(12) United States Patent
Kumar et al.

(10) Patent No.: US 12,427,329 B2
(45) Date of Patent: *Sep. 30, 2025

(54) EXTERNAL DEFIBRILLATOR

(71) Applicant: ELEMENT SCIENCE, INC., San Francisco, CA (US)

(72) Inventors: Uday N. Kumar, San Francisco, CA (US); Zachary J. Malchano, Boston, MA (US); Maarten Dinger, San Francisco, CA (US); Timothy Bahney, Edwards, CO (US); Frank Garcia, Redwood City, CA (US)

(73) Assignee: Element Science, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/627,158

(22) Filed: Apr. 4, 2024

(65) Prior Publication Data
US 2024/0359024 A1    Oct. 31, 2024

Related U.S. Application Data

(63) Continuation of application No. 17/501,805, filed on Oct. 14, 2021, now Pat. No. 11,975,209, which is a
(Continued)

(51) Int. Cl.
*A61N 1/00* (2006.01)
*A61N 1/04* (2006.01)
(Continued)

(52) U.S. Cl.
CPC .......... *A61N 1/3968* (2013.01); *A61N 1/046* (2013.01); *A61N 1/3975* (2013.01);
(Continued)

(58) Field of Classification Search
CPC .... A61N 1/3968; A61N 1/046; A61N 1/3975; A61N 1/3987; A61N 1/0496;
(Continued)

(56) References Cited

U.S. PATENT DOCUMENTS 3,706,313 A    12/1972 Milani et al.
3,924,641 A    12/1975 Weiss
(Continued)

FOREIGN PATENT DOCUMENTS

CN    102316795 A    1/2012
CN    103354756 A    10/2013
(Continued)

OTHER PUBLICATIONS

3M Health Care; Tegaderm high performance foam adhesive dressing (Product Description); 8 pages retrieved from the internet (https://multimedia.3m.com/mws/media/7946980/tegaderm-hp-foam.pdf); on Sep. 22, 2021.
(Continued)

*Primary Examiner* — Scott M. Getzow
(74) *Attorney, Agent, or Firm* — Shay Glenn LLP

(57) ABSTRACT

A wearable external defibrillator with a plurality of ECG sensing electrodes and a first defibrillator pad electrode and a second defibrillator pad electrode. The ECG sensing electrodes and the defibrillator pad electrodes are configured for long term wear.

15 Claims, 90 Drawing Sheets

Related U.S. Application Data continuation of application No. 16/721,506, filed on Dec. 19, 2019, now Pat. No. 11,185,709, which is a continuation of application No. 15/120,655, filed as application No. PCT/US2015/017366 on Feb. 24, 2015, now abandoned.

(60) Provisional application No. 61/944,008, filed on Feb. 24, 2014.

(51) Int. Cl.
| | | |
|---|---|---|
| *A61N 1/39* | (2006.01) | |
| *G16H 20/30* | (2018.01) | |
| *G16H 50/20* | (2018.01) | |
| *A61N 1/36* | (2006.01) | |
| *A61N 1/362* | (2006.01) | |

(52) U.S. Cl.
CPC .......... *A61N 1/3987* (2013.01); *G16H 20/30* (2018.01); *G16H 50/20* (2018.01); *A61N 1/0496* (2013.01); *A61N 1/36014* (2013.01); *A61N 1/3625* (2013.01); *A61N 1/3904* (2017.08)

(58) Field of Classification Search
CPC .............. A61N 1/36014; A61N 1/3625; A61N 1/3904; G16H 20/30; G16H 50/20
See application file for complete search history.

(56) References Cited

U.S. PATENT DOCUMENTS

| | | |
|---|---|---|
| 4,023,573 A | 5/1977 | Pantridge et al. |
| 4,184,493 A | 1/1980 | Langer et al. |
| 4,328,808 A | 5/1982 | Charbonnier et al. |
| 4,473,078 A | 9/1984 | Angel |
| 4,499,907 A | 2/1985 | Kallok et al. |
| 4,504,773 A | 3/1985 | Suzuki et al. |
| 4,523,595 A | 6/1985 | Zibell |
| 4,548,203 A | 10/1985 | Tacker et al. |
| 4,574,810 A | 3/1986 | Lerman |
| 4,576,170 A | 3/1986 | Bradley et al. |
| 4,595,009 A | 6/1986 | Leinders |
| 4,614,192 A | 9/1986 | Imran et al. |
| 4,637,397 A | 1/1987 | Jones et al. |
| 4,706,680 A | 11/1987 | Keusch et al. |
| 4,708,145 A | 11/1987 | Tacker et al. |
| 4,727,877 A | 3/1988 | Kallok |
| 4,768,512 A | 9/1988 | Imran |
| 4,777,954 A | 10/1988 | Keusch et al. |
| 4,800,883 A | 1/1989 | Winstrom |
| 4,821,723 A | 4/1989 | Baker et al. |
| 4,823,796 A | 4/1989 | Benson |
| 4,834,100 A | 5/1989 | Charms |
| 4,850,357 A | 7/1989 | Bach |
| 4,869,252 A | 9/1989 | Gilli |
| 4,928,690 A | 5/1990 | Heilman et al. |
| 4,953,551 A | 9/1990 | Mehra et al. |
| 4,989,607 A | 2/1991 | Keusch et al. |
| 4,996,984 A | 3/1991 | Sweeney |
| 5,014,701 A | 5/1991 | Pless et al. |
| 5,078,134 A | 1/1992 | Heilman et al. |
| 5,083,562 A | 1/1992 | de Coriolis et al. |
| 5,092,332 A | 3/1992 | Lee et al. |
| 5,107,834 A | 4/1992 | Ideker et al. |
| 5,111,813 A | 5/1992 | Charbonnier et al. |
| 5,143,071 A | 9/1992 | Keusch et al. |
| 5,163,427 A | 11/1992 | Keimel |
| 5,172,690 A | 12/1992 | Nappholz et al. |
| 5,174,288 A | 12/1992 | Bardy et al. |
| 5,179,946 A | 1/1993 | Weiss |
| 5,184,616 A | 2/1993 | Weiss |
| 5,205,284 A | 4/1993 | Freeman |
| 5,207,219 A | 5/1993 | Adams et al. |
| 5,222,492 A | 6/1993 | Morgan et al. |
| 5,230,336 A | 7/1993 | Fain et al. |
| 5,251,624 A | 10/1993 | Bocek et al. |
| 5,261,400 A | 11/1993 | Bardy |
| 5,271,417 A | 12/1993 | Swanson et al. |
| 5,292,338 A | 3/1994 | Bardy |
| 5,314,430 A | 5/1994 | Bardy |
| 5,324,309 A | 6/1994 | Kallok |
| 5,334,219 A | 8/1994 | Kroll |
| 5,344,429 A | 9/1994 | Smits |
| 5,352,239 A | 10/1994 | Pless |
| 5,360,435 A | 11/1994 | DeGroot |
| 5,366,484 A | 11/1994 | Kroll |
| 5,366,485 A | 11/1994 | Kroll et al. |
| 5,366,497 A | 11/1994 | Ilvento et al. |
| 5,372,606 A | 12/1994 | Lang et al. |
| 5,381,803 A | 1/1995 | Herleikson et al. |
| 5,391,186 A | 2/1995 | Kroll et al. |
| 5,395,395 A | 3/1995 | Hedberg |
| 5,405,366 A | 4/1995 | Fox et al. |
| 5,411,547 A | 5/1995 | Causey |
| 5,413,591 A | 5/1995 | Knoll |
| 5,431,687 A | 7/1995 | Kroll |
| 5,431,693 A | 7/1995 | Schroeppel |
| 5,439,484 A | 8/1995 | Mehra |
| 5,456,690 A | 10/1995 | Duong Van |
| 5,466,244 A | 11/1995 | Morgan |
| 5,468,254 A | 11/1995 | Hahn et al. |
| 5,474,574 A | 12/1995 | Payne et al. |
| 5,483,165 A | 1/1996 | Cameron et al. |
| 5,489,293 A | 2/1996 | Pless et al. |
| 5,507,778 A | 4/1996 | Freeman |
| 5,540,723 A | 7/1996 | Ideker et al. |
| 5,540,724 A | 7/1996 | Cox |
| 5,545,182 A | 8/1996 | Stotts et al. |
| 5,545,183 A | 8/1996 | Altman |
| 5,578,062 A | 11/1996 | Alt et al. |
| 5,591,211 A | 1/1997 | Meltzer |
| 5,591,212 A | 1/1997 | Keimel |
| 5,594,287 A | 1/1997 | Cameron |
| 5,607,454 A | 3/1997 | Cameron et al. |
| 5,620,467 A | 4/1997 | Wagner |
| 5,622,168 A | 4/1997 | Keusch et al. |
| 5,632,267 A | 5/1997 | Hognelid et al. |
| 5,643,324 A | 7/1997 | Persson |
| 5,645,586 A | 7/1997 | Meltzer |
| 5,650,750 A | 7/1997 | Leyde et al. |
| 5,658,319 A | 8/1997 | Kroll |
| 5,662,690 A | 9/1997 | Cole et al. |
| 5,670,557 A | 9/1997 | Dietz et al. |
| 5,674,250 A | 10/1997 | de Coriolis et al. |
| 5,674,275 A | 10/1997 | Tang et al. |
| 5,683,424 A | 11/1997 | Brown et al. |
| 5,718,718 A | 2/1998 | Kroll et al. |
| 5,720,767 A | 2/1998 | Velez |
| 5,725,560 A | 3/1998 | Brink |
| 5,735,879 A | 4/1998 | Gliner et al. |
| 5,741,306 A | 4/1998 | Glegyak et al. |
| 5,766,226 A | 6/1998 | Pedersen |
| 5,769,872 A | 6/1998 | Lopin et al. |
| 5,792,188 A | 8/1998 | Starkweather et al. |
| 5,803,927 A | 9/1998 | Cameron et al. |
| 5,817,151 A | 10/1998 | Olson et al. |
| 5,824,017 A | 10/1998 | Sullivan et al. |
| 5,824,018 A | 10/1998 | Dreher et al. |
| 5,833,712 A | 11/1998 | Kroll et al. |
| 5,849,025 A | 12/1998 | Owens et al. |
| 5,889,388 A | 3/1999 | Cameron et al. |
| 5,891,173 A | 4/1999 | Brewer |
| D409,752 S | 5/1999 | Bishay et al. |
| 5,902,249 A | 5/1999 | Lyster |
| 5,902,323 A | 5/1999 | Brewer et al. |
| 5,908,443 A | 6/1999 | Brewer et al. |
| 5,928,270 A | 7/1999 | Ramsey |
| 5,929,601 A | 7/1999 | Kaib et al. |
| 5,944,669 A | 8/1999 | Kaib |
| 5,951,598 A | 9/1999 | Bishay et al. |
| 5,974,339 A | 10/1999 | Baker et al. |
| 5,978,705 A | 11/1999 | KenKnight et al. |

(56) References Cited

U.S. PATENT DOCUMENTS

| | | |
|---|---|---|
| 5,987,354 A | 11/1999 | Cooper et al. |
| 5,991,658 A | 11/1999 | Brewer et al. |
| 6,041,255 A | 3/2000 | Kroll |
| 6,065,154 A | 5/2000 | Hulings et al. |
| 6,093,982 A | 7/2000 | Kroll |
| 6,097,982 A | 8/2000 | Glegyak et al. |
| 6,101,413 A | 8/2000 | Olson et al. |
| 6,104,953 A | 8/2000 | Leyde |
| 6,108,578 A | 8/2000 | Bardy et al. |
| 6,119,039 A | 9/2000 | Leyde |
| 6,125,298 A | 9/2000 | Olson et al. |
| 6,128,531 A | 10/2000 | Smith |
| 6,134,479 A | 10/2000 | Brewer et al. |
| 6,148,222 A | 11/2000 | Ramsey |
| 6,148,233 A | 11/2000 | Owen et al. |
| 6,169,387 B1 | 1/2001 | Kaib |
| 6,173,204 B1 | 1/2001 | Sullivan et al. |
| 6,208,896 B1 | 3/2001 | Mulhauser |
| 6,208,898 B1 | 3/2001 | Gliner et al. |
| 6,219,222 B1 | 4/2001 | Shah et al. |
| 6,230,054 B1 | 5/2001 | Powers |
| 6,234,990 B1 | 5/2001 | Rowe et al. |
| 6,241,751 B1 | 6/2001 | Morgan et al. |
| 6,253,099 B1 | 6/2001 | Oskin et al. |
| 6,280,461 B1 | 8/2001 | Glegyak et al. |
| 6,289,243 B1 | 9/2001 | Lin et al. |
| 6,298,267 B1 | 10/2001 | Rosborough et al. |
| 6,304,773 B1 | 10/2001 | Taylor et al. |
| 6,304,783 B1 | 10/2001 | Lyster et al. |
| 6,327,499 B1 | 12/2001 | Alt |
| 6,337,995 B1 | 1/2002 | Mower |
| 6,347,248 B1 | 2/2002 | Gliner |
| 6,411,844 B1 | 6/2002 | Kroll et al. |
| 6,421,563 B1 | 7/2002 | Sullivan et al. |
| 6,441,582 B1 | 8/2002 | Powers |
| 6,451,947 B1 | 9/2002 | Benz et al. |
| 6,480,734 B1 | 11/2002 | Zhang et al. |
| 6,490,478 B1 | 12/2002 | Zhang et al. |
| 6,496,729 B2 | 12/2002 | Thompson |
| 6,539,255 B1 | 3/2003 | Brewer et al. |
| 6,539,258 B1 | 3/2003 | Sullivan et al. |
| 6,546,285 B1 | 4/2003 | Owen et al. |
| 6,546,287 B1 | 4/2003 | Havel et al. |
| 6,549,807 B1 | 4/2003 | Kroll |
| 6,556,863 B1 | 4/2003 | O'Phelan et al. |
| 6,597,949 B1 | 7/2003 | Dhurjaty |
| 6,625,487 B2 | 9/2003 | Herleikson |
| 6,633,778 B2 | 10/2003 | Sherman |
| 6,647,290 B2 | 11/2003 | Wuthrich |
| 6,678,559 B1 | 1/2004 | Breyen et al. |
| 6,681,003 B2 | 1/2004 | Linder et al. |
| 6,687,117 B2 | 2/2004 | Liu et al. |
| 6,738,664 B1 | 5/2004 | McDaniel |
| 6,760,621 B2 | 7/2004 | Walcott et al. |
| 6,766,193 B1 | 7/2004 | Mouchawar et al. |
| 6,834,050 B1 | 12/2004 | Madour et al. |
| 6,856,835 B2 | 2/2005 | Bardy et al. |
| 6,871,094 B1 | 3/2005 | Allen et al. |
| 6,873,133 B1 | 3/2005 | Kavounas |
| 6,873,874 B2 | 3/2005 | Ware et al. |
| 6,954,669 B1 | 10/2005 | Fishler et al. |
| 6,963,773 B2 | 11/2005 | Waltman et al. |
| 6,965,796 B2 | 11/2005 | Kelly |
| 6,965,799 B2 | 11/2005 | Nova et al. |
| 6,968,230 B2 | 11/2005 | Waltman |
| 6,980,856 B2 | 12/2005 | Sullivan et al. |
| 6,983,183 B2 | 1/2006 | Thiagarajan et al. |
| 6,990,373 B2 | 1/2006 | Jayne et al. |
| 6,993,386 B2 | 1/2006 | Lin et al. |
| 6,996,436 B2 | 2/2006 | Allen et al. |
| 7,006,865 B1 | 2/2006 | Cohen et al. |
| 7,027,864 B2 | 4/2006 | Snyder et al. |
| 7,047,072 B2 | 5/2006 | Walker et al. |
| 7,050,850 B2 | 5/2006 | Norton |
| 7,054,686 B2 | 5/2006 | MacDonald |
| 7,062,321 B2 | 6/2006 | Lyster et al. |
| 7,079,894 B2 | 7/2006 | Lyster et al. |
| 7,085,601 B1 | 8/2006 | Bardy et al. |
| 7,095,210 B2 | 8/2006 | Tamura et al. |
| 7,096,062 B2 | 8/2006 | Kelly et al. |
| 7,107,099 B1 | 9/2006 | O'Phelan et al. |
| 7,149,576 B1 | 12/2006 | Baura et al. |
| 7,151,963 B2 | 12/2006 | Havel et al. |
| 7,174,204 B2 | 2/2007 | Hadley et al. |
| 7,174,208 B2 | 2/2007 | DeGroot et al. |
| 7,194,303 B2 | 3/2007 | Rissmann et al. |
| 7,200,434 B2 | 4/2007 | Havel et al. |
| 7,242,979 B1 | 7/2007 | Kelly et al. |
| 7,245,974 B2 | 7/2007 | Dupelle et al. |
| 7,257,441 B2 | 8/2007 | Swerdlow et al. |
| 7,272,441 B1 | 9/2007 | Chapman et al. |
| 7,277,751 B2 | 10/2007 | Dupelle et al. |
| 7,379,772 B2 | 5/2008 | Bardy et al. |
| 7,383,085 B2 | 6/2008 | Olson |
| 7,385,802 B1 | 6/2008 | Ribble et al. |
| 7,392,081 B2 | 6/2008 | Wagner et al. |
| 7,463,923 B2 | 12/2008 | Brewer et al. |
| 7,570,994 B2 | 8/2009 | Tamura et al. |
| 7,570,996 B2 | 8/2009 | Crespi et al. |
| 7,667,954 B2 | 2/2010 | Lessner et al. |
| 7,684,864 B2 | 3/2010 | Olson et al. |
| 7,706,864 B2 | 4/2010 | Kroll et al. |
| 7,729,770 B2 | 6/2010 | Cabelka et al. |
| 7,734,345 B2 | 6/2010 | Cinbis |
| 7,840,265 B2 | 11/2010 | Perschbacher et al. |
| 7,920,918 B2 | 4/2011 | Ideker et al. |
| 7,962,207 B2 | 6/2011 | Nassif |
| 7,974,689 B2 | 7/2011 | Volpe et al. |
| 8,000,786 B2 | 8/2011 | Sweeney |
| 8,024,037 B2 | 9/2011 | Kumar |
| 8,050,759 B2 | 11/2011 | Stegemann et al. |
| 8,086,312 B2 | 12/2011 | Nielsen et al. |
| 8,108,043 B2 | 1/2012 | Markowitz et al. |
| 8,116,865 B2 | 2/2012 | Linder et al. |
| 8,121,683 B2 | 2/2012 | Bucher et al. |
| 8,145,303 B2 | 3/2012 | Rubin et al. |
| 8,195,280 B2 | 6/2012 | Van Dam et al. |
| 8,209,007 B2 | 6/2012 | Mcintyre et al. |
| 8,239,012 B2 | 8/2012 | Felix et al. |
| 8,343,644 B2 | 1/2013 | Vaisnys et al. |
| 8,364,260 B2 | 1/2013 | Kumar |
| 8,369,945 B2 | 2/2013 | Youker et al. |
| 8,386,035 B2 | 2/2013 | Valsnys et al. |
| 8,401,637 B2 | 3/2013 | Kroll et al. |
| 8,401,638 B2 | 3/2013 | Swerdlow et al. |
| 8,423,136 B2 | 4/2013 | Ostroff |
| 8,433,404 B2 | 4/2013 | Chavan et al. |
| 8,473,051 B1 | 6/2013 | Wessels et al. |
| 8,706,215 B2 | 4/2014 | Kaib et al. |
| 8,838,236 B2 | 9/2014 | Debardi et al. |
| 9,101,780 B2 | 8/2015 | Cheng et al. |
| 9,237,858 B2 | 1/2016 | Krusor et al. |
| 9,592,403 B2 | 3/2017 | Sullivan |
| 9,597,004 B2 | 3/2017 | Hughes et al. |
| 9,724,008 B2 | 8/2017 | Sullivan et al. |
| 9,757,579 B2 | 9/2017 | Foshee et al. |
| 9,757,581 B2 | 9/2017 | Sullivan et al. |
| 9,789,327 B2 | 10/2017 | Brown et al. |
| 9,827,434 B2 | 11/2017 | Kaib et al. |
| 9,833,607 B2 | 12/2017 | Crone et al. |
| 10,271,754 B2 | 4/2019 | Bahney et al. |
| 10,328,275 B2 | 6/2019 | Donnelly et al. |
| 10,953,234 B2 | 3/2021 | Kumar et al. |
| 11,076,792 B2 | 8/2021 | Tompkins et al. |
| 11,185,709 B2 | 11/2021 | Kumar et al. |
| 11,253,715 B2 | 2/2022 | Kumar et al. |
| 11,701,521 B2 | 7/2023 | Kumar et al. |
| 11,975,209 B2 | 5/2024 | Kumar et al. |
| 2001/0037093 A1 | 11/2001 | Benkowski et al. |
| 2002/0188216 A1 | 12/2002 | Kayyali et al. |
| 2003/0055460 A1 | 3/2003 | Owen et al. |
| 2003/0095648 A1 | 5/2003 | Kaib et al. |
| 2003/0125771 A1 | 7/2003 | Garrett |
| 2003/0167075 A1 | 9/2003 | Fincke |

(56) References Cited

U.S. PATENT DOCUMENTS

| | | |
|---|---|---|
| 2003/0201752 A1 | 10/2003 | Locke et al. |
| 2004/0143297 A1 | 7/2004 | Ramsey |
| 2004/0267322 A1 | 12/2004 | Kavounas et al. |
| 2005/0070963 A1 | 3/2005 | Wilson et al. |
| 2005/0090868 A1 | 4/2005 | Cansell |
| 2005/0107833 A1 | 5/2005 | Freeman et al. |
| 2005/0131465 A1 | 6/2005 | Freeman et al. |
| 2005/0234515 A1 | 10/2005 | Freeman |
| 2006/0116724 A1 | 6/2006 | Snyder |
| 2006/0129192 A1 | 6/2006 | Greatbatch et al. |
| 2006/0149346 A1 | 7/2006 | Dupelle et al. |
| 2006/0173499 A1 | 8/2006 | Hampton et al. |
| 2006/0178706 A1 | 8/2006 | Lisogurski et al. |
| 2006/0229679 A1 | 10/2006 | Joo |
| 2006/0241700 A1 | 10/2006 | Ghanem et al. |
| 2006/0259091 A1 | 11/2006 | Ries et al. |
| 2006/0285302 A1 | 12/2006 | Kim |
| 2007/0100381 A1 | 5/2007 | Snyder et al. |
| 2008/0177342 A1 | 7/2008 | Snyder |
| 2008/0183230 A1 | 7/2008 | Kemmetmueller et al. |
| 2008/0255625 A1 | 10/2008 | Powers |
| 2008/0312708 A1 | 12/2008 | Snyder |
| 2009/0005827 A1 | 1/2009 | Weintraub et al. |
| 2009/0076345 A1 | 3/2009 | Manicka et al. |
| 2009/0076559 A1 | 3/2009 | Libbus et al. |
| 2009/0306730 A1 | 12/2009 | Roso |
| 2010/0030290 A1 | 2/2010 | Bonner et al. |
| 2010/0241181 A1 | 9/2010 | Savage et al. |
| 2010/0292544 A1 | 11/2010 | Sherman et al. |
| 2011/0071611 A1 | 3/2011 | Khuon et al. |
| 2011/0125040 A1 | 5/2011 | Crawford et al. |
| 2011/0279963 A1 | 11/2011 | Kumar et al. |
| 2011/0288604 A1 | 11/2011 | Kaib et al. |
| 2012/0025521 A1 | 2/2012 | Baller et al. |
| 2012/0046706 A1 | 2/2012 | Anderson et al. |
| 2012/0089037 A1 | 4/2012 | Bishay et al. |
| 2012/0116472 A1 | 5/2012 | Pittaro |
| 2012/0158075 A1 | 6/2012 | Kaib et al. |
| 2012/0169287 A1 | 7/2012 | Lopin et al. |
| 2012/0191149 A1 | 7/2012 | Freeman |
| 2012/0197353 A1 | 8/2012 | Donnelly et al. |
| 2012/0215123 A1 | 8/2012 | Kumar et al. |
| 2012/0265264 A1 | 10/2012 | Vaisnys et al. |
| 2012/0289809 A1 | 11/2012 | Kaib et al. |
| 2012/0302860 A1 | 11/2012 | Volpe et al. |
| 2012/0325096 A1 | 12/2012 | Holt |
| 2013/0018432 A1 | 1/2013 | Garrett et al. |
| 2013/0053909 A1 | 2/2013 | Elghazzawi et al. |
| 2013/0085538 A1 | 4/2013 | Volpe et al. |
| 2013/0123870 A1 | 5/2013 | Heinrich et al. |
| 2013/0158614 A1 | 6/2013 | Azar et al. |
| 2013/0325096 A1 | 12/2013 | Dupelle et al. |
| 2014/0025131 A1 | 1/2014 | Sullivan et al. |
| 2014/0039594 A1 | 2/2014 | Savage et al. |
| 2014/0207201 A1 | 7/2014 | Piha et al. |
| 2014/0243694 A1 | 8/2014 | Baker et al. |
| 2014/0277226 A1 | 9/2014 | Poore et al. |
| 2014/0371806 A1 | 12/2014 | Raymond et al. |
| 2014/0378782 A1 | 12/2014 | Herken et al. |
| 2015/0148854 A1 | 5/2015 | Whiting et al. |
| 2015/0217121 A1 | 8/2015 | Subramanian et al. |
| 2015/0238094 A1 | 8/2015 | Lai et al. |
| 2015/0321022 A1 | 11/2015 | Sullivan et al. |
| 2017/0056682 A1 | 3/2017 | Kumar et al. |
| 2022/0126107 A1 | 4/2022 | Kumar et al. |
| 2024/0091545 A1 | 3/2024 | Kumar et al. |

FOREIGN PATENT DOCUMENTS

| | | |
|---|---|---|
| CN | 103405851 A | 11/2013 |
| CN | 103443794 A | 12/2013 |
| CN | 106470593 A | 3/2014 |
| EP | 95726 B1 | 11/1988 |
| EP | 362093 A2 | 4/1990 |
| EP | 445800 A1 | 9/1991 |
| EP | 487776 A1 | 6/1992 |
| EP | 612253 A1 | 8/1994 |
| EP | 503778 B1 | 7/1996 |
| EP | 469817 B1 | 2/1997 |
| EP | 465241 B1 | 11/1998 |
| EP | 589251 B1 | 11/2000 |
| EP | 1263497 A1 | 12/2002 |
| EP | 988087 B1 | 1/2003 |
| EP | 998328 B1 | 10/2003 |
| EP | 687479 B1 | 8/2004 |
| EP | 973582 B1 | 5/2005 |
| EP | 888149 B1 | 7/2005 |
| EP | 1742700 A2 | 1/2007 |
| EP | 1759732 A1 | 3/2007 |
| EP | 1827594 A1 | 9/2007 |
| EP | 1954345 A2 | 8/2008 |
| EP | 2047886 A1 | 4/2009 |
| EP | 1530983 B1 | 9/2009 |
| EP | 2446927 A1 | 5/2012 |
| JP | H04184831 A | 7/1992 |
| JP | H06105917 A | 4/1994 |
| JP | H07541 A | 1/1995 |
| JP | H10509334 A | 9/1998 |
| JP | 2002514107 | 5/2002 |
| JP | 2007150180 A | 6/2007 |
| JP | 2008520306 A | 6/2008 |
| JP | 2013542787 | 11/2013 |
| JP | 2014533525 A | 12/2014 |
| JP | 2015521085 A | 7/2015 |
| JP | 2017506121 | 3/2017 |
| WO | WO97/031680 A1 | 9/1997 |
| WO | WO2001/085251 A1 | 11/2001 |
| WO | WO2006/115778 A2 | 11/2006 |
| WO | WO2007/092543 A2 | 8/2007 |
| WO | WO2007/113452 A1 | 10/2007 |
| WO | WO2010/096774 A2 | 8/2010 |
| WO | WO2011/163339 A1 | 12/2011 |
| WO | WO2013/033238 A1 | 3/2013 |
| WO | WO2013/181607 A1 | 12/2013 |
| WO | WO2014/007307 A1 | 1/2014 |
| WO | WO2014/151925 A1 | 9/2014 |
| WO | WO2015/017727 A1 | 2/2015 |

OTHER PUBLICATIONS

Aliexpress; Car wrapping cut tool double head carbon vinyl film cutter knife with paperback slitter blade mo-1108; 4 pages; retrived from the internet (https://www.aliexpress.us/item/2261800118493818.html?gatewayAdapt=glo2usa4itemAdapt) on Apr. 2021.

Birgersdotter-Green; Advances in AEDs and wearable defibrillators (presentation slides): 23 pages; 2013 (year of pub. sufficiently earlier than effective US filing date and any foreign priority date; available to applicants(s) at least as of Jun. 4, 2013).

Calle et al.; Equivalence of the standard monophasic waveform shocks delivered by automated external defibrillators; Resuscitation; 53(1); pp. 41-46; Apr. 2002.

Caterham; Half-side screen with armrests, left carbon vinyl, S3, R500; 6 pages; retrieved from the internet (https://caterhamshop.official.ec/items/23847744) on Apr. 21, 2023.

Field et al.; Part 1: Executive Summary: 2010 American heart association guidelines for cardiopulmonary resuscitation and emergency cardiovascular care; Circulation; 122 (18 Suppl. 3); pp. S640-S656; Nov. 2, 2010.

International Chemical Co.; Saturated silver/silver chloride reference electrode with double junction holder; 1 page; retrieved from the internet (https://www.autolabj.com/construction.files/electrode.files/E-agagcl.htm) on Apr. 21, 2023.

Jones et al.; improved safety factor for triphasic defibrillator waveforms; Cir. Res.; 64(6); pp. 1172-1177; Jun. 1989.

Jones et al.; Increasing fibrillation duration enhances relative asymmetrical biphasic versus monophasic defibrillator waveform efficacy; Circ. Res.; 67(2); pp. 376-384; Aug. 1990.

Kotobank; Silver-silver chloride electrode; 3 pages; retrieved from the internet (https://kotobank.jp/word/%E9%8A%80-%E5%A1%A9%E5%80%96%E9%8A%80%E9%9B%BB%E6%A5%B5-764277) on May 1, 2023.

(56) References Cited

OTHER PUBLICATIONS

Pariaut et al; Evaluation of shock waveform configuration on the defibrillation capacity of implantable cardioverter defibrillators in dogs; J. Vet. Cardiol.; 14(3); pp. 389-398; Sep. 2012.

Swartz et al.; Conditioning prepulse of biphasic defibrillator waveforms enhances refractoriness to fibrillation wavefronts; Circulation Res.; 68(2); pp. 438-449; Feb. 1991.

Walsh et al.; Novel rectangular biphasic and monophasic waveforms delivered by a radiofrequency-powered defibrillator compared with conventional capacitor-based waveforms in transvenous cardioversion of atrial fibrillation; Europace; 8(10); pp. 873-880; Oct. 2006.

Zipes et al.; ACC/AHA/ESC 2006 guidelines for management of patients with ventricular arrhythmias and the prevention of sudden cardiac death; Europace; 8(9); pp. 746-837; Sep. 2006.

Zoll; LifeVest model 4000 Patient Manual; 16 pages retrieved from the internet (https://www.accessdata.fda.gov/cdrh_docs/pdf/P010030S056c.pdf0; on Sep. 22, 2021.

Kumar et al.; U.S. Appl. No. 18/954,331 entitled "Wearable medical device with disposable and reusable components," filed Nov. 20, 2024.

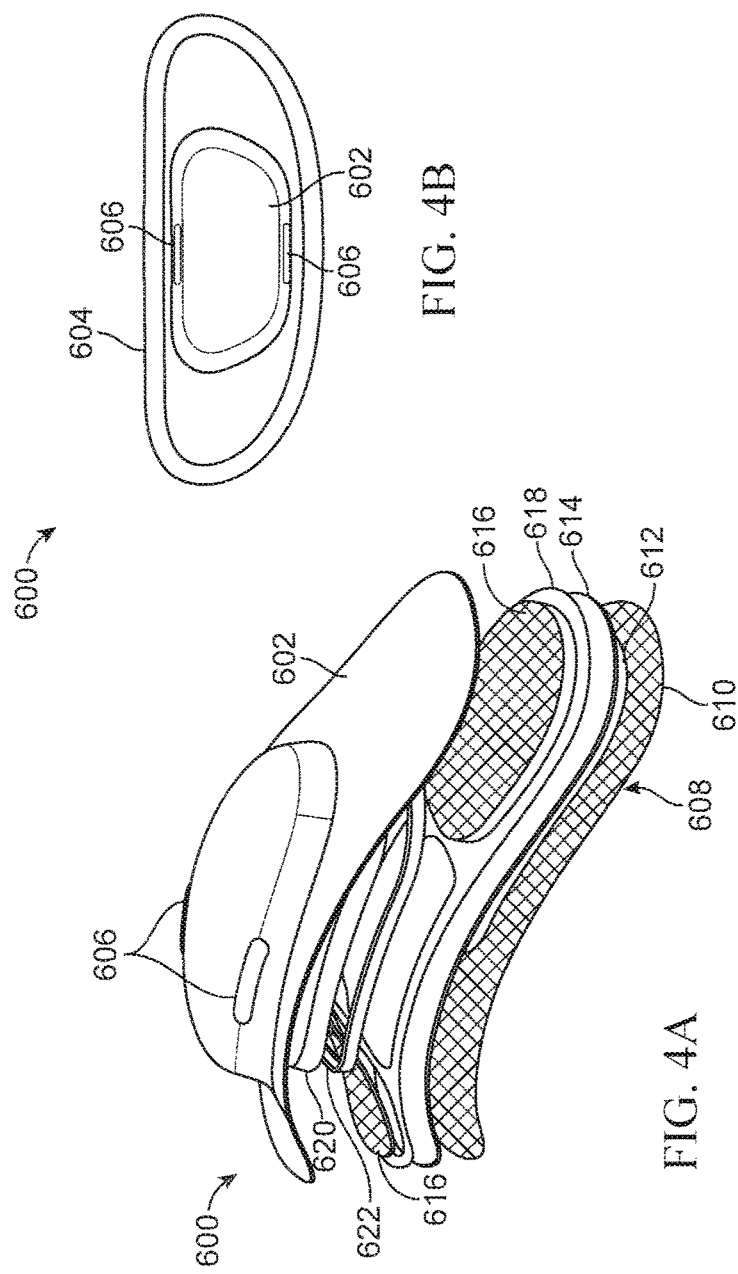

| PSA | Wear Duration | Tact | MTVR | Moisture Resistance | Absorption | Elastic | Cost |
|---|---|---|---|---|---|---|---|
| Acrylate | □□ | □□□ | □ | □ | □ | □ | □ |
| Silicone | □□ | □□ | □□ | □□□ | □ | □□ | □□□ |
| Hydrocolloid | □□□ | □□□ | □ | □□ | □□□ | □□□ | □□ |

| Property | Acrylic | Natural Rubber | Synthetic Rubber | Polyolefin | Polyurethane | Silicone |
|---|---|---|---|---|---|---|
| Tack | low to high | high | high | medium | low | low to high |
| Peel Adhesion | medium to high | high | high | medium | low to medium | medium |
| Cohesive Strength | low to high | high | high | low | low to medium | high |
| Adhesion Stability Upon Aging | poor | poor | poor | medium | medium | excellent |
| Plasticizer Resistance | low to medium | low | low | low | medium | good |
| Oxidation Resistance | good | poor | poor | poor | good | excellent |
| Adhesive Color | clear | yellow | clear to straw | clear to straw | clear to straw | clear |
| Solvent Resistance | high | fair | fair | fair | high | excellent |
| Permeability to Air | poor | poor | poor | poor | poor | excellent |
| MVTR | good | poor | poor | poor | good | fair |
| Repositionability on Skin | poor | poor | poor | poor | fair | excellent |
| Low Skin Sensitivity | good | poor | good | good | good | excellent |
| Low Skin Trauma | poor | poor | poor | good | good | excellent |
| Cost | medium | low | low | medium | high | high |

FIG. 14

| | | | | | |
|---|---|---|---|---|---|
| AC | Motor Start | – | – | Snap | -20 / +65 |
| ACC | Low ESR | Long Life, Switch Mode Apps | 70000 @ +55 | Snap | -40 / +85 |
| ACS | Low ESR | Long Life, Switch Mode Apps | 70000 @ +55 | Snap | -40 / +85 |
| AK | Overvoltage Protected | Flame Retardant | 2000R @ +105 | Snap | -25 / +105 |
| AKS | Low ESR | Long Life, Switch Mode Apps | 70000 @ +55 | Pin | -40 / +85 |
| ALP10 | General Purpose | Board Mounting | 2000 @ +85 | Pin | -40 / +85 |
| ALS10 | Computer Grade | – | 2000 @ +85 | Screw | -40 / +85 |
| ALS11 | Computer Grade | Stud Mount | 2000 @ +85 | Screw | -40 / +85 |
| ALS20 | Computer Grade | Long Life | 5000 @ +85 | Screw | -55 / +85 |
| ALS21 | Computer Grade | Stud Mount, Long Life | 5000 @ +85 | Screw | -55 / +85 |
| ALS27 | Computer Grade | Stud Mount, Long Life, Dimensions Meet CO37/39 | 5000 @ +85 | Screw | -55 / +85 |
| ALS29 | Computer Grade | Long Life, Dimensions Meet CO37/39 | 5000 @ +85 | Screw | -55 / +85 |
| ALS30 | Large, Screw, Long Life | High ripple, long life | 5000 @ +85 | Screw | -40 / +85 |
| ALS30 | Large, Screw, Long Life | High ripple, long life | 5000 @ +85 | Screw | -40 / +85 |
| ALS31 | Large, Screw, Long Life | High ripple, long life | 5000 @ +85 | Screw | -40 / +85 |
| ALS31 | Large, Screw, Long Life | High ripple, long life | 5000 @ +85 | Screw | -40 / +85 |
| ALS40 | Large, Screw, Long Life | High Ripple | 2000 @ +105 | Screw | -40 / +105 |
| ALS41 | Large, Screw, Long Life | High Ripple | 2000 @ +105 | Screw | -40 / +105 |
| ALS60 | Large, Screw, Long Life | High Ripple | 2000 @ +125 | Screw | -55 / +125 |
| ALS61 | Large, Screw, Long Life | High Ripple | 2000 @ +125 | Screw | -55 / +125 |
| ALT10 | General Purpose | Solder Tag Terminals | 2000 @ +85 | Lug | -40 / +85 |
| ALT11 | General Purpose | Solder Tag Terminals, Stud Mount | 2000 @ +85 | Lug | -40 / +85 |
| AR | High Reliability | Long Life, High Cap | 110000 @ +55 | Screw | -40 / +85 |
| AR-HG | High Reliability | Very High CV | 110000 @ +55 | Screw | -40 / +85 |
| ARU | High Reliability | Long Life, High Cap | 110000 @ +55 | Screw | -40 / +85 |
| ARU-HG | High Reliability | Very High CV | 110000 @ +55 | Screw | -40 / +85 |
| AS | High Reliability | Long Life, High Surge Voltage | 150000 @ +55 | Screw | -40 / +85 |
| ASM | General Purpose | Miniature | 1000 @ +105 | Radial | -55 / +105 |
| ASU | High Reliability | Long Life, High Surge Voltage | 150000 @ +55 | Screw | -40 / +85 |
| AT | High Reliability | Long Life, Extended Temp Range | 330000 @ +55 | Screw | -55 / +105 |
| ATC | Low ESR | Extended Temp Range, Switch Mode Apps | 120000 @ +55 | Snap | -25 / +105 |
| ATS | Low ESR | Extended Temp Range, Switch Mode Apps | 120000 @ +55 | Snap | -25 / +105 |
| ATU | High Reliability | Long Life, Extended Temp Range | 330000 @ +55 | Screw | -55 / +105 |
| AUP | General Purpose | – | 2000 @ +105 | Screw | -40 / +105 |
| AY-HR | High Voltage | Long Life, High Ripple Current | 130000 @ +55 | Screw | -40 / +85 |
| AYU-HR | High Voltage | Long Life, High Ripple Current | 130000 @ +55 | Screw | -40 / +85 |

FIG. 20

| | | | | | |
|---|---|---|---|---|---|
| 110 / 160 | 40 / 150 | – | Sanyo | $Al_2O_3$ | |
| 25 / 500 | 68 / 47000 | 0.006CV (5min) | Itelcond | $Al_2O_3$ | – |
| 25 / 500 | 68 / 47000 | 0.006CV (5min) | Itelcond | $Al_2O_3$ | Two Terminals |
| 200 / 400 | 33 / 1200 | 3*SQRT(CV) | Nichicon | $Al_2O_3$ | Four Terminals |
| 40 / 450 | 100 / 100000 | 0.006CV (5min) | Itelcond | $Al_2O_3$ | – |
| 10 / 385 | 100 / 68,000 | 0.006*SQRT(CV)+4 max. (5 min.) | BHC | $Al_2O_3$ | For Printed Wiring Board |
| 10 / 450 | 68 / 470,000 | 4*SQRT(CV) or 6 mA max. (5 min.) | BHC | $Al_2O_3$ | – |
| 10 / 450 | 68 / 470,000 | 4*SQRT(CV) or 6 mA max. (5 min.) | BHC | $Al_2O_3$ | – |
| 6.3 / 450 | 68 / 330,000 | 0.003*SQRT(CV)+4 max. (5 min.) | BHC | $Al_2O_3$ | – |
| 6.3 / 450 | 68 / 330,000 | 0.003*SQRT(CV)+4 max. (5 min.) | BHC | $Al_2O_3$ | – |
| 6.3 / 450 | 68 / 470,000 | 0.003*SQRT(CV)+4 max. (5 min.) | BHC | $Al_2O_3$ | |
| 6.3 / 450 | 68 / 470,000 | 0.003*SQRT(CV)+4 max. (5 min.) | BHC | $Al_2O_3$ | |
| 10 / 600 | 68 / 1,000,1200 | – | BHC | $Al_2O_3$ | – |
| 10 / 600 | 68 / 1,000,000 | – | BHC | $Al_2O_3$ | – |
| 10 / 600 | 68 / 1,000,000 | – | BHC | $Al_2O_3$ | – |
| 10 / 600 | 68 / 1,000,000 | – | BHC | $Al_2O_3$ | Stud mount version of ALS30 |
| 10 / 500 | 100 / 1,000,000 -/+20% | =<0.003CV or 10mA (5 min) | BHC | $Al_2O_3$ | – |
| 10 / 500 | 100 / 1,000,000 +/-20% | =< 0.003CV or 10mA (5 min) | BHC | $Al_2O_3$ | |
| 16 / 100 | 1000 / 150,000 +/-20% | =<0.003CV or 10mA (5 min) | BHC | $Al_2O_3$ | |
| 16 / 100 | 1000 / 150,000 +/-20% | =< 0.003CV or 10mA (5 min) | BHC | $Al_2O_3$ | – |
| 10 / 385 | 100 / 68,000 | 0.006*SQRT(CV)+4 max. (5 min.) | BHC | $Al_2O_3$ | |
| 10 / 385 | 100 / 68,000 | 0.006*SQRT(CV)+4 max. (5 min.) | BHC | $Al_2O_3$ | – |
| 16 / 450 | 100 / 470000 | 0.006CV (5min) | Itelcond | $Al_2O_3$ | – |
| 16 / 450 | 100 / 470000 | 0.006CV (5min) | Itelcond | $Al_2O_3$ | Ring Clip Mount |
| 16 / 450 | 100 / 470000 | 0.006CV (5min) | Itelcond | $Al_2O_3$ | Ring Clip Mount, Reduced Volume |
| 16 / 450 | 100 / 470000 | 0.006CV (5min) | Itelcond | $Al_2O_3$ | Threaded Stud Mount |
| 25 / 500 | 100 / 330000 | 1.5*SQRT(CV) (5min) | Itelcond | $Al_2O_3$ | Threaded Stud Mount, Reduced Volume |
| 6.3 / 50 | 0.1 / 100 | – | NCC | $Al_2O_3$ | Ring Clip Mount |
| 25 / 500 | 100 / 330000 | 1.5*SQRT(CV) (5min) | Itelcond | $Al_2O_3$ | CE04 |
| 25 / 350 | 220 / 150000 | 1.5*SQRT(CV) (5min) | Itelcond | $Al_2O_3$ | Threaded Stud Mount |
| 200 / 450 | 68 / 1500 | 0.006CV (5min) | Itelcond | $Al_2O_3$ | Ring Clip Mount |
| 200 / 450 | 68 / 1500 | 0.006CV (5min) | Itelcond | $Al_2O_3$ | Two Terminals |
| 25 / 350 | 220 / 150000 | 1.5*SQRT(CV) (5min) | Itelcond | $Al_2O_3$ | Four Terminals |
| 10 / 400 | 150 / 470,000 | – | NCC | $Al_2O_3$ | Threaded Stud Mount |
| 16 / 500 | 1000 / 22000 | 0.006CV (5min) | Itelcond | $Al_2O_3$ | CE331 |
| 16 / 500 | 1000 / 22000 | 0.006CV (5min) | Itelcond | $Al_2O_3$ | Ring Clip Mount |

FIG. 20 (Cont.)

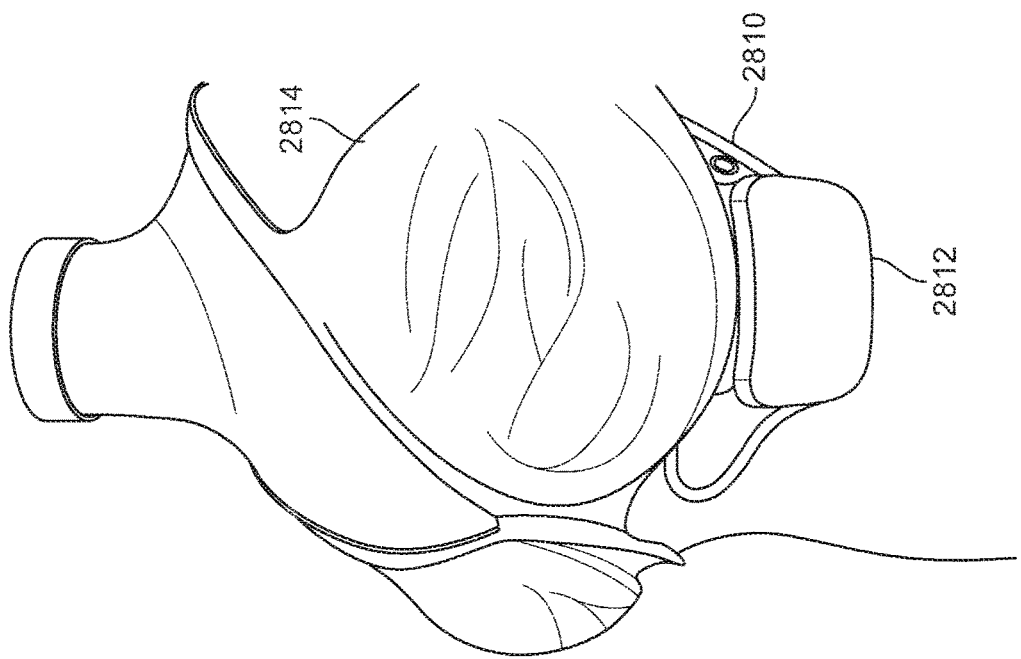
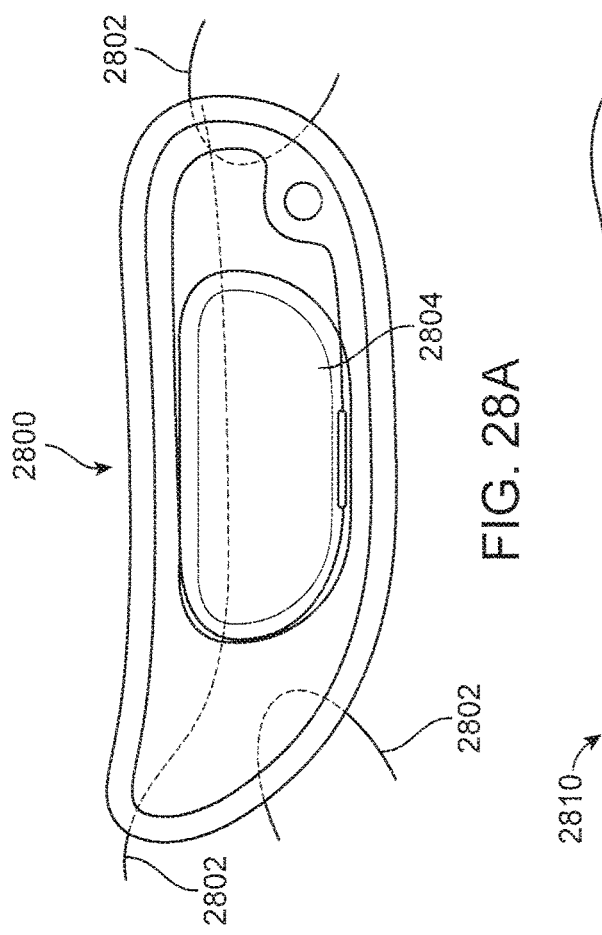
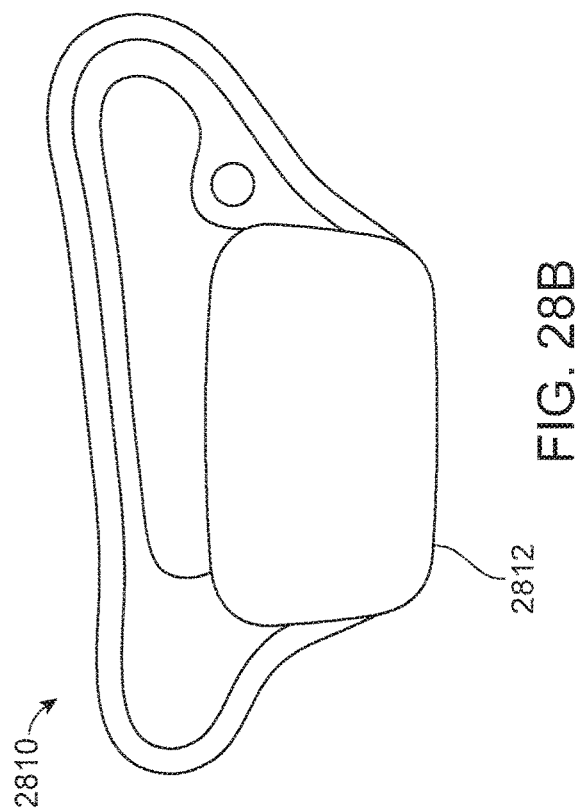
FIG. 28C
FIG. 28A
FIG. 28B

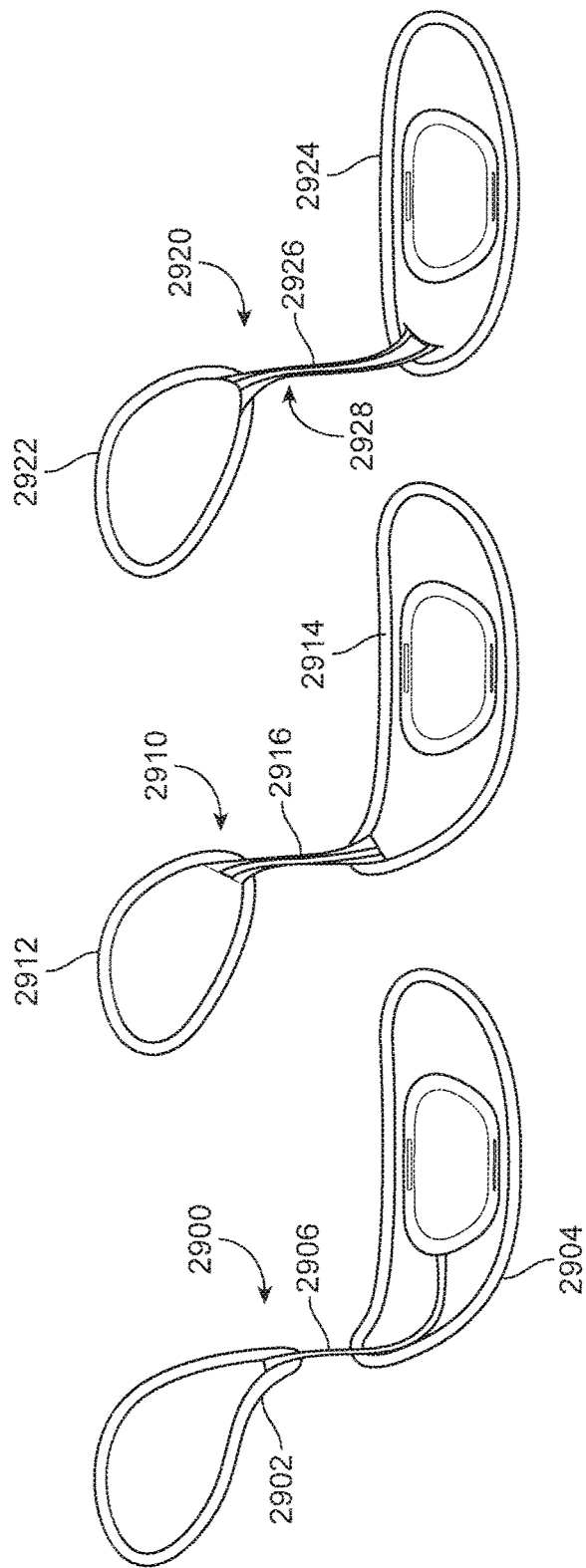

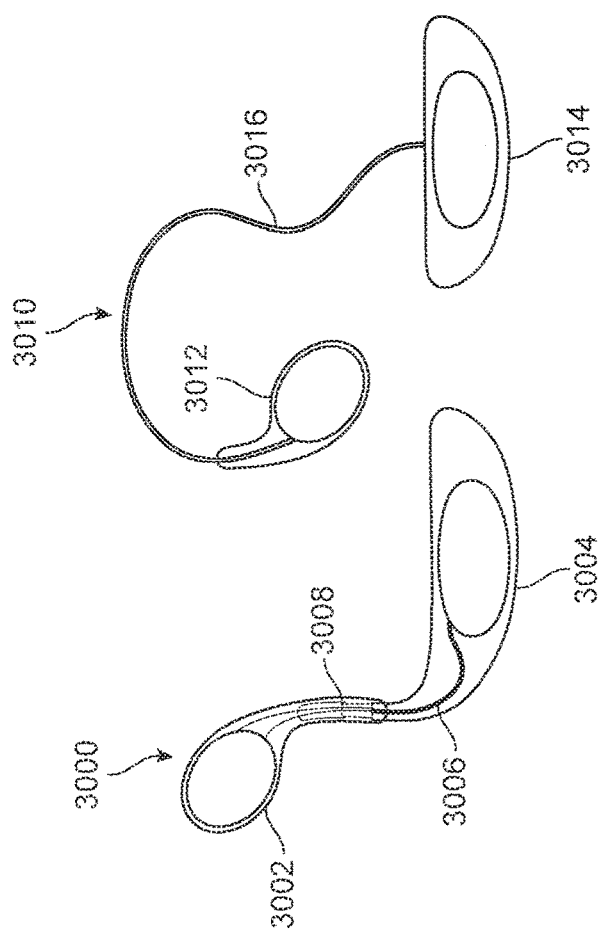
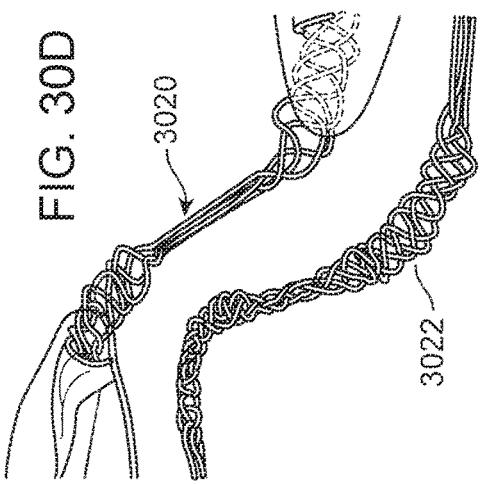
FIG. 30A  FIG. 30B  FIG. 30C  FIG. 30D

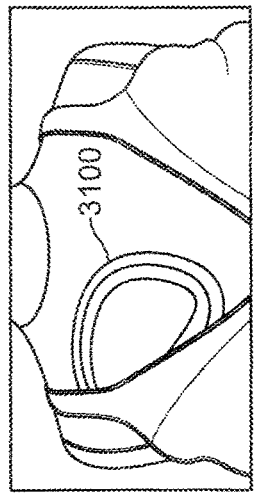
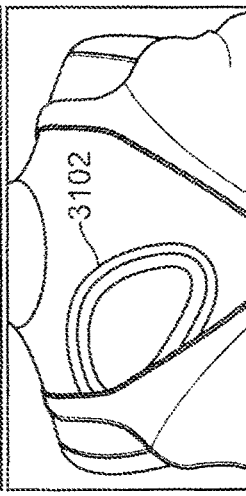
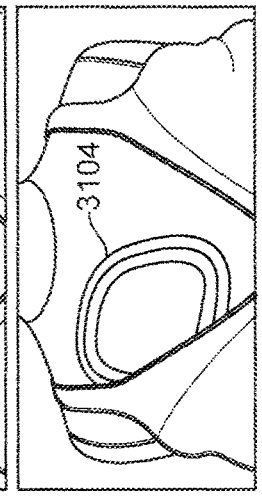
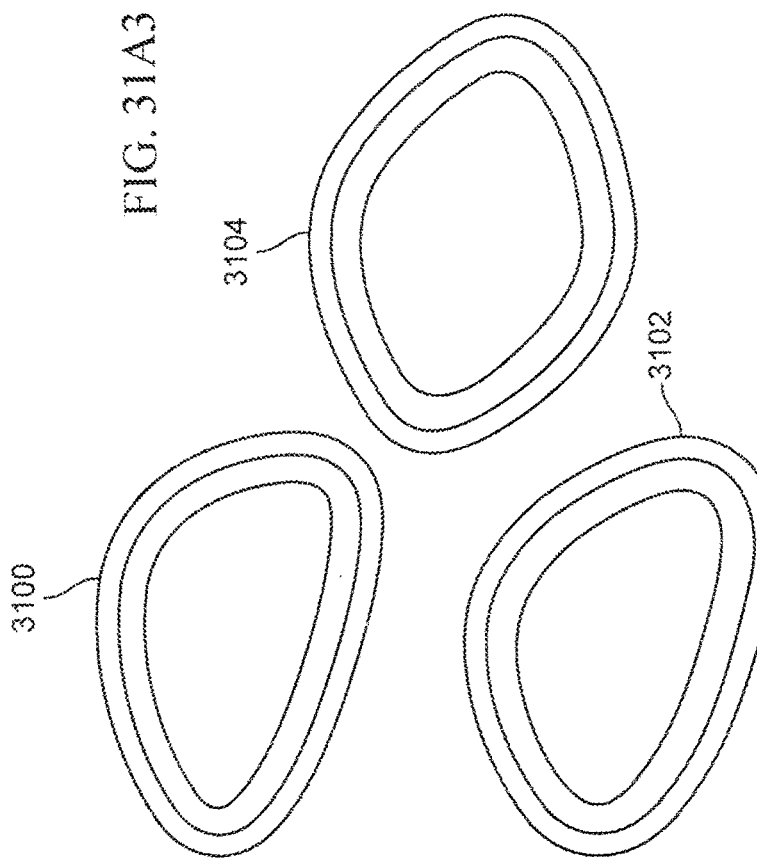

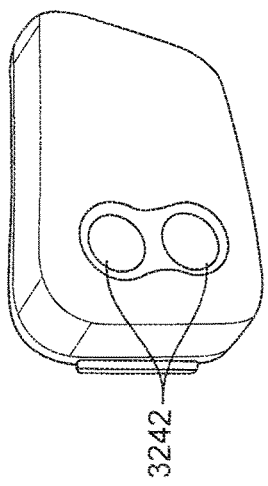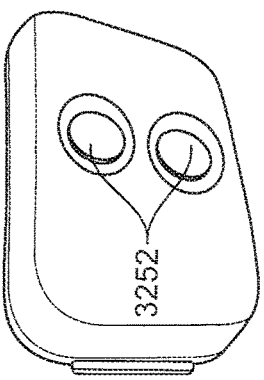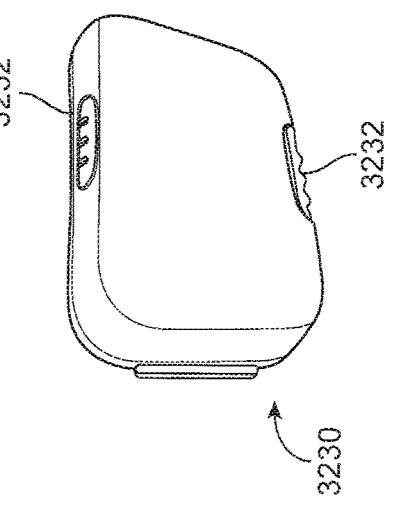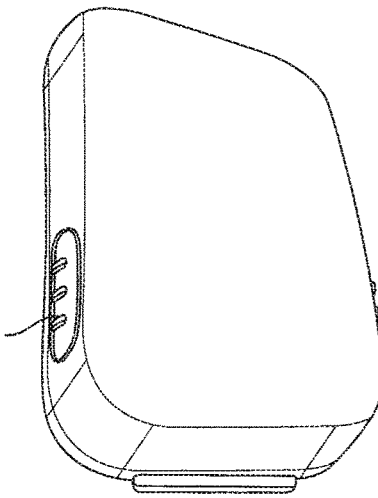

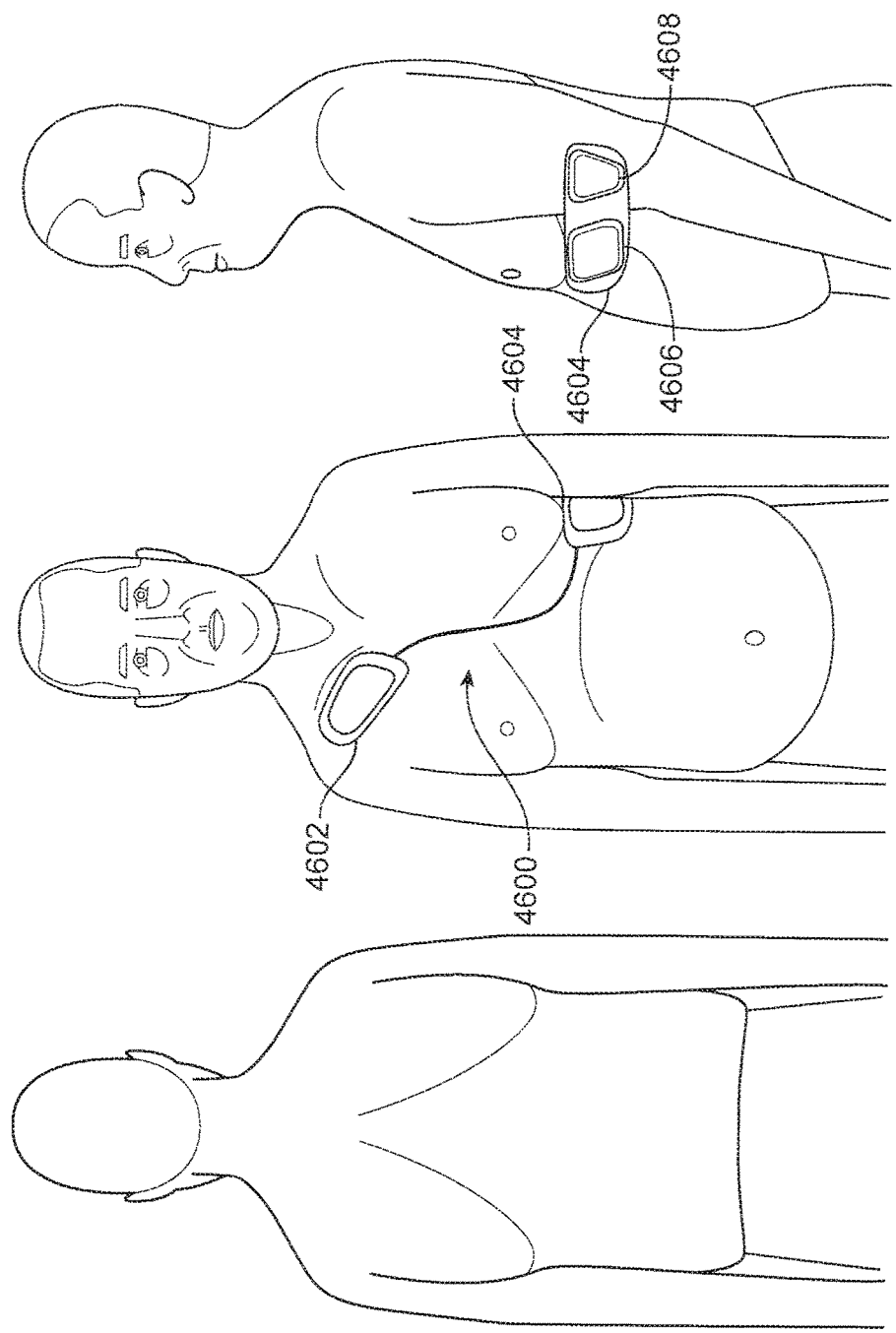

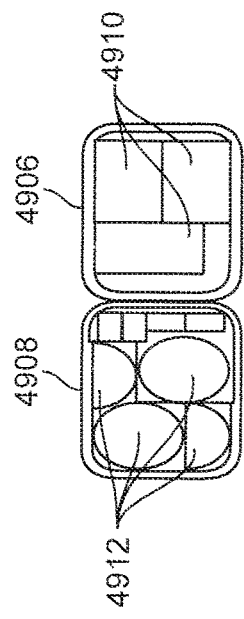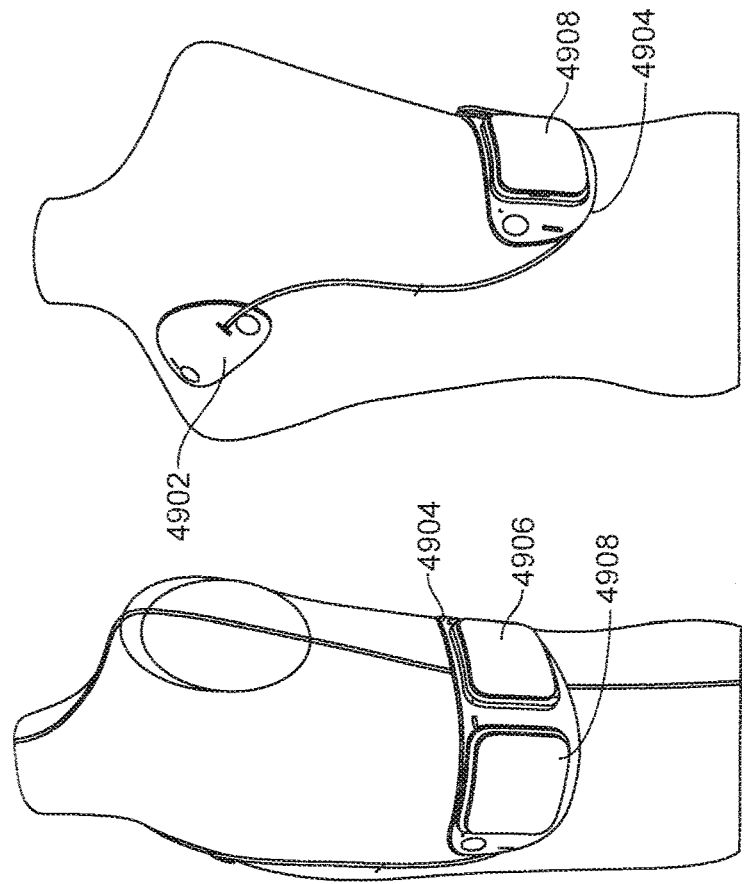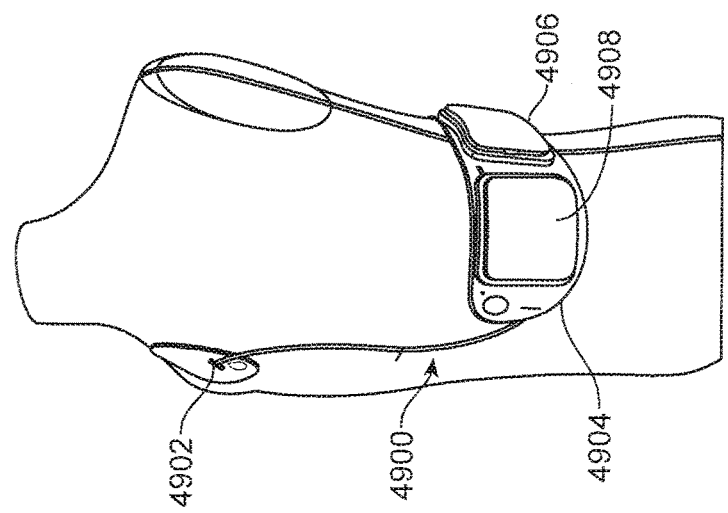
FIG. 49A
FIG. 49B
FIG. 49C
FIG. 49D

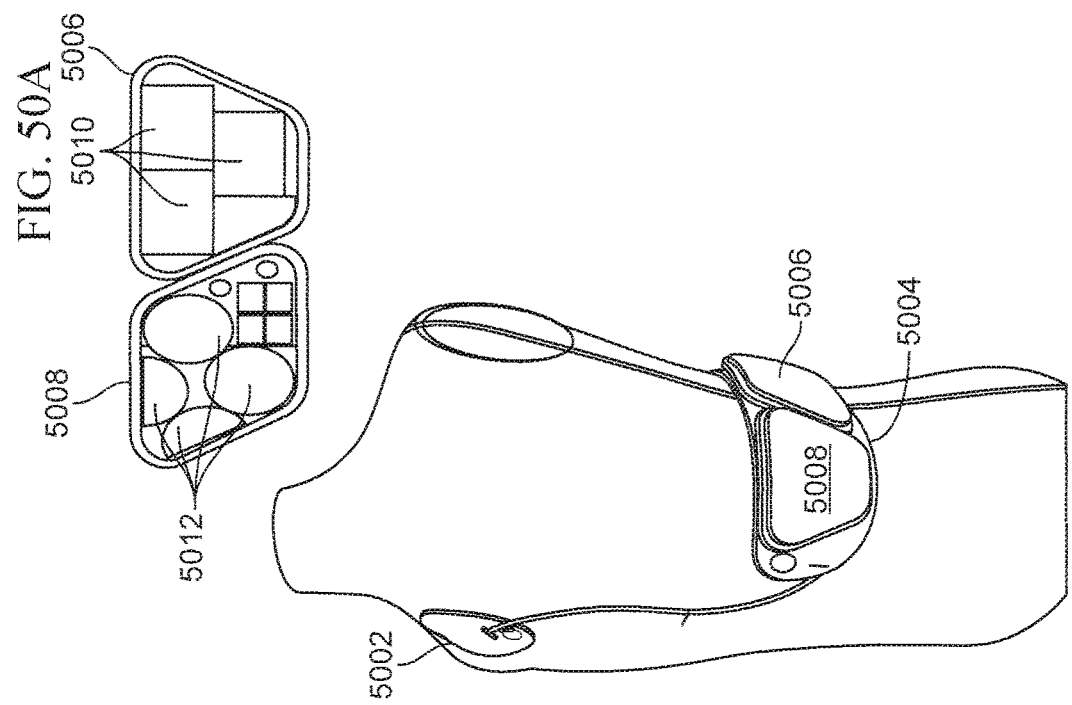
FIG. 50A
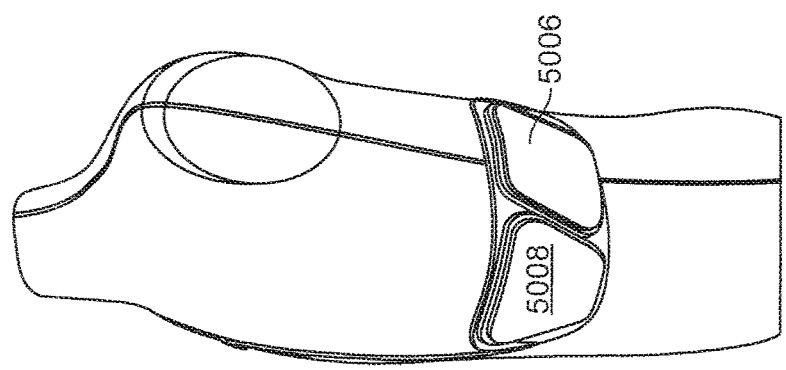
FIG. 50D
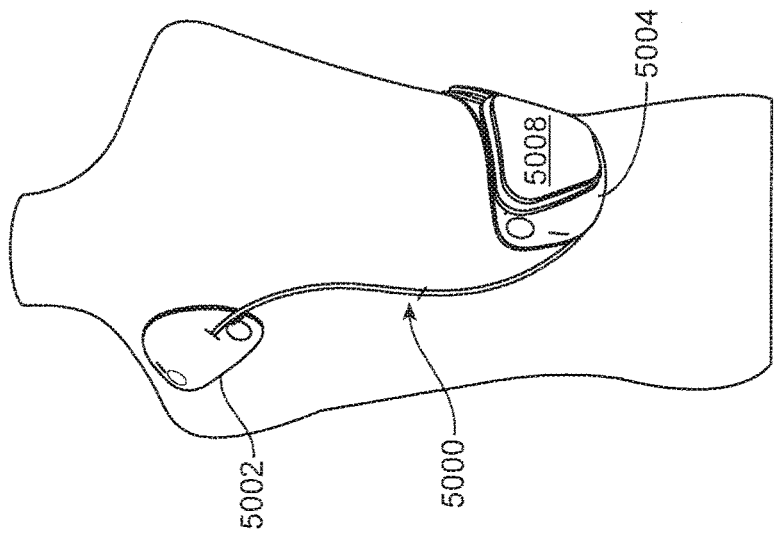
FIG. 50C
FIG. 50B

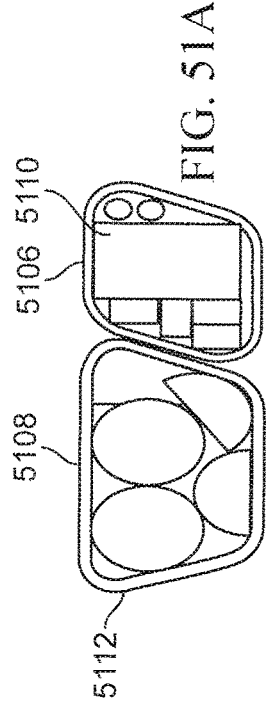
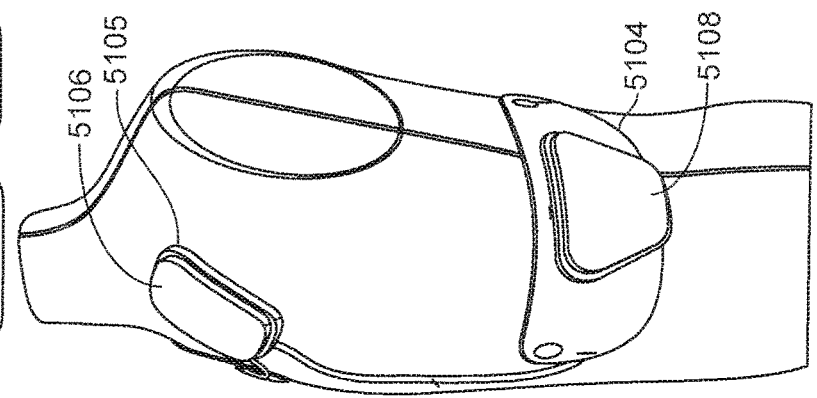
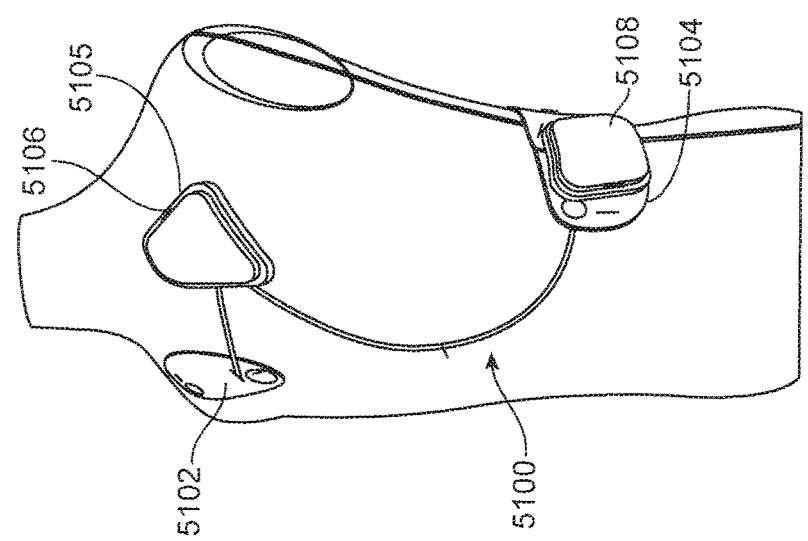
FIG. 51A  FIG. 51B  FIG. 51C  FIG. 51D

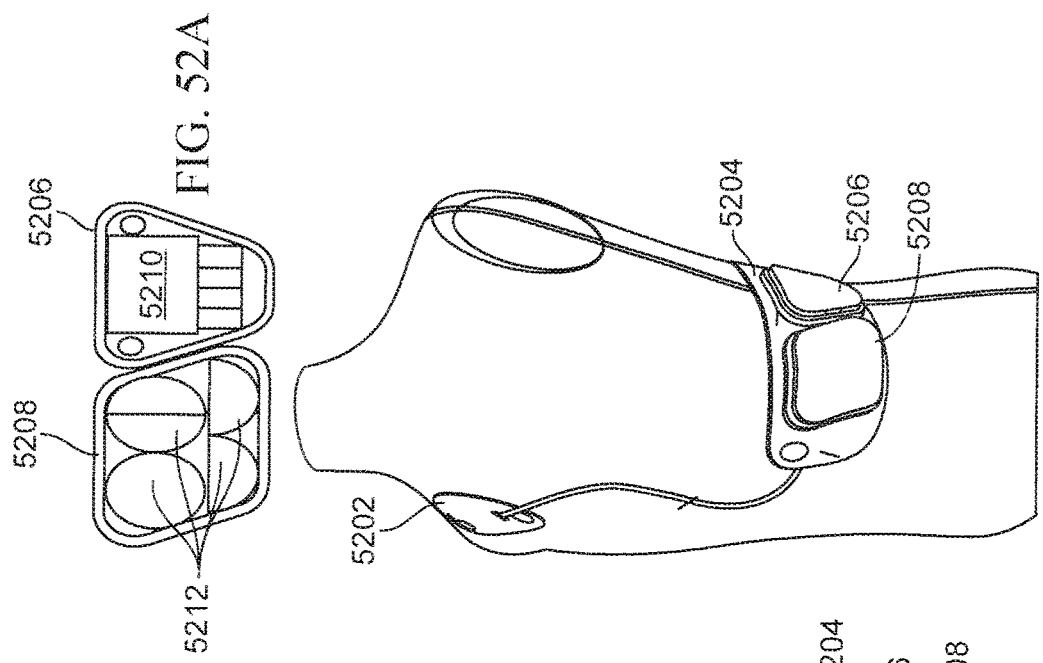
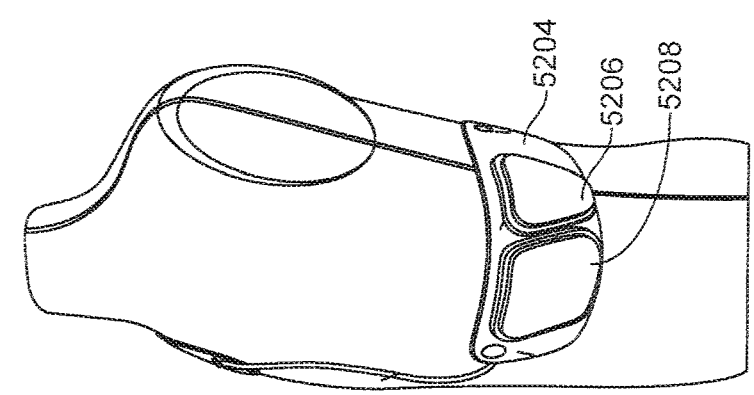
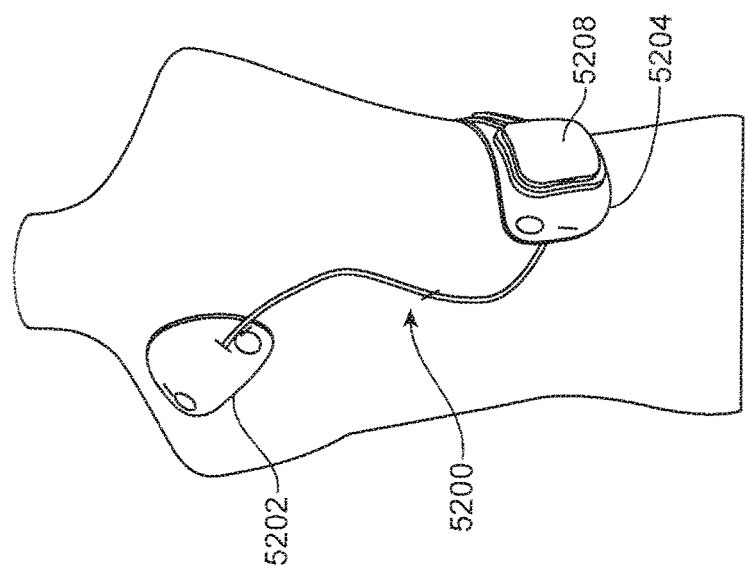

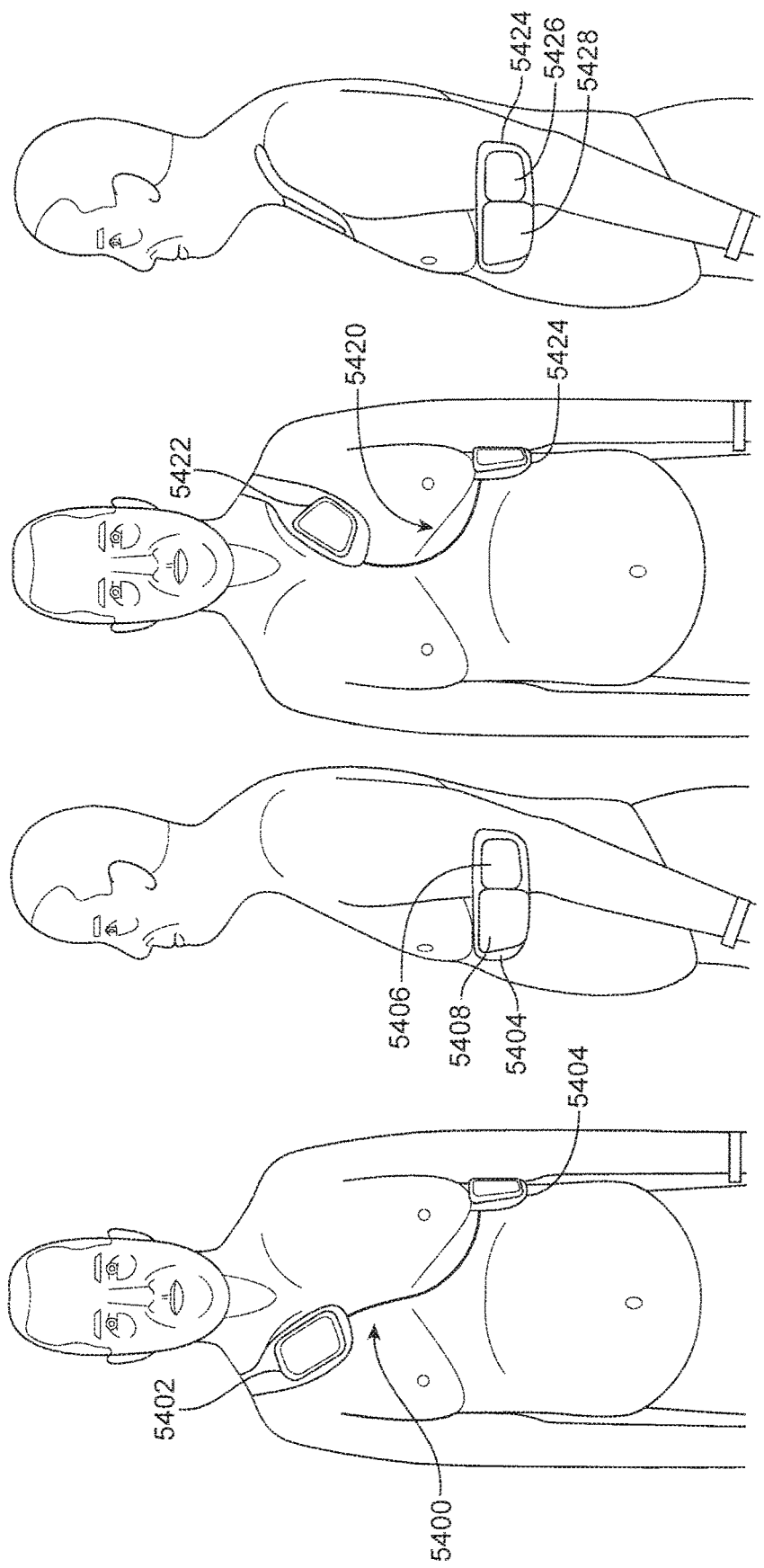

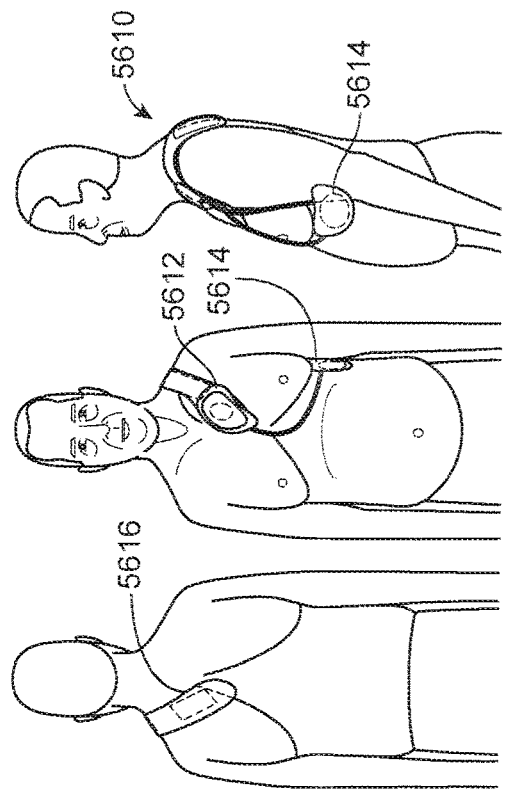
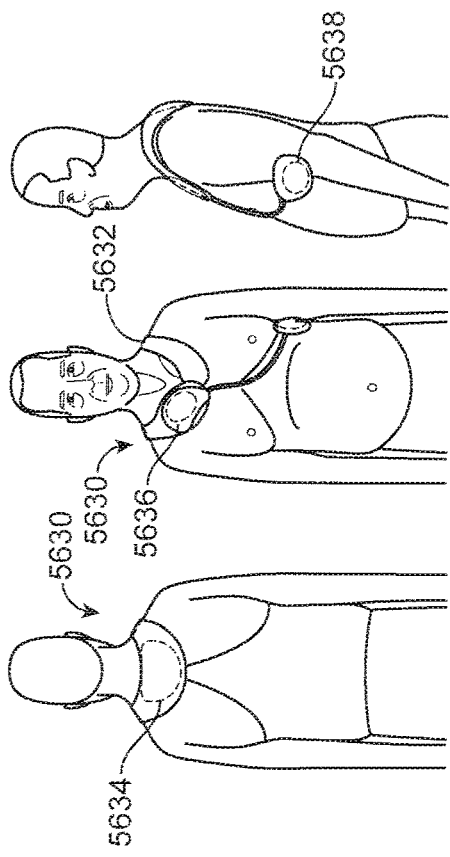
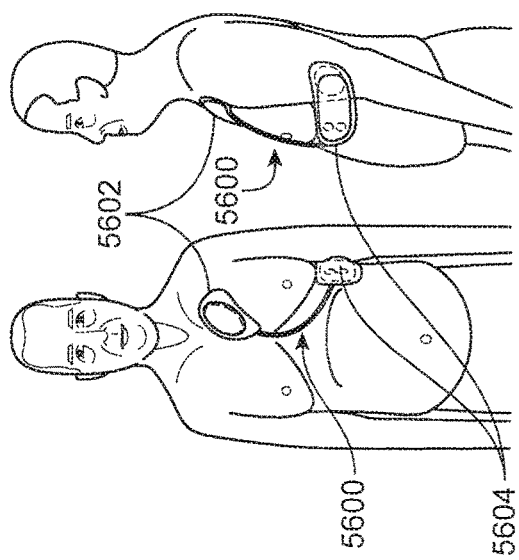
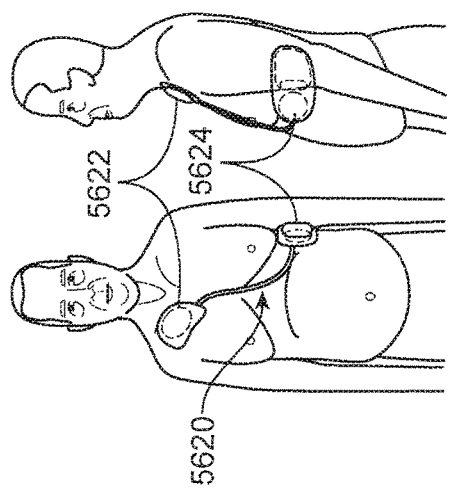

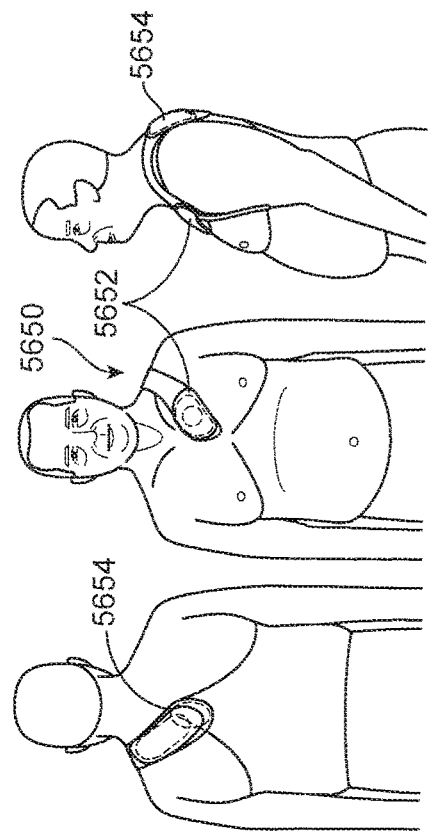
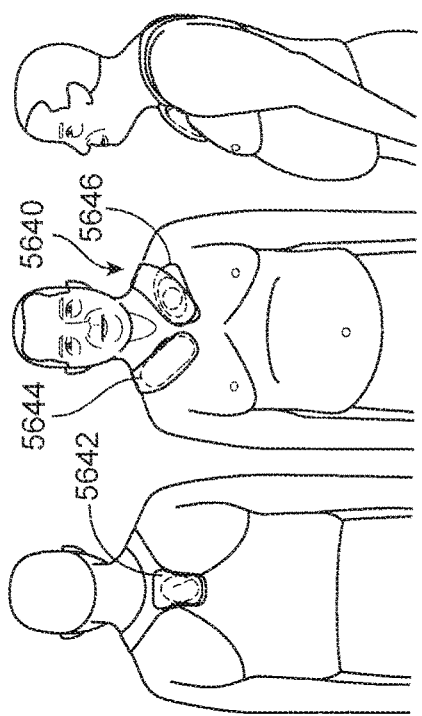
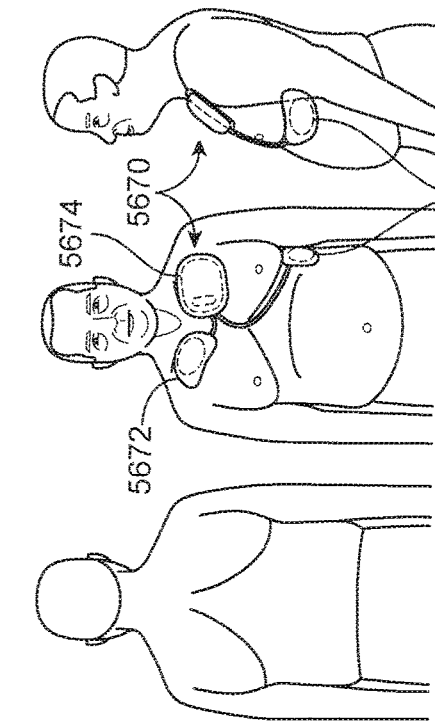
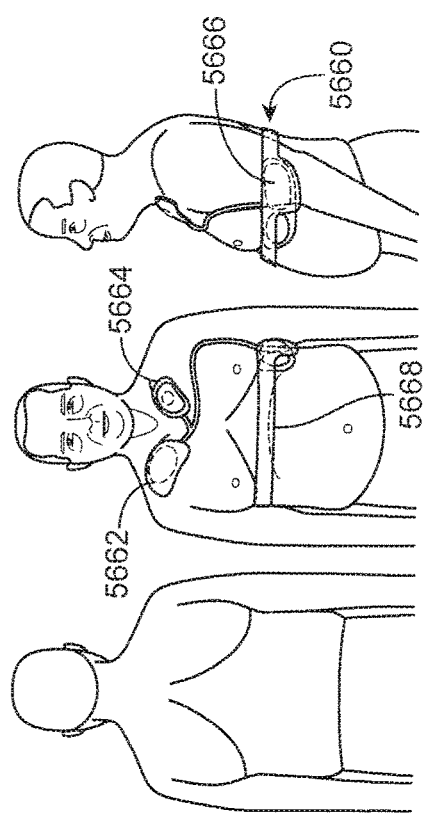

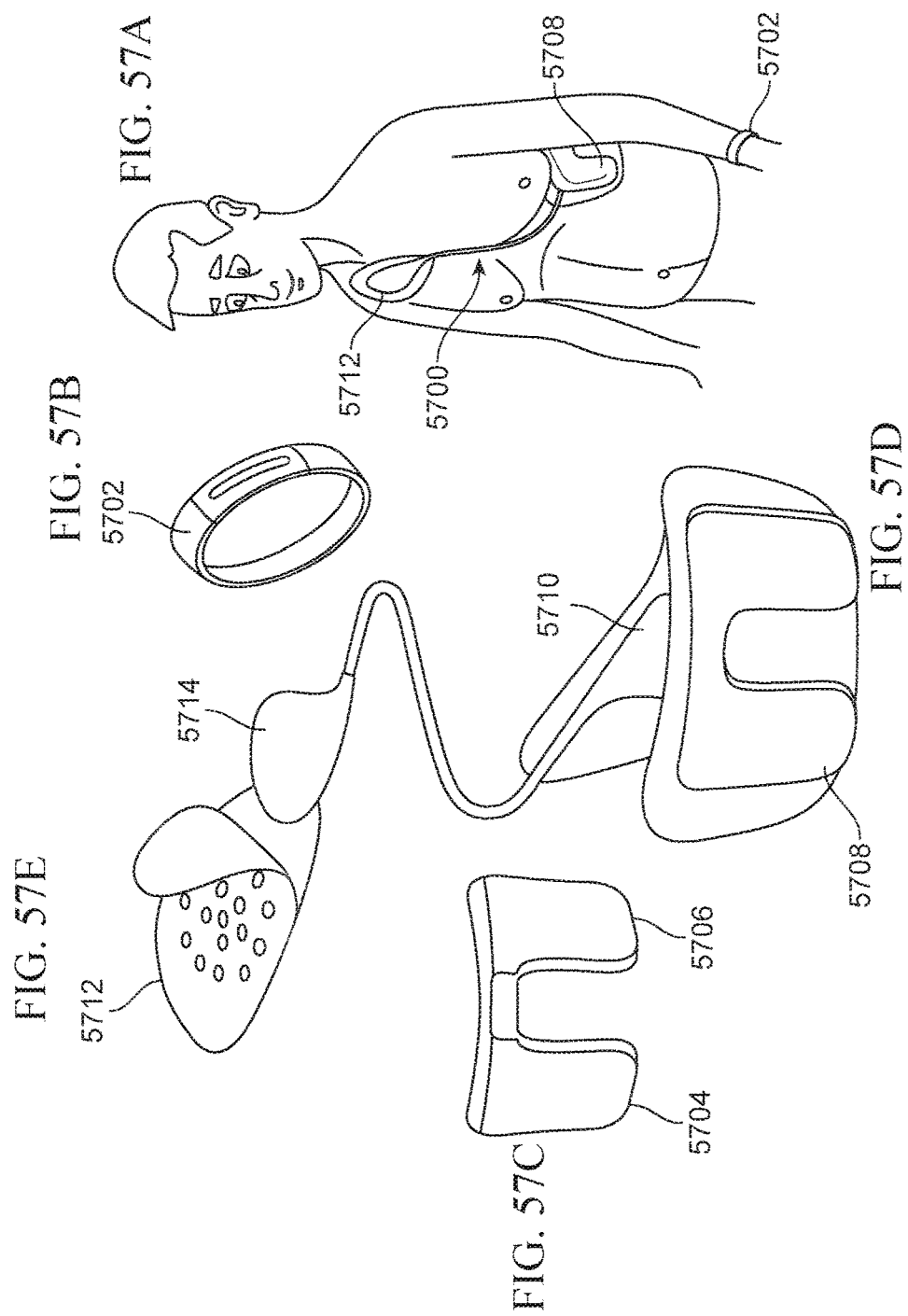

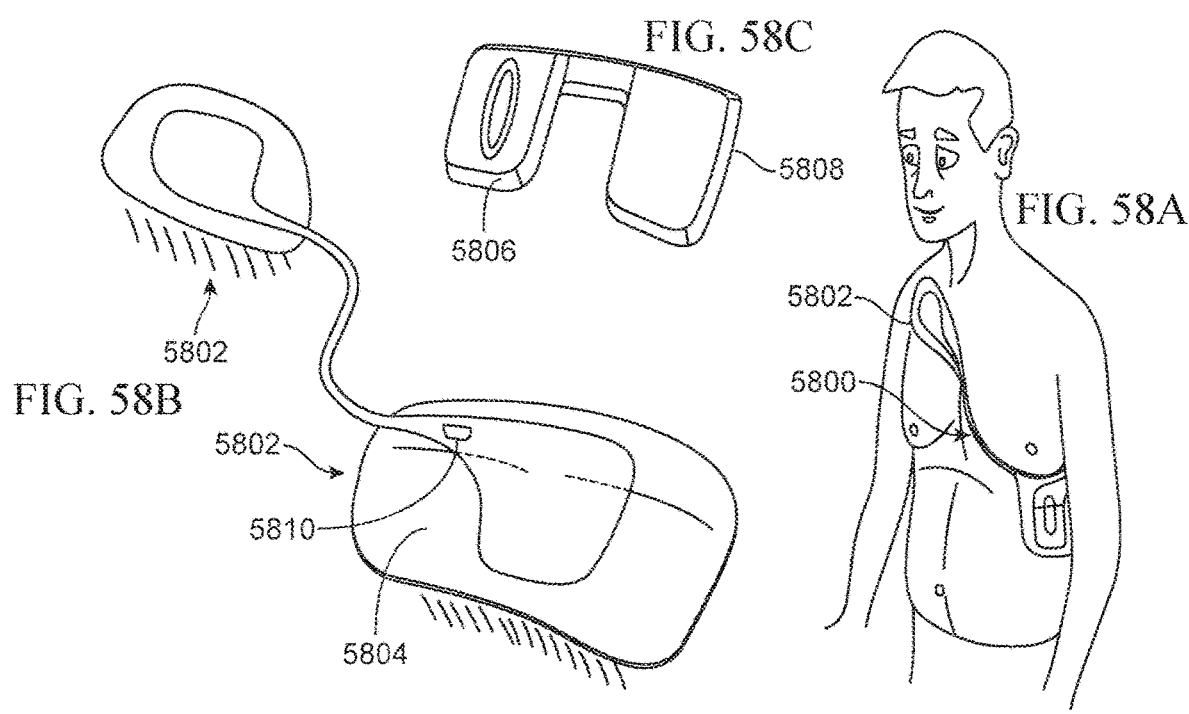

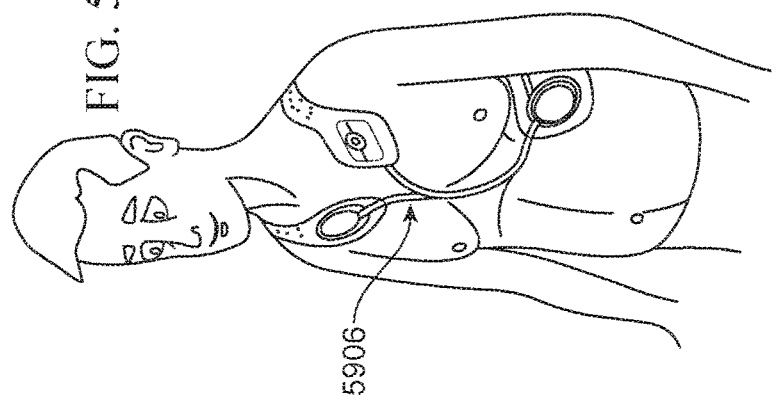
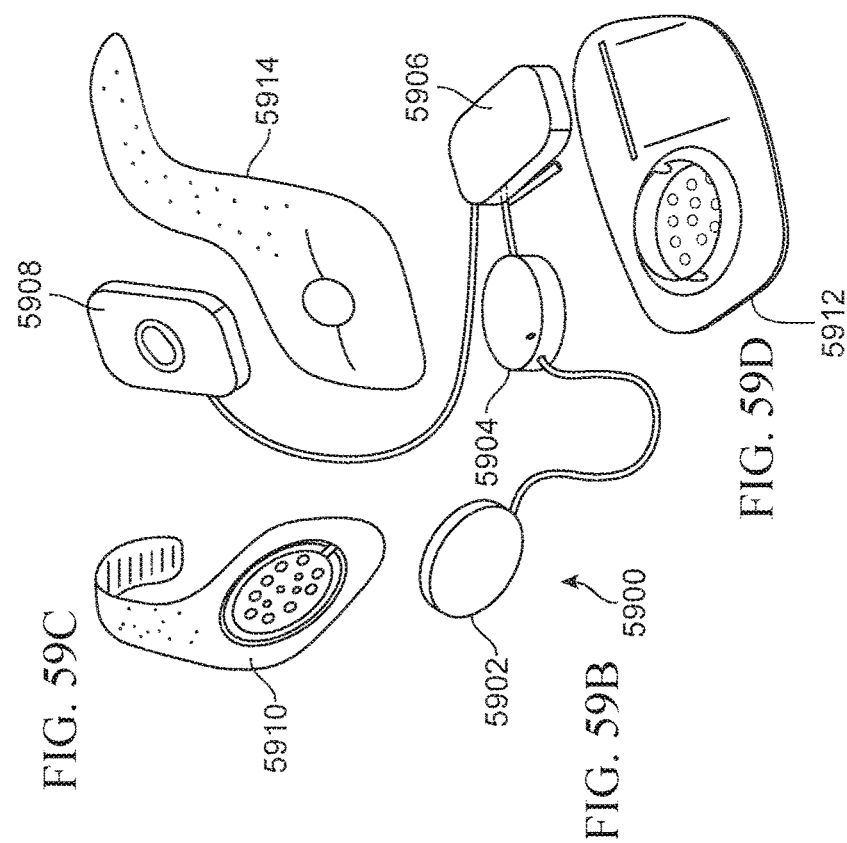

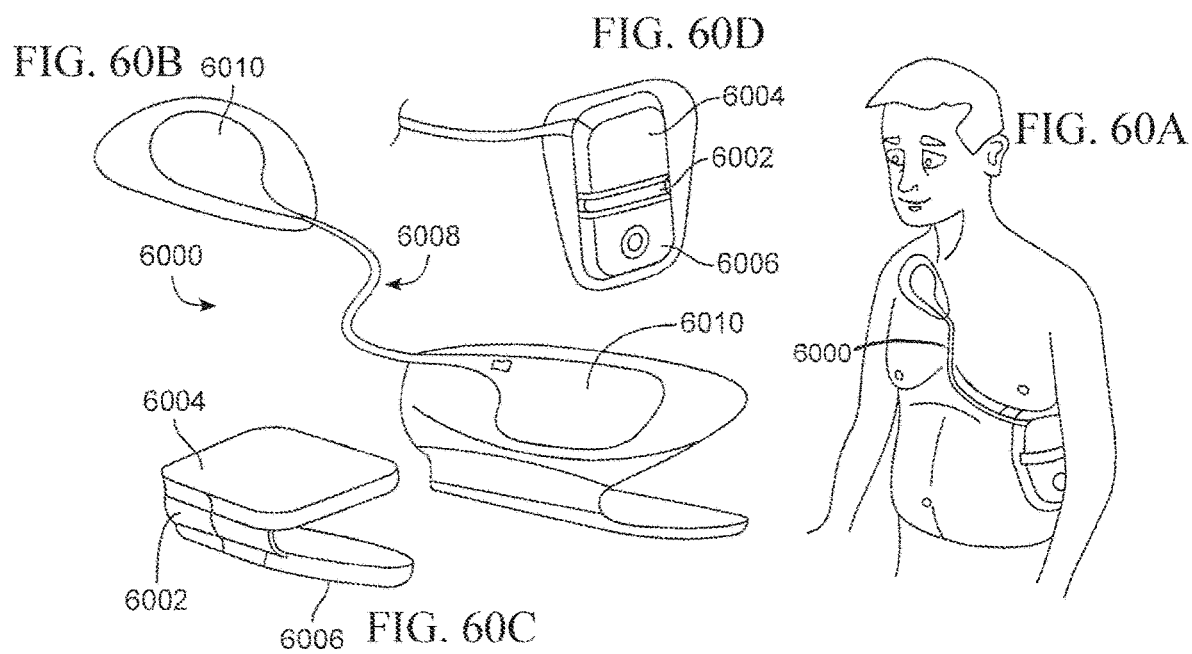

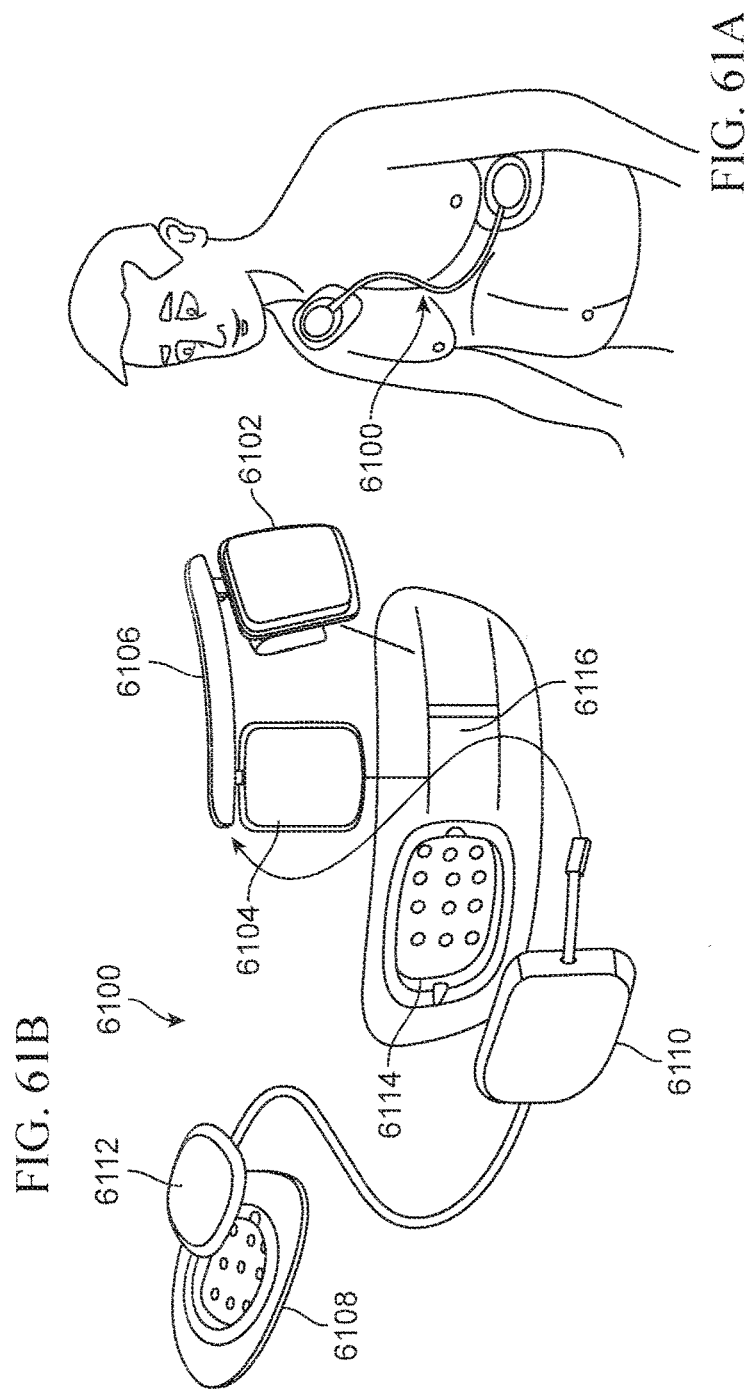

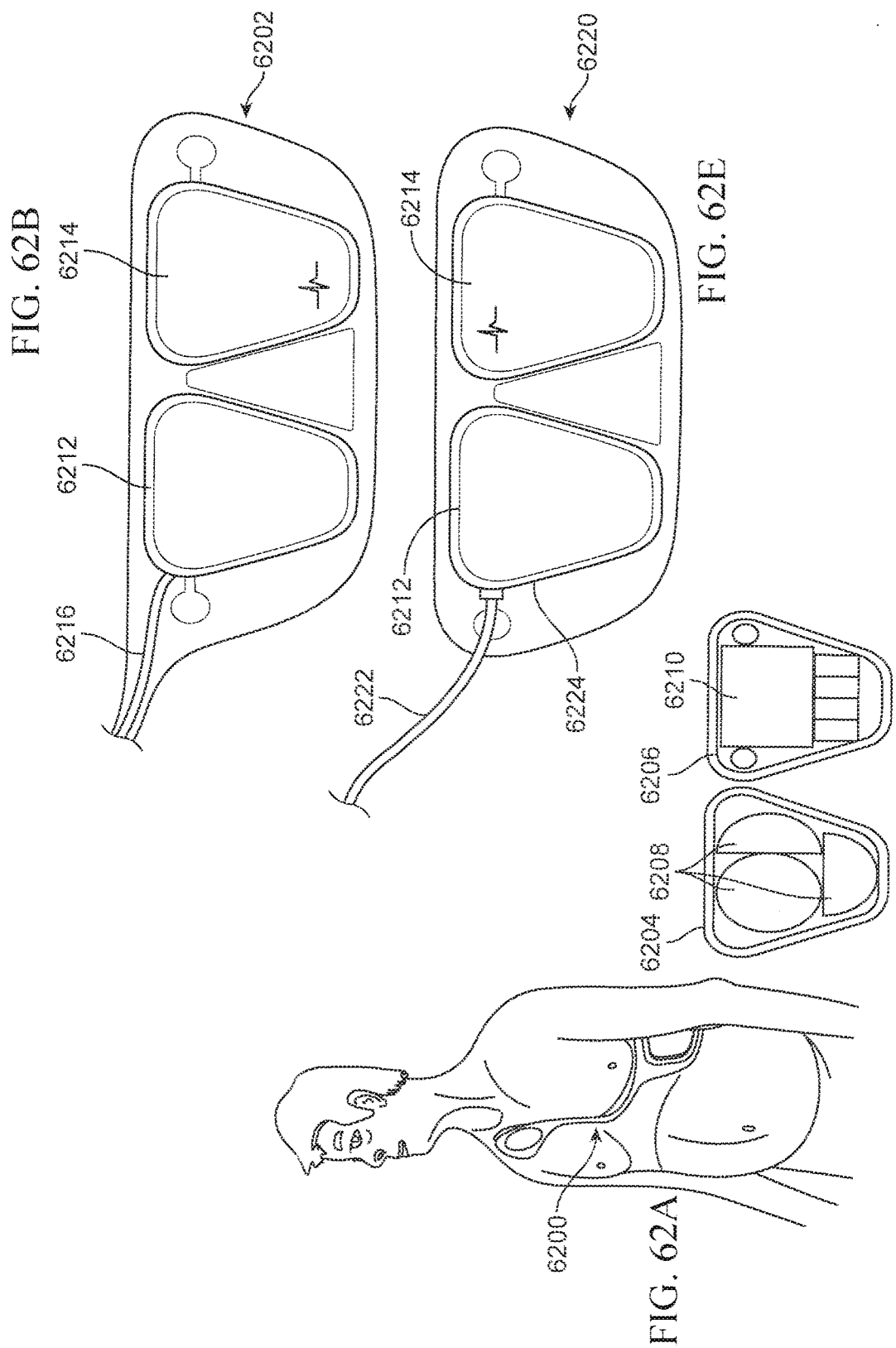

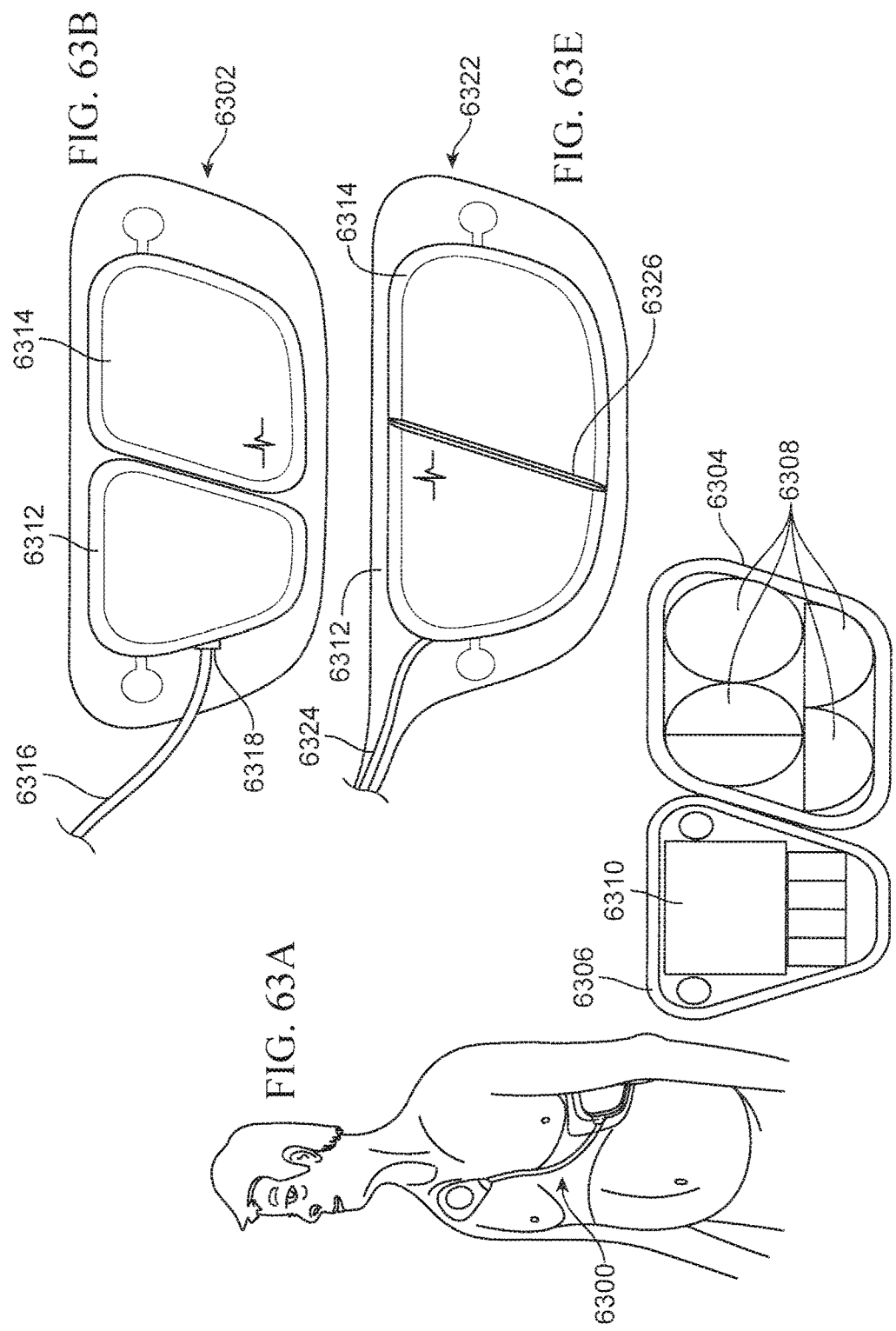

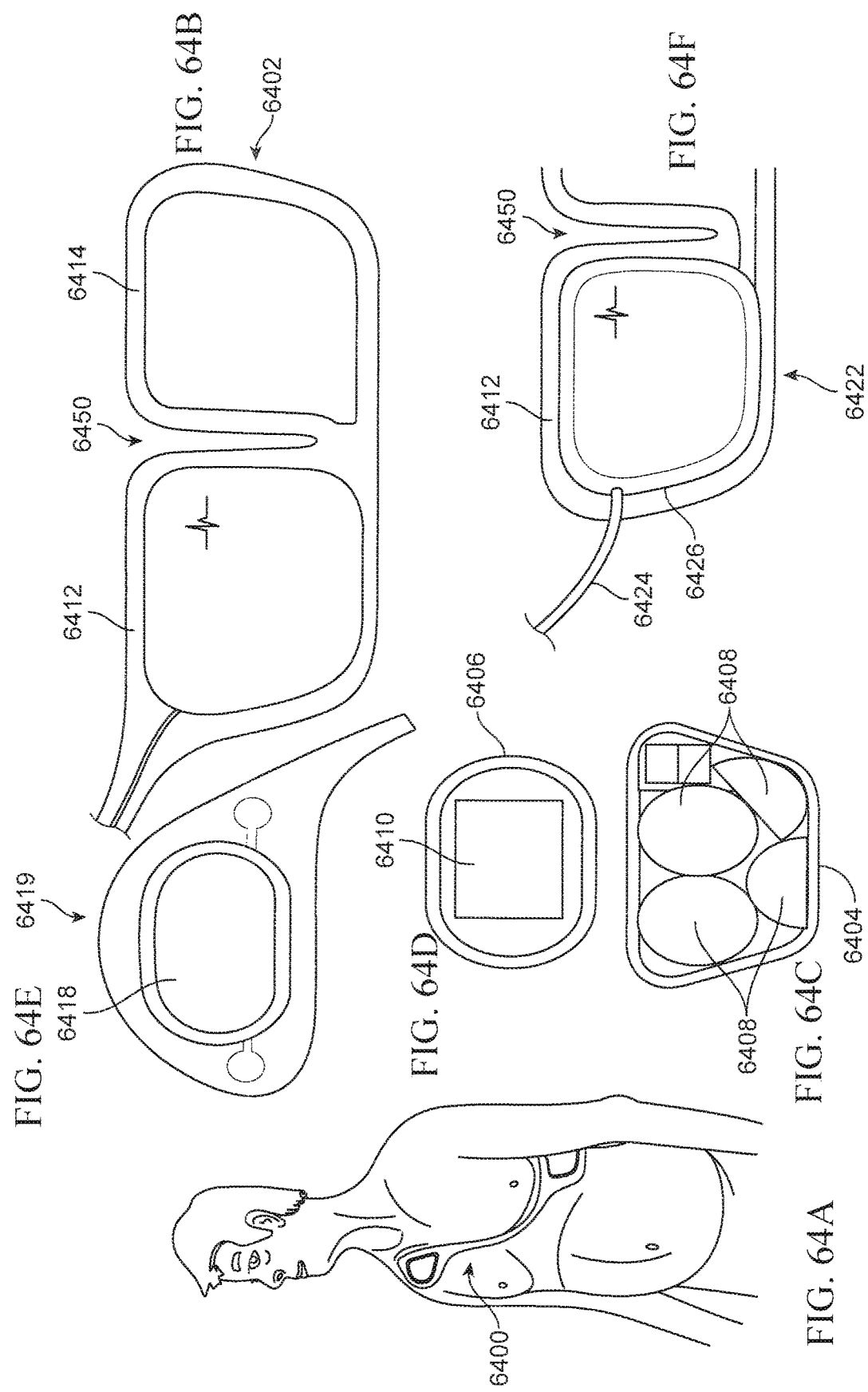

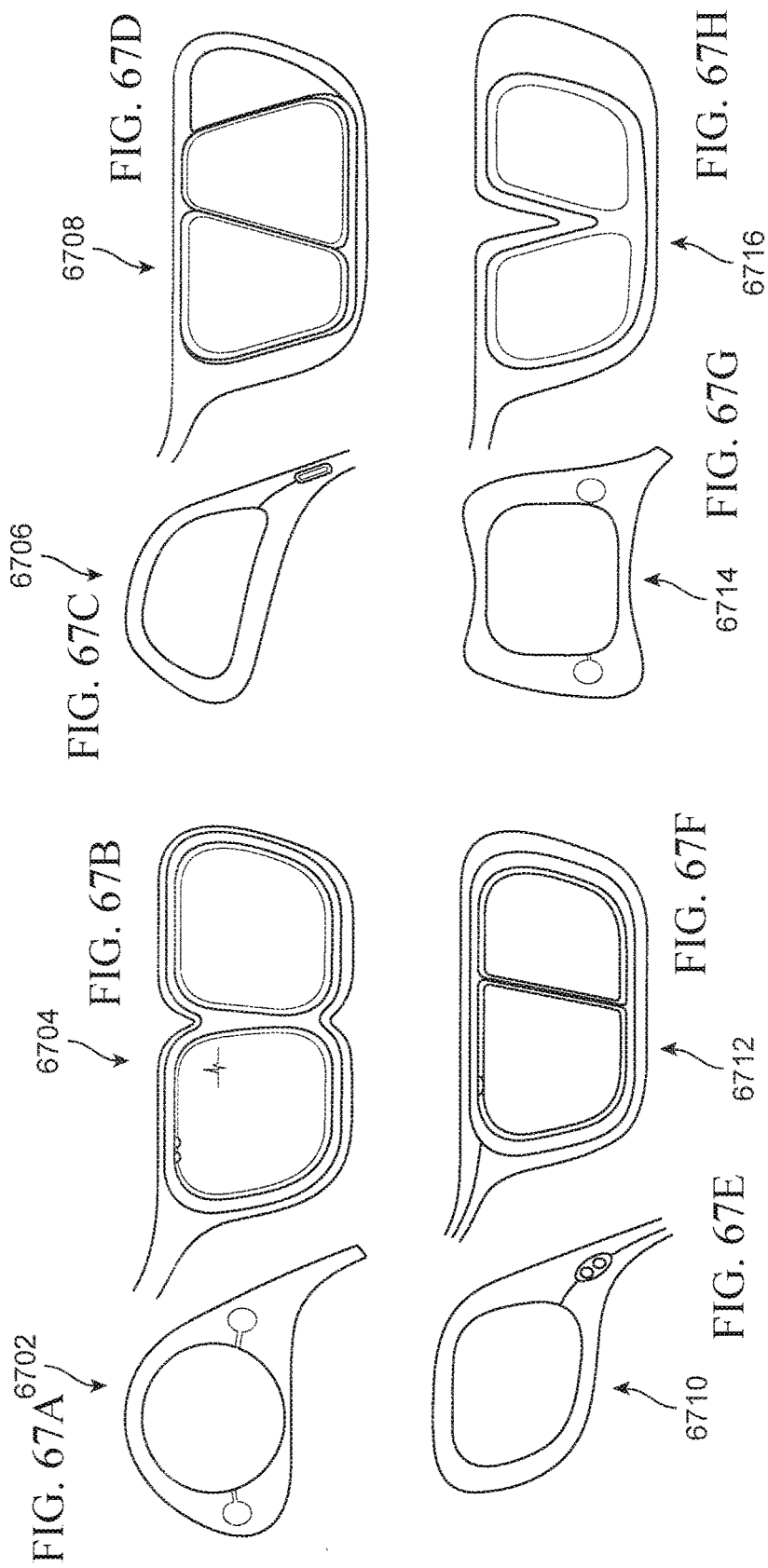

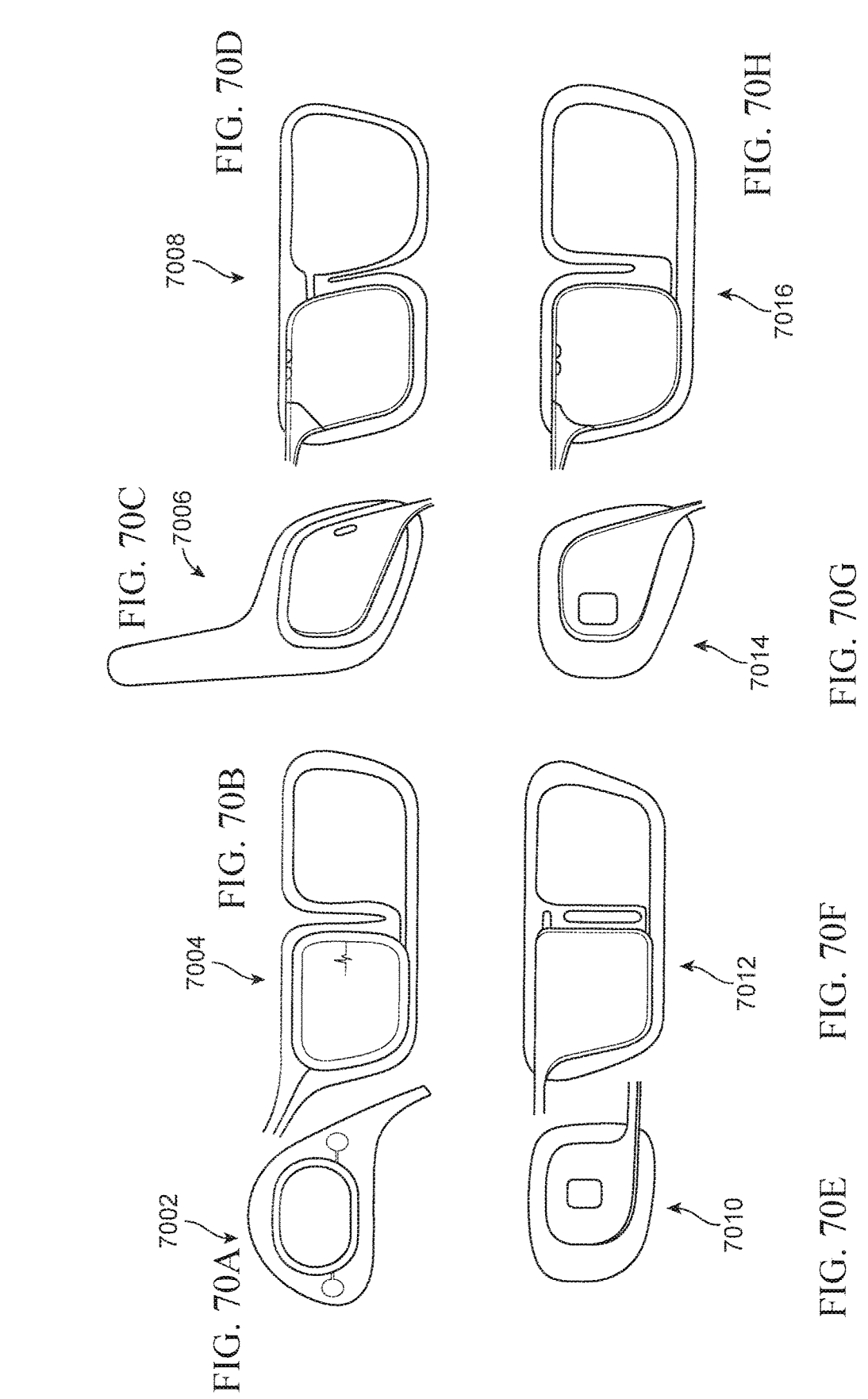

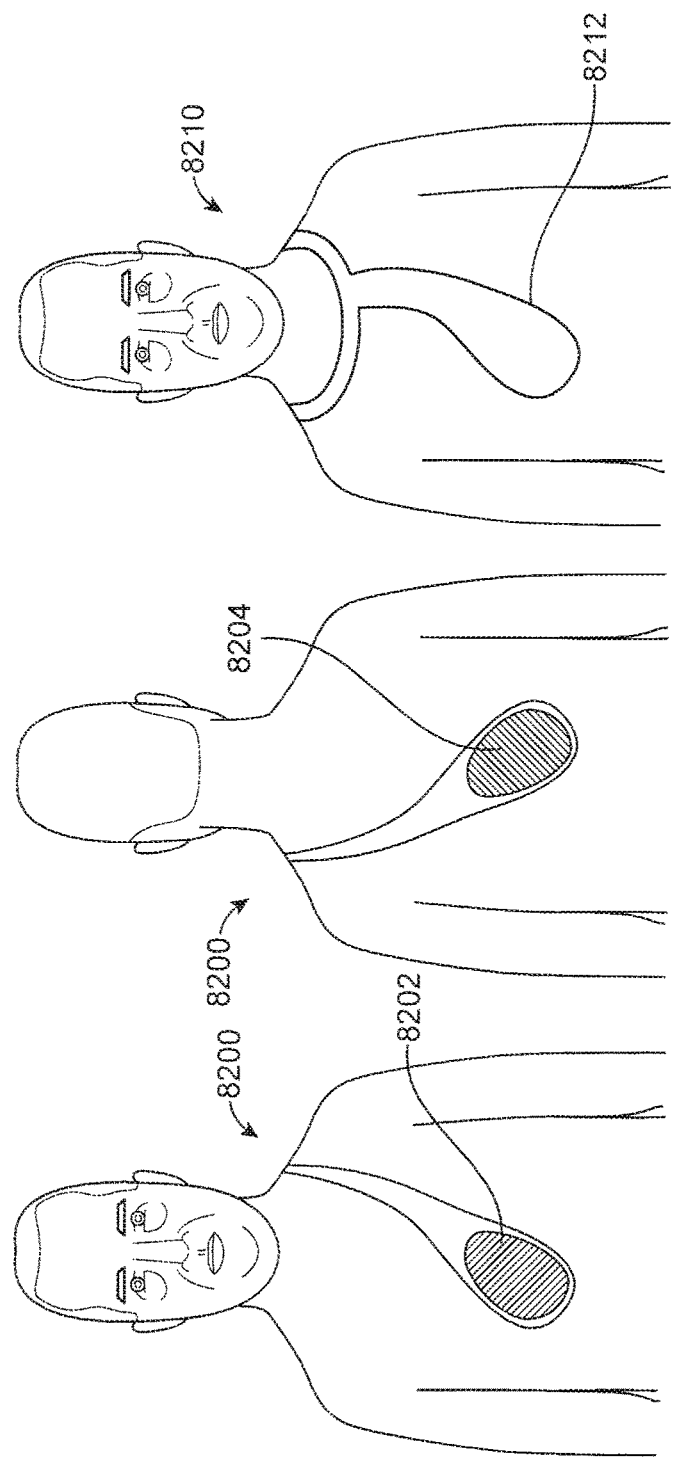

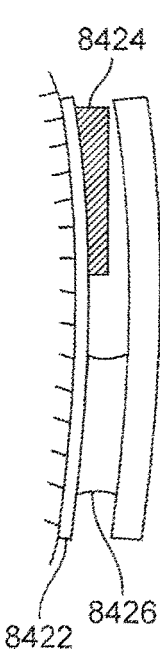
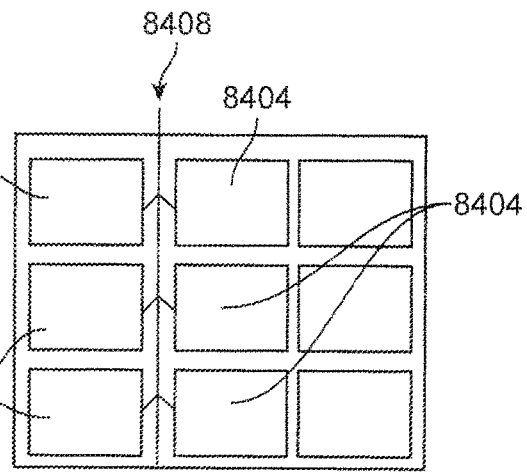
FIG. 84A1
FIG. 84A2
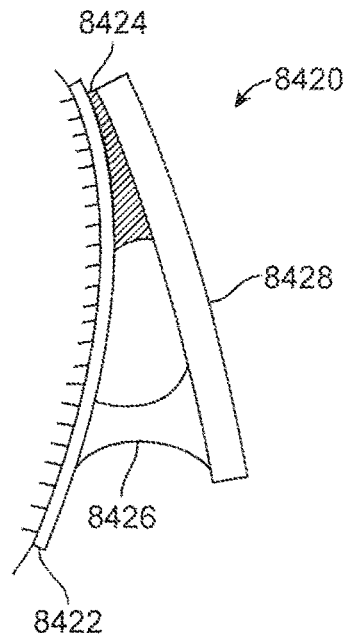
FIG. 84B

FIG. 87A
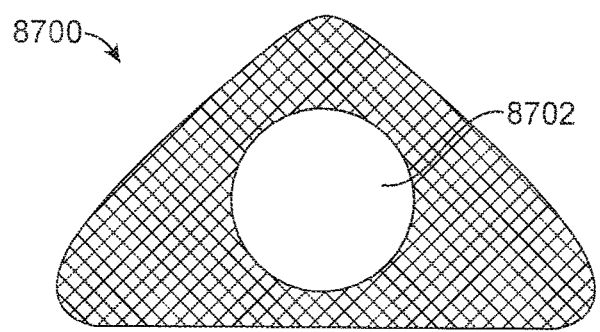
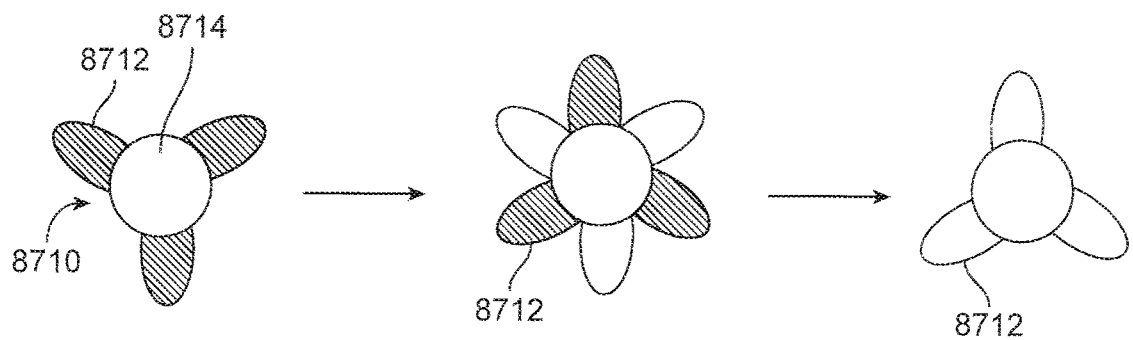
FIG. 87B

EXTERNAL DEFIBRILLATOR

CROSS REFERENCE TO RELATED APPLICATIONS

The present application is a continuation of U.S. patent application Ser. No. 17/501,805, filed Oct. 14, 2021, which is a continuation of U.S. patent application Ser. No. 16/721,506, filed Dec. 19, 2019, now U.S. Pat. No. 11,185,709, titled "External Defibrillator," which application is a continuation of U.S. patent application Ser. No. 15/120,655, filed Aug. 22, 2016, titled "External Defibrillator," now abandoned, which application is the national stage of International Application No. PCT/US2015/017366, filed Feb. 24, 2015, which application claims priority to U.S. Provisional Application No. 61/944,008 filed Feb. 24, 2014, titled "External Defibrillator," the disclosures of which are incorporated by reference in their entirety.

The present application is related to U.S. Pat. No. 8,024,037 filed Jul. 27, 2007, and U.S. Pat. No. 8,364,260 filed Aug. 5, 2011, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates generally to external defibrillators. In particular, the disclosure relates to automatic external defibrillators that can be continuously and comfortably worn by a patient for an extended period of time.

BACKGROUND

Every year in the US, over 800,000 individuals have a heart attack, or myocardial infarction (MI). After an MI, a patient is at increased risk for experiencing potentially life-threatening abnormal heart rhythms, or arrhythmias. This increased risk is caused by numerous structural and electrical abnormalities in the recently damaged heart. For most patients, however, this increased risk is temporary. After patients have been treated with various procedures and medications to help their heart heal, their risk of experiencing a life-threatening arrhythmia usually drops back to their risk prior to the MI. This drop in risk typically occurs after a few days to weeks after the MI has taken place.

In addition to the post-MI setting, there are other situations in which a patient's arrhythmia risk is temporarily increased, such as after certain types of heart surgery or when starting certain medications with pro-arrhythmic properties. In patients who are known to be at risk for an arrhythmia and who have an ICD or S-ICD in place, if the ICD/S-ICD needs to be removed for a short period of time due to an infection or malfunction, the patient is also left vulnerable. In other patients, such as those with a condition known as heart failure (new diagnosis or acute exacerbation) or cardiomyopathy, certain medications and/or procedures can lead to an improvement in the heart's function and reduce a patient's susceptibility to an arrhythmia such that a permanently implanted device, such as an ICD or S-ICD, would not be needed. However, during the time of treatment when heart function is recovering or when the patient is receiving treatment, these patients are still temporarily at risk for a life-threatening arrhythmia.

More than 750,000 patients are at risk for sudden cardiac death (SCD) in the U.S. each year. Based on event rates of up to 4% in the higher risk subgroups of the populations improved treatments could save up to 30,000 lives annually in the U.S. There are about 3.7 million worldwide incidence of SCD due to ventricular arrhythmias with a survival rate of less than 1%. Improved methods and devices are also needed to treat patients at risk for SCD. The devices and methods disclosed herein can be used for patients with a temporarily increased risk for SCD or with a chronically increased risk for SCD. Clinical conditions in which a patient's temporary risk for experiencing a lethal arrhythmia or SCD is elevated include, but are not limited to: in patients after explanation of an ICD or S-ICD (due to infection or a mechanical failure, for instance), in patients with sleep apnea when it is severe, in patients who have certain arrhythmia syndromes, in pediatric patients with structural heart diseases, in certain patients with significant valvular heart disease, in pregnant or recently pregnant patients who develop pregnancy-related cardiomyopathy, and in patients with end-stage renal disease or on dialysis. Additional examples of conditions that can cause, increase the likelihood of SCD, or make a patient prone to SCD include: after cardiac surgery, new cardiomyopathy, after a heart attack, new heart failure, and heart failure exacerbation. FIG. 1 illustrates statistics and factors that elevate risk for SCD.

Various studies of this population of patients have shown that certain medications, especially those with anti-arrhythmic properties, do a poor job at reducing this temporarily increased arrhythmia risk. Implantable cardioverter defibrillators (ICDs) and subcutaneous ICD (S-ICDs), which can continuously monitor the patient for an arrhythmia and effectively reset the heart rhythm when an arrhythmia occurs, carry significant risks during implantation such that their overall benefit during this short period of increased risk is limited. Implanting ICDs and S-ICDs in many patients whose risk of an arrhythmia would eventually return to normal also has significant unwanted health, economic, and societal consequences. FIG. 2C and FIG. 2D include illustrations of examples of an S-ICD 104 and an ICD 106, respectively.

Automatic external defibrillators (AEDs) are stored on walls apart from patients in highly populated places such as airports and do not monitor patients for arrhythmias. They are only useful if an AED is present when the patient needs it and if other people capable of using the AED are present at the time an arrhythmia occurs, can identify that a patient needs defibrillation and is able to apply the sensing and defibrillation electrodes to the patient. An example of an AED 102 is illustrated in FIG. 2B. Wearable external defibrillators and external cardioverter defibrillators are described in U.S. Pat. Nos. 5,741,306; 6,065,154; 6,280,461; 6,681,003 and US 2003/0095648. A similar product is currently being sold as the Zoll Lifecor Life Vest™ wearable cardioverter defibrillator (WCD). FIG. 2A illustrates an example of a WCD 100. Wearable cardioverter defibrillators are able to monitor a patient for arrhythmias while they are worn without the need for implantation surgery, and they can be removed when the need for such monitoring (and possible cardioversion or defibrillation shock) has passed.

One drawback of currently available wearable defibrillators (such as the Life Vest product) is lack of patient compliance. Because of the size, shape and weight of these wearable devices, patients are reluctant to wear them due to discomfort, their bulkiness under clothes or limitations in the devices themselves. In particular, such devices cannot be worn in the shower or bath, and they often are difficult, if not impossible, to sleep in. The device therefore is not useful in providing treatment to the patient while sleeping or in the shower. Patients also complain that the Life Vest is too large and uncomfortable. Many patients also have increased anxiety over the many alarms and notifications from the Life-Vest. The increased anxiety further increases instances of non-compliance. Given the bulkiness of these devices, some patients do not like using these wearable devices outside in public as it draws unnecessary attention to them, which they might find uncomfortable or embarrassing. This may affect their well-being and may lead them to avoid performing their normal routine activities. All of these factors increase patient noncompliance and prevent the treatment of a treatable arrhythmia. In one study 60% of Life Vest wearers were not saved due to patient non-compliance (Tanawuttiwat T, et al. PACE Online 12.3.2013). The device can also be easily taken off, which prevents the vest from providing treatment to the patient when it is not being worn.

Another drawback is that it is possible to incorrectly wear a wearable vest like the Life Vest, such that the vest will not properly detect a patient arrhythmia. Incorrectly wearing the vest can also prevent the vest from delivering a defibrillating shock to the patient. The design of the vest can also result in increased false positives of arrhythmias measured by the vest. The vest also has a complicated electrode design. Because the vest is put and taken off multiple times a day, no gel is applied between the defibrillation electrodes and the patient's skin unless and until a shock is required. The gel releasing mechanism can fail or may not work when the vest is worn incorrectly.

What is needed, therefore, is a non-invasive, temporary device that can continuously monitor the patient's heart rhythm to detect arrhythmias; can record and store all detected rhythms for future evaluation if necessary; can automatically and reliably defibrillate the heart if an arrhythmia is detected; can be used for a short period of time (days to weeks, possibly months) when the temporary risk of an arrhythmia exists; is entirely non-invasive and reversible and causes no significant or potentially permanent bodily harm from its use; and/or, most importantly, is unobtrusive and water resistant and requires only minimal maintenance or care so that it can seamlessly integrate into patients' lives such that they are protected from life-threatening arrhythmias during this entire period of time and can perform their normal daily routines without impediments to their physical or mental well-being. If the device is required to defibrillate a patient during this time, this patient can then be referred for evaluation to determine whether they need a permanent ICD or S-ICD, if appropriate. If nothing occurs and the patient doesn't have persistent pro-arrhythmic risk factors after this temporary period, the device can be removed and the implantation of a permanent device can be avoided. In this way, a functional, easy-to-use device for cardiac defibrillation to protect patients during a period of temporarily increased arrhythmia risk could also more efficiently identify patients who would benefit from more permanently implanted devices and those who would not.

A need also exists for treating temporary periods of elevated risk for sudden cardiac death in a successful and cost-effective manner while delivering an outstanding patient experience. A need also exists for improved treatment for patients with a need for an ICD but not getting one today, patients not initially indicated for ICD but found to be at elevated risk for SCD, and patients that would die of SCD without wearable defibrillator.

U.S. Pat. Nos. 8,024,037 and 8,364,260 disclose wearable external defibrillators. Wearable external defibrillators are desired that have improved adhesives for long term-wear, improved electrodes for long-term wear, improved weight distribution of the electrical components, improved and reduced size, and improved comfort to increase patient compliance.

The Zio® Patch by iRhythm® is designed to record heartbeats for up to 14 days. The Zio Patch has a relatively small profile and is lightweight because it does not have to accommodate the electrodes for delivering a defibrillating shock or support the electronic components required to deliver a defibrillating shock.

There are many challenges in developing biocompatible adhesives and electrodes for long-term wear. It is difficult to design adhesives that can be worn for longer than 10 days. Skin sloughing also occurs naturally over time, typically on the order of about 10-30 days, with variation related to the age of the patient. The natural sloughing of skin cells also presents technical challenges that need to be solved by the design of the adhesive material and design of the electrodes. Adhesives and electrodes also typically will cause skin irritation and redness during long term wear. It is desirable to also develop an improved adhesive and electrode design that can be used to comfortably attach the wearable defibrillator to the patient for long term wear. Developing a device that also is small enough to allow a weight distribution while adhered to the patients such that the device can be used constantly for long term wear is a challenging task. Additionally, developing a device small enough to be concealed such that its use in public does not draw attention or can be easily hidden under normal clothing is desired.

SUMMARY OF THE DISCLOSURE

Improved wearable defibrillators are disclosed herein that can be comfortably worn by the patient around the clock. The wearable defibrillators can be worn during showering, sleeping, and normal activities. The adhesives and electrodes are designed for long term wear and to be ready to deliver an effective amount of energy for defibrillation.

In general, in one embodiment, a wearable external defibrillator includes one or more sensing electrodes configured to engage with a patient's skin to detect a cardiac signal, a defibrillator electrode pad configured to engage with the patient's skin and to deliver an electrical therapy to the patient, the defibrillator electrode pad configured to be in continuous electrical communication with the patient's skin, a patient engagement substrate comprising an adhesive, the one or more sensing electrodes, the defibrillator electrode pad, and a fluid transport element configured to transport fluid away from the skin to allow the wearable external defibrillator to be worn continuously during movement and showering activities, an energy source; and a controller configured to detect the cardiac signal with the sensing electrodes and to deliver a therapeutic shock through the defibrillator pad to the patient while the patient engagement substrate is engaged with the patient.

In general, in one embodiment, a wearable external defibrillator includes one or more sensing electrodes configured to engage with a patient's skin to detect a cardiac signal; a defibrillator electrode pad configured to engage with the patient's skin and to deliver an electrical therapy to the patient, the defibrillator electrode pad configured to be in continuous electrical communication with the patient's skin;

a patient engagement substrate comprising the one or more sensing electrodes, the defibrillator electrode pad, and an elastic element configured to conform to, and stretch with, the patient's skin to allow the wearable external defibrillator to be worn continuously during movement and showering activities, an electrical energy source, and a controller configured to detect the cardiac signal with the sensing electrodes and to deliver a therapeutic shock through the defibrillator pad to the patient while the patient engagement substrate is engaged with the patient.

This and other embodiments can include one or more of the following features. The wearable external defibrillator can further include a second patient engagement substrate including a second defibrillator electrode pad, a second adhesive, and a second plurality of sensing electrodes, the second defibrillator electrode pad can be configured to engage with the patient's skin and to deliver an electrical therapy to the patient, the second defibrillator electrode pad can be configured to be in continuous electrical communication with the patient's skin, the second defibrillator electrode in electrical communication with the electrical energy source. The wearable defibrillator can further include a battery, one or more capacitors, wherein the controller can be configured to charge the one or more capacitors with the battery and to discharge the one or more capacitors through the defibrillator electrode pad and the second defibrillator electrode pad, wherein the electrical energy source can include the one or more capacitors. The battery, one or more capacitors, and the controller can be enclosed in a housing connected to the patient engagement substrate. The battery, one or more capacitors, and the controller can be enclosed in two or more separate housing connected to the patient engagement substrate. The housing can be configured to allow water vapor to pass from an interior surface of the housing through the housing to an exterior surface. The interior surface of the housing can be permeable to water vapor such that water vapor can pass from the interior surface to the exterior surface with an average moisture transmission rate of greater than about 250 $g/m^2$ per day based on a surface area of the patient engagement substrate. The housing can be air permeable. The exterior surface of the housing can be hydrophobic. The exterior surface of the housing can be water resistant. The wearable defibrillator can further include a fluid transport layer within the housing in fluid communication with the patient engagement substrate, the fluid transport layer can be configured to improve the flow of fluid across the patient engagement substrate. The fluid transport layer can have an absorption capacity of greater than about 500%. The fluid transport element can include the adhesive and the fluid transport layer. The fluid transport layer can be configured to transport fluid across a dominant surface area of the fluid transport layer. The wearable defibrillator can further include an absorbent material within the housing. The transport element can include the absorbent material. The transport element can include the housing. The wearable defibrillator can further include one or more waterproof housings surrounding the one or more capacitors, battery, and controller. The wearable defibrillator can further include a support layer configured to engage with and support the controller, one or more capacitors, and battery. A ratio of a combined weight of the one or more capacitors, battery, and controller to the surface area of the patient engagement substrate can be less than about 2 $g/cm^2$. The battery, one or more capacitors, and the controller can be enclosed in a housing separate from the patient engagement substrate and the second patient engagement substrate. The patient engagement surface can have an average moisture transmission rate of greater than about 10 $g/m^2$ per day based on a surface area of the patient engagement substrate. The patient engagement surface can have an average moisture transmission rate of greater than about 50 $g/m^2$ per day based on a surface area of the patient engagement substrate. The patient engagement surface can have an average moisture transmission rate of greater than about 100 $g/m^2$ per day based on a surface area of the patient engagement substrate. The patient engagement surface can have an average moisture transmission rate of greater than about 150 $g/m^2$ per day based on a surface area of the patient engagement substrate. The patient engagement surface can have an average moisture transmission rate of greater than about 200 $g/m^2$ per day based on a surface area of the patient engagement substrate. The patient engagement surface can have an average moisture transmission rate of greater than about 250 $g/m^2$ per day based on a surface area of the patient engagement substrate. The elastic element can have an average modulus of elasticity of about 0.40 MPa to about 0.9 MPa. The patient engagement substrate can have an average modulus of elasticity of about 0.40 MPa to about 0.9 MPa. The patient engagement substrate can have an average modulus of elasticity of greater than about 0.40 MPa. The patient engagement substrate can have an average modulus of elasticity of less than about 5.0 MPa. The patient engagement substrate can have an average modulus of elasticity of less than about 2.0 MPa. The one or more capacitors can have a total nominal capacitance of greater than about 50 µF. The one or more capacitors can have a total voltage greater than about 100 V. The wearable defibrillator can further include a flexible bridge connecting the first and second patient engagement substrates. The flexible bridge can include an electrical conductor configured to provide electrical communication between the second defibrillator pad electrode and the second plurality of ECG sensing electrodes to one or more of the controller and the one or more capacitors. The adhesive can include an adhesive border along a perimeter of the first patient engagement substrate configured to adhere to the wearable defibrillator and the skin of the patient, wherein the wearable defibrillator can have a tapered cross-sectional profile along the adhesive border from a side of the adhesive border towards a center of the wearable defibrillator to an outer edge of the adhesive border. The wearable defibrillator can further include a wireless data communication module within the housing. The wearable defibrillator can further include one or more sensors within the housing. The sensors can include one or more of: a GPS sensor, accelerometer, microphone, and a gyroscope. The wearable defibrillator can have a moisture transport rate of greater than about 250 $g/m^2$ per day from the first patient engagement substrate to the exterior of the housing based on a surface area of the first patient engagement substrate. The first defibrillator pad electrode can include a hydrogel and a woven carbon fiber structure. The wearable defibrillator can have a moisture transport rate of greater than about 250 $g/m^2$ per day from the second patient engagement substrate to an exterior of an outer layer based on a surface area of the second patient engagement substrate. The wearable defibrillator can further include a user interface. The patient engagement substrate can have an average moisture transmission rate of greater than about 500 $g/m^2$ per day. The fluid transport element can have an average moisture transmission rate of greater than about 50 $g/m^2$ per day based on a surface area of the patient engagement substrate. The fluid transport element can have an average moisture transmission rate of greater than about 250 $g/m^2$ per day based on a surface area of the patient engagement substrate. The adhesive in the patient engagement substrate can include perforations. The perforations can have a diameter of about 0.5 mm to about 2 mm. The perforations in the adhesive can have an open area of about 10% to about 25% of an overall surface area of the adhesive. The elastic element can include the adhesive. The wearable external defibrillator can be configured to be worn continuously during movement and showering activities for greater than about 24 hours. The wearable external defibrillator can be configured to be worn continuously during movement and showering activities for greater than about 5 days. The wearable external defibrillator can be configured to be worn continuously during movement and showering activities for greater than about 7 days. The wearable external defibrillator can be configured to be worn continuously during movement and showering activities for greater than about 10 days.

In general, in one embodiment, a wearable external defibrillator including a patient engagement substrate comprising an adhesive, one or more sensing electrodes, and a defibrillator electrode pad, a fluid communication layer in fluid communication with the patient engagement substrate, a battery, one or more capacitors, and a controller within one or more electronics housings, a support layer connected to the electronics housing and the patient engagement substrate, and an exterior housing connected to a portion of the patient engagement substrate such that the one or more electronics housings are between the exterior housing and the patient engagement substrate.

This and other embodiments can include one or more of the following features. The wearable defibrillator can further include an absorption layer in fluid communication with the fluid communication layer. The patient engagement substrate can have an average moisture transmission rate of greater than about 250 g/m$^2$ per day based on a surface area of the patient engagement substrate. The wearable defibrillator can further include a second patient engagement substrate including a second defibrillator electrode pad, a second adhesive, and a second plurality of sensing electrodes and a second fluid communication layer in fluid communication with the second patient engagement substrate, the second defibrillator electrode pad configured to engage with the patient's skin and to deliver an electrical therapy to the patient, the second defibrillator electrode pad configured to be in continuous electrical communication with the patient's skin. The second patient engagement substrate can have an average moisture transmission rate of greater than about 250 g/m$^2$ per day based on a surface area of the second patient engagement substrate. The exterior housing can be air permeable. An outer surface of the exterior housing can be hydrophobic. An outer surface of the exterior housing can be water resistant. The fluid communication layer can have an absorption capacity of greater than about 500%. The wearable defibrillator can further include a waterproof housing surrounding the one or more capacitors, battery, and controller. The patient engagement substrate can have an average modulus of elasticity of about 0.40 MPa to about 0.9 MPa. The patient engagement substrate can have an average modulus of elasticity of greater than about 0.40 MPa. The one or more capacitors can have a total nominal capacitance of greater than about 50 µF. The one or more capacitors can have a total voltage greater than about 100 V. The wearable defibrillator can further include a wireless data communication module within the housing. The wearable defibrillator can further include one or more sensors within the housing. The sensors can include one or more of: a GPS sensor, accelerometer, microphone, and a gyroscope. The adhesive in the patient engagement substrate can include perforations. The perforations can have a diameter of about 0.5 mm to about 2 mm. The perforations in the adhesive can have an open area of about 10% to about 25% of an overall surface area of the adhesive. The fluid communication layer can have an average moisture transmission rate of greater than about 50 g/m$^2$ per day based on a surface area of the patient engagement substrate. The fluid communication layer can have an average moisture transmission rate of greater than about 250 g/m$^2$ per day based on a surface area of the patient engagement substrate.

In general, in one embodiment, a wearable external defibrillator includes a first patient engagement substrate including an adhesive, one or more sensing electrodes, and a first defibrillator electrode pad, the one or more sensing electrodes configured to engage with a patient's skin to detect a cardiac signal, the first defibrillator electrode pad configured to engage with the patient's skin and to deliver an electrical therapy to the patient, the first defibrillator electrode pad configured to be in continuous electrical communication with the patient's skin, a housing connected to the first patient engagement substrate to form an interior space between the housing and the first patient engagement substrate, the interior portion comprising a battery, one or more capacitors, and a controller, wherein the first defibrillator electrode pad is in electrical communication with the one or more capacitors, a second patient engagement substrate comprising a second defibrillator electrode pad, second adhesive, and second plurality of sensing electrodes, the second defibrillator electrode pad configured to engage with the patient's skin and to deliver an electrical therapy to the patient, the second defibrillator electrode pad configured to be in continuous electrical communication with the patient's skin, the second defibrillator electrode in electrical communication with the one or more capacitors, and a fluid transport element configured to transport fluid away from the skin to allow the wearable external defibrillator to be worn continuously for greater than 24 hours, wherein the controller is configured to charge the one or more capacitors with the battery and to discharge the one or more capacitors through the first defibrillator electrode pad and the second defibrillator electrode pad.

This and other embodiments can include one or more of the following features. The wearable external defibrillator can be configured to be worn continuously during movement and showering activities for greater than about 5 days. The wearable external defibrillator can be configured to be worn continuously during movement and showering activities for greater than about 7 days. The wearable external defibrillator can be configured to be worn continuously during movement and showering activities for greater than about 10 days. The wearable defibrillator can have an average moisture transmission rate of greater than about 250 g/m$^2$ per day from the first patient engagement substrate through the housing connected to the first patient engagement substrate based on a surface area of the first patient engagement substrate. The first patient engagement substrate can have an average moisture transmission rate of greater than about 500 g/m$^2$ per day. The first and second patient engagement substrates can have an average modulus of elasticity of about 0.40 MPa to about 0.9 MPa. The patient engagement substrate can have an average modulus of elasticity of greater than about 0.40 MPa. The housing can be air permeable. An outer surface of the housing can be hydrophobic. The outer surface of the housing can be water resistant. The fluid transport element can further include a fluid transport layer within the housing in fluid communication with the first patient engagement substrate, the fluid transport layer can be configured to improve the flow of water across the first patient engagement substrate. The fluid transport layer can have an absorption capacity of greater than about 500%. The wearable defibrillator can further include an absorbent material within the housing. The wearable defibrillator can further include one or more waterproof housings surrounding the one or more capacitors, battery, and controller. The wearable defibrillator can further include a support layer configured to engage with and support the controller, one or more capacitors, and battery. A ratio of a combined weight of the one or more capacitors, battery, and controller to the surface area of the patient engagement substrate can be less than about 2 g/cm$^2$. The one or more capacitors can have a total nominal capacitance of greater than about 50 µF. The one or more capacitors can have a total voltage greater than about 100 V. The wearable defibrillator can further include a flexible bridge connecting the first and second patient engagement substrates. The flexible bridge can include an electrical conductor configured to provide electrical communication between the second defibrillator pad electrode and the second plurality of ECG sensing electrodes to one or more of the controller and the one or more capacitors. The adhesive can include an adhesive border along a perimeter of the first patient engagement substrate configured to adhere to the wearable defibrillator and the skin of the patient, wherein the wearable defibrillator can have a tapered cross-sectional profile along the adhesive border from a side of the adhesive border towards a center of the wearable defibrillator to an outer edge of the adhesive border. The wearable defibrillator can further include a wireless data communication module within the housing. The wearable defibrillator can further include one or more sensors within the housing. The sensors can include one or more of: a GPS sensor, accelerometer, microphone, and a gyroscope. The first defibrillator pad electrode can include a hydrogel and a woven carbon fiber structure. The adhesive in the patient engagement substrate can include perforations. The perforations can have a diameter of about 0.5 mm to about 2 mm. The perforations in the adhesive can have an open area of about 10% to about 25% of an overall surface area of the adhesive.

In general, in one embodiment a patient engagement surface includes one or more sensing electrodes configured to engage with a patient's skin to detect a cardiac signal, a defibrillator electrode pad configured to engage with the patient's skin and to deliver an electrical therapy to the patient, the defibrillator electrode pad configured to be in continuous electrical communication with the patient's skin, and a patient engagement substrate comprising an adhesive, the one or more sensing electrodes, the defibrillator electrode pad, and a fluid transport element configured to transport fluid away from the skin to allow the wearable external defibrillator to be worn continuously during movement and showering activities.

This and other embodiments can include one or more of the following features. The patient engagement surface can further include elastic element an elastic element configured to conform to, and stretch with, the patient's skin to allow the wearable external defibrillator to be worn continuously during movement and showering activities for greater than seven days. The patient engagement surface can be configured to be worn continuously during movement and showering activities for greater than about 24 hours. The patient engagement surface can be configured to be worn continuously during movement and showering activities for greater than about 5 days. The patient engagement surface can be configured to be worn continuously during movement and showering activities for greater than about 10 days. The defibrillator pad can include a woven carbon fiber structure. The patient engagement surface can further include a second defibrillator electrode pad. The patient engagement surface can further include an electronics module in electrical communication with the defibrillator electrode pad and second defibrillator electrode pad. The patient engagement substrate can have an average modulus of elasticity of greater than about 0.40 MPa. In general, in one embodiment a kit including the wearable external defibrillator and one or more of: an adhesive remover, a skin cleaner, hair removal tool, and instructions for applying the wearable defibrillator.

In general, in one embodiment a method of monitoring and defibrillating a patient's heart, including adhering to a first skin surface portion of the patient a first patient engagement substrate comprising a first plurality of sensing electrodes and a first defibrillator pad, the first defibrillator pad in electrical communication with an electrical energy source sufficient to provide a defibrillating shock, the first patient engagement substrate part of a wearable defibrillator comprising a fluid transport element configured to transport fluid away from the first skin surface portion of the patient to allow the wearable external defibrillator to be worn continuously during movement and showering activities, adhering to a second skin surface portion of the patient a second patient engagement substrate comprising a second plurality of sensing electrodes and a second defibrillator pad, the second defibrillator pad in electrical communication with the electrical energy source sufficient to provide the defibrillating shock, the second patient engagement part of the wearable defibrillator; and measuring electrical data corresponding to a cardiac signal of the patient with the first plurality of sensing electrodes and the second plurality of sensing electrodes.

This and other embodiments can include one or more of the following features. The fluid transport element can move fluid away from the first skin portion and towards an exterior of a housing of the wearable defibrillator. The fluid transport element can move fluid across a dominant cross-sectional area of the fluid transport element. The fluid transport element can provide an average moisture transmission rate of greater than about 50 g/m$^2$ per day to the first skin surface portion of the patient. The fluid transport element can provide an average moisture transmission rate of greater than about 250 g/m$^2$ per day to the first skin surface portion of the patient. The fluid transport element can include an adhesive and a wicking material, wherein the adhesive can be part of the first patient engagement substrate and the second patient engagement substrate. The method can further include analyzing the electrical data to determine if the patient has a treatable arrhythmia. The method can further include detecting one or more of the pulse, breathing rate, heart sounds, and heart rate of the patient. The method can further include analyzing the detected one or more of the pulse, breathing rate, heart sounds, and heart rate of the patient to confirm a treatable arrhythmia. The method can further include delivering an electrical shock after determining that the patient has a treatable arrhythmia. The method can further include measuring a transthoracic impedance of the patient between the first defibrillator pad electrode and the second defibrillator pad electrode prior to delivering the electrical shock. The method can further include continuously wearing the wearable defibrillator for greater than about 24 hours. The method can further include continuously wearing the wearable defibrillator for greater than about 5 days. The method can further include continuously wearing the wearable defibrillator for greater than about 7 days.

In general, in one embodiment a method for treating a patient with a wearable defibrillator includes receiving ECG data from a plurality of ECG sensing electrodes configured for long term wear and continuous electrical contact with a skin of the patient, the plurality of ECG sensing electrodes being part of the wearable defibrillator, analyzing the ECG data to determine whether the patient has a treatable arrhythmia, upon determination of a treatable arrhythmia, detecting one or more of a pulse, a breathing rate, heart sounds, and a heart rate of the patient, analyzing the detected one or more of the pulse, breathing rate, heart sounds, and heart rate of the patient to confirm a treatable arrhythmia, measuring a transthoracic impedance of the patient between a first defibrillator pad electrode and a second defibrillator pad electrode, the first defibrillator pad and second defibrillator pad configured for long term wear and continuous electrical contact with the skin of the patient, the first defibrillator pad and second defibrillator pad being part of the wearable defibrillator, instructing a controller to charge a plurality of capacitors in the wearable defibrillator, and delivering a therapeutic electrical shock to the patient through the first defibrillator electrode pad and the second defibrillator electrode pad.

This and other embodiments can include one or more of the following features. The method can further include after determination of a treatable arrhythmia wirelessly transmitting data corresponding to a location of the patient to an emergency medical service. The method can further include after determination of a treatable arrhythmia wirelessly transmitting data corresponding to a location of the patient to an emergency contact of the patient. Measuring a transthoracic impedance can include determining if the first defibrillator pad and second defibrillator pad electrode are in electrical contact with the skin of the patient. The method can further include tailoring the therapeutic electrical shock based on the transthoracic impedance. The method can further include prior to instructing the controller to charge the plurality capacitors, generating an audible alarm to warn the patient of a possible therapeutic electrical shock. The method can further include instructing the controller to charge the plurality of capacitors if a shutoff button on the wearable defibrillator is not pushed.

In general in one embodiment a method of monitoring and defibrillating a patient's heart includes engaging a patient engagement substrate with skin of the patient, the patient engagement substrate comprising an adhesive, one or more sensing electrodes, and a defibrillator electrode pad and an elastic element, measuring a cardiac signal with the one or more sensing electrodes, supporting in electrical contact with the one or more sensing electrodes and the defibrillator electrode pad, a battery, an electrical energy source, and a controller configured to monitor the one or more sensing electrodes, to charge the one or more capacitors with the battery and to discharge the electrical energy source through the defibrillator electrode pad to deliver an electrical therapy to the patient, and performing the engaging, measuring and supporting steps continuously for at least 24 hours. The elastic element can have an average modulus of elasticity of about 0.40 MPa to about 0.9 MPa. The engaging, measuring and supporting steps can be performed continuously for at least 48 hours. The engaging, measuring and supporting steps can be performed continuously for at least 5 days. The engaging, measuring and supporting steps can be performed continuously for at least 7 days. The engaging, measuring and supporting steps can be performed continuously for at least 10 days. The engaging, measuring, and supporting steps can be performed continuously through movement and showering activities.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4B illustrate multiple views of a portion of an embodiment of a wearable defibrillator.

FIG. 14 illustrates properties of various adhesives.

FIGS. 18-20 illustrate various types of capacitor materials and properties.

FIGS. 24A-24C illustrate a q-cap capacitor configuration in accordance with some embodiments.

FIGS. 28A-28D illustrate different lower patch shapes in accordance with some embodiments and how the lower patch and housing can be placed on a female user.

FIGS. 29A-29C and 30A-30D illustrate different cable designs that can be used between the lower patch and upper patch.

FIGS. 31A1-31D illustrate various form factors for an upper patch in accordance with some embodiments along with examples of the placement of the upper patch on a chest of a female user.

FIGS. 32A-32E illustrate different housing shapes and designs that can be used with the wearable defibrillators disclosed herein.

FIGS. 45A-45C, 46A-46C, 47A-47C, and 48A-48C illustrate embodiments of wearable defibrillators attached to a patient.

FIGS. 49A-49D, 50A-50D, 51A-51D, and 52A-52D show pictures of weighted models of wearable defibrillators in accordance with some embodiments.

FIGS. 53A-74 illustrate various embodiments of wearable defibrillators. FIGS. 53A-53D show wearable defibrillators with a patch attached to the chest. FIGS. 54A-54D show embodiments of wearable defibrillators with an upper patch and a lower patch. FIGS. 56A-56H3 illustrate additional embodiments of wearable defibrillators with various supports. FIGS. 57A-57E illustrate an embodiment of a wearable defibrillator with a bracelet. FIGS. 58A-58C illustrate an embodiment of a wearable defibrillator with replaceable adhesive electrode assemblies. FIGS. 59A-59E illustrate an embodiment of a wearable defibrillator with replaceable adhesive patches and pockets. FIGS. 60A-60D illustrate an embodiment of a wearable defibrillator with a flexible hinge. FIGS. 61A-61B illustrate an embodiment of a wearable defibrillator with the electronics and battery component connected to the capacitors by a bridge. FIGS. 62A-62E illustrate an embodiment of a wearable defibrillator with a capacitor module and a battery/electronics module. FIGS. 63A-63E illustrate another embodiment of a wearable defibrillator with a capacitor module and a battery/electronics module. FIGS. 64A-64F illustrate another embodiment of a wearable defibrillator with a capacitor module and a battery/electronics module. FIG. 65 illustrates an embodiment of a wearable defibrillator on a male and a female patient. FIG. 66 illustrates an embodiment of a wearable defibrillator with a side support patch. FIGS. 67A-67H illustrate different designs for the foot print of the upper patch and the lower patch/side support. FIG. 69 shows another embodiment of a wearable defibrillator with a lower patch supporting a capacitor module and defibrillator pad electrode. FIGS. 70A-70H show various embodiments of different foot prints for the upper patch and lower patch of wearable defibrillators. FIGS. 72, 73A-73B, and 74 illustrate wearable defibrillators with different profiles to conform to the body.

FIGS. 77A-78 illustrate various features of an embodiment of a wearable defibrillator. FIGS. 77A-77C illustrate different views of a wearable defibrillator with a bracelet. FIG. 78 illustrates a wearable defibrillator with a lower patch supporting electronics modules.

FIGS. 82A-82C illustrate sketches of wearable defibrillators with various configurations of interconnect structures in accordance with some embodiments.

FIGS. 84A1-84A2 illustrate cross-sectional and top views, respectively of wearable defibrillators in accordance with some embodiments. FIG. 84B illustrates a device with an adhesive and stretchable anchor.

FIGS. 87A-87B illustrate wearable electrodes in accordance with some embodiments.

DETAILED DESCRIPTION

Figure 1:
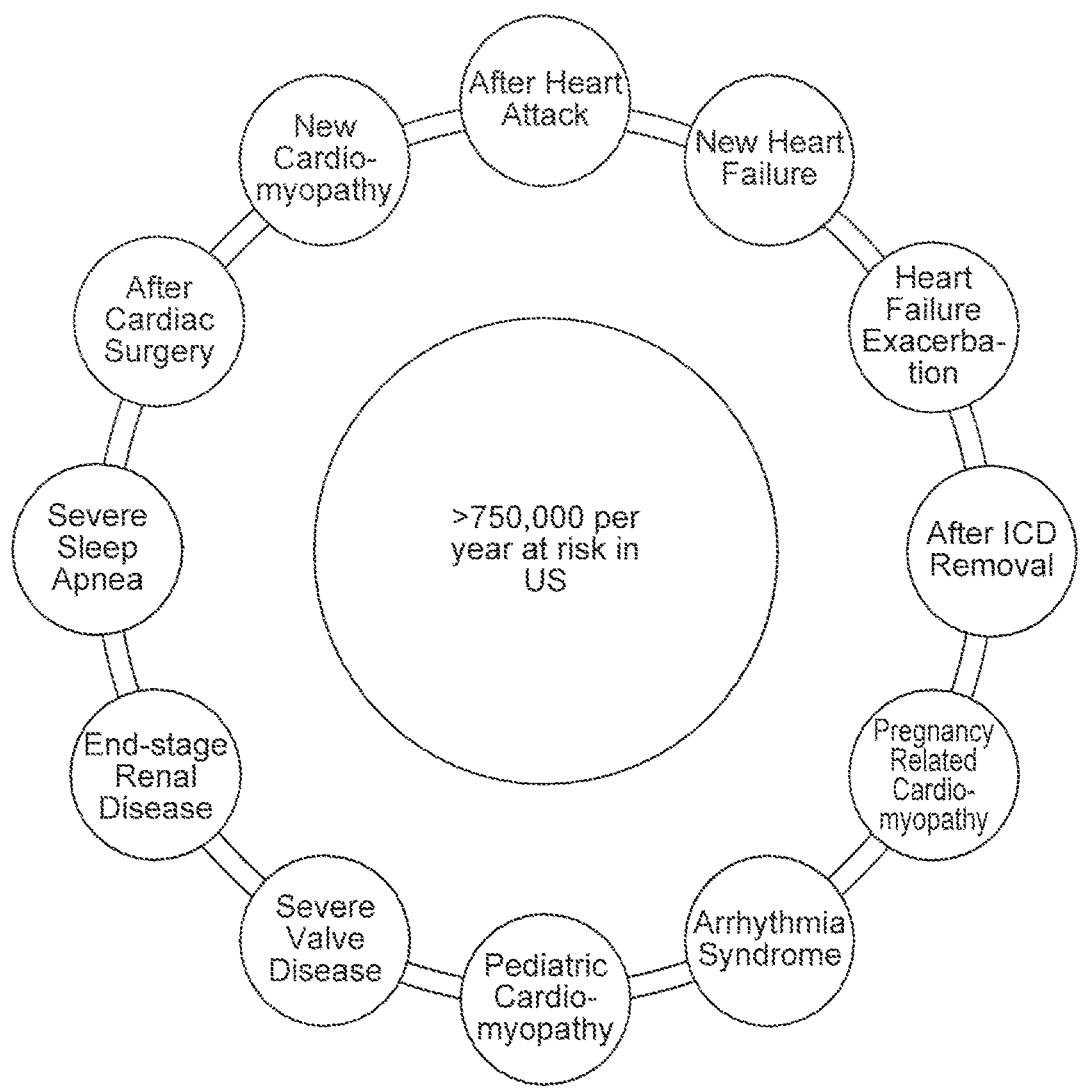
FIG. 1 illustrates examples of conditions that elevate risk for sudden cardiac death (SCD).
Figure 2D:
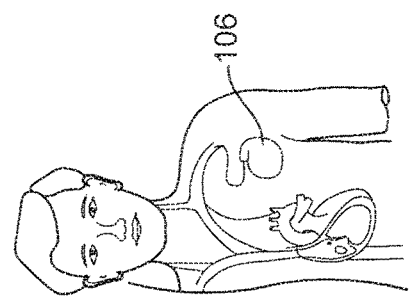
FIGS. 2A-2D illustrate various prior art defibrillators.
Figure 2C:
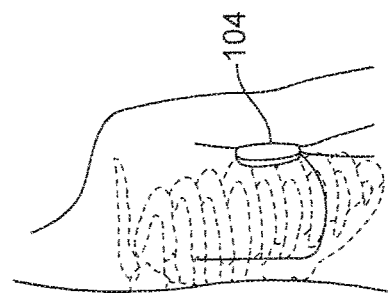
Figure 2B:
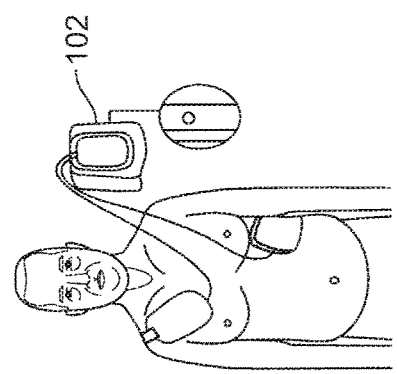
Figure 2A:
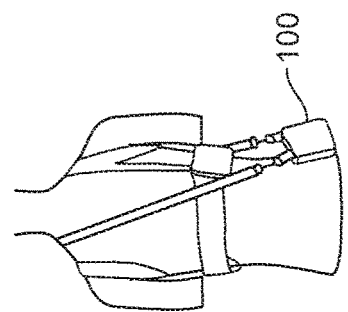

Improved wearable defibrillators are described herein. The wearable defibrillators can be comfortably worn by the patient throughout the day, including during showering and sleeping. The electrodes and adhesive are designed for long term wear while minimizing discomfort and skin irritation from the electrodes and adhesive.

The wearable defibrillator can only detect and treat arrhythmia when it is worn. When the device is not worn then a lifesaving therapy can't be provided. The efficacy of the device is maximized by continuous wear. A goal is to make the device as small, lightweight, comfortable, and unobtrusive as possible in order to increase patient compliance. It is desirable to minimize the size and weight of the components of the device; however, the components also need to be reliable and rugged to withstand showering and other forces encountered during normal human activity. The parts of the device that are attached to the patient's skin also need to accommodate perspiration and skin stretching beneath the attachment substrate in order to stay comfortably attached while maintaining skin health.

A number of different aspects of the defibrillators are disclosed herein. The defibrillators typically include defibrillation electrodes (also called defibrillation pads), ECG monitoring electrodes (also called sensing electrodes), electronics components to determine when a defibrillation shock is necessary, a battery, one or more capacitors, etc.

One challenge is designing components, including the capacitor and battery to be rugged and reliable while also being lightweight and small enough to be attached to the patient's body. Another challenge is designing the profile of the device and components to distribute the weight across the body of the patient in a comfortable, ergonomic, and non-obtrusive manner.

Also, because they are attached to the patient's skin for an extended period of time (e.g., 7-10 days or longer), the defibrillators of this invention include patient engagement substrates that, in addition to supporting the ECG sensing electrodes and the defibrillation pads in sufficient electrical contact with the skin, include elements designed to accommodate perspiration produced by the skin beneath the defibrillator and elements designed to stretch and move as the skin beneath the defibrillator stretches and moves to maintain skin health and comfort during the long term wear. Thus, because the electrodes and other defibrillator components may not be permeable to water or water vapor from the skin, one or more other elements of the substrate can perform that function. Failure to absorb and/or remove perspiration may result in failure of the adhesive and/or skin irritation, limiting the ability to attach the defibrillator (including the sensing and defibrillation electrodes) to the skin for an extended period of time. Deterioration of the skin beneath the patient engagement substrate might also limit the patient's ability to attach a new defibrillator engagement structure to the same skin location for a subsequent monitoring period. A breathable outer housing can also be used to further improve the moisture vapor transmission rate of the wearable defibrillator.

Another challenge is to design a wearable defibrillator that can be worn continuously, including during normal activities like movement and showering. The Lifevest™ is not suitable for use during showering and must be removed prior to showering. Other conventional AED are not can't be used when the patient is wet (e.g., in the shower) and are therefore not capable of providing protection to the patient during showering. The wearable defibrillators disclosed herein are suitable to be worn continuously during movement and showering activities. The wearable defibrillators described herein are also able to monitor ECG signals and provide a defibrillating shock to the patient when they are in the shower. In some embodiments the wearable external defibrillators described herein are configured to be worn continuously during movement and showering activities for greater than about 24 hours. In some embodiments the wearable external defibrillators described herein are configured to be worn continuously during movement and showering activities for greater than about 48 hours. In some embodiments the wearable external defibrillators described herein are configured to be worn continuously during movement and showering activities for greater than about 5 days. In some embodiments the wearable external defibrillators described herein are configured to be worn continuously during movement and showering activities for greater than about 7 days. In some embodiments the wearable external defibrillators described herein are configured to be worn continuously during movement and showering activities for greater than about 10 days.

Another challenge is designing an adhesive material that can reliably and comfortably attach the device to the skin of the patient while minimizing skin irritation for long term wear. Many types of adhesives cause skin irritation when worn for more than a few hours. Skin irritation can bother the patient and result in non-compliance when the patient removes the device due to excessive skin irritation. The adhesive material of the patient engagement substrate should be comfortable for a typical wear duration, e.g., about 7-14 days.

Natural skin sloughing can also change the impedance of the skin. The electrode design and contact should also account for changes to the impedance of the skin. Natural skin sloughing typically occurs over a period of about 10-30 days. The natural skin sloughing can make it challenging to design an electrode that can maintain an acceptable impedance and electrical contact with the skin for a duration of over 10 days in some patients. One possible solution to this problem is to re-position the electrode after a set time period such that it contacts a different area of the skin.

Long term wear can be considered any wear duration over 5 days. In some embodiments the patient engagement substrate is configured to be worn in one position on the skin for greater than about 7 days, greater than about 10 days, between about 10 to about 14 days, between about 14 and about 21 days, or between about 21 days and about one month (approximately 30 days). After being worn for a specified duration, e.g., about 10 to 14 days, the device can be shifted such that the electrodes and adhesive contact new areas of the skin of the patient, after which the device can be worn in the second position for a period of 10 to 14 days. This process can be repeated as necessary for the entire time the defibrillator is worn. The total wear duration of the device can vary based on the patient and condition to be treated. In some embodiments the wear duration of the wearable defibrillator is greater than about 30 days, greater than about 45 days, greater than about 60 days, greater than about 90 days, greater than about 120 days, greater than about 150 days, greater than about 180 days, greater than about 210 days, greater than about 240 days, greater than about 270 days, greater than about 300 days, greater than about 330 days, or greater than about 360 days. In some patients in whom there are permanent contraindications to an implantable device, such as an ICD or S-ICD, or for certain patients who refuse an implantable solution, the duration of wear could be lifelong.

A variety of different long-term wear electrode configurations and electrode materials are disclosed herein that can be used in the wearable defibrillators described herein. Commercially available electrode pads, such as those from Zoll and 3M, are not suitable for long term wear. Most of the Zoll and 3M pads are indicated for 8 hours of use. In contrast, the patient engagement substrate designs and materials described herein can enable long term wear of the defibrillator.

A variety of properties of the device can be selected to improve the comfort of the device to improve the long term wear of the device. Skin stretches as the body moves, then returns to its original position when the body moves back. The properties of the portion of the device contacting the skin can be tailored to match these elastic properties of the skin. While some of the components in the patient engagement substrate are more or less inelastic, one or more elastic elements can be added to the substrate to make the overall elasticity of the patient engagement substrate match the elasticity of the skin. These improved properties can greatly increase the comfort of the wearable defibrillator and allow for long term wear of the device while minimizing skin irritation and patient non-compliance.

Figure 3B:
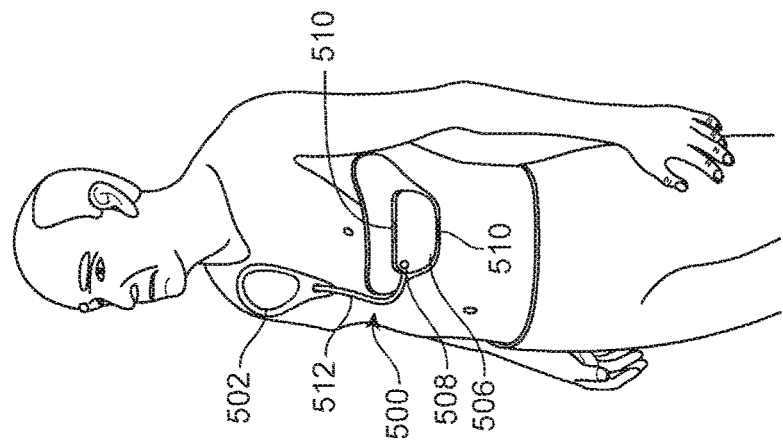
FIGS. 3A-3B illustrate a wearable defibrillator in accordance with some embodiments.
Figure 3A:
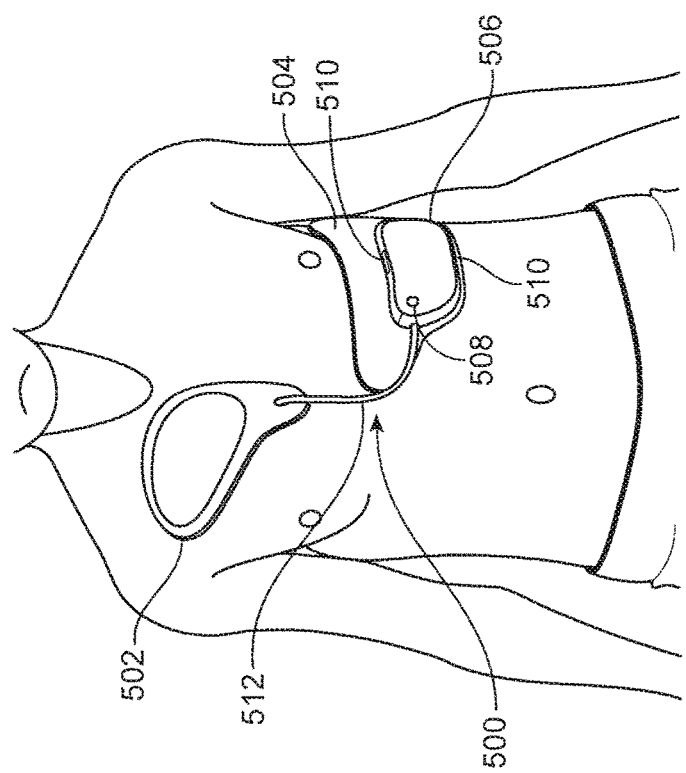

FIG. 3A and FIG. 3B illustrate a wearable defibrillator 500 with an upper patch 502 having two sensor electrodes and a defibrillator electrode and a lower patch 504 having three sensor electrodes and a defibrillator electrode. The patient engagement substrate of the upper patch 502 and lower patch 504 includes the defibrillator pad electrodes and the sensing electrodes. The lower patch 504 supports a housing 506 that includes a LED light indicator 508 to provide system feedback. The housing 506 includes buttons 510 that can be pushed by the user. The upper patch electrodes are connected to the electronics in the lower patch by conductive cabling 512. The lower patch 504 has a larger surface area than the upper patch 502 that can be used to spread the shear weight of the electronics module (e.g., battery, capacitors, and controller). The lower patch 504 is configured to follow the lower rib line of the wearer. The ECG sensors can be evenly spread across the vector. The housing 506 on the lower patch 504 includes user interface controls for easy access by the wearer. In some cases the upper patch 502 can include a feedback system, such as a speaker, for improved communication with wearers that have decreased hearing function. In some embodiments the upper patch can include an override button. In some embodiments the upper patch can include a speaker and override button. In other embodiments the speaker and/or override button can be on the lower patch. The illustrated cables 512 can include a cable management system to deploy or remove slack in the cable connecting the upper patch 502 and lower patch 504 to accommodate a spectrum of body sizes.

The illustrated patient engagement substrate of the first patch/portion and second patch/portion can include an elastic element made from flexible materials that have an elasticity similar to the skin, such as an elastic element. The elastic element can improve the wearability of the defibrillator and allow for continuous wear during movement and showering activities. The modulus of elasticity for skin typically ranges from 0.42 to 0.85 MPa. Skin typically has an ultimate strength ranging from 5 to 30 MPa. The elastic element can enable the upper patch 502 and lower patch 504 to conform to and stretch with the patient's skin to allow the wearable defibrillator to be worn long term. In some embodiments the elastic element can have an average elasticity of about 0.40 MPa to about 0.90 MPa. In some embodiments the elastic element includes the adhesive in the patient engagement substrate. In some embodiments the adhesive that make up the patient engagement element or substrate can have an average elasticity of about 0.40 MPa to about 0.90 MPa. In some embodiments the defibrillator pad electrodes and sensing electrodes can have an average elasticity of about 0.40 MPa to about 0.90 MPa. In some embodiments the patient engagement substrate has an average elasticity of about 0.40 MPa to about 0.90 MPa. In some embodiments the patient engagement substrate has an average elasticity of greater than about 0.40 MPa. In some embodiments the patient engagement substrate has an average elasticity of less than about 5.0 MPa. In some embodiments the patient engagement substrate has an average elasticity of less than about 2.0 MPa. In some embodiments the elasticity of the patient engagement surface can vary such that it is less elastic in areas adjacent to rigid components like the electronics (capacitors, battery, circuit boards, etc.) and more elastic in other areas. For example the areas of the patient engagement surface that are not next to the electronics can have an elasticity of about 0.40 MPa to about 0.90 MPa. Matching the elasticity of the electrodes and adhesive to the elasticity of the skin can make the wearable defibrillator more comfortable.

The fluid transport properties of the wearable defibrillator can be enhanced to increase comfort, skin health, and long term wearability of the wearable defibrillator. In some embodiments the wearable defibrillator includes a fluid transport element configured to transport fluid away from the skin. In some embodiments the fluid transport element can be configured to transport fluid away from the skin to allow the wearable external defibrillator to be worn continuously during movement and showering activities. One way of quantifying the fluid transport properties of the device or portions of the device, such as the fluid transport element, is the moisture transmission rate. The moisture transmission rate can include the transmission rate of fluid and vapor. In some embodiments the moisture transmission rate of the overall wearable defibrillator can be selected to meet or exceed the average human transpiration rate. The average human transpiration rate can be about 250 $g/m^2$ per day. High physical exertion can produce moisture at a rate of up to about 1,100 $g/m^2$ per hour; however that transpiration rate is unlikely to be sustained for long. Embodiments of the wearable defibrillators disclosed herein can be configured to transport higher transpiration rates as necessary for short duration of high physical exertion. For example, for high transpiration rates the wicking layer can transport moisture across the patient interface area. The moisture can be absorbed by an absorption layer so that the fluid can then be evaporated at a slower rate through the housing.

The fluid transport element can be a single material or multiple materials or structures in the wearable defibrillator. In some embodiments the fluid transport element can include a portion of the patient engagement substrate. In some embodiments the fluid transport element can include an adhesive. In some embodiments the fluid transport element can include a fluid transport layer or material, such as a wicking layer. In some embodiments the fluid transport element can include an absorbing layer. In some embodiments the fluid transport element can include a breathable outer housing.

In some embodiments the fluid transport element has an average moisture transmission rate of greater than about 10 $g/m^2$ per day based on a surface area of the patient engagement substrate. In some embodiments the fluid transport element has an average moisture transmission rate of greater than about 50 $g/m^2$ per day based on a surface area of the patient engagement substrate. In some embodiments the fluid transport element has an average moisture transmission rate of greater than about 100 $g/m^2$ per day based on a surface area of the patient engagement substrate. In some embodiments the fluid transport element has an average moisture transmission rate of greater than about 150 $g/m^2$ per day based on a surface area of the patient engagement substrate. In some embodiments the fluid transport element has an average moisture transmission rate of greater than about 200 $g/m^2$ per day based on a surface area of the patient engagement substrate. In some embodiments the fluid transport element has an average moisture transmission rate of greater than about 250 $g/m^2$ per day based on a surface area of the patient engagement substrate. In some embodiments the fluid transport element has an average moisture transmission rate of greater than about 500 $g/m^2$ per day based on a surface area of the patient engagement substrate.

In some embodiments the fluid transport properties of the adhesive can be quantified. In some embodiments the adhesive has an average moisture transmission rate of greater than about 10 $g/m^2$ per day based on a surface area of the patient engagement substrate. In some embodiments the fluid transport properties of the adhesive can be quantified. In some embodiments the adhesive has an average moisture transmission rate of greater than about 50 g/m² per day based on a surface area of the patient engagement substrate. In some embodiments the adhesive has an average moisture transmission rate of greater than about 100 g/m² per day based on a surface area of the patient engagement substrate. In some embodiments the adhesive has an average moisture transmission rate of greater than about 150 g/m² per day based on a surface area of the patient engagement substrate. In some embodiments the adhesive has an average moisture transmission rate of greater than about 200 g/m² per day based on a surface area of the patient engagement substrate. In some embodiments the adhesive has an average moisture transmission rate of greater than about 250 g/m² per day based on a surface area of the patient engagement substrate. The defibrillator pad electrodes and sensing electrodes can also have any of the moisture vapor transport properties as the adhesive.

The moisture vapor transmission rate of the patient engagement substrate can be configured to transport moisture from the skin. In some embodiments the wearable defibrillator has a patient engagement substrate including the adhesive, sensing electrodes, and defibrillator pad electrode with a moisture transmission rate of greater than about 250 g/m² per day based on the surface area of the patient engagement substrate. The moisture vapor transmission rate can be the average moisture vapor transmission across the total surface area of the patient engagement surface (e.g., surface area of the adhesive, defibrillator pad electrode, and sensor electrodes). In some embodiments the patient engagement surface has an average moisture transmission rate of greater than about 10 g/m² per day based on a surface area of the patient engagement substrate. In some embodiments the patient engagement surface has an average moisture transmission rate of greater than about 50 g/m² per day based on a surface area of the patient engagement substrate. In some embodiments the patient engagement surface has an average moisture transmission rate of greater than about 100 g/m² per day based on a surface area of the patient engagement substrate. In some embodiments the patient engagement surface has an average moisture transmission rate of greater than about 150 g/m² per day based on a surface area of the patient engagement substrate. In some embodiments the patient engagement surface has an average moisture transmission rate of greater than about 200 g/m² per day based on a surface area of the patient engagement substrate. In some embodiments the patient engagement substrate has a moisture vapor transmission rate of greater than about 500 g/m² per day. In some embodiments the patient engagement substrate has a moisture vapor transmission rate of greater than about 1,000 g/m² per day.

The housing can also facilitate moisture vapor transmission from the surface of the skin through the patient engagement substrate and out through the housing to the exterior of the wearable defibrillator. In some embodiments the interior surface of the housing can be permeable to water vapor such that water vapor can pass from the interior of the device through the housing to the exterior of the device. In some embodiments the interior surface of the housing is permeable to water vapor such that water vapor can pass from the interior surface to the exterior surface with a moisture vapor transmission rate of greater than about 250 g/m² per day based on the surface area of the patient engagement surface. In some embodiments the moisture vapor transmission rate of the housing is greater than about 500 g/m² per day based on the surface area of the patient engagement surface. In some embodiments the moisture vapor transmission rate of the housing is greater than about 1,000 g/m² per day based on the surface area of the patient engagement surface. In some embodiments the moisture vapor transmission rate of the housing is greater than about 1,500 g/m² per day based on the surface area of the exterior of the housing. In some embodiments the moisture vapor transmission rate of the housing is greater than about 2,000 g/m² per day based on the surface area of the exterior of the housing. In some embodiments the moisture vapor transmission rate of the housing is greater than about 5,000 g/m² per day based on the surface area of the exterior of the housing. In some embodiments the moisture vapor transmission rate of the housing is greater than about 10,000 g/m² per day based on the surface area of the exterior of the housing. In some embodiments the moisture vapor transmission rate of the housing can be as high as about 25,000 g/m² per day based on the surface area of the exterior of the housing.

The wearable defibrillators disclosed herein can have a multi-layer construction that can further improve the long term wearability of the defibrillator. FIG. 4A-FIG. 4B illustrate multiple views of a portion of a lower patch 600 of a wearable defibrillator 600 in accordance with some embodiments. A top view of the lower patch 600 shows the outer housing 602 and adhesive border 604. The housing 602 includes two buttons 606. The adhesive border 604 can be used to prevent moisture from entering the space between the skin and the electrodes and defibrillator pad. Adhesive border 604 can also be used to prevent the device from being inadvertently peeled off due to mechanical abrasion across the edges of the device. The adhesive border can have a thickness of less than about 0.010 inches. In some embodiments the adhesive border has a thickness of about 0.001 inches to about 0.005 inches. The second view of the lower patch 600 is an isometric view illustrating the multi-layer construction of the lower patch 600. The lower patch 600 includes a layer 608 configured to contact the patient's skin for long term wear. The layer 608 that contacts the patient's skin includes adhesive 610, sensing electrodes, and a defibrillator pad electrode 612 configured to contact the skin for long term wear. The adhesive 610, sensing electrodes, and defibrillator pad 612 can include complementary structures to fit together to form the layer or substrate that contacts the skin. In some embodiments the adhesive can be part of a fluid transport element. In some embodiments the adhesive can be modified to improve the fluid transport properties.

A wicking layer 614 can be in contact with the layer 608 containing one or more of the adhesive 610, hydrogel electrodes, sensor electrodes, and defibrillation pads 612. In some embodiments the wicking layer 614 is part of a fluid transport element. The wicking layer 614 can improve the diffusion of fluid, such as water liquid, vapor and moisture, from the skin across the layer (e.g., adhesive and electrodes) contacting the patient's skin. In addition to wicking fluid across the adhesive and electrodes the wicking layer can also diffuse fluids across a dominant surface area of the wicking layer. The wicking layer can have a flexible sheet-like structure that can conform to the desired surface morphology for the device and skin of the patient. The flexible sheet-like structure has a dominant surface area that is the surface area of the flat sheet surface of the layer. The dominant surface area can be either the side of the layer closer to the patient engagement/skin side of the layer or the side of the layer closer to the external housing side of the layer. Spreading the fluid out across the dominant surface area of the wicking layer can greatly improve the fluid transport properties of the device by spreading the fluid out over a larger surface area to improve evaporation and fluid transport across the outer housing. The improved fluid transport can increase the comfort for the user and increase the long term wearability of the device by, e.g., preventing skin perspiration from affecting the electrical contact between the sensing and defibrillation electrodes and the skin and from interfering with the adhesive properties of the adhesive. An absorbing section 616 or plurality of sections 616 can be used in conjunction with the wicking layer 614 to further improve the moisture transport between the skin and the device. In some embodiments the absorbing section can be part of the fluid transport element. The adhesive 610 used in the patient engagement substrate can also be perforated in some embodiments to further improve moisture transport across the adhesive layer. The perforated adhesive layer can be part of the fluid transport element.

A semi rigid base chassis 618 can be used to provide additional structural support for the heavier components of the device, such as the device electronics. The illustrated chassis can have the electronics module 620 or modules mounted to the chassis 618. The illustrated defibrillator mounts the electronics 620 to the chassis 618 using a mount frame 622. The electronics can be included within one or more waterproof housings within the device housing(s). The electronics can be connected to the sensor electrodes and defibrillator pads using flexible conductive material that can be routed through the multi-layer structure in the device. Examples of materials that can be used for the semi-rigid chassis 618 include polyester, polyethylene, polystyrene, polyurethane, and vinyl.

The housing 602 can be flexible. In some embodiments the flexible housing can be used to hold the device together. The flexible housing can also be elastic. The housing can be resistant to impacts, tearing, dirt, chemicals, and bacteria. The outer surface of the housing can be low friction to reduce wear and decrease the likelihood of catching on clothing and objects. In some embodiments the outer surface of the housing is water resistant. In some embodiments the outer surface of the housing is hydrophobic. The housing can be waterproof to prevent water from entering the interior of the device through the housing. In some embodiments the housing can be permeable to air. Examples of materials that can be used for the housing include polyester or polyurethane based fabrics. The fabric can be knitted, woven, or non-woven. In some embodiments the housing can be part of the fluid transport element.

The properties of the individual layers can be selected to achieve a wearable defibrillator with the desired mechanical, strength, flexibility, adhesive, electrical, and chemical properties.

Figure 5:
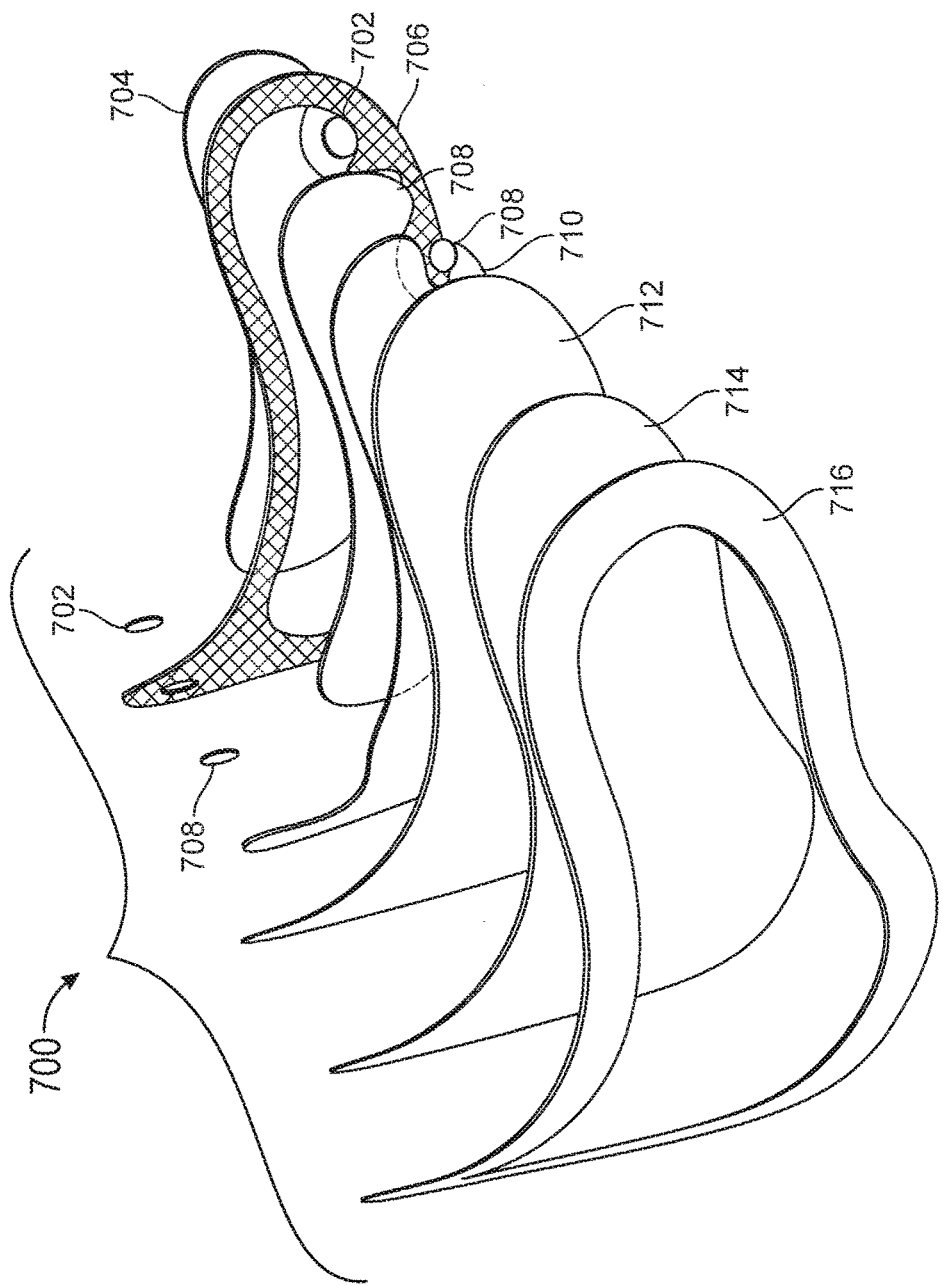
FIG. 5 illustrates an embodiment of a portion of a wearable defibrillator with a multi-layer construction.

FIG. 5 illustrates an embodiment of a portion 700 of a wearable defibrillator with a multi-layer construction. FIG. 5 shows discrete sections of the sensor electrode hydrogel 702, the defibrillator electrode hydrogel 704, and the adhesive 706 having complementary shapes such that the sensor electrode hydrogel 702, defibrillator electrode hydrogel 704, and adhesive 706 can be combined and arranged in one substrate having a substantially planar layer or shape such that each of the sensing electrodes, defibrillator pad electrode, and adhesive can conform to the skin of the patient. The patient engagement substrate includes the sensor electrode hydrogel 702, defibrillator electrode hydrogel 704, and adhesive 706 and is configured to contact the patient's skin and be suitable for long term wear. The sensor electrode hydrogel 702 can be arranged in multiple discrete electrodes to sense or acquire a cardiac signal at different contact points. The defibrillator electrode hydrogel 704 has a larger surface area to provide sufficient contact with the skin while delivering a defibrillating energy pulse. The adhesive 706 can be a high-tack breathable adhesive. In some embodiments the adhesive 706 can be a gel that is perforated as shown in FIG. 5 to improve the breathability and/or moisture transport properties of the adhesive. The hydrogels used for the defibrillator pad electrode 704 and sensing electrodes 702 can also have adhesive properties to improve electrical contract with the skin and to provide additional structural support for the device.

The adhesive can be selected to support the weight of the wearable defibrillator through activities for a duration of 10-14 days. The adhesive can also be selected for moisture management, to be comfortable and non-irritating, and to be easy to remove. In some embodiments multiple different types of adhesives can be used. Examples of adhesive types that can be used include hydrocolloid, silicone, acrylic, polyolefin, etc. Hydrocolloid adhesive typically have high strength but can be more difficult to remove. Silicone has good strength and can be removed more easily. Perforated silicone in combination with a wicking layer can achieve excellent moisture transport properties while maintaining adhesion to the skin.

A conductive electrode film 708 is illustrated. The conductive electrode film 708 can be in electrical communication with one or more of the sensing electrodes 702 and defibrillator electrode hydrogel 704. In some embodiments the conductive electrode film 708 can be laminated to the support structure, such as a polyester (PET) chassis 710, to form a flex circuit. In some embodiments the additional sensors described herein can also be manufactured within the flex circuit for easier manufacturing. A support structure 710 is illustrated in FIG. 5. The support structure 710 can be used to support the device electronics and spread the shear load of the device across the footprint of the device. The support structure 710 can be semi-rigid to provide support for the electronics and to improve weight distribution. A moisture transport material 712 can be used to improve moisture transport from the electrode and adhesive side of the device towards the exterior of the device. The moisture transport material 712 can be a wicking fabric. Examples of wicking materials include materials such as cotton, polyester, and non-woven constructions. The moisture transport layer can pull moisture from the skin through the adhesive and hydrogels. In some embodiments the moisture or fluid transport layer has an absorption capacity of greater than about 500%. In some embodiments the fluid transport or wicking layer is a non-woven fabric that is a mixture of polyester and cellulose. In some embodiments the ratio of cellulose to polyester can be from about 45/55 to 65/35 with a basis weight from 30-120 $g/m^2$. In one example the layer is a 50/50 mixture of cellulose and polyester with a basis weight of 70 $g/m^2$ and has an absorption capacity of about 850%.

An outer housing material 714 is illustrated. The outer housing material 714 can be made out of a fabric, laminate, or other material or structure that is breathable and has some water resistance. The outer housing material 714 can be flexible and abrasion resistant to reduce friction between the outer housing material and clothing. Examples of outer housing materials 714 include nonwoven fabrics, laminate structures, and laminate fabric structures. In some embodiments a non-woven polyurethane fabric material can be used as the outer housing. Laminate structures can include an outer layer, membrane layer, and inner layer. The outer layer, membrane layer, and inner layer materials can be selected to provide a breathable laminate structure with a hydrophobic outer surface to provide water resistance. In some embodiments the outer housing material is water resistant. In some embodiments the outer housing material is hydrophobic. In some embodiments the outer housing material is waterproof.

An outer adhesive border 716 is illustrated. The adhesive border 716 is configured to connect to the perimeter of the device and to adhesively engage with the skin to improve adhesion between the portion of the wearable defibrillator and the patient's skin. The adhesive border 716 can be made out of a thin and flexible non-woven polyurethane with a high-tack adhesive. The adhesive border 716 can form a substantially waterproof seal between the perimeter of the device and the patient's skin to prevent water from passing from the exterior of the device to the area between the electrodes and the patient's skin. The adhesive border 716 can have a tapered cross section as shown in FIG. 6; 818.

Figure 6:
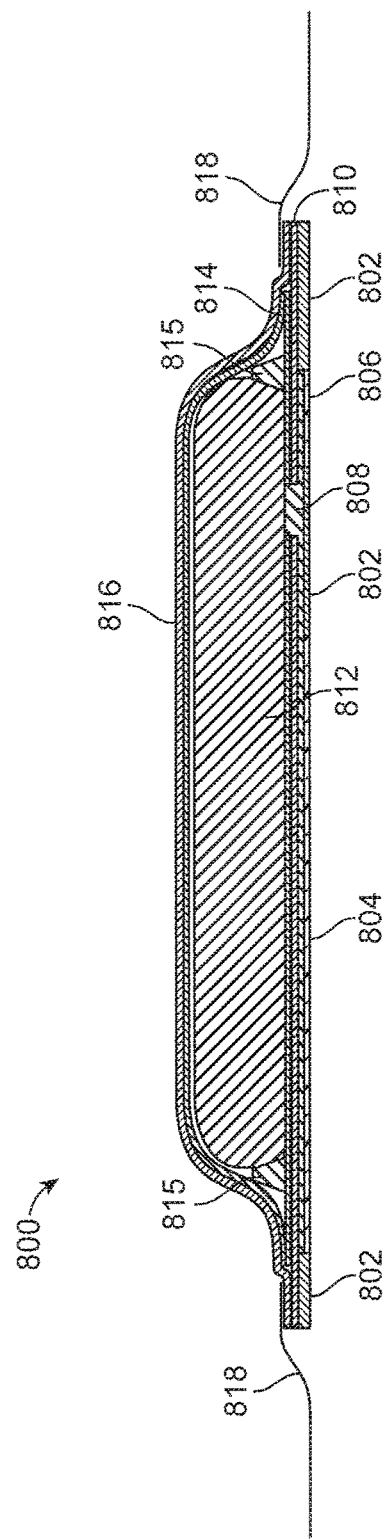
FIG. 6 illustrates a cross section of a portion of a wearable defibrillator in accordance with some embodiments.

FIG. 6 illustrates a cross section of a portion of a wearable defibrillator in accordance with some embodiments. The patient interface substrate includes an adhesive 802 and hydrogels for the defibrillator pad electrode 804 and sensing electrodes 806. A conductive layer 808 provides electrical communication between the electronics module and the hydrogel electrodes 804, 806. The patient interface substrate includes a breathable wicking layer 810 serving as a moisture transport element that improves the moisture transport across the hydrogel electrodes 804, 806 and adhesive 802. The electronics module 812 can be enclosed in a water resistant or waterproof housing 814. A support layer (not pictured) can be used to spread the sheer weight of the electronics module between the wicking layer 812 and the housing 814. An electronics housing mount 815 can be optionally used to mount the electronics to the device or an optional support layer. The support layer can be on the electrode side or exterior housing side of the electronics module 812 or on both sides. The outer housing material 816 can be made of a water repellant and breathable material. The layers can be welded together along the perimeter of the device. A thin polyurethane adhesive film 818 can be used along the perimeter of the device to improve adhesion. The thin adhesive film 818 can improve the profile of the device along the edges such that the cross section of the device is tapered towards the exterior of the device. The tapering can reduce the likelihood of the device edges peeling up or getting caught on clothing or other items and breaking the seal of the adhesive border 818.

Figure 7:
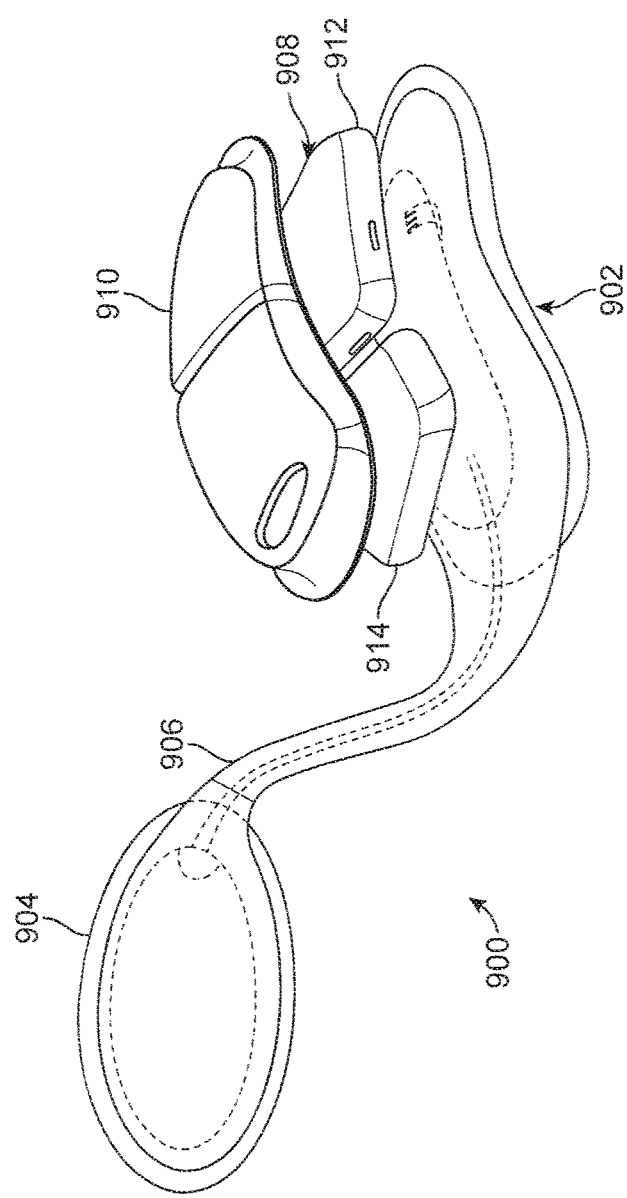
FIG. 7 illustrates an embodiment of a wearable defibrillator.

FIG. 7 illustrates an embodiment of a wearable defibrillator 900. The wearable defibrillator includes a first portion or patch 902 with a patient engagement substrate including a defibrillator pad and sensor electrodes and a second portion or patch 904 with a patient engagement substrate including a defibrillator pad and sensor electrodes. The first portion 902 and second portion 902 can be connected by a cable bridge 906 as illustrated in FIG. 7. The cable bridge 906 can be flexible, stretchable, and/or adjustable to accommodate different patient anatomy. The illustrated first portion 902 includes an electronics module 908 and housing 910. The illustrated electronics module 908 includes a first compartment 912 and second compartment 914 in electrical communication. The first and second compartments 912, 914 are configured to hold the battery, controller, and capacitors. The illustrated housing 910 is configured to connect to the first portion 902 of the wearable defibrillator to enclose the electronics module 908 within the housing 910. The housing material can have one or more of the following properties: water resistance, tear resistance, dirt resistance, anti-microbial properties, flexibility, chemical resistance, moldable/formable, smooth outer surface, and a hydrophobic outer surface. In some embodiments the housing has a waterproof exterior and an interior surface that is permeable to water vapor and liquid such that the water can flow through the housing to the exterior of the device. The electronics module can have a rigid housing that is impact resistant, water resistant, and light weight. The electronics module can include LED and button features. The first portion and second portion can be made out of a material with one or more of the following properties: breathability, anti-fungal, anti-microbial, hydrophobic, opaque, translucent, colored, laminate multi-layer structure, etc. The first and second portions can be co-molded. The multi-layer structure can include electronics routing and can support flex circuits and interconnects.

Figure 8:
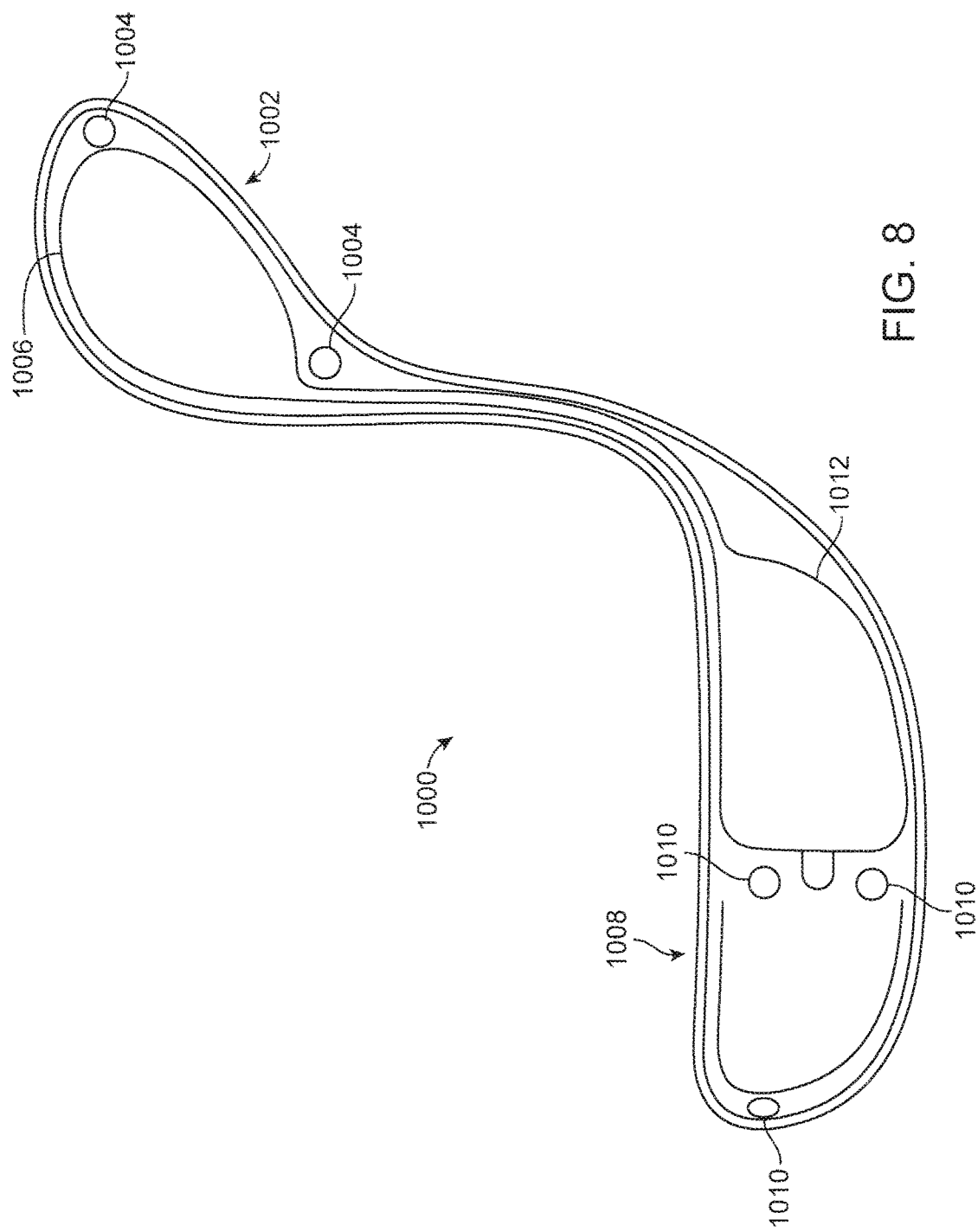
FIG. 8 illustrates an embodiment of a wearable defibrillator.

FIG. 8 illustrates an embodiment of a wearable defibrillator 1000. The wearable defibrillator 1000 has an upper patch 1002 with a patient engagement substrate including two ECG sensing electrodes 1004 and a defibrillator pad electrode 1006. The wearable defibrillator has a lower patch 1008 with a patient engagement substrate including three ECG sensing electrodes 1010 and a defibrillator pad electrode 1012. The lower patch includes the electronics module. The electronics module includes the controller, capacitor, and battery. The battery can charge the capacitors followed by the capacitors delivering electrical energy to each of the defibrillator pads to provide an electrical therapy to the patient wearing the wearable defibrillator.

Figure 9:
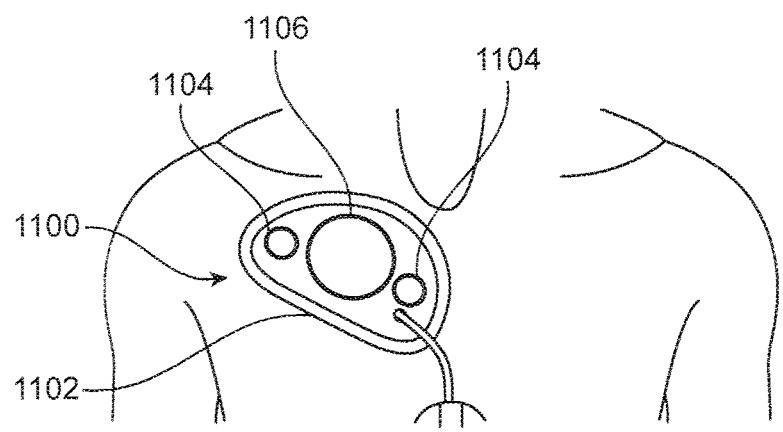
FIGS. 9-10 illustrate an embodiment of a wearable defibrillator.
Figure 10:
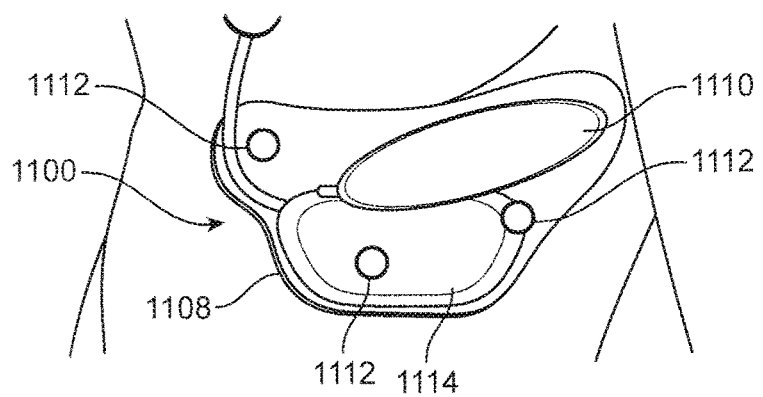

FIGS. 9 and 10 illustrate an embodiment of a wearable defibrillator 1100. FIGS. 9 and 10 illustrate the electrodes to show the relative location on the patient even though the electrodes are on the side of the wearable defibrillator 1100 that contacts the skin. The wearable defibrillator 1100 has an upper patch 1102 with a patient engagement substrate including two ECG sensing electrodes 1104 on either side of a defibrillator pad electrode 1106. The wearable defibrillator 1100 has a lower patch 1108 with a patient engagement substrate including a defibrillator pad electrode 1110 and three ECG sensing electrodes 1112 spaced across the surface area of the device. The lower patch includes the electronics module 1114.

Figure 11:
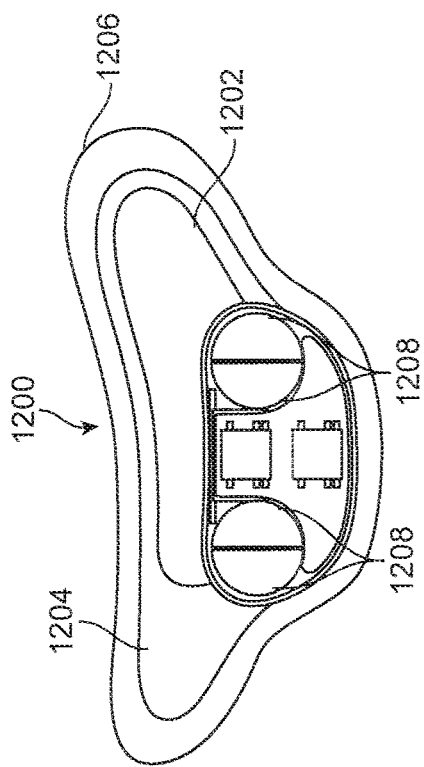
FIGS. 11-13 illustrate three different profiles for embodiments of the lower patch.
Figure 13:
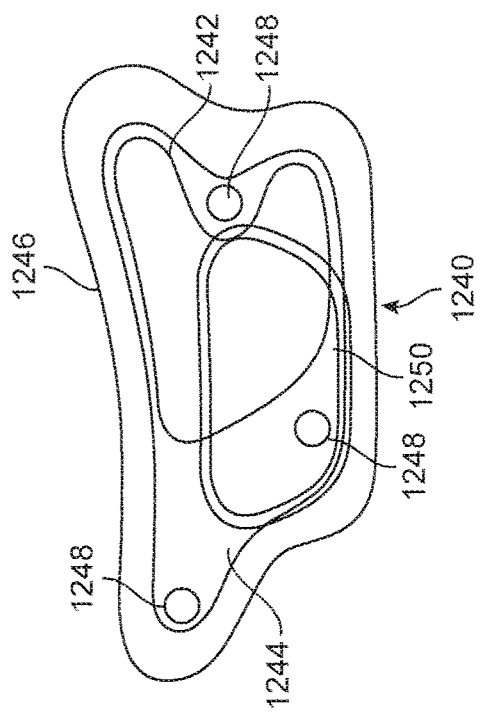
Figure 12:
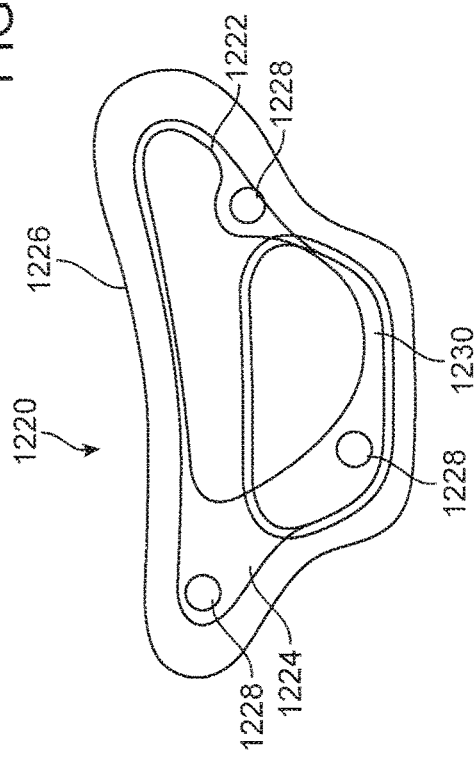

FIGS. 11-13 illustrate three different profiles of embodiments for the shape of the lower patch. Each of the lower patch arrangements include a patient engagement substrate having three ECG sensor electrodes and a defibrillator pad electrode in a substrate configured to contact the skin of user. FIG. 11 illustrates a lower patch 1200 with a patient engagement substrate having a defibrillator pad electrode 1202, adhesive 1204, and adhesive border 1206. FIG. 11 shows an open view of the electronics housing with the capacitors 1208 having a half-circular cross section. FIG. 12 illustrates a lower patch 1220 with a patient engagement substrate having a defibrillator pad electrode 1222, adhesive 1224, adhesive border 1226, ECG sensor electrodes 1228, and housing 1230. FIG. 13 illustrates a lower patch 1240 with a patient engagement substrate having a defibrillator pad electrode 1242, adhesive 1244, adhesive border 1246, ECG sensor electrodes 1248, and housing 1250. The different lower patches have different defibrillator electrode pad shapes, each of which are configured to provide a defibrillating pulse of electrical energy to the skin of the user. The lower patch can utilize a patch shape and housing shape that conforms to the contours of the body and can move with the body during wear. The patch and housing can have a compact component configuration that can be shaped to follow the rib line for more stable long term wear and adhesion. The patch can be worn such that it extends laterally under the arm. The housing preferably does not extend laterally under the arm because that configuration can be less comfortable for the wearer during sleep. The housing can be placed over the rib cage as the skin articulates less over the rib cage. The lower patch and housing can arranged such that the housing flows and stays within the rib cage line when it is worn by the user to minimize the obtrusiveness of the device. In some embodiments, each of the patches can have fluid transport elements and/or elastic elements, as discussed above.

Capacitors having different shapes and cross-sections can be used in the embodiments of wearable defibrillators disclosed herein. In some embodiments round aluminum capacitors, flatpack aluminum capacitors, and a tantalum/aluminum capacitor with a semi-circular shape can be used in the wearable defibrillators disclosed herein. Multiple capacitors can be used to provide the desired voltage and capacitance to the wearable defibrillator while maintaining a light weight small profile. Six of the standard round aluminum capacitors can provide the desired electrical properties for the capacitor bank. Four of the custom round aluminum capacitors can provide the desired electrical properties for the capacitor bank. Four of the custom round aluminum capacitors can provide the desired electrical properties for the capacitor bank. Five of the custom round aluminum capacitors can provide the desired electrical properties for the capacitor bank.

Figure 16:
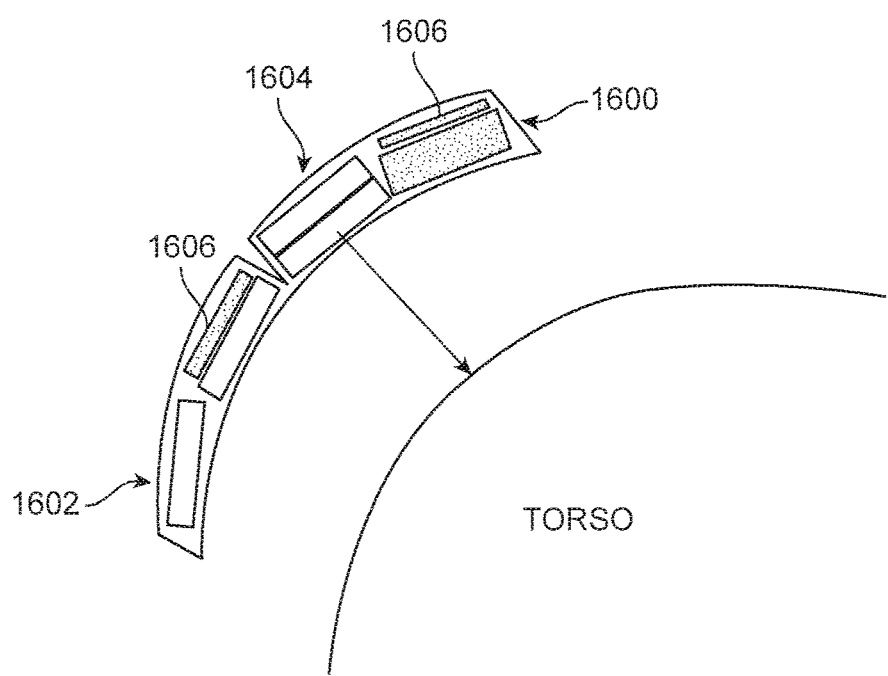
FIGS. 16 and 17A-17C illustrate side profile views of housing shapes used in embodiments of wearable defibrillators.
Figure 17A:
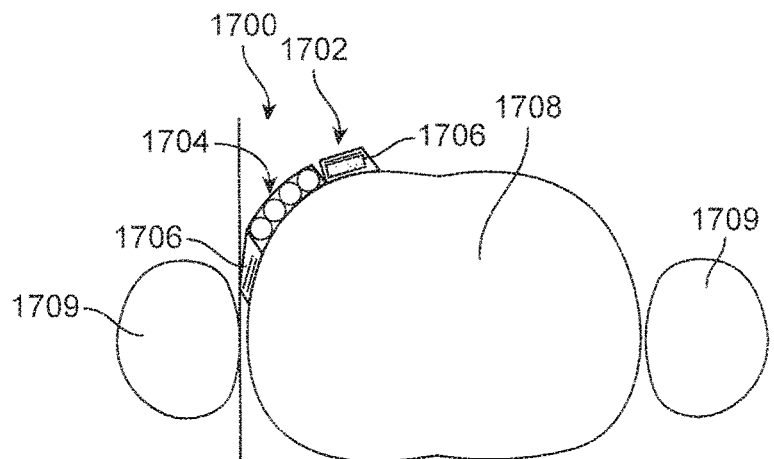
Figure 17B:
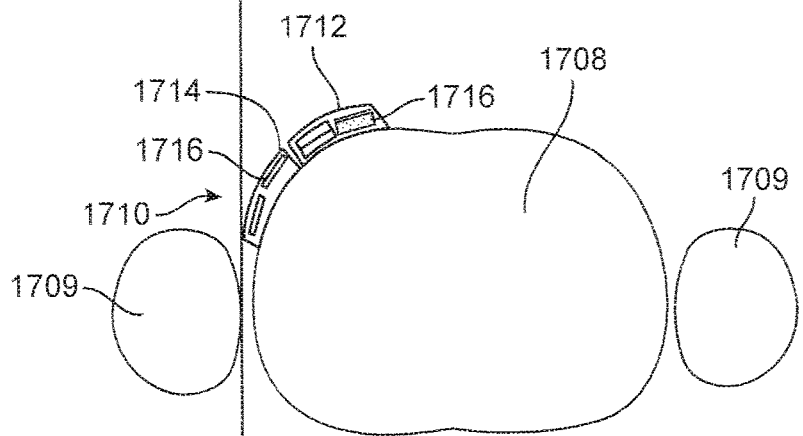
Figure 17C:
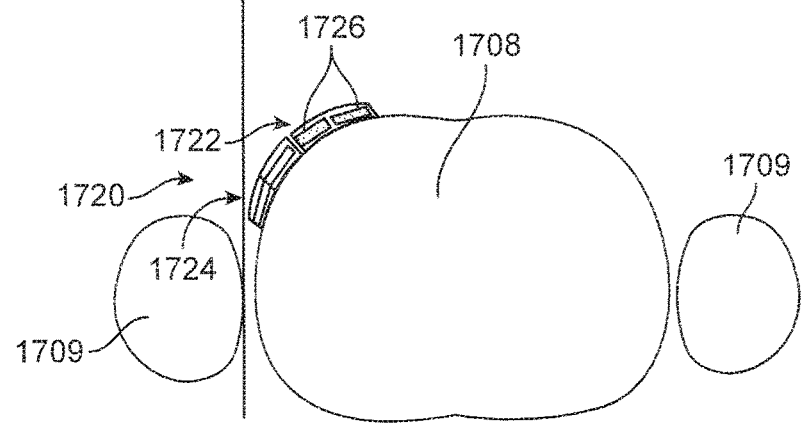

FIGS. 16-17C illustrate side profile views of housing shapes used in embodiments of wearable defibrillators. The contouring of the housing and hardware within the housing can be designed to conform to the size and shape of the patient torso. The housing 1600 and hardware can be contained in multiple sections 1602, 1604 as shown in FIG. 16 to improve the flexibility of the wearable defibrillator and to improve conformity with the patient torso. The housing can be made out of a flexible material to allow the housing to flex and mirror the profile of the patient torso. The arrangement of the electronics and capacitors 1606 can be made to follow the contours of the torso and to minimize the overall product thickness. The housing can be mounted on the patch such that the housing stays within the rib line area for improved comfort and support.

FIGS. 17A-17C illustrate several embodiments of capacitor and housing arrangements relative to the torso 1708 and arms 1709. The size and configuration for the capacitors can be selected to keep the housing small and to try to avoid interference with limbs where possible. For example the housing can be arranged to limit or minimize the profile of the housing extending under the arm. FIG. 17A shows a cross-section of a device 1700 with a first housing section 1702 and a second housing section 1704. The first housing 1702 and second housing 1704 include commercially available capacitors 1706. FIG. 17B shows a cross-section of a device 1710 with a first housing section 1712 and a second housing section 1714. The first housing 1712 and second housing 1714 include custom capacitors 1716. FIG. 17C shows a cross-section of a device 1720 with a first housing section 1722 and a second housing section 1724. The first housing 1722 and second housing 1724 include custom capacitors 1726.

Figure 28D:
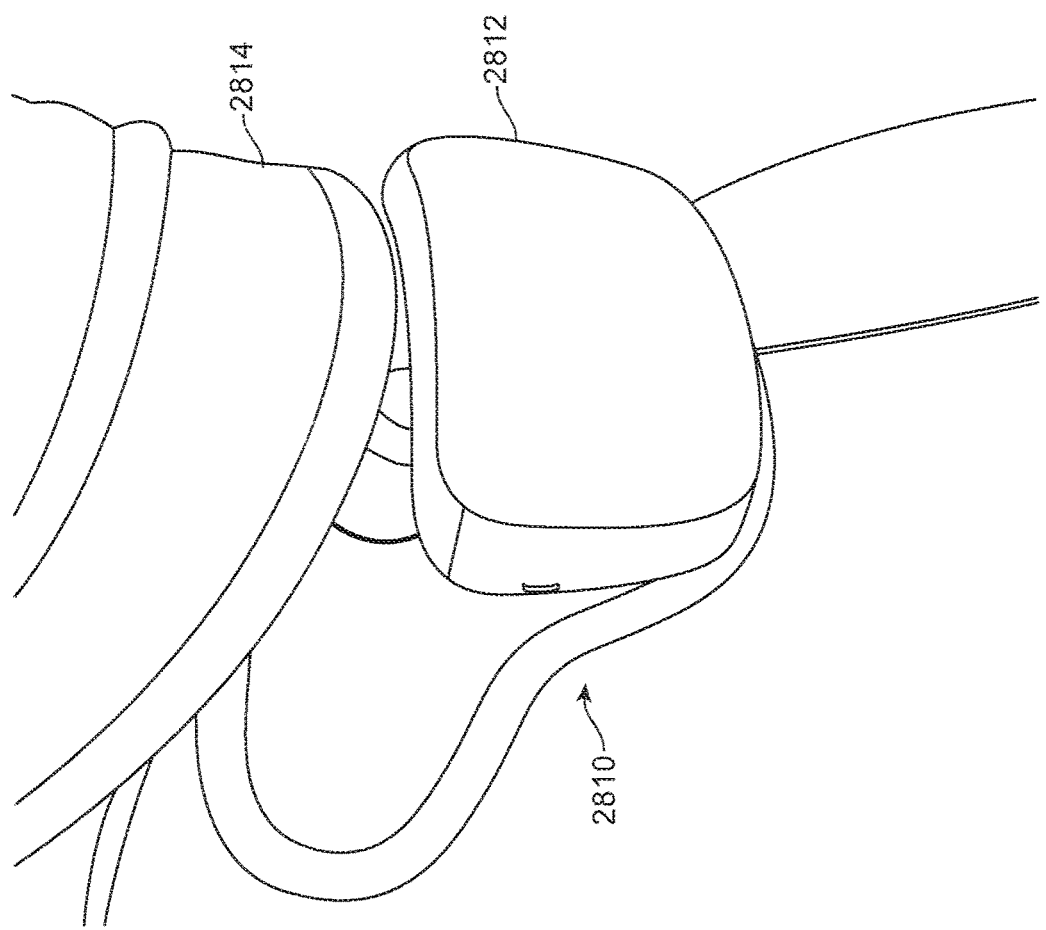

FIGS. 28A-28D illustrate different lower patch shapes in accordance with some embodiments and how the lower patch and housing can be placed on a female user. FIG. 28A illustrates a lower patch 2800 and housing 2804 with wear lines 2802 for locations that may experience additional wear and strain. In some embodiments the layered structures adjacent to these areas can be reinforced or strengthened to improve wear resistance.

FIG. 28B illustrates a lower patch 2810 with an electronics housing 2812. The lower patch of the wearable defibrillator can be designed such that the lower patch is placed on a female user on the rib cage below the bra such that the housing extends below the bra 2814 as shown in FIGS. 28C and 28D. The wearable defibrillators can be designed to avoid undergarment areas to improve overall comfort. The wearable defibrillators can be designed to be unisex and can be adjustable to one size fits all body types. The wearable defibrillators can include shape landmarks on the housing or patches to inform the user of correct placement to guide the user to locating the defibrillator pads in the proper areas.

FIGS. 29A-29C and 30A-30D illustrate different cable designs that can be used between the lower patch and upper patch. The cable section connecting the upper and lower patches can be designed to be flexible, extendable, and to provide articulation between the upper and lower patch. The cable section can also be designed to have a low profile to minimize interference with clothing and undergarments. In one example the wires can be braided to move freely and extend when necessary. The cable section can have a tapered construction along the sternum and breast bone area to avoid excessive skin irritation. The cable section can have elastic properties to minimize tension between the upper and lower patches. In some embodiments the cable section can include an elastic multi-core cable inside of a water resistant sleeve. In some embodiments the cabling can receive excess cabling. FIG. 29A illustrates a wearable defibrillator 2900 with an upper patch 2902, lower patch 2904, and a cable section 2906 with a free hanging exposed cable system. FIG. 29B illustrates a wearable defibrillator 2910 with an upper patch 2912, lower patch 2914, and an integrated cable 2916 that can slide within a flexible casing. FIG. 29C illustrates a wearable defibrillator 2920 with an upper patch 2922, lower patch 2924, and a braided cable 2926 within a flexible casing 2928. FIG. 30A illustrates a wearable defibrillator 3000 with an upper patch 3002, lower patch 3004, and a cable 3006 within a slidably adjustable sleeve 3008. FIG. 30B illustrates a wearable defibrillator 3010 with an upper patch 3012, lower patch 3014, and a cable section 3016 that can extend from a middle section of the lower patch to avoid the sternum. FIGS. 30C and 30D illustrate two different braided cable patterns 3020, 3022 that can be used with any of the wearable defibrillator embodiments disclosed herein.

FIGS. 31A1-31D illustrate various form factors for an upper patch in accordance with some embodiments along with examples of the placement of the upper patch on a chest of a female user. FIGS. 31A1-31A3 illustrate upper patches 3100, 3102, and 3104. FIG. 31B shows upper patch 3100 on the chest of a female user. FIG. 31C shows upper patch 3102 on the chest of a female user. FIG. 31D shows upper patch 3104 on the chest of a female user. The shape of the upper patch can be optimized to the fit on the pectoral region of the wearer. The upper patch can be shaped to minimize overlap with bra straps and other types of common undergarments. Typically, the wearable defibrillators disclosed herein are configured to be unisex; however, in some embodiments the upper and lower patches can be configured specifically for male or female anatomy with different sizes and shapes.

FIGS. 32A-32E illustrate different housing shapes and designs that can be used with the wearable defibrillators disclosed herein. The different housing shapes have control buttons in different arrangements. FIG. 32A illustrates a housing 3210 with buttons 3212 on the side of the housing.

FIG. 32B illustrates a housing 3220 with buttons 3222 on the side of the housing. FIG. 32C illustrates a housing 3230 with buttons 3232 on the side of the housing. FIG. 32D illustrates a housing 3240 with buttons 3242 on the front of the housing. FIG. 32E illustrates a housing 3250 with buttons 3252 on the front of the housing. The two control buttons can require simultaneous pushing for an input to avoid accidental pressing or contact. The buttons can be ergonomically located for easy reaching by the wearer to pinch or press the buttons simultaneously. The housing can be countered to draw the wearer's fingers towards the button. The housing can also include a surface projection or contour to help guide the wearer towards the buttons because clothing worn over the housing can block visualization of the housing buttons.

When the electrodes are in continuous electrical content with the patient's skin, skin sloughing can increase the impedance of the skin. One way of minimizing issues associated with skin sloughing is to move the electrodes around after about 10 to 14 days or at least once during the first month of use.

In some embodiments a passive electrode arrangement can be used. For example a hydrogel can be used that is in continuous contact with the skin. The hydrogel can be modified to improve the compatibility with the skin and to reduce skin irritation. For example, the hydrogel can be hydrated, could be matched to the elasticity of the skin, or could be made to match physiological parameters of the skin including pH and moisture transport. In addition, the hydrogel would exclude chemicals which would breakdown the skin such as shampoos, which may attack the lipids of the stratum corneum.

The electrode can be conformable to the body. The electrode can be designed to be conformable to a specific anatomy of the body.

In some embodiments the elasticity of the electrode is modified to match the elastic nature of the skin. Matching the elasticity of the electrode to the skin can decrease the skin irritation and make the electrode more comfortable for long term wear. In some embodiments the electrodes can have a spiral type design. In some embodiments the electrode can include a slit or hinge to allow for bending and flexing while being adhered to the skin. In some embodiments a material can be added over the electrode. The material can be added to modify the properties of the electrode. For example, a hydrogel or electrode gel can be applied over the electrode, such as AgCl or Sn, to improve heat current spreading and limit resistive heating of tissue.

In some embodiments defibrillation pads suitable for long term wear are provided. For example, a patient engagement surface can include one or more sensing electrodes configured to engage with a patient's skin to detect a cardiac signal, a defibrillator electrode pad configured to engage with the patient's skin and to deliver an electrical therapy to the patient, the defibrillator electrode pad configured to be in continuous electrical communication with the patient's skin; and a patient engagement substrate comprising an adhesive, the one or more sensing electrodes, the defibrillator electrode pad, and a fluid transport element configured to transport fluid away from the skin to allow the wearable external defibrillator to be worn continuously during movement and showering activities.

In some embodiments the defibrillator pad electrodes used in the wearable defibrillators described herein can include a hydrogel and a woven carbon fiber structure. The woven carbon fiber electrode structure can conform to the skin and deliver electrical energy to the skin during a defibrillating shock. An adhesive border can be used around the hydrogel-carbon fiber defibrillator pad to minimize edge lift and moisture ingress.

The electrode design can be selected to maintain a local environment between the skin and electrode. For example, the electrode can be designed to limit ingress of water during showering and to prevent the egress of water from the hydrogel or other electrode material. A proper hydration for the skin and hydrogel can be maintained to improve the electrical contact and the health of the skin for long term wear. Dehydration of the hydrogel can lead to higher electrode-patient interface impedance. Shampoo and soaps can also modify the hydrogel properties and adhesive. A barrier can also be used to keep shampoo and soaps from modifying the properties of the electrode. In some embodiments the electrode can contain a material to break down the stratum corneum, such as a soap. In some embodiments an adhesive border can be used to limit ingress of water and materials to the environment between the electrodes and the skin. The adhesive border could be around the perimeter of the patch and/or around a perimeter of each of the individual defibrillator pad electrodes and sensing electrodes.

The wearable defibrillator can include a structure, such as electrode monitoring structure, to monitor the electrodes to ensure that they properly contact the patient's skin in the correct position. For example, the capacitance and/or impedance can be sensed by the system to determine if the electrodes are fully adhered to the patient and/or in the appropriate position to allow for deployment during an arrhythmia to deliver an effective defibrillation pulse.

Another option for minimizing skin irritation from continuous electrode contact or to minimize changes in impedance associated with skin sloughing is to use an electrode that is not in continuous electrical contact with the skin. In some embodiments the long term wear electrode can be an active electrode that can release a gel to improve electrical contact with the patient's skin. The gel can be a conductive material. This design is also less affected by increased impedance from skin sloughing as the electrical contact is made with the skin immediately before delivery of a defibrillating pulse. Additional active electrode embodiments are discussed below.

Additional structures for active electrodes to deploy a conductive material are disclosed herein. In some embodiments the electrodes are adhered to the skin such that a defined space is created between the skin and electrode. A conductive material is deployed between the electrode and skin to increase the conductivity between the electrode and skin. Other mechanical and chemical arrangements can be used to increase the conductivity between the electrode and skin.

In some embodiments a hydrogel can be deployed as the conductive material. The hydrogel can be heat activated, pressure activated (vacuum or positive pressure), voltage activated, or deployed in the space between the electrodes and skin using other means.

Microfluidics can also be used to deploy a conductive material in some embodiments. For example, microfluidics, wicking, and capillary action can be used to deploy the conductive material instead of injecting the conductive material.

Additional options for deploying a conductive gel include: electroporation, melt/burn a sacrificial layer, phase change, puncture/tear sacrificial barrier layer, extrusion, vacuum, pressure, electric field, magnetic field, heat, mechanical (e.g., pump or spring), chemical means (e.g., osmotic pressure or reaction), ultrasound ejection, etc.

The sodium content or other salt content of the electrodes is another design concern. An increased sodium content or other salt can dry the skin out through osmotic diffusion. The sodium or salt content can be minimized (or selected to be isosmotic) in some embodiments to reduce drying of the skin.

In some embodiments an eluting agent can be used with any of the electrodes disclosed herein. The eluting agent can reduce impedance in long term wear. In one example a steroid can be eluted.

The outer layer of the skin (stratum corneal layer) can have poor conductivity. In some embodiments the electrical contact between the electrode and skin can be enhanced by removing or penetrating the stratum corneal layer. Microneedles can be deployed to penetrate the stratum corneal layer prior to delivering the defibrillator pulse. The top layer of the skin can be removed prior to delivering the defibrillator pulse. Another option is to do controlled removal rate of dead skin cells or the outer layer of skin to impede growth of that layer. Removing the outer layer of skin or achieving electrical contact with the body below the outer layer of the skin can reduce the transthoracic impedance between the electrode and patient. Another option is to deliver short electrical spikes prior to the defibrillator pulse to reduce thoracic impedance.

Various configurations can be used for the long-term ECG monitoring electrodes. Structure can be used to isolate the monitoring electrode from the device assembly to minimize combined motion artifacts. The electrode can have a low-profile design and can be conformable to the device to minimize peeling. The electrode can be on an external surface of the device and can include an outer slip layer to minimize external physical interactions with clothing and/or during sleeping.

Various adhesive designs can be used to attach the device to the body for long term wear. The adhesive can be designed to allow for distributing the device weight and shear force across the adhesive area. In some embodiments the adhesive is selected to avoid primary skin irritation symptoms, such as redness (erythema), swelling (edema), and skin sensitization. Other design considerations for the adhesive include the mobility and flow of the adhesive along with the tack, peel adhesion, and shear strength of the adhesive. In some embodiments the adhesive has a surface energy that is less than the surface energy of the skin, which is typically around 28 dyn/cm$^3$. Various skin adhesives and their properties are illustrated in FIG. 14, including acrylate, silicone, hydrocolloid, acrylic, natural rubber, synthetic rubber, polyolefin, and polyurethane.

In some embodiments the adhesive type and configuration can be selected based on the moisture vapor transmission rate. In some cases perforations or openings can be made in the adhesive to improve the moisture vapor transmission rate. The perforations can be holes having a diameter of about 0.5 mm to about 2 mm. The perforations can have substantially uniform shapes or can have different or varying sizes and shapes. In some embodiments the adhesive can include an open cell structure. The overall open area can be selected to achieve an adhesive portion of the device with the desired properties, such as moisture vapor transmission rate. In some embodiments the perforations have an open area of about 10% to about 25% of the overall adhesive surface area. In some embodiments a wicking layer can be used to further improve the moisture vapor transmission rate. An absorbent material can be used to also improve the moisture vapor transmission rate.

Figure 15:
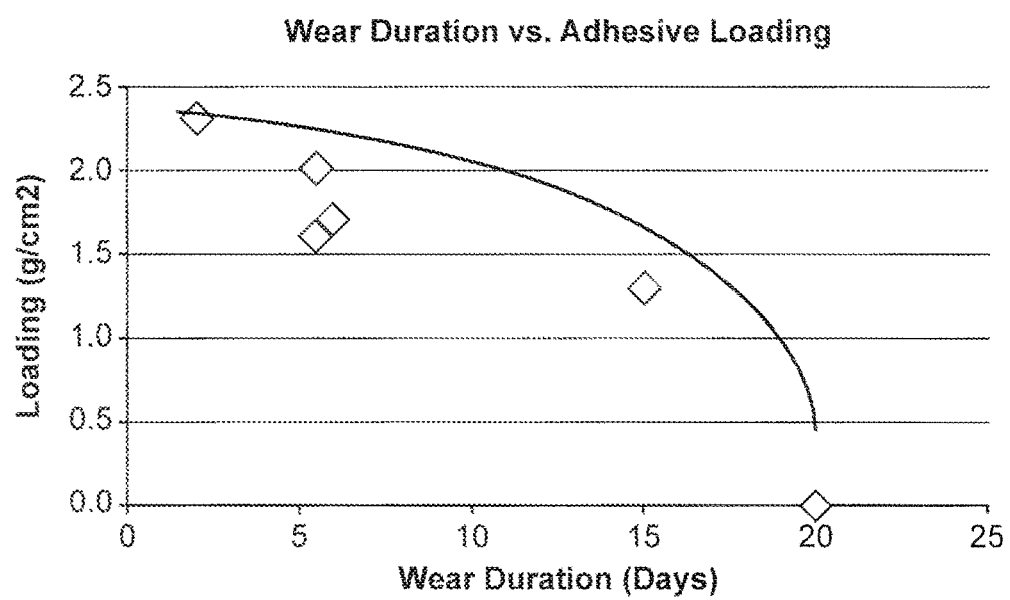
FIG. 15 illustrates examples of testing adhesives and wear duration of various weights in accordance with some embodiments.

The device weight and form-factor affect the wear duration and comfort of the device. The wear duration is inversely proportional to the device weight. FIG. 15 illustrates data for wear duration versus adhesive loading for various weights. In some embodiments the hydrogel electrodes can provide additional adhesion to the skin to further support the device.

In some embodiments the adhesive is designed to attach the wearable defibrillator to the skin of the patient for 10-14 days without significant skin irritation. After 10-14 days the adhesive can be replaced or the device can be shifted such that he adhesive contacts different areas of the patient's skin. In other embodiments, the adhesive may be designed to be used for up to about 1 month (approximately 30 days) after which it can be replaced or the device can be shifted.

In some embodiments the device can include changeable adhesive pockets. The adhesive pockets can be replaced after a specific duration of use. The replaced adhesive pockets can be used to contact a different area of the patient's skin to support the wearable defibrillator. The adhesive pockets can be periodically replaced to achieve the total duration of wear for the defibrillator.

In some embodiments the device can have an adhesive profile that is configured to adhere to the body in alternating positions between device applications. For example, the adhesive can be used with a checkerboard (A/B) configuration or can have rotational symmetry. The device can be rotated periodically to minimize skin irritation while maintaining electrode contact with the skin as shown in FIG. 87B. The configuration illustrated in FIG. 87B can be rotated about 60° to change the areas that the adhesive contacts the skin to minimize skin irritation.

In some embodiments the device includes a structure to protect the adhesive edges, such as hydrocolloid adhesive edges, from lifting or peeling off of the skin. The structure can prevent or minimize water contact with the edges during showering. The edges can also be configured to have a low profile to minimize the chances of the edges getting stuck on clothing or other items.

In some embodiments a thin polyurethane layer with an adhesive is used to protect the edges of the device from contact with water. Keeping the adhesive layer dry and the area between the device and the user's skin dry can increase long term comfort.

In some embodiments a silicone adhesive can be used which may do better with water contact than a material such as a hydrocolloid adhesive.

The adhesive can be selected or arranged such that the adhesive accommodates or allows for stretching of the skin.

In some embodiments two or more different adhesives can be used. The adhesives can be arranged in a pattern such as multiple rings or in an alternating pattern. The stronger adhesive may be more irritating to the skin so alternating a stronger adhesive with a lower strength adhesive can improve comfort and long term wear.

In some embodiments a chemical or substance can be used with a hydrocolloid adhesive to decrease the adhesion of the hydrocolloid and reduce skin irritation.

In some embodiments an ultrasonic suture can be used to ultrasonically weld the device to the skin so the device could be semi-permanently attached to the user.

In some embodiments the adhesive can be arranged in onion layers, with the onion layers of the adhesive shedding over time.

In some embodiments the wearable defibrillator can be configured such that an outer slip layer of the device can be changed periodically while keeping the device in place. The slip layer can be designed to minimize interactions between the outer device layer and clothing and other items.

The wearable defibrillator can be provided with a material that can be used to reliably remove the adhesive from the skin. In one example the adhesive remover can be infused with the device. The adhesive and device can be removed after a specified period of time.

The patient's skin can be prepared prior to attaching the wearable defibrillator to improve contact with the patient's skin. In one example automated ways can be used for skin preparation, such as using ultrasonic derma abrasion. In another example a skin cleaning material can be used to prepare the skin prior to attaching the wearable defibrillator. A stick and peel structure can be provided. The stick and peel structure can be applied to the skin and removed. An adhesive material on the stick and peel structure can remove dirt, oil, and skin cells.

In some embodiments the wearable defibrillator can be provided to the patient as part of a kit. The kit can include items such as: an adhesive remover, a skin cleaner, hair removal tool, tools for applying the wearable defibrillator, and instructions for applying the wearable defibrillator. Examples of tools include tools that can make the application process easier for the patient, such as by allowing for two-handed operation. Examples of tools include a strap harness, molded carrier frame, template to hold the device close to body to keep hands free for device application. Other examples of tools include a projected template or mirror template that patients can use to help properly orientate the device by aligning themselves to match the device placement on the body.

Skin cleaning and hair removal tools can also be provided with the device. Wipes containing alcohol can be used to degrease the skin surface. In some embodiments a single-use glove can be provided with a cleaning material that can be used to clean the skin surface and apply the device. The glove could include a surface with a solvent such as alcohol. In other case the glove could include a roughened surface or fastener surface to receive interchangeable cleaning pads. Other skin cleaning tools include a hair removal strip. Another example of a hair removal tool is a disposable razor. The tools can be used in a sequence to remove hair, scrub the surface of the skin, and clean the skin followed by applying the device.

The packaging for the device can also include built in support features, such as an instruction guide built into box to help user manage the different application steps. A video could also be provided to guide the user to properly apply the device.

In some embodiments a doctor or medical professional will apply the electrodes and attach the device to the patient's skin for the first time. The device position or orientation on the patient's body can be changed about every two weeks to minimize skin irritation. For future device removal and application a caregiver, spouse, or the patient can apply the electrodes and device. The device can include clear instructions for correct positioning of the electrodes and device. The device can also sense the location of the device and provide feedback or an alert to the user during placement of the device. Feedback can be provided through a light on the device, auditory indication, tactile feedback, vibration, or other types of feedback. In some cases the skin preparation prior to attachment can include cleaning and shaving the skin area prior to applying the electrodes.

The wearable defibrillator can have a high reliability and be ready to deliver a defibrillating pulse within about 10 seconds. The wearable defibrillator components may be able to deliver a set maximum number of shocks to the patient. In some embodiments the device is configured to deliver at least 10 shocks to the patient. The device can also measure the transthoracic impedance, be suitable for long term wear time, be comfortable and conformable, have a low profile, and the ability to assess electrode contact with the skin. The wearable defibrillator may also purposely take a longer time to defibrillate (anywhere from 10 seconds or up to one minute) during which time it may perform additional analyses in order to increase the accuracy of making a determination to deliver a defibrillating shock. The additional time might also allow for certain arrhythmias to self-terminate, thereby eliminating the need for a shock.

The wearable defibrillator can include ECG electrodes, defibrillator electrodes, a contact sensing element to determine if the defibrillator electrodes are contacting the skin, defibrillator circuitry, ECG circuitry, batteries, capacitors, power management, wireless communication, user interface elements, operating software, and any of the additional structures and features described herein.

For the ECG monitor the wearable defibrillator can use a two-lead electrode system with 2-4 sensing electrodes or a three-lead system can be used with six or more sensing electrodes.

The battery and electronics components can be considered part of a low voltage block and the capacitors can be considered part of a high voltage block. The batteries are used to charge the capacitors prior to delivering the defibrillating pulse. The batteries may store a large amount of energy while keeping down the weight. In some embodiments batteries can be used that are similar to cell phone batteries. In some embodiments secondary cells can be used. In some embodiments primary cells can be used. The battery weight can vary between about 50 grams and 150 grams. In some embodiments the battery weight is about 50 grams to about 100 grams. Different batteries can be used based on the specific components used and the sampling frequency and other device settings.

Wearable devices that are worn close to the body, such as in an adhered application should have a low profile, low gravimetric density, and be able to withstand daily physical activities like exercise, showering, sleeping, etc. Safety mechanisms may also be used to allow for mitigations of failures modes caused by factors such as water ingress, physical shock, etc. The capacitors used in the wearable defibrillators disclosed herein provide an electric energy storage and discharge mechanism that exhibits high power density, high energy density, physical robustness, low gravimetric density, and can be worn safely in close proximity to the body.

The capacitors disclosed herein and used in the wearable defibrillators can meet one or more of the following design criteria: capacitance of greater than 400 µF, voltage rating of greater than 350 V, a compact volume, and a density of about 2.5 g/cm$^3$ or less.

A variety of different types of capacitor materials, arrangements, and properties are illustrated in FIGS. 15, 18-27C. FIG. 15 illustrates shapes and cross-sections of various capacitors that can be used in the embodiments of wearable defibrillators disclosed herein. FIG. 15 illustrates two different round aluminum capacitors, a flatpack aluminum capacitor, and a tantalum/aluminum capacitor with a semi-circular shape. Multiple capacitors can be used to provide the desired voltage and capacitance to the wearable defibrillator while maintaining a light weight small profile.

Figure 18:
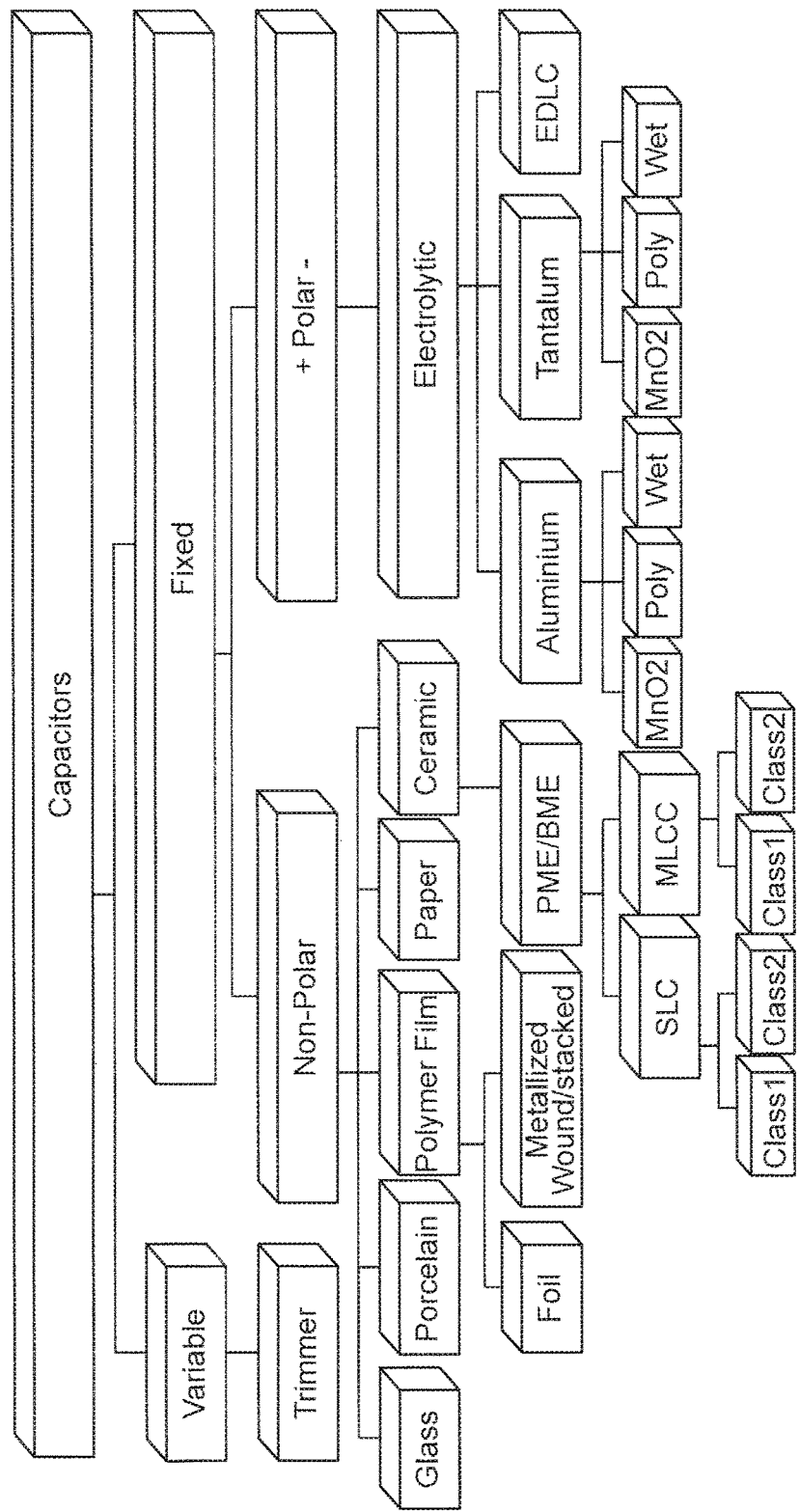
Figure 19:
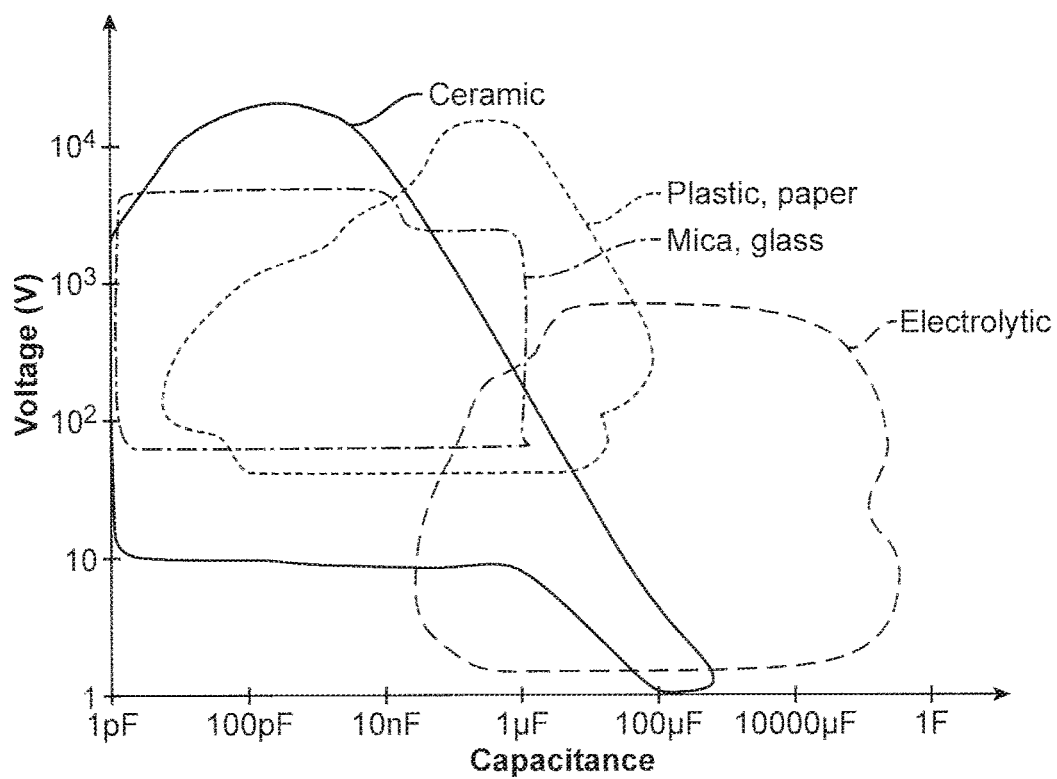
Figure 21B:
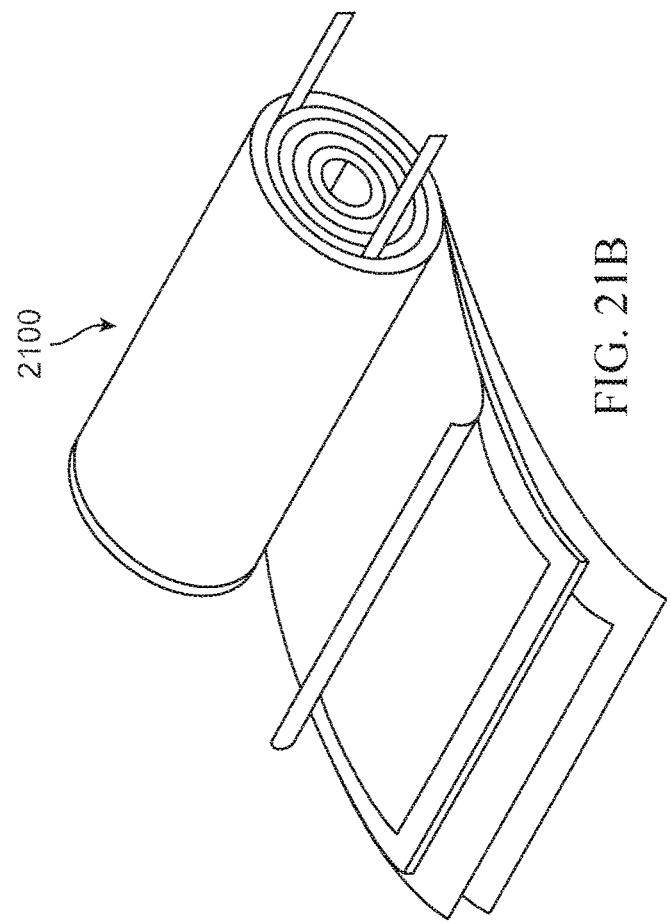
FIGS. 21A-21B illustrate aspects of aluminum electrolytic capacitor configurations in accordance with some embodiments.
Figure 21A:
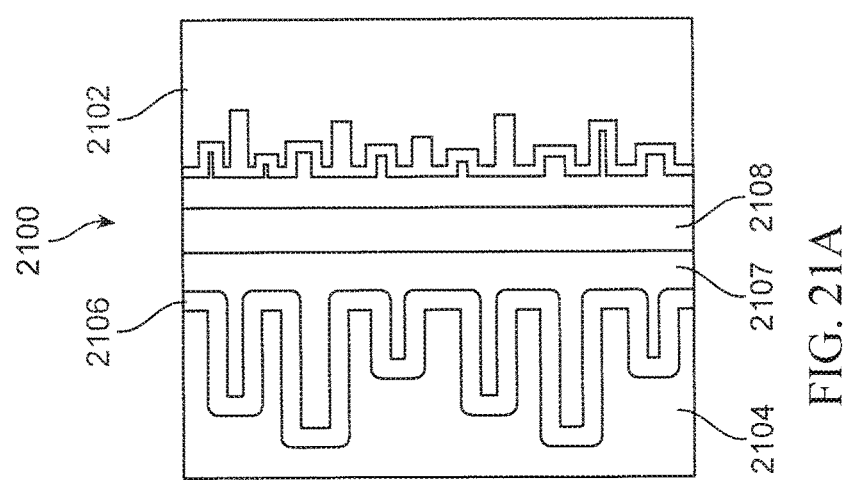
Figure 22:
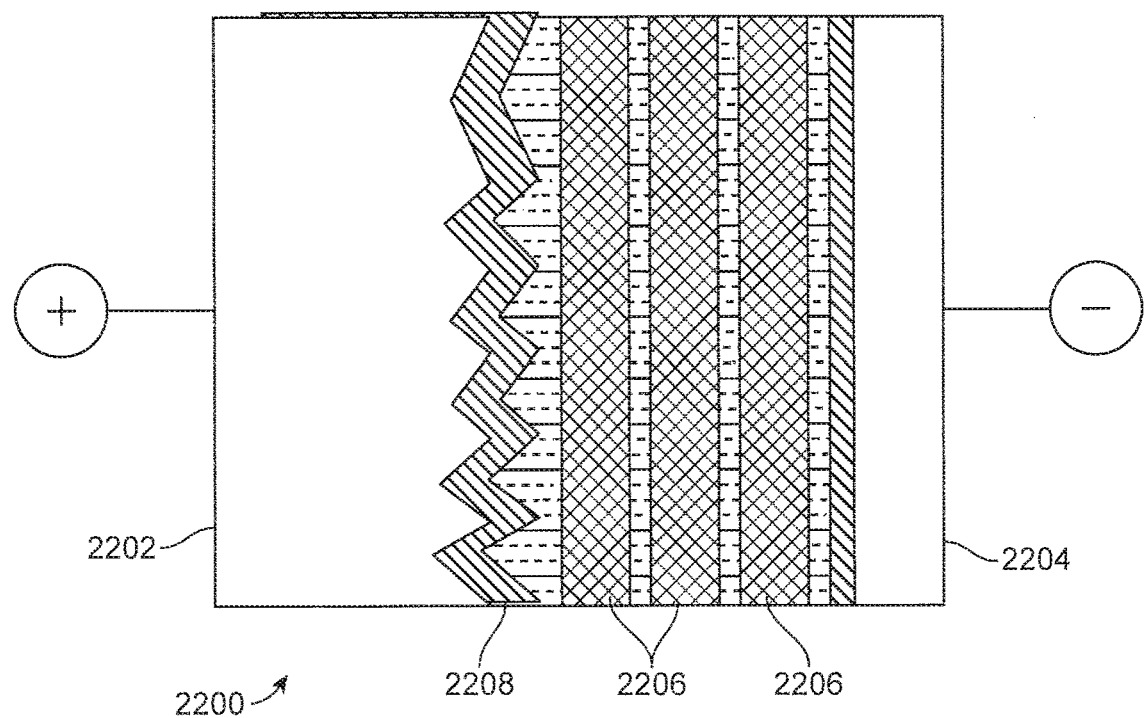
FIG. 22 illustrates aspects of another aluminum electrolytic capacitor configuration in accordance with some embodiments.
Figure 23:
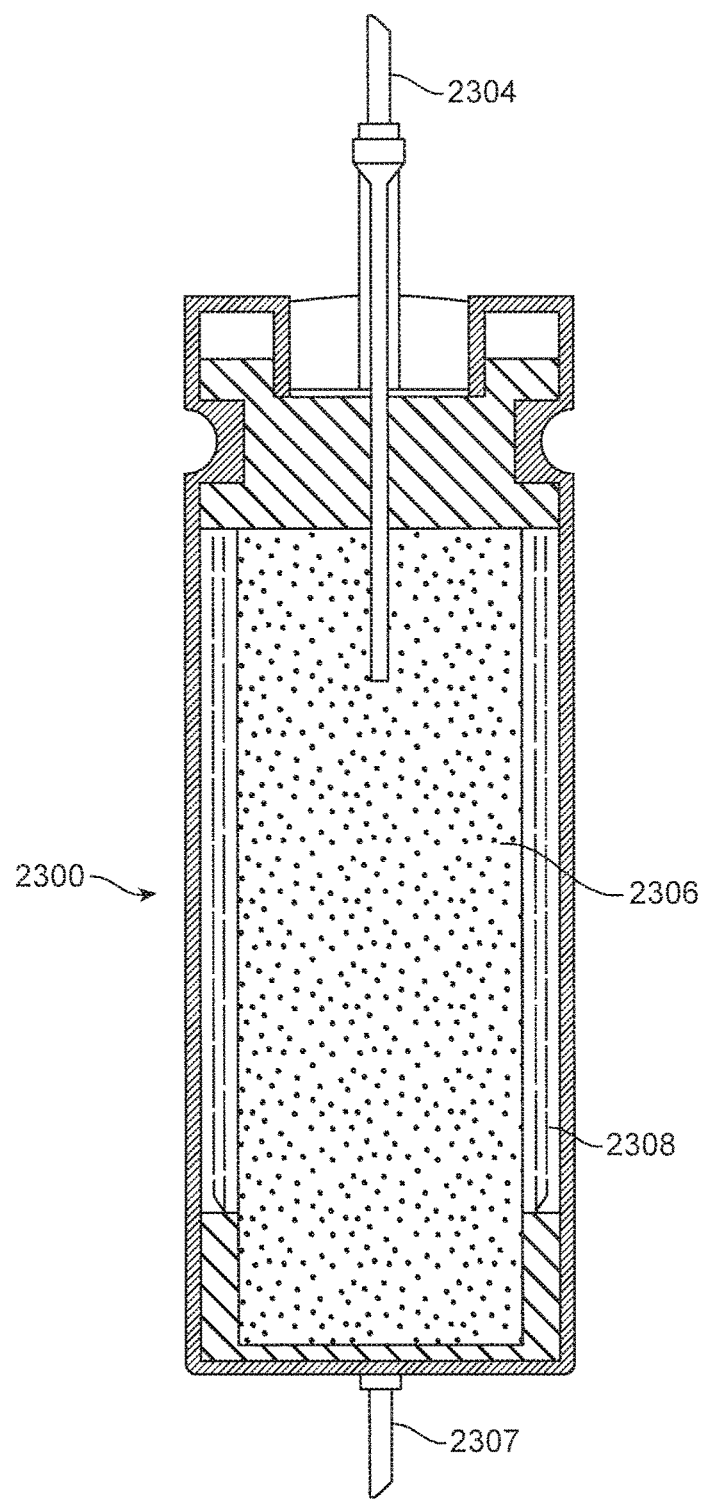
FIG. 23 illustrates a wet tantalum electrolytic capacitor configuration in accordance with some embodiments.
Figure 24:
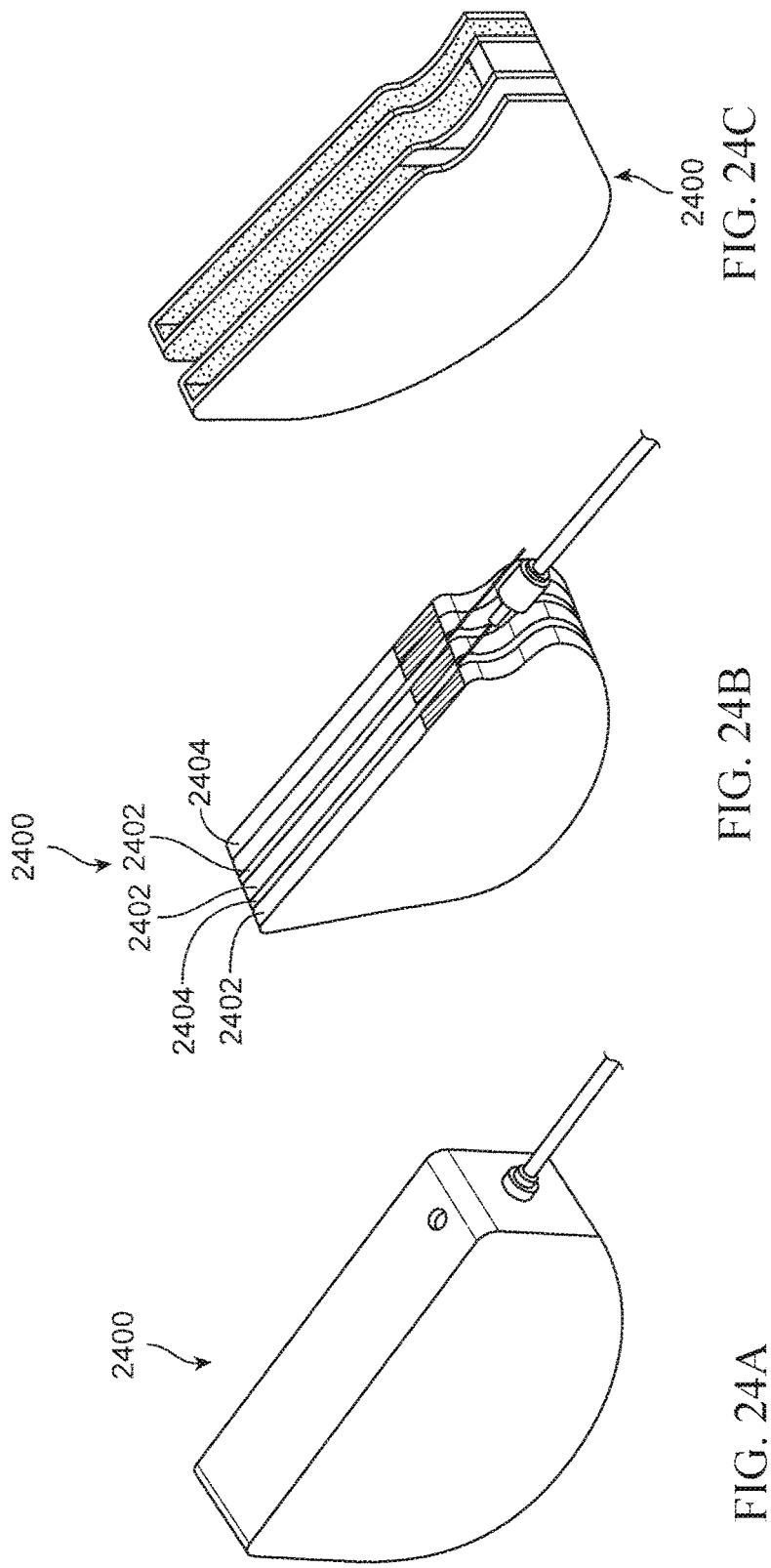
Figure 25:
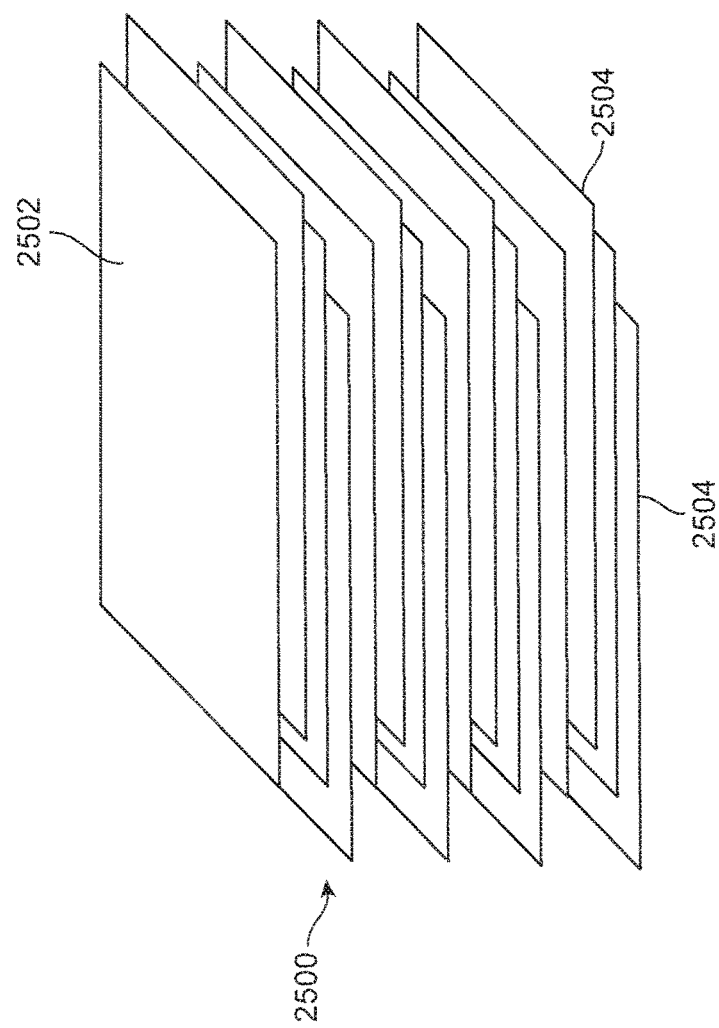
FIG. 25 illustrates an alternate design for an aluminum capacitor configuration in accordance with some embodiments.
Figure 26:
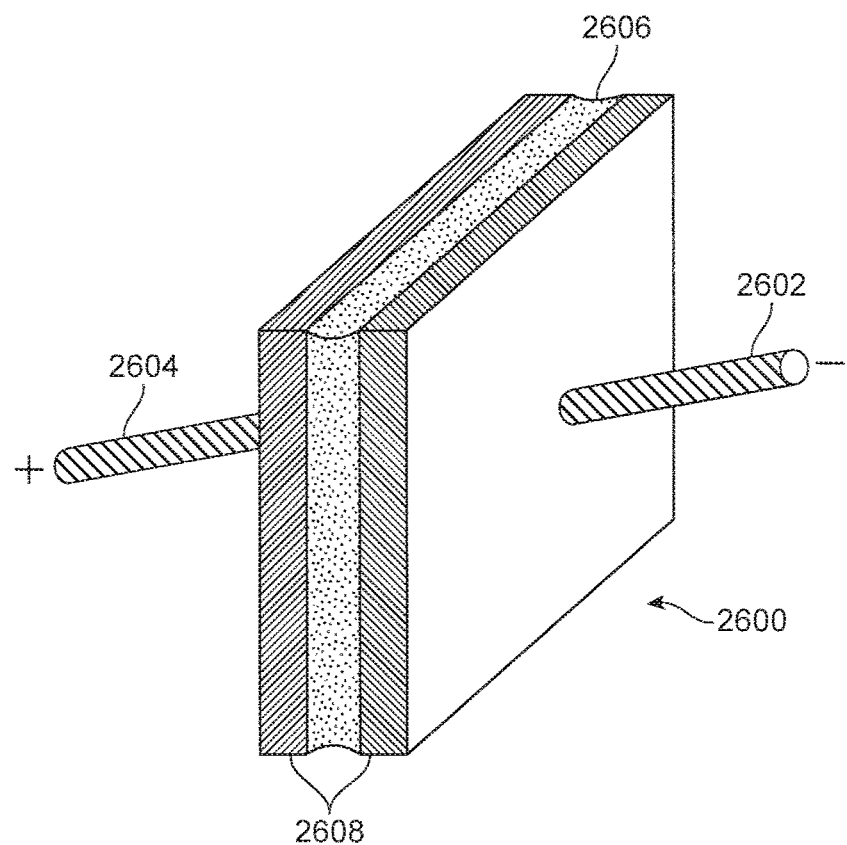
FIG. 26 illustrates a capacitor in accordance with some embodiments.
Figure 27A:
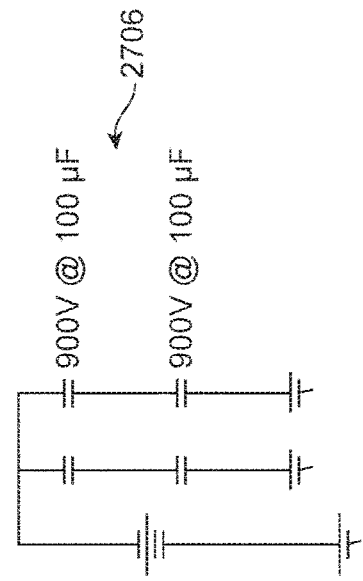
FIGS. 27A-27C illustrate various capacitor arrangements in accordance with some embodiments.
Figure 27B:
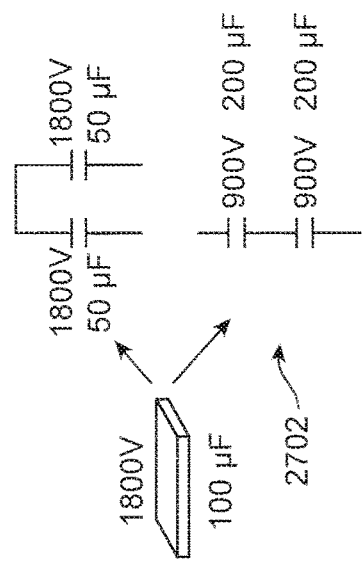
Figure 27C:
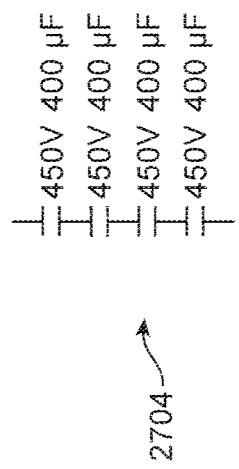

FIG. 18 illustrates various types of capacitor materials, types, and configurations. FIG. 19 illustrates the voltage and capacitance for different types of capacitors. FIG. 20 is a chart listing various capacitor properties for capacitors that can be used in the devices disclosed herein. FIGS. 21A-21B illustrate a wet/wound aluminum capacitor 2100 with a cathode 2102, anode 2104, dielectric 2106, electrolyte 2107, and paper soaked electrolyte 2108. FIG. 22 illustrates a capacitor 2200 with a cathode 2204, anode 2202, dielectric 2208, and electrolyte support 2206. FIG. 23 illustrates a wet tantalum capacitor 2300 with a cathode 2302, anode lead 2304, tantalum anode 2306, and electrolyte 2308. FIG. 24A-FIG. 24C illustrate Q-capacitor 2400 with anodes 2402 and spaces 2404 between the anodes 2402. FIG. 25 illustrates stacked capacitor 2500 with dielectric or electrolyte support 2502 and conductive foils 2504. FIG. 26 illustrates a capacitor 2600 with a cathode 2602, anode 2604, dielectric 2606, and foils 2608. FIG. 27A-FIG. 27C illustrate various capacitor arrangements 2702, 2704, 2706 that can be used to generate a voltage of 1800 V and a capacitance of 100 µF.

In some embodiments wet/electrolytic tantalum or wet/electrolytic aluminum capacitors can be used. Capacitor configurations in accordance with some embodiments are illustrated in FIGS. 21A-24C.

Examples of capacitor configurations include rolled, sandwich, stacked, and other configurations. Wet tantalum capacitors can have a working voltage of about 125 V. Aluminum capacitors can have a working voltage of about 450 V. Other capacitor materials can be used that meet the general design criteria described herein, such as wet or dry electrolytic Titanium.

One or more capacitors can be used in the wearable defibrillator. The size and number of the capacitors can be varied based on the electrical requirements of the pulse to be delivered. In some embodiments about 4 capacitors to about 20 capacitors can be used. In some embodiments six or more capacitors are used. In some embodiments about 12 to 18 capacitors are used. In some embodiments about 15 to 18 capacitors are used. In some embodiments six or less capacitors can be used. In some embodiments five or less capacitors can be used. In some embodiments four or less capacitors can be used.

In some embodiments the capacitors have a density of about 3.0 g/cm$^3$ or less. In some embodiments the capacitors have a density of about 2.5 g/cm$^3$ or less. In some embodiments the capacitors have a density of about 2.0 g/cm$^3$ or less. In some embodiments the capacitors have a density of about 1.5 g/cm$^3$ or less. In some embodiments the capacitors have a density of about 1.0 g/cm$^3$ or less. In some embodiments a denser capacitor can be used with a density of greater than about 3.0 g/cm$^3$. In some embodiments the capacitor has a density of between about 3.0 g/cm$^3$ to about 10.0 g/cm$^3$.

In some embodiments the plurality of capacitors occupy a volume of less than about 20 cm$^3$. In some embodiments the plurality of capacitors occupy a volume of less than about 16 cm$^3$. In some embodiments the plurality of capacitors occupy a volume of less than about 15 cm$^3$. In some embodiments the plurality of capacitors occupy a volume of less than about 12 cm$^3$. In some embodiments the plurality of capacitors occupy a volume of less than about 10 cm$^3$. In some embodiments the plurality of capacitors occupy a volume of less than about 7.5 cm$^3$. In some embodiments the plurality of capacitors occupy a volume of less than about 5 cm$^3$.

In some embodiments the plurality of capacitors can have a total nominal capacitance of greater than about 25 micro Farads (µF). In some embodiments the plurality of capacitors can have a total nominal capacitance of greater than about 50 micro Farads (µF). In some embodiments the plurality of capacitors can have a total nominal capacitance of greater than about 100 micro Farads (µF). In some embodiments the plurality of capacitors can have a total nominal capacitance of greater than about 125 micro Faradays (µF). In some embodiments the plurality of capacitors can have a total nominal capacitance of greater than about 150 micro Farad (µF). In some embodiments the one or more capacitors have a total nominal capacitance of greater than about 400 µF.

In some embodiments the capacitors can have a discharge time constant of less than about 3 ms.

The plurality of capacitors can have a weight of less than about 500 grams. In some embodiments the plurality of capacitors can have a weight of less than about 200 grams. In some embodiments the weight of the plurality of the capacitors is about 100 grams to about 200 grams. In some embodiments the weight of the plurality of capacitors is about 125 grams to about 175 grams.

The capacitor can have various shapes. For example, the capacitors can have a pencil-like or cylindrical shape, coin-cell type shape, a lasagna type shape, or a spiral or circular type shape. The capacitor configuration can be selected to minimize the overall volume occupied by the capacitors to increase the wearability of the defibrillator.

In some embodiments one dimension of the capacitor shape can be minimized below a set depth. In some embodiments one dimension of the capacitor can be kept to about 20 mm or less. In some embodiments one dimension of the capacitor can be kept to about 15 mm or less. In some embodiments one dimension of the capacitor can be kept to about 10 mm or less.

Multiple capacitors can be used to meet the capacitor design requirements. The capacitors can be arranged in parallel, series, or combinations of the two. In some embodiments the capacitors are selected and arranged to achieve a total working voltage of about 1800 V with a total nominal capacitance of about 100 µF. FIGS. 27A-27C illustrate a variety of capacitor configurations 2702, 2704, 2706 that can be used to achieve a total working voltage of about 1800 V and a total nominal capacitance of about 100 µF. In one example two capacitors each having a working voltage of 900 V and a nominal capacitance of 200 µF can be arranged in series to achieve a capacitance of 100 µF and voltage of 1800 V. In another example two capacitors each having a working voltage of 1800 V and a nominal capacitance of 50 µF could be arranged in parallel to achieve a capacitance of 100 µF and voltage of 1800 V. In another example two capacitors each having a working voltage of 450 V and a nominal capacitance of 400 µF can be arranged in series to achieve a capacitance of 100 µF and voltage of 1800 V. In another example four capacitors each having a working voltage of 900 V and a nominal capacitance of 100 µF could be arranged in a 2×2 parallel configuration to achieve a capacitance of 100 µF and voltage of 1800 V.

In certain multiple capacitor arrangements and configurations one capacitor can discharge while some of the remaining capacitors are being charged.

In some embodiments a combination of different capacitors with different electrical properties can be used. Each capacitor can have a unique identifier that contains individual information on the particular capacitor. The unique identifier can be recognized by the electronics components and considered by the software during the operation of the wearable defibrillator. In one example the unique identifier on the capacitor could perform a digital hand shake with the electronics components and software such that the operating conditions can be tailored to the specific capacitors used in the device.

In some embodiments the capacitors can be removed from a used wearable defibrillator and reused in a new or refurbished device. A testing protocol can be used to ensure that the capacitors still meets the design specifications. A refurbishing protocol can also be used to test and replace portions of the device that may be more prone to failure.

In some embodiments alternate designs for providing the defibrillator pulse may not use a capacitor. For example, parallel or interlocked power converters, solid state batteries, or a compensating resistor could possibly be used.

The wearable defibrillator can deliver energy to the patient using any conventional waveform. In one embodiment a truncated biphasic waveform is used. In some cases the waveform can be modulated. In some embodiments the waveform can be tweaked to increase the efficiency, for example the waveform could be truncated so the negative voltage tail is smaller.

The amount of energy delivered during the defibrillator pulse can be predetermined and monitored. In some embodiments about 50 joules to about 200 joules are delivered during the defibrillator pulse. In some embodiments about 75 joules to about 150 joules are delivered during the defibrillator pulse. In some embodiments about 100 joules to about 200 joules are delivered during the defibrillator pulse. In some embodiments about 130 joules to about 150 joules are delivered during the defibrillator pulse. In some embodiments a pulse of about 150 joules can be delivered. In one example a pulse of 130 joules can be delivered, which is likely to achieve a 99% efficacy. In another embodiment, the defibrillator may deliver up to 200 joules. In another embodiment in which a non-biphasic pulse is used, up to 360 joules may be delivered. The amount of energy required may be dependent on a patient's size or body mass, with generally higher energy requirements needed for larger individuals The wearable defibrillator can include an impedance circuit to measure the transthoracic impedance of the electrodes prior to and during delivery of the defibrillator pulse. The circuit can measure an analog value or a threshold value. The wearable defibrillator is adhered to the body so the transthoracic voltage can be measured in real time with a high degree of accuracy in relation to competitive products. The transthoracic impedance can vary based on the position of electrodes and defibrillator equipment. The transthoracic impedance of the patient does not need to be measured before installing the wearable defibrillator on the patient. The transthoracic impedance measured during the defibrillator pulse can be used to tailor the waveform to deliver a set amount of energy during the defibrillator pulse. The defibrillation waveform and impedance measurement may be as disclosed in U.S. Pat. No. 5,607,454 or U.S. Pat. No. 5,735,879.

A variety of patient vital signs and data can be measured by the wearable defibrillator described herein. The ECG sensing electrodes in the upper and lower patch can measure ECG data for the patient. The ECG sensing electrodes and defibrillator pad electrodes of the wearable defibrillator can be adhered to the body of the patient. The ECG sensing electrodes, defibrillator pad electrodes and adhesive adhered to the skin of the patient can provide a moisture vapor transmission rate of greater than about 250 g/m$^2$ per day to the skin surface portion of the patient. In some embodiments the ECG sensing electrodes, defibrillator pad electrodes, and adhesive can provide any of the moisture vapor transmission rates described herein to the skin contacted by the ECG sensing electrodes, defibrillator pad electrodes, and adhesive.

In addition to ECG data, data can be collected from any of the sensors disclosed herein, including sensors integral with the wearable defibrillator and sensors separate from the wearable defibrillator. For example, a microphone can be used to listen for heart sounds (e.g., a heartbeat), patient breathing, or voice commands. A variety of parameters and data can be extracted from the ECG sensing electrodes and other sensors. For example, data can be collected corresponding to the patient's heart rate, heart rate variability, pulse, heart sounds, breathing rate, breath sounds, voice commands, etc.

The patient data can be analyzed to determine if the patient may be in need of a treatment or if the device may need to be adjusted or replaced. The patient data can be analyzed to determine the cardiopulmonary state of the patient, to check if the patient has a pulse, to check the cardiac rhythm for ventricular fibrillation, and to determine if the patient is conscious. The device and electrode status can also be interrogated using the patient data. The impedance of the electrodes can be analyzed to confirm that the electrodes are in proper engagement with the skin of the patient. The wearable defibrillator can also be interrogated using the patient data to check for a device error.

Based on the analysis of the patient data the device can take a number of different actions or provide notifications to the patient. The ECG data can be analyzed to determine if the patient has a treatable arrhythmia. If the patient is determined to have a treatable arrhythmia then the wearable defibrillator can provide a therapeutic shock to the patient. The wearable defibrillator can provide an auditory or tactile warning to the patient prior to providing an electrical shock. The wearable defibrillator can also confirm the absence of a heart beat or pulse prior to providing an electrical shock to the patient. In some embodiments the transthoracic impedance of the patient between the first defibrillator pad electrode and the second defibrillator pad electrode can be measured prior to delivering the electrical shock. The impedance can be measured to confirm proper electrical contact and to tailor the characteristics of the waveform based on the transthoracic impedance to deliver the desired amount of electrical energy to the patient.

The data analysis combining different parameters can provide a higher sensitivity and specificity than what can be achieved by any individual parameter alone. Combining data from different sensors can be used to remove interference by providing redundant measurements. Measuring and analyzing physiologic parameters can improve clinical relevance by enabling validation of intermediate values such as the heart rate. The measurement of physiological parameters provides advantages over deep learning nets and other "blind" algorithms that do not analyze physiological parameters.

In some embodiments VF/VT can be detected using ECG as a primary input to achieve sensitivity and with phonocardiography to determine specificity. Heart sounds are absent during cardiac arrest. The combination of ECG sensor analysis and listening for a heartbeat can maximize sensitivity and specificity for the detection and treatment.

The use of ECG data and determining the heartbeat can also indicate contradictory information on the state of the patient. For example, the ECG data could show VF but the microphone picks up heart sounds, which could indicate the need to repair the device, replace the device, adjust electrode placement or adhesion, or to correct the overall adhesion of the device to the body. In addition, concurrent acoustic and electrical heart sensing may also give indication for other heart pathologies (such as MI, CHF exacerbation, pulmonary edema) which may not be able to be detected with sufficient accuracy with one sensor alone.

The data from the various sensors can also provide additional information about the status of the wearable defibrillator. For example, battery status, memory status, device performance history, and therapy readiness can be estimated from a combination of worn sensors. Sensors do not need to be worn with the wearable defibrillator or integral with the wearable defibrillator. The additional sensors can be worn on peripherals with the data sent to the algorithm processing unit. These sensors can also be used to trigger in-device events, including determining a patient fall or the presence of a magnetic field. Sensors do not have to directly correspond to biological features that can be observed by a human. For example, the acoustic sensor could measure sounds in the ultrasonic range. The auxiliary data can be used to determine additional information about the patient, such as posture. In some cases the auxiliary data can be sued to determine if a delay in treatment may be appropriate based on the time of day or patient posture.

The sensor data can be analyzed to check for potential issues with the wearable defibrillator and electrode adhesion to the patient. If any potential issues are detected by the sensor data then a notification message or alert can be provided to the patient and/or healthcare professional. The message or alert can provide the user or healthcare provider with instructions to adjust the ECG electrode, to adjust other device features, or to replace the device.

Figure 34:
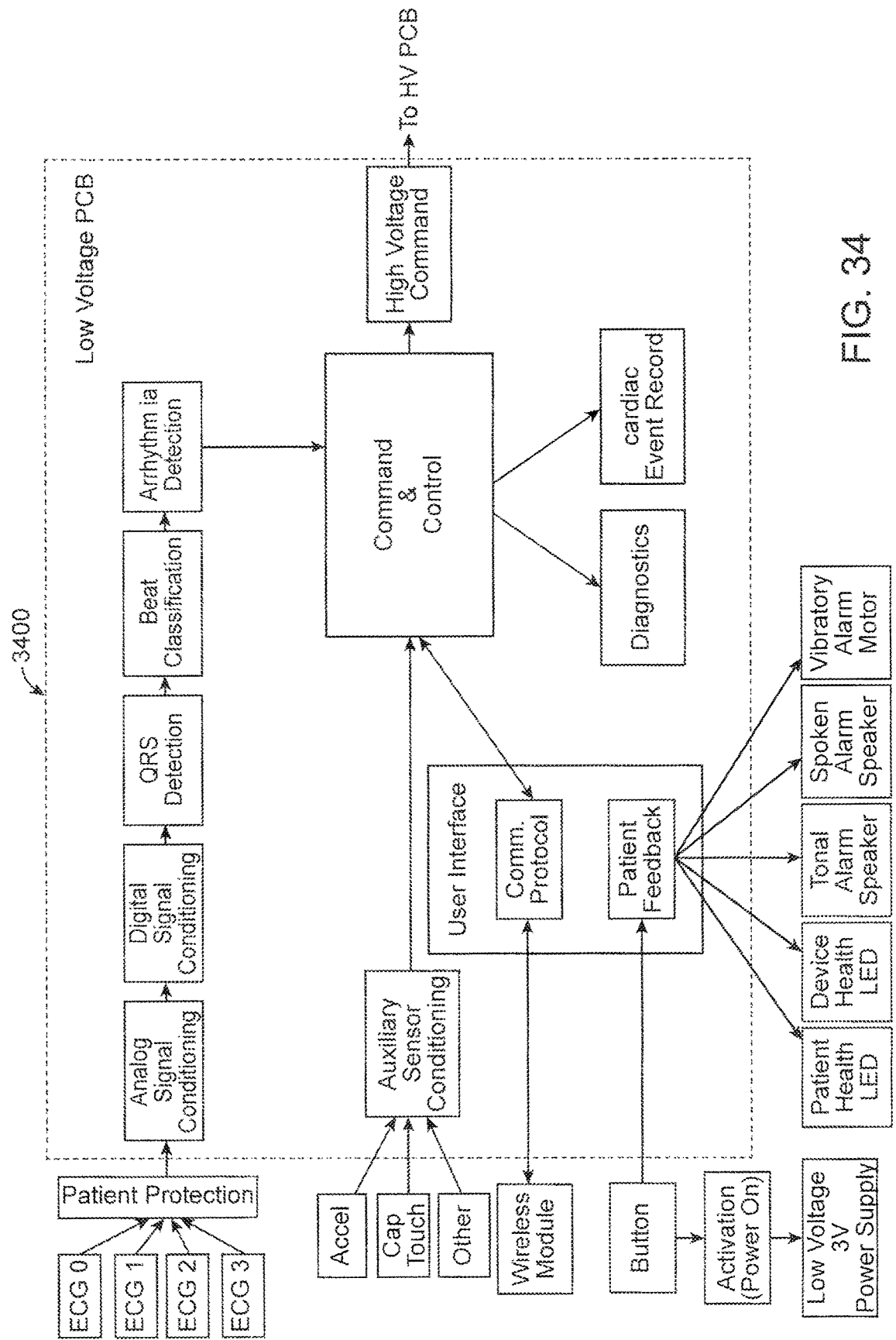
FIG. 34 is a schematic illustration of a portion of a wearable defibrillator in accordance with some embodiments.

FIG. 34 is a schematic illustration of a portion 3400 of a wearable defibrillator in accordance with some embodiments. Data from a plurality of ECG electrodes (ECG 0, ECG 1, ECG 2, ECG 3) can be processed with analog and digital signal conditioning. The conditioned ECG signals can be analyzed for QRS detection and beat detection followed by arrhythmia detection. The ECG signals and the results of the arrhythmia detection can be sent to the command and control module of the device. Signals from auxiliary sensors like an accelerometer, capacitive touch, and any of the other sensors described herein can be conditioned and analyzed with the signals sent to the command and control module. The command and control module of the device can perform diagnostics on the device and the collected data. The command and control module can also record cardiac event records and other data collected by the sensors interfacing with the command and control module. In some cases the command and control module can store all of the raw data collected by the wearable defibrillator. The raw data can be downloaded or transmitted to a healthcare provider for analysis.

A user interface of the device can include a patient feedback module and communication protocol such as a wireless data transmission module. The patient feedback module can output an indication of the patient health and device health with one or more LEDs. Additional patient feedback can be provided by one or more of: a tonal alarm, spoken alarm, and vibratory alarm. The device can be turned on by the patient using a button interacting with the patient feedback module.

The command and control module can also send commands to the high voltage section of the device. Upon detection of a treatable arrhythmia the command and control section can send instructions to the high voltage section of the device to charge the capacitors with the device battery. After the capacitors are properly charged the command and control module can instruct the device to provide an electrical shock to the defibrillator pad electrodes.

Figure 35:
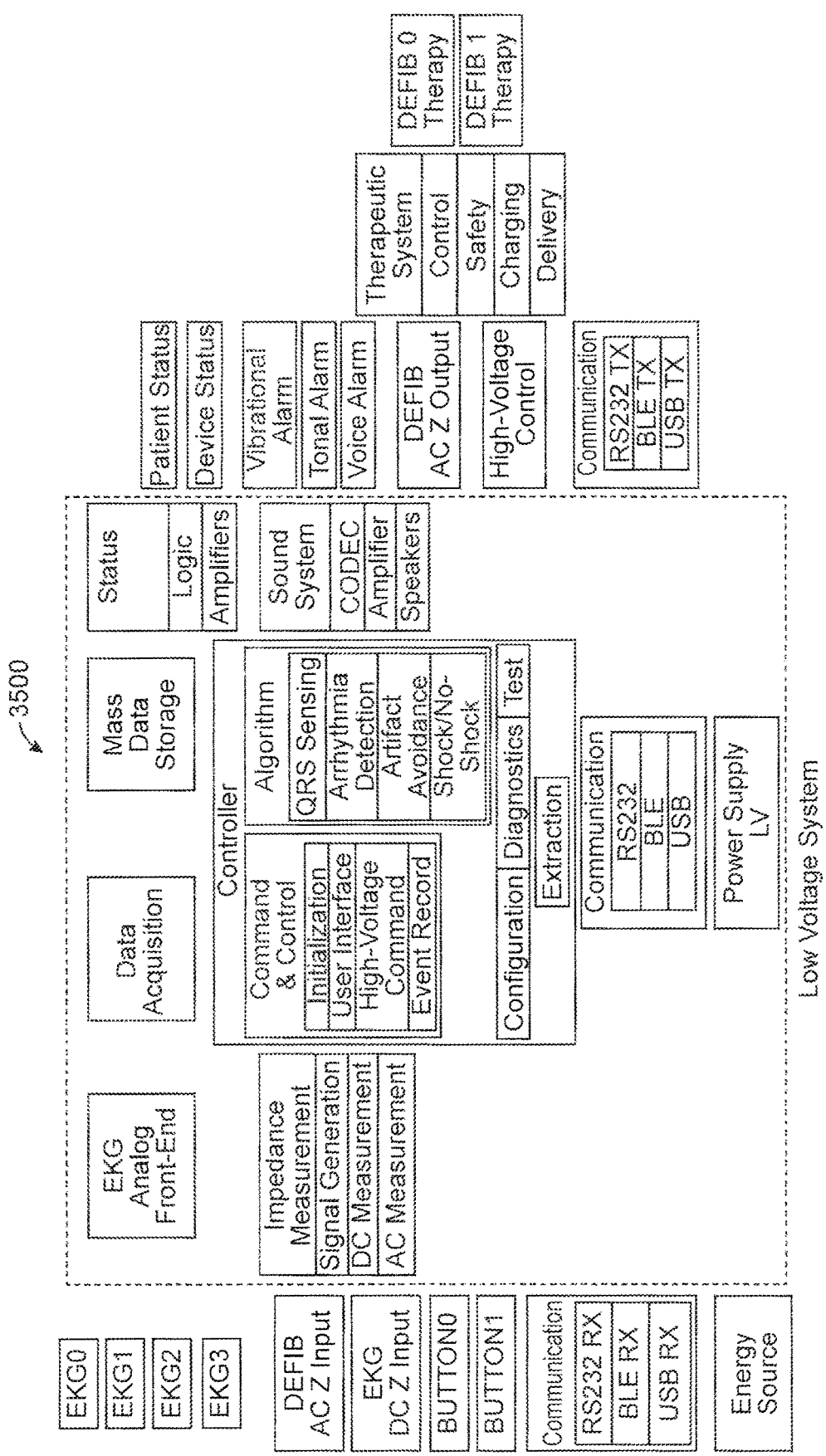
FIG. 35 is a schematic illustration of a portion of a wearable defibrillator in accordance with some embodiments.

FIG. 35 is a schematic illustration of a portion 3500 of a wearable defibrillator in accordance with some embodiments. The wearable defibrillator includes an impedance measurement module as part of the low voltage system. The controller can include a command and control module, algorithm module, configuration module, diagnostic module, test module, and extraction module. The algorithm module includes a QRS sensing module, arrhythmia detection module, artifact avoidance module, and shock/no-shock determination module. The illustrated schematic also includes a therapeutic system with a control module, safety module, charging module, and electrical energy delivery module.

The wearable defibrillator can include circuits with components to carry out any of the functions described herein. In some embodiments the wearable defibrillator includes one or more discrete circuits for carrying out the functions described herein. In some embodiment the wearable defibrillator can include an application-specific integrated circuit (ASIC).

Figure 36:
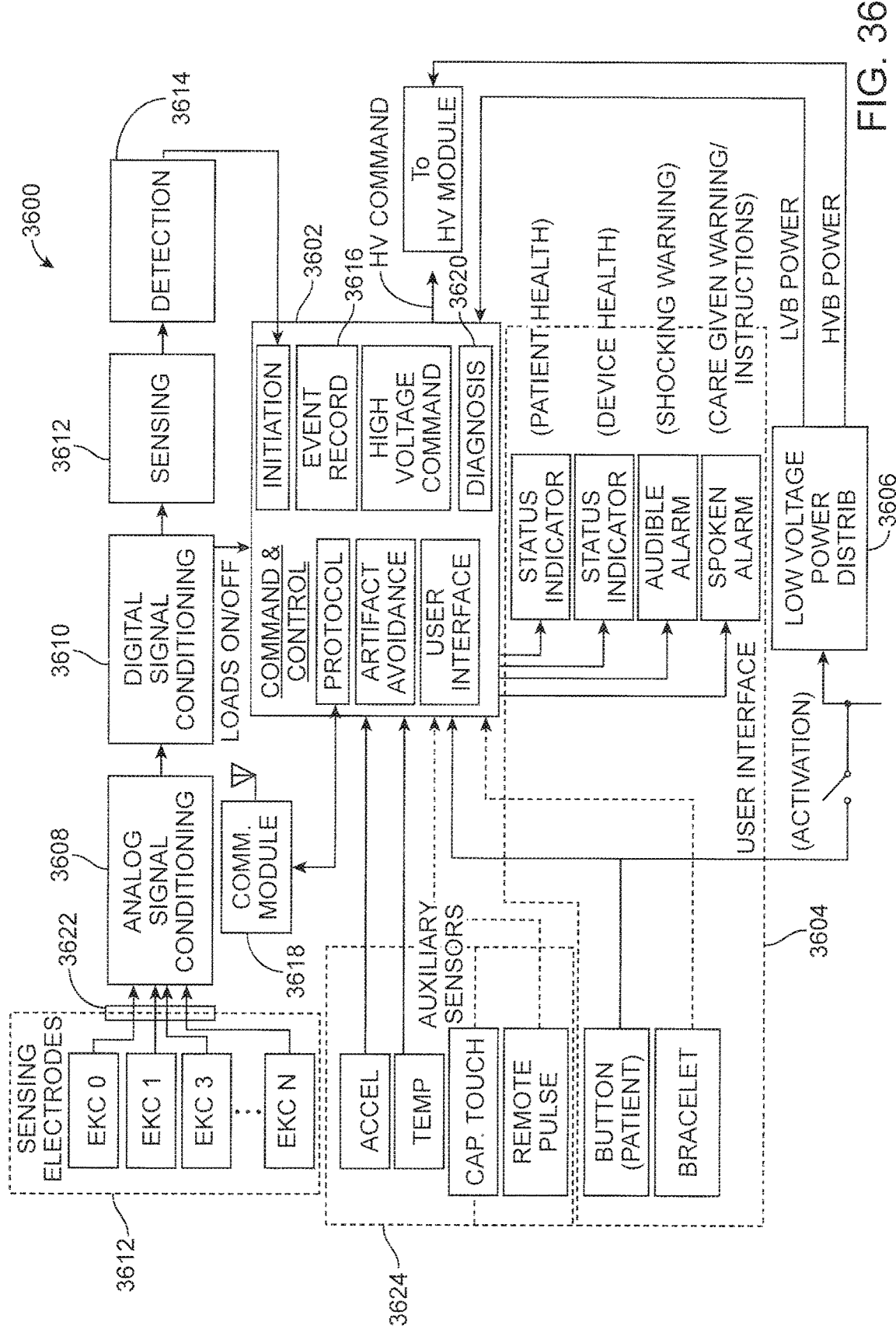
FIGS. 36-37 illustrate additional examples of control blocks and circuit designs that can be used in the wearable defibrillators disclosed herein.
Figure 37:
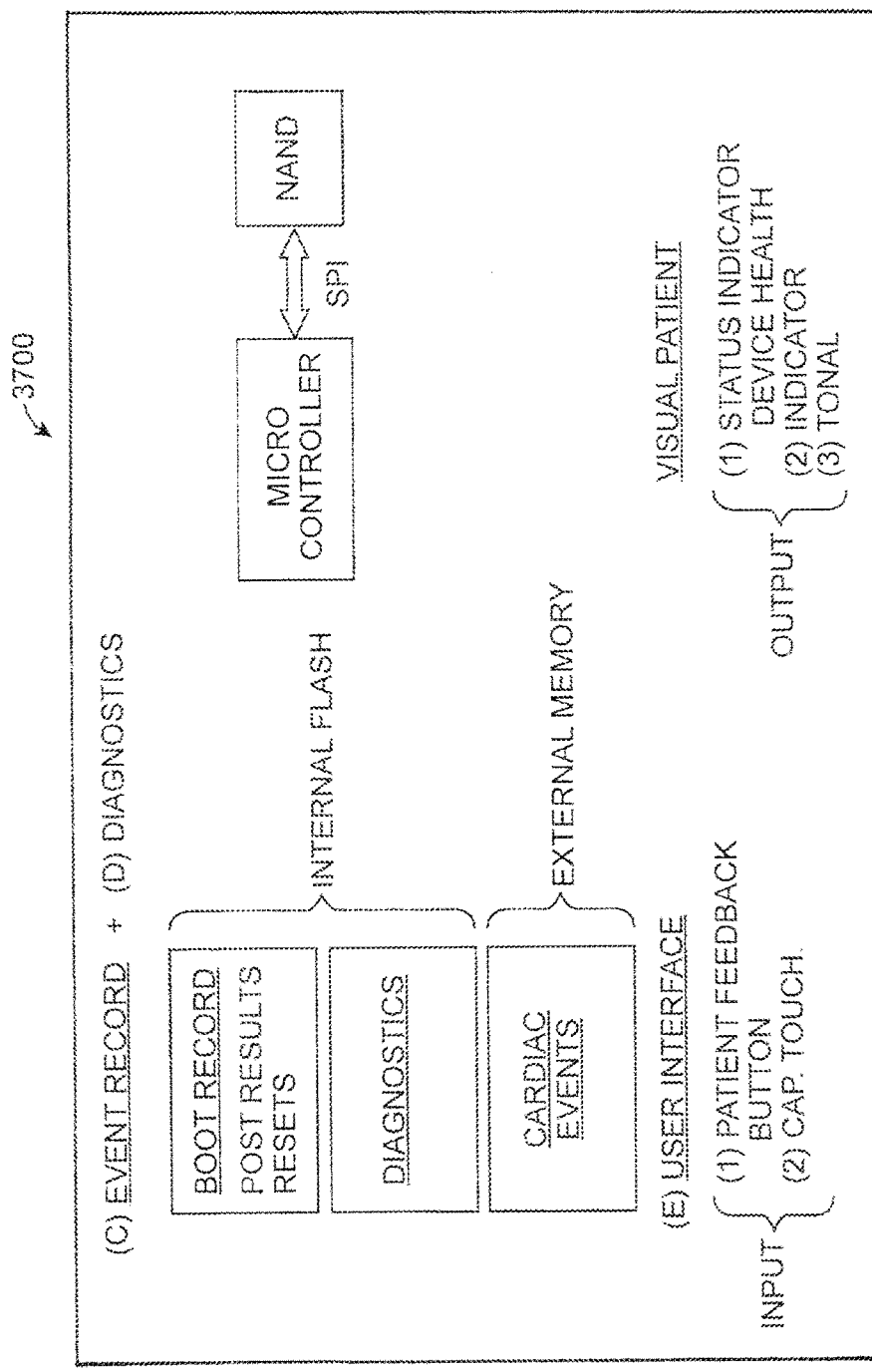

FIGS. 36-37 illustrate additional examples of control blocks 3600, 3700 and circuit designs that can be used in the wearable defibrillators disclosed herein. In some embodiments the wearable defibrillator can be composed of six basic components: a low voltage block, a high voltage block, a battery block, and defibrillator pads (leading, trailing, and sensing electrodes).

The low voltage bock can have responsibilities including: command and control of the device, user interface, low voltage power distribution, ECG signal conditioning, R-wave sensing, arrhythmia detection, diagnostics, and communication. Analog signal conditioning can include amplification and filtering of the signals. The digital signal conditioning can include linear filters, pacing, spike, and removal.

As illustrated in FIG. 36, the low voltage block can include one or more of: a command and control block (3602), user interface block (3604), low voltage power distribution block (3606), analog signal conditioning block (3608), digital signal conditioning block (3610), sensing block (3612), detection block (3614), event record block (3616), communication block (3618), diagnostics block (3620), patient protection block (3622), and auxiliary block (3624).

Command and Control (3602) can include the logical center of the device that is responsible for the high-level control of the device. From a de-energized state the command and control block will be activated by a button press. The device will have one button which will act as the power-on as well as the patient feedback input: activation/patient feedback button and micro controller. The initial button press can close a switch between the voltage regulator and battery. Closing the switch will provide enough power to the command and control block to perform the initialization procedure and shift control of the power supply toe the command and control block. Once this has occurred the function of the button shifts to patient feedback. Once the device is powered on it can remain in a low power state with the leads on detection. In some embodiments the device can have an off button.

The event record can store all of the events (event record, diagnostics) detected by the device that can be categorized as a significant event. Significant events can range from results of the power on self-test procedure, calibration at manufacturing, diagnostics during wear, diagnostics during storage, as well as arrhythmic events. The categories of these events can be listed as: i) cardiac events; ii) post events, iii) diagnostic. The event record can be stored in a NAND flash external to the microcontroller.

The command and control block can thus control: activation, initialization, event record, diagnostics, user experience, high voltage command, artifact avoidance, and communication protocol.

Activation and diagnostics functions can include checking the device to ensure that the batteries are at an appropriate charge and that all subsystems are functioning as expected. This could be performed when the device is off the patient on every button press. The test could be initiated in the same way while on the patient. When the button is pressed, while the device is off the body and in a low power state, the device will generate an interrupt that will awaken the microcontroller and in doing so will instigate a diagnostic check (see circuit design in FIGS. 44A-44N). The diagnostic test will have a refractory period in order to limit the risk of excessive current consumption from an overabundance of button presses.

In some embodiments an independent tester can be used in light of the flurry of AED failures (e.g., devices not ready when required. The independent tester can provide an inexpensive way to test the device and to provide confirmation that the device is in working order and capable of providing a defibrillating shock when necessary. In some cases the separate independent tester can be built into the package enclosure to provide a reasonable evaluation of the state of the device as well as the query the device for health related information. The patient or medical professional could use the independent tester immediately prior to placing the device on the patient to ensure the integrity of the device.

Initialization occurs after activation when control of the supply shifts from the user/button to the microcontroller. It is at this step that the microcontroller can perform all of the necessary procedures to begin monitoring the patient.

In some cases capacitive touch sensor can be used to provide an alternate way (e.g., other than impedance) for detecting a proper patient/electrode interface. Capacitive touch could be implemented on the electrode itself so as not to affect sensing.

For the event record and diagnostics an internal flash memory can be used to store the boot record, post results, resets and diagnostic information. Cardiac events can be stored in an external memory as illustrated in FIG. 37. The user interface can include inputs such as a patient feedback button, capacitive touch sensor and other inputs. The outputs can include a status indicator of device health and other device information.

The high voltage control system can provide a high level interface to the high voltage module. At a minimum the microcontroller should be able to command the high voltage module to execute the following functions: on/off, enable/arm, charge, disarm, shock, status, and self-check.

Artifact avoidance can be implemented by software based ECG analysis and by making use of external auxiliary sensors such as an accelerometer, capacitive touch sensor, temperature, remote pulse measure, and data from other sensors disclosed herein.

The wearable defibrillator can include a communication protocol capable of communicating with wireless external sensors as well as methods of providing real-time feedback as requested from a remote provider.

Figure 38:
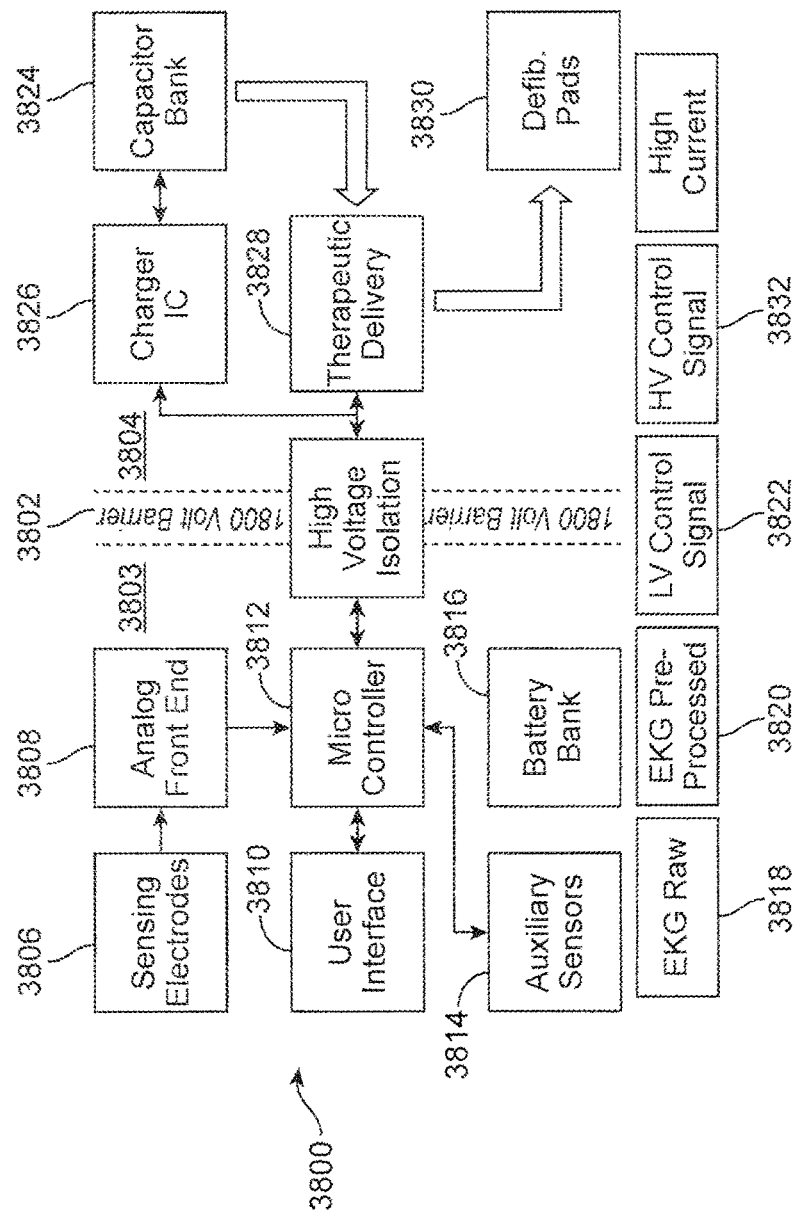
FIG. 38 illustrates a block diagram of a wearable defibrillator system.

FIG. 38 illustrates a block diagram 3800 of a wearable defibrillator system. The illustrated diagram includes high voltage isolation 3802 between the low voltage section 3803 and high voltage section 3804. The low voltage section 3803 includes the sensing electrodes 3806, analog front end 3808, user interface 3810, micro controller 3812, auxiliary sensors 3814, battery bank 3816, EKG raw signals 3818, EKG pre-processed signals 3820, and low voltage control signal 3822. The high voltage section 3804 includes the capacitor bank 3824, the charger module 3826, therapeutic delivery module 3828, defibrillator pads 3830, and high voltage control signal 3832.

Figure 39:
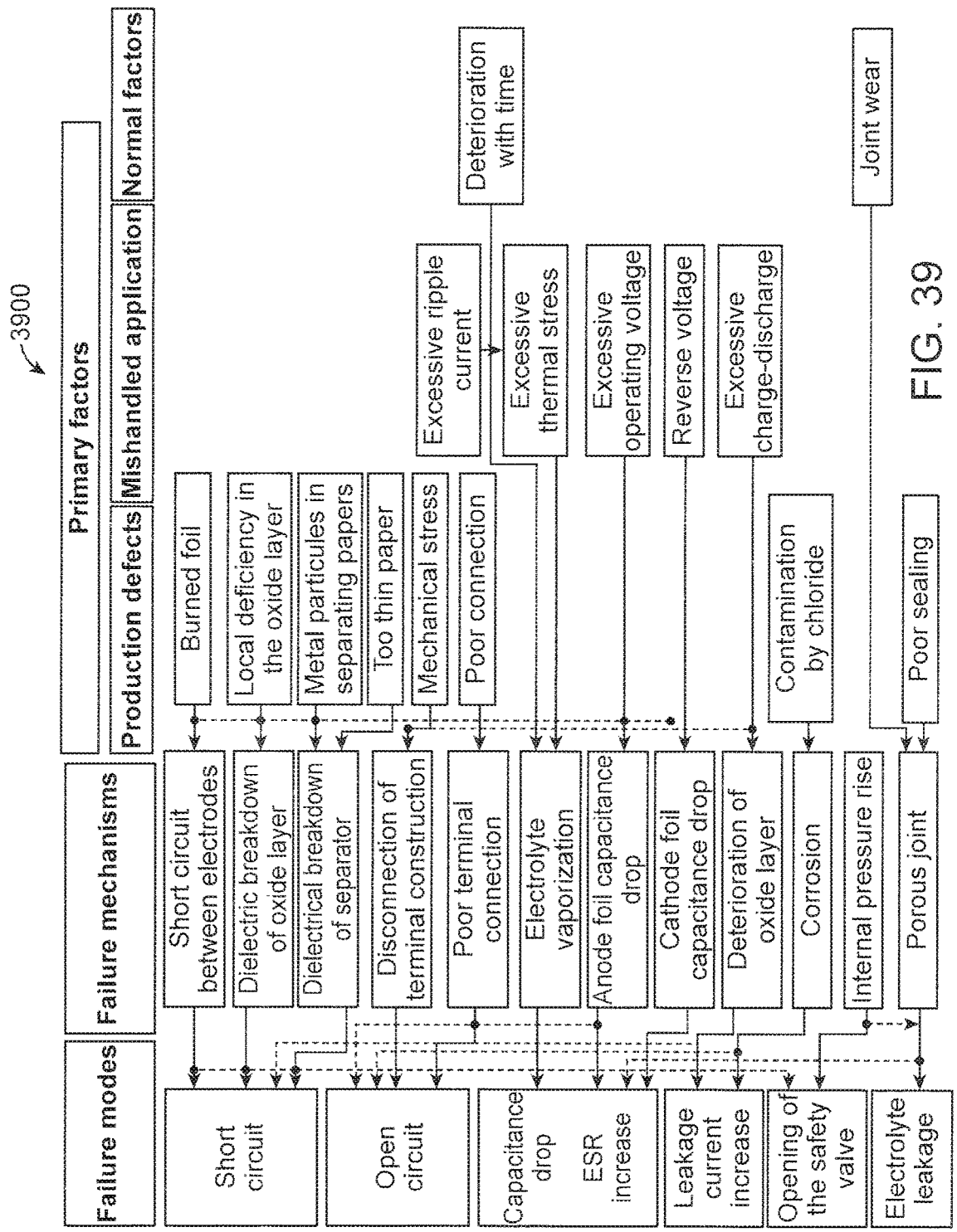
FIG. 39 illustrates a diagram of safety features used in embodiments of the wearable defibrillators.

Placing a high voltage capacitor, in particular electrolytic capacitors, near the body in a wearable device also presents some safety concerns. The wearable defibrillator can include failure mitigation protocols to avoid unsafe conditions arising from certain device failure types, in particular failures associated with electrolytic capacitors. FIG. 39 illustrates a block diagram 3900 with a number of failure modes and possible causes for the failures. The wearable defibrillator software can analyze the operating conditions to detect and analyze any of the failure conditions shown in FIG. 39. The failure can be determined and an appropriate action can be taken to avoid an unsafe condition or environment for the patient wearing the defibrillator. When appropriate an alert can be provided to the user regarding the type of device failure with a suggested action.

The wearable defibrillator includes software to perform any of the functions described herein. The software can analyze the ECG monitor data, determine when an arrhythmic condition occurs that is treatable through a defibrillator pulse, determine the transthoracic impedance, and provide a therapeutic defibrillator pulse.

The software can include a learning mode to learn the specific ECG patterns of the patient. The software can analyze the data from the impedance sensors to determine if the electrodes are in good electrical contact. Excessive impedance can also be detected, which can be caused by dehydration of the electrode, drying of the skin, skin irritation, skin deterioration, etc.

The software can tailor treatment based on any of the sensors disclosed herein. For example the treatment can be different if the patient is sleeping, if humidity is present like the patient is in the shower, etc. The software can analyze any of the failure conditions shown in FIG. 39 and determine the potential sources of failure.

The wearable defibrillator is worn under the patient's clothes. It can be useful for the wearable defibrillator to communicate data wirelessly with other devices. Data can be transmitted relating to the status of the device, history of the use of the device, warnings, etc. Examples of data communication methods that can be used with and incorporated in the wearable defibrillators include: Bluetooth, Wi-Fi, cellular, radio, or any other suitable data modem communication method. The wearable defibrillator can be configured to communicate wirelessly with a smartphone or tablet computer.

The wearable defibrillator can be wirelessly interrogated. Programs have been developed to interrogate an ICD, S-ICD, or pacemaker. The wearable defibrillator can be configured to be interrogated with equipment currently used in hospitals to interrogate the status of ICDs, S-ICD, and pacemakers. The wearable defibrillator can also be designed for home interrogation using a smartphone, tablet, laptop, or computer.

In some embodiments the device software and firmware can be updated using wireless data transfer.

The wearable defibrillator can communicate wirelessly with a bracelet, watch, or other wearable device separate from the wearable defibrillator. The bracelet or wearable device separate from the defibrillator can store data on the status, history, or any other useful data relating to the defibrillator. The bracelet can be accessed more easily by an emergency medical technician or other health care provider to get data from the defibrillator.

Data on a cardiac event can be transmitted wirelessly. An emergency medical technician can receive data on the event from a display on the wearable defibrillator, a bracelet, wireless data transfer, or any other method for transmitting data on the event from the wearable defibrillator.

In some embodiments the wearable defibrillator can automatically transmit position data wirelessly regarding a cardiac event or if the device provides a shock to a cellular or data network. The position data can be determined by a GPS sensor on the device. The position of the defibrillator can be automatically sent and reported to an emergency medical network. In some cases a request for emergency medical treatment can also be automatically made by the device.

In some embodiments a small visual display can be provided on the defibrillator to provide information and/or instructions to the user.

In some embodiments the device does not include a visual display in order to minimize the weight and profile of the device. Visual communication between the device and the user can be difficult without a visual display on the wearable defibrillator. The device can communicate information to the user using one or more of alarms, buttons, auditory notifications or warnings (using a build-in speaker, for instance), tactile feedback, vibration, electrical shock, etc. The information can also be triggered by various events, such as when an impending shock is about to be delivered.

For example, a system status button can be on one or both of the electrode areas. The system status button can display a green light for normal operation or a red light to indicate a potential problem.

In some embodiments the wearable defibrillator can include an override control switch or button on the capacitor bank, battery module, or any other portion of device. These switches may take various forms such as pinch sensors, buttons requiring pressure, or capacitive sensors.

In some embodiments the device can vibrate to try to wake the patient before delivering a defibrillating pulse because the therapy could be different if the patient is asleep or unconscious. The incidence of false positives can be reduced by attempting to wake patient. Another option for waking the patient is to deliver a small shock or transcutaneous ping prior to providing the defibrillating pulse. In some embodiments the device can include a dead man switch.

Additional information can be displayed to the user using a bracelet, smart phone, tablet, or other device having a display as disclosed herein.

The wearable defibrillator device can include additional sensors, features, and additional wearable device. In some embodiments the wearable defibrillator includes an additional sensor such as an accelerometer, microphone, gyroscope, GPS localization, temperature sensors, and any other discrete sensors.

In some embodiments the wearable defibrillator can include a sensing circuit to monitor electrode contact to measure device health and the quality of the adherence of the electrodes to the body. The electrodes can have capacitive sensors to measure if the electrode is peeling away or losing contact with the patient. The capacitive sensors can use low power consumption and measure the impedance to determine whether the electrode is in good contact with the skin or is peeling off. If the electrode is peeling off a notice could be provided to the user to push the electrode back on.

Figure 79D:
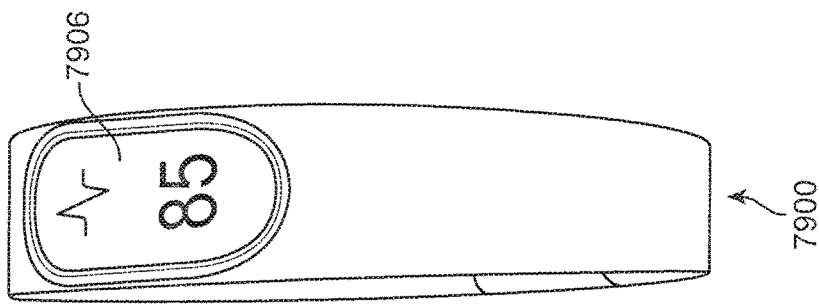
FIGS. 79A-80 illustrate embodiments of a wearable bracelet that can be used with the wearable defibrillators disclosed herein.
Figure 79C:
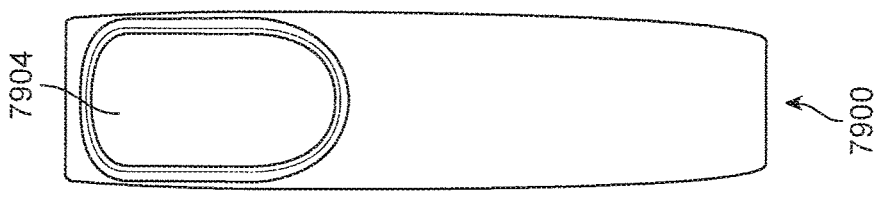
Figure 79B:
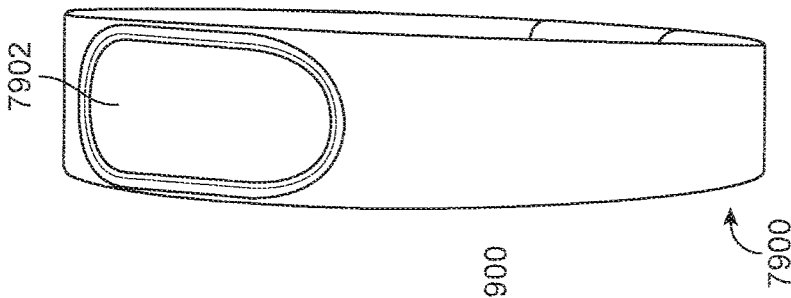
Figure 79A:
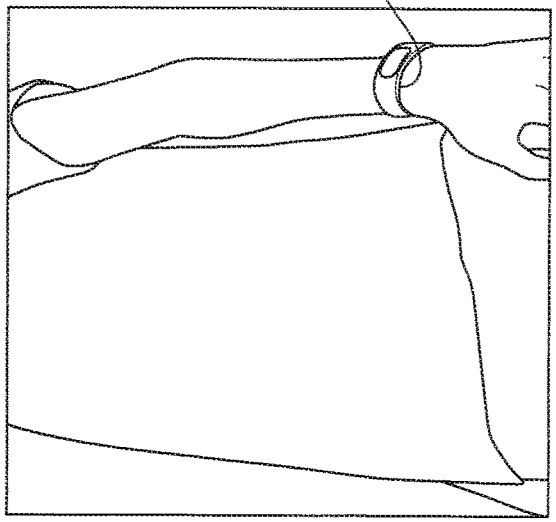
Figure 80:
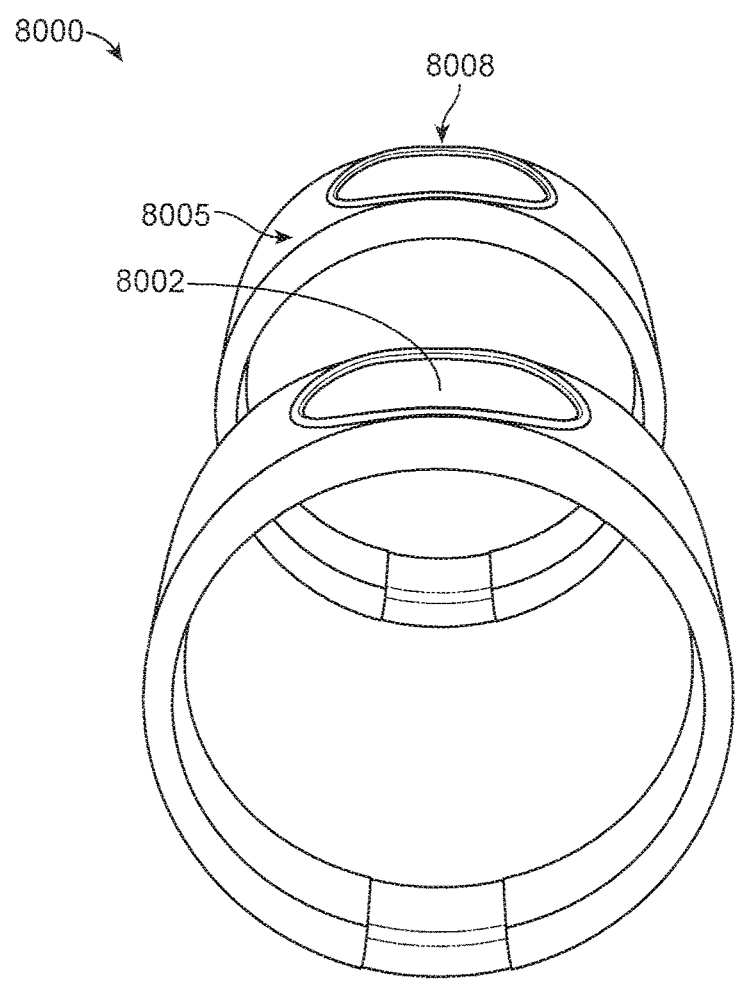

Examples of additional wearable devices include a wearable bracelet, watch, or other similar device. The bracelet can include a hemodynamic sensor to verify the pulse of the patient. The pulse data could be useful if the chest device loses contact but the pulse could still be measured by the bracelet. The bracelet could have an override switch. The bracelet can include a display and touch screen. The bracelet could also store data and transfer information. Information that can be provided by the bracelet includes system status, battery status, warnings, notifications, user response buttons, etc. A visual indicator can be on the bracelet, watch, or device to notify the user of a problem with the device that should be corrected. Examples of bracelets and functions are shown in FIGS. 79A-80.

A spouse could also wear a bracelet to receive notification about the status of the wearable defibrillator and patient health. A watch could also be used with any of the features described herein with regard to the watch.

Figure 40:
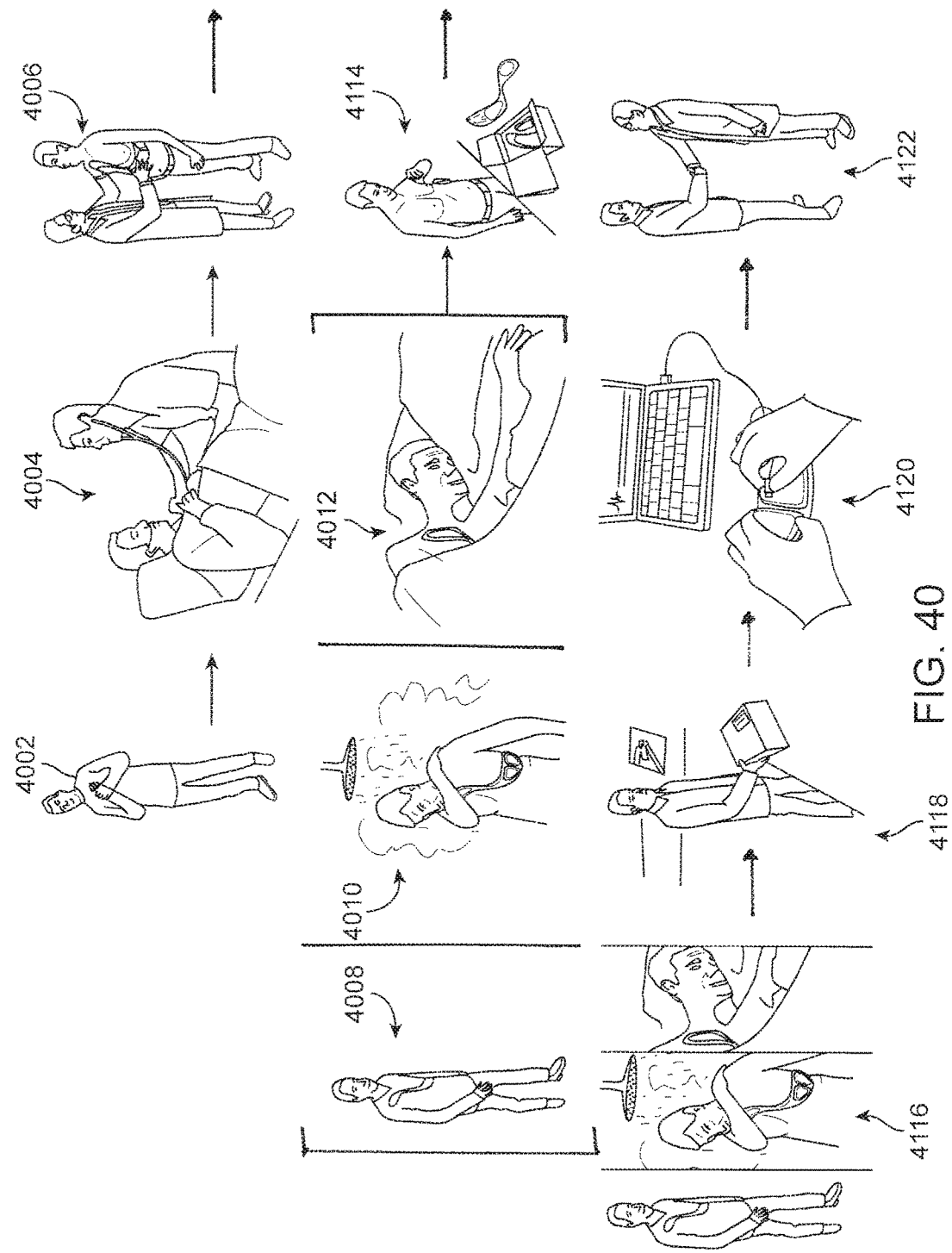
FIG. 40 illustrates images of a user being prescribed, receiving, and using a wearable defibrillator in accordance with the embodiments disclosed herein.

FIG. 40 illustrates a typical series of events for a patient that is prescribed a wearable defibrillator. The patient can suffer a cardiac condition 4002 leading to medical treatment 4004. The doctor can place the wearable defibrillator on the patient initially 4006. The patient can then go about normal life activities such as exercising 4008, showering 4010, and sleeping 4012. After the initial wear period the user receives replacement parts, such as new adhesive pads 4014. The user then installs the device with the new adhesive pads 4014 followed by normal activities 4016. After the end of the treatment period with the wearable defibrillator the user can return or mail back the device 4018. A health professional can download and analyze the data 4020 taken and stored by the wearable defibrillator, which can be used in follow up treatment and diagnosis 4022.

The overall device profile can be designed to increase the comfort for the user by designing how the device contacts the skin and hangs off of the body. The device can be designed to improve the ergonomics and to decrease the skin irritation. The weight can be evenly spread over the profile of the device to increase the comfort for the user. The device profile can also be designed to use parts of the body for additional support of the heavier parts of the device, such as by wearing the device over the shoulder. A variety of device profile embodiments are illustrated in FIGS. 45A-74.

The heavier components on the defibrillator device are the capacitors and the battery components. For example, the capacitors can have a total weight of about 100-200 grams, but may be as heavy as 500 grams. In one example the capacitors weigh about 160 grams. The battery components can have a weight of about 50-100 grams. The overall device profile (e.g., surface area contacting the skin) can be designed to spread the weight out across the body. The weight distribution and device profile can also be based on the desired wear duration and device weight. In some embodiments the overall device weight per surface area is no greater than about 0.5 $g/cm^2$, no greater than about 1.0 $g/cm^2$, no greater than about 1.1 $g/cm^2$, no greater than about 1.2 $g/cm^2$, no greater than about 1.3 $g/cm^2$, no greater than about 1.4 $g/cm^2$, no greater than about 1.5 $g/cm^2$, no greater than about 1.6 $g/cm^2$, no greater than about 1.7 $g/cm^2$, no greater than about 1.8 $g/cm^2$, or no greater than about 1.9 $g/cm^2$. In some embodiments the overall device weight per surface area is no greater than about 2 $g/cm^2$, no greater than about 2.3 $g/cm^2$, no greater than about 3 $g/cm^2$, or no greater than about 5 $g/cm^2$.

The device can hold the capacitors and battery in separate sections to distribute the heavier components. The device can have flexes to account for the curvature of body and to provide additional degrees of freedom. For example a flexible hinge, living hinge, bridge, flexible interconnect, or articulation point can be used between the heavier and rigid components, such as the battery and capacitors. In some embodiments the battery, capacitors, and other heavier components can be enclosed in a housing that is separate from the patient engagement surfaces. The separate housing can be supported by adhesive attachment to the body, clipping on to a garment, or be supported off of the anatomy of the body.

Figure 81B:
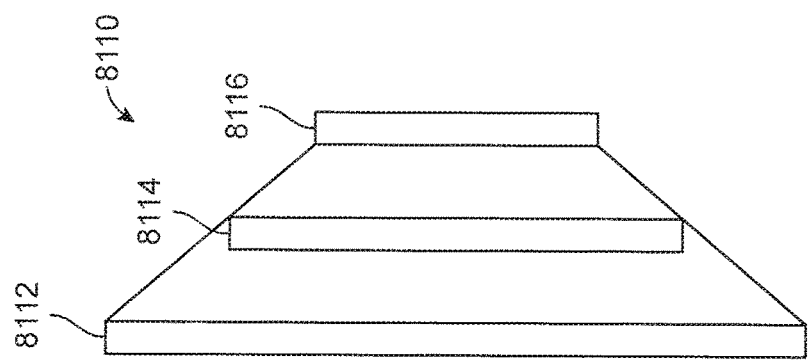
FIG. 81B illustrates a cross-section of a wearable electrode in accordance with some embodiments.

In some embodiments, the device's patient engagement substrate includes an elastic element, such as a layered structure which can be used to transition between the elastic modulus of the skin to the rigid components in the housing. The layers can transition from elastic closer to the skin to more rigid and less elastic towards the rigid components as shown in FIG. 81B.

In some embodiments the device profile can be designed to use common anatomy as the anchor points to the body. For example the device can be designed to attach to the sternum because the sternum does not vary between patients as much as other anatomy points.

In some embodiments the device can include a sling with an over the shoulder support or neck support to provide additional support for the weight of the device by the shoulder and/or neck as shown in FIGS. 47A-47C, 48A-48C, 56A-56H, 59A-59E and 77A-77C.

The defibrillator device can also be designed with tapered edges so that the edges of the device do not catch on clothing or get caught on other items.

In some embodiments the device profile can be designed such that the device can be rotated such that the adhesive and electrodes can attach to different parts of the skin. Supporting the device with different areas of the skin improves the device comfort and improves the long term wear. For example, a triangular or flower petal device profile design can be used as illustrated in FIGS. 87A-87B.

In some embodiments different form designs can be used around the electrodes when switching between units to allow the skin previously contacted by the adhesive to heal.

In some embodiments the electronics, capacitors, and batteries can be broken up into multiple parts or sections.

In some embodiments different device profiles can be used depending on the treatment regime for the patient and patient characteristics.

In some embodiments electrical components can be switched out if they last for less than the wear duration. For example, a new battery could be used to replace an old battery.

In some embodiments the device can include adjustable sections between the attachment points to minimize the number of device profile variants.

In some embodiments one or more of the capacitor bank, electronic board, and batteries can be selected based on specific characteristics of the patient and treatment for use with the device form factor. For example, the capacitor can be selected based on the size of the patient or thoracic impedance. The electronics board could be different for a patient with a pacemaker so that the device can have a higher sampling rate. Different batteries can be paired with the specific electronics board.

In some embodiments the capacitors and electrical contacts can be reused. In some cases the capacitors and electrical contacts can be refurbished before reusing in another device.

Figure 41A:
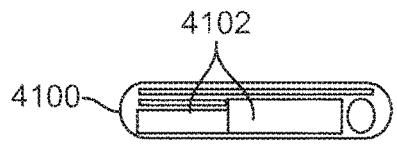
FIGS. 41A-41U illustrate various component layouts for embodiments of wearable defibrillators.
Figure 41B:
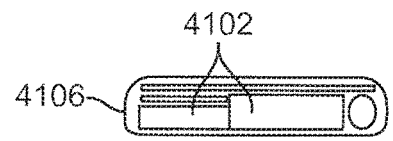
Figure 41C:
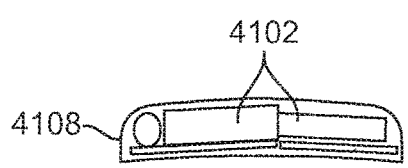
Figure 41D:
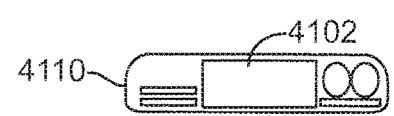
Figure 41E:
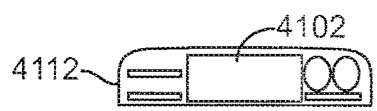
Figure 41F:
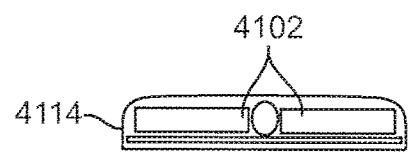
Figure 41G:
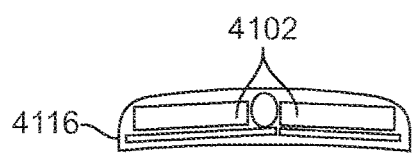
Figure 41H:
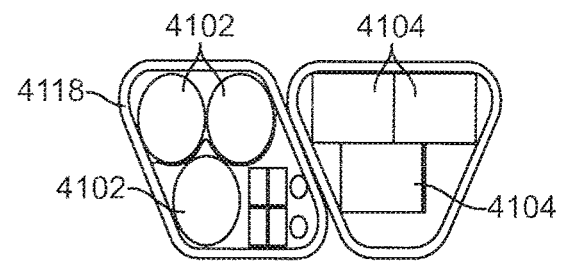
Figure 41I:
Figure 41J:
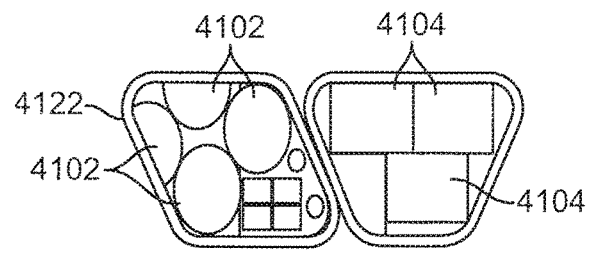
Figure 41K:
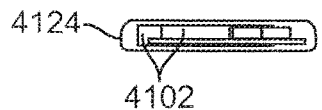
Figure 41L:
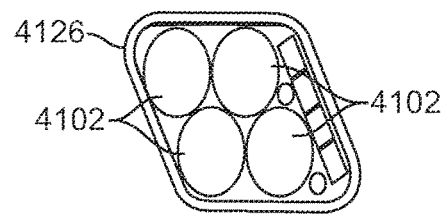
Figure 41M:
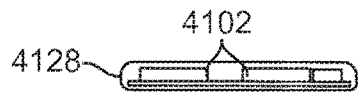
Figure 41N:
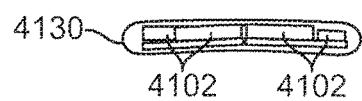
Figure 41O:
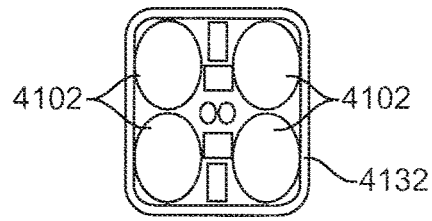
Figure 41P:
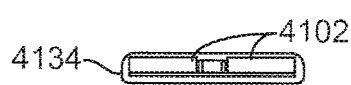
Figure 41Q:
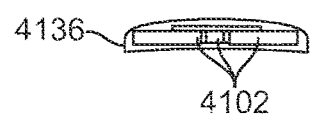
Figure 41R:
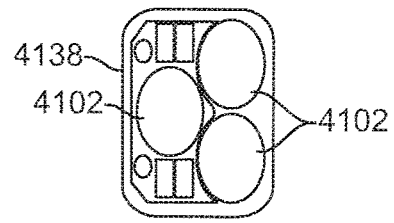
Figure 41S:
Figure 41T:
Figure 41U:
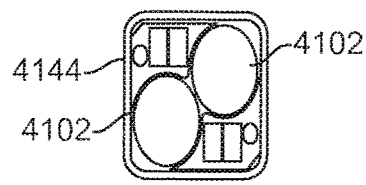
Figure 42A:
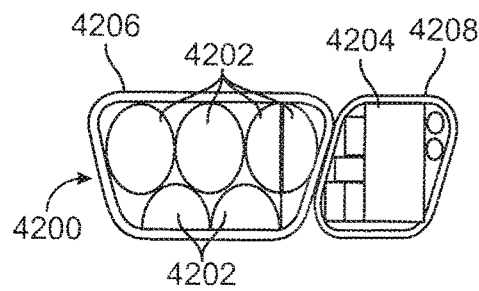
FIGS. 42A-42L illustrate various component layouts for embodiments of wearable defibrillators.
Figure 42B:
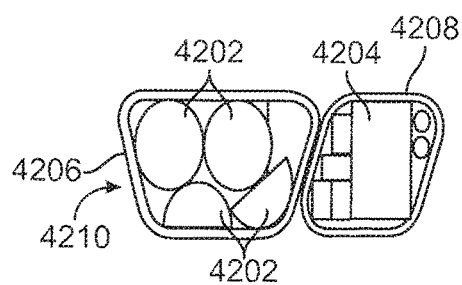
Figure 42C:
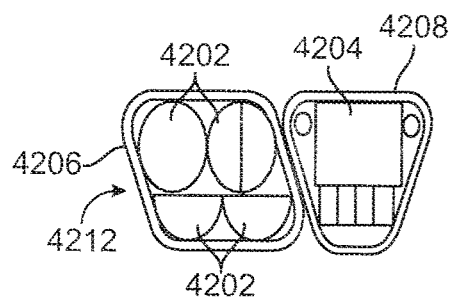
Figure 42D:
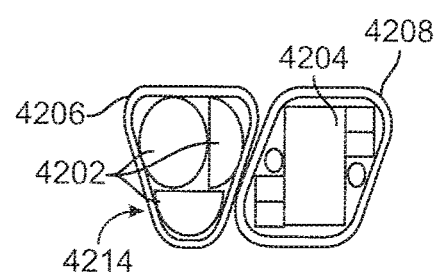
Figure 42E:
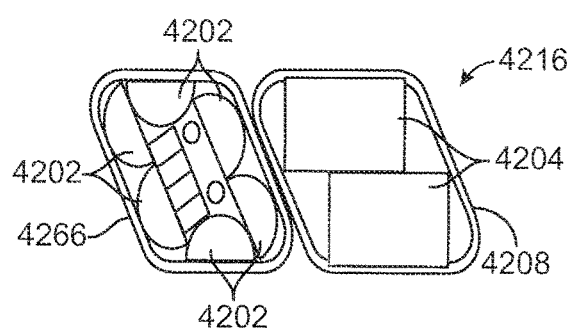
Figure 42F:
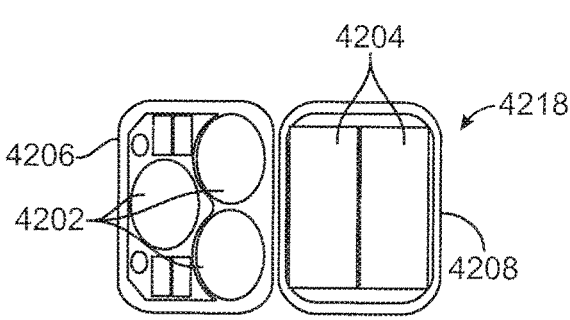
Figure 42G:
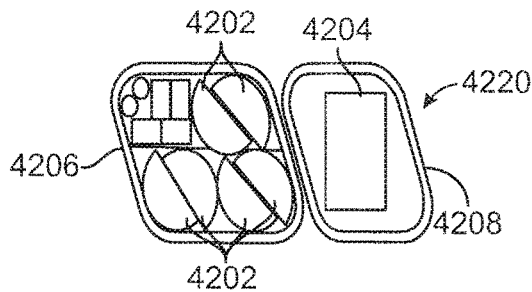
Figure 42H:
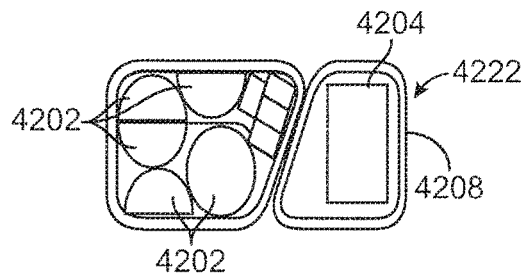
Figure 42I:
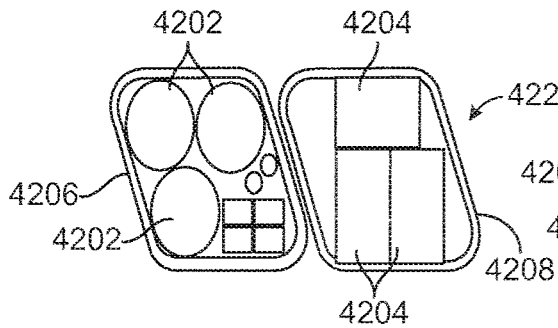
Figure 42J:
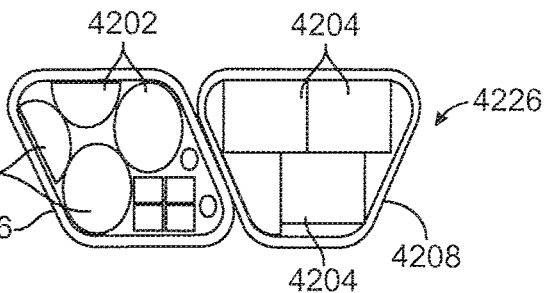
Figure 42K:
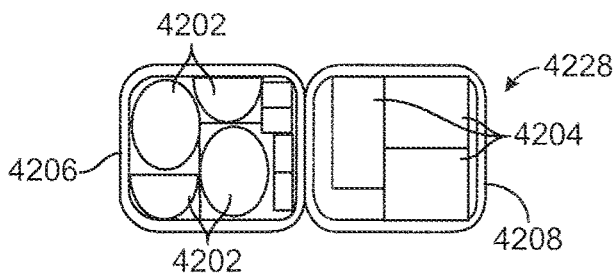
Figure 42L:
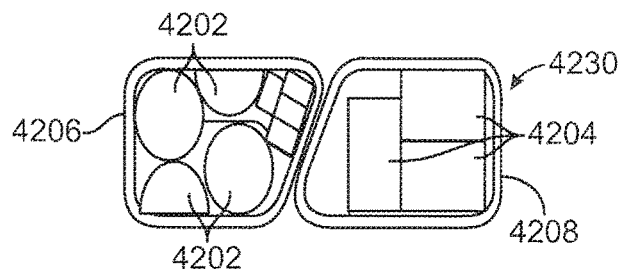

FIGS. 41A-41U and 42A-42L illustrate various component layouts for embodiments of wearable defibrillators. FIGS. 41A-41U illustrate component layouts of capacitors 4102 and batteries 4104 in various configurations 4100, 4106, 4108, 4110, 4112, 4114, 4116, 4118, 4120, 4122, 4124, 4126, 4128, 4130, 4132, 4134, 4136, 4138, 4140, 4142, and 4144. The capacitors 4104 can be arranged in the high voltage module. The capacitors 4104 can be arranged such that they have a low profile and weight distribution across the surface of the wearable defibrillator. FIGS. 42A-42L illustrate additional layouts (4200, 4210, 4212, 4214, 4216, 4218, 4220, 4222, 4224, 4226, 4228, and 4230) for capacitors 4202 and batteries 4204 on a first section 4206 and a second section 4208 of the wearable defibrillator. The capacitors can be arranged in one module of the wearable defibrillator and the battery and low power/voltage components can be arranged in a separate second module or section of the wearable defibrillator.

Figure 43:
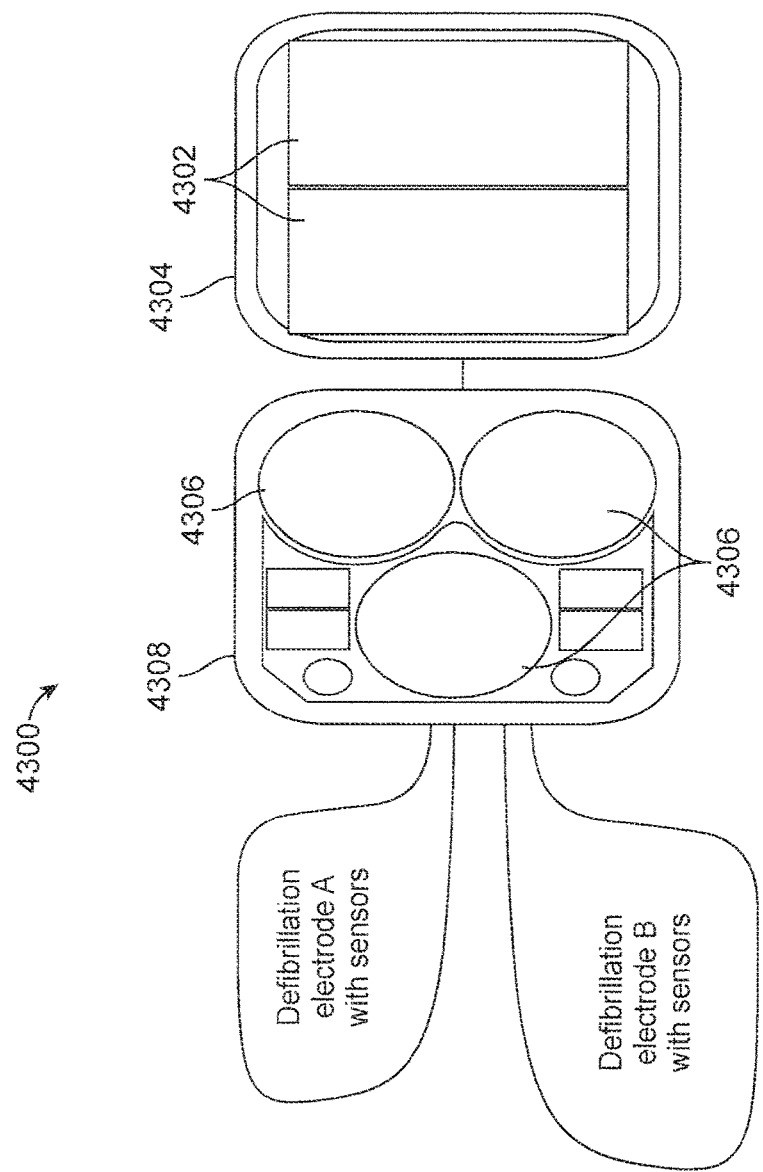
FIG. 43 illustrates a component layout for an embodiment of wearable defibrillators.

FIG. 43 illustrates a component layout for an embodiment of a wearable defibrillator 4300. The batteries 4302 are arranged in a first module 4304 or section of the wearable defibrillator that can be referred to as the low voltage module. The capacitors 4306 are arranged in a separate second module 4308 or section of the wearable defibrillator that can be referred to as the high voltage module. The defibrillation electrodes are in electrical communication with the high voltage module. The low voltage module can monitor the patient heart rate through the sensors and control the energy transfer when a shock needs to be administered. The batteries charge the capacitors in the high voltage module, which then send the electrical energy to the defibrillator pad electrodes to deliver the electrical therapy to the patient.

Figure 44A:
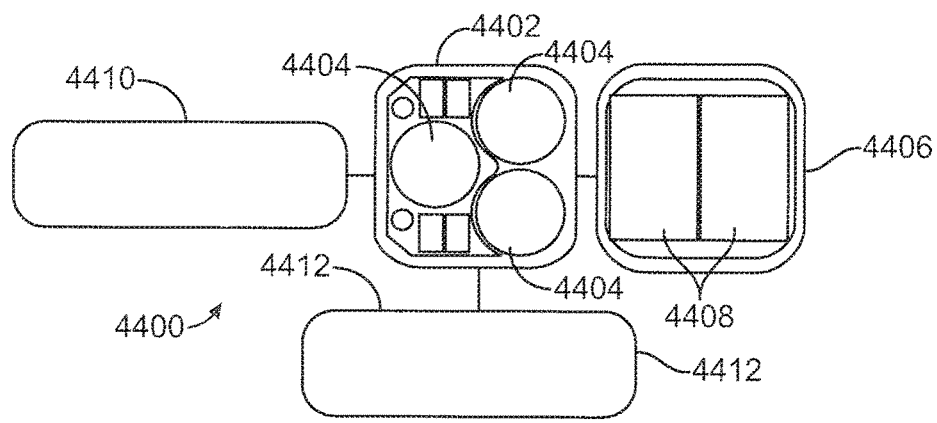
FIGS. 44A-44N illustrate various component layouts for embodiments of wearable defibrillators.
Figure 44B:
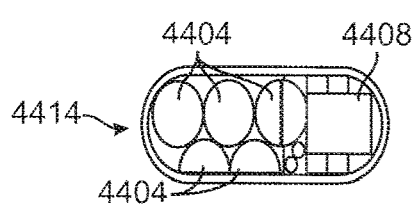
Figure 44C:
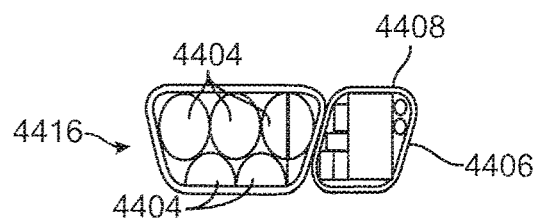
Figure 44D:
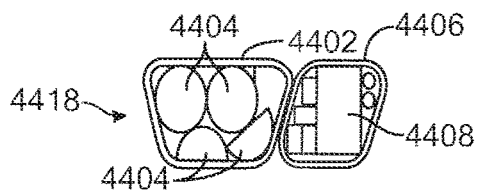
Figure 44E:
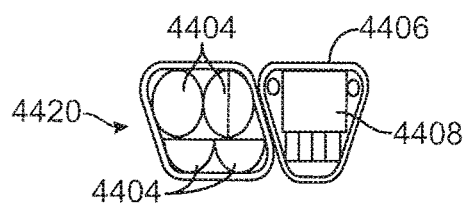
Figure 44F:
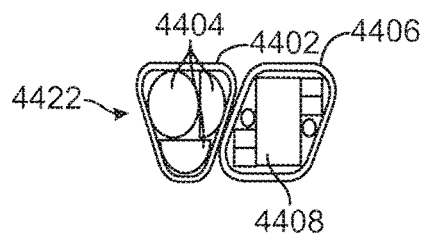
Figure 44G:
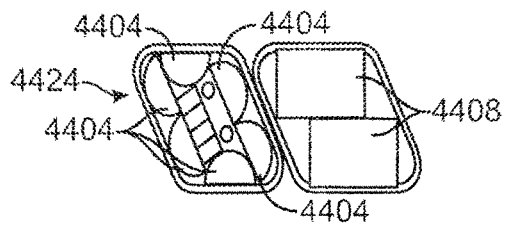
Figure 44H:
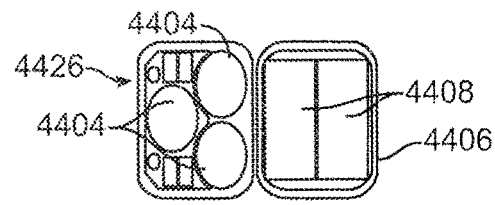
Figure 44I:
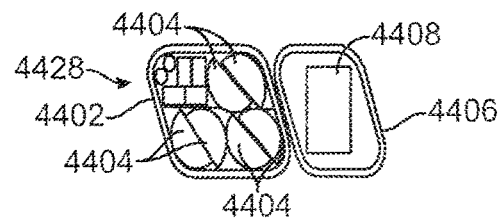
Figure 44J:
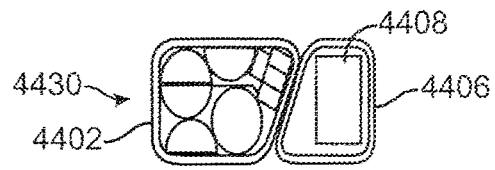
Figure 44K:
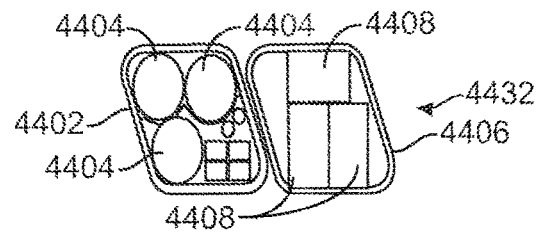
Figure 44L:
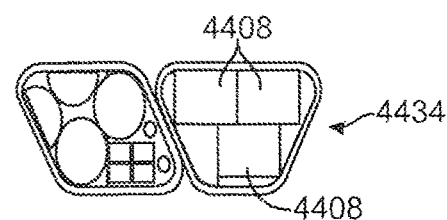
Figure 44M:
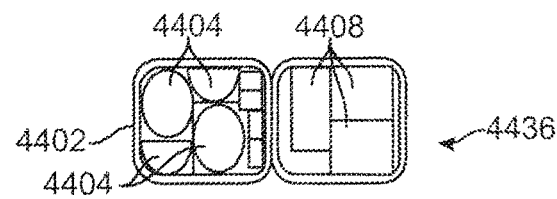
Figure 44N:
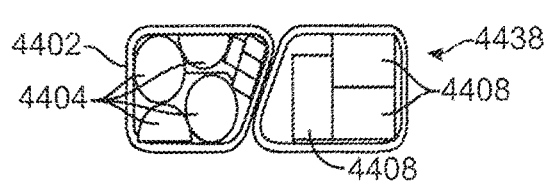

FIGS. 44A-44N illustrate various component layouts for embodiments of wearable defibrillators. FIG. 44A illustrates an embodiment of a wearable defibrillator 4400 with a high voltage module 4402 with capacitors 4404 and a low voltage module 4406 having batteries 4408. The high voltage module 4402 and capacitors 4404 are configured to deliver an electrical therapy via the defibrillator electrodes 4410, 4412. FIGS. 44A-44N illustrate different layouts (4414, 4416, 4418, 4420, 4422, 4424, 4426, 4428, 4430, 4432, 4434, 4436, and 4438) for the high voltage module 4402 and capacitors 4404 and the low voltage module 4406 and batteries 4408. The capacitors are configured in circular and semi-circular cross-sectional shapes. The capacitors are spread across the high voltage module and the batteries are arranged on the low voltage module. The duration of wear can be determined by balancing the weight of the device versus the area of adhesion to the body. FIG. 15 illustrates data for wear duration versus adhesive loading for various adhesive types and weights.

Figures 45A, 45B, 45C:
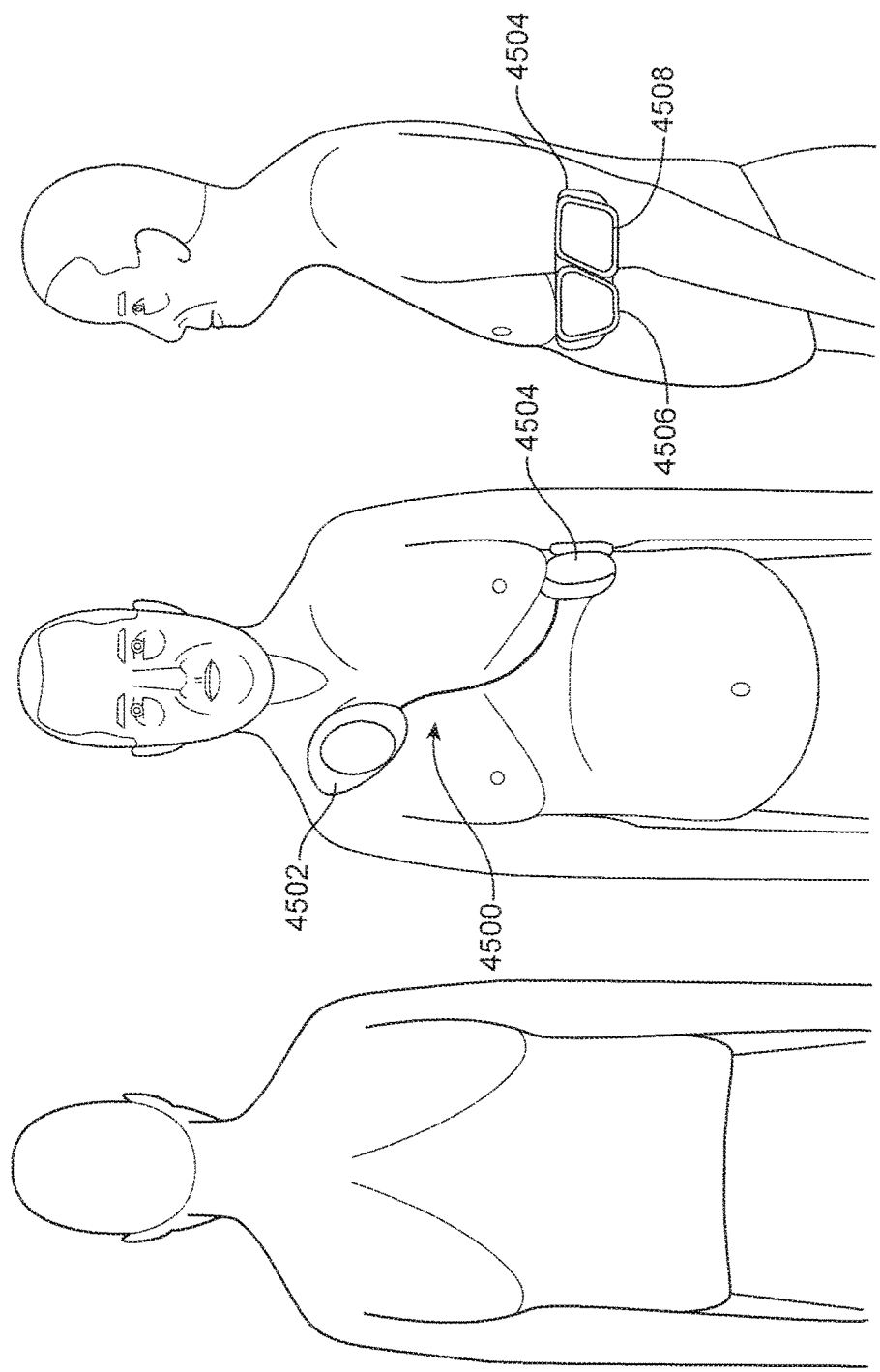
Figures 47A, 47B, 47C:
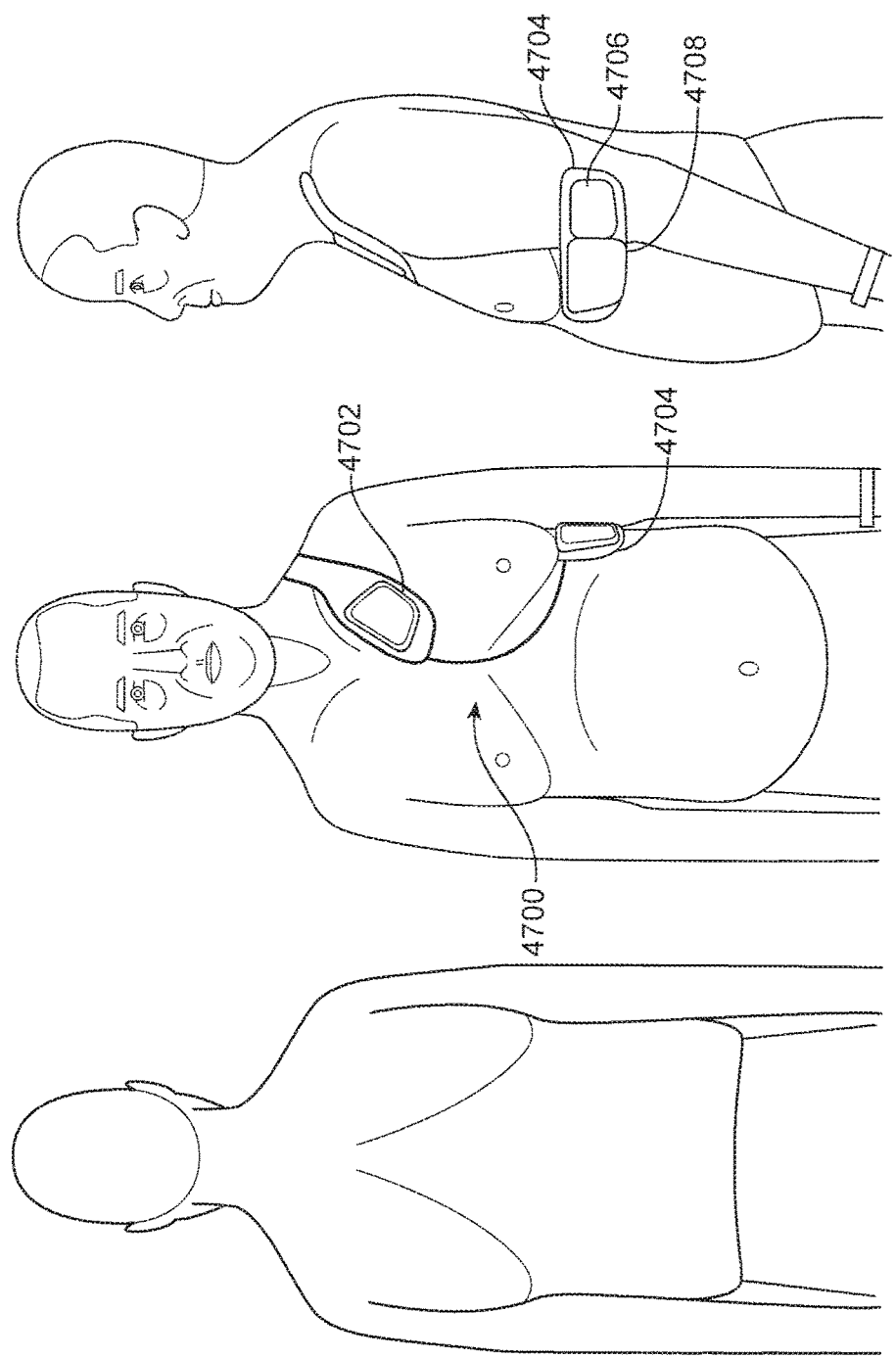
Figure 48C:
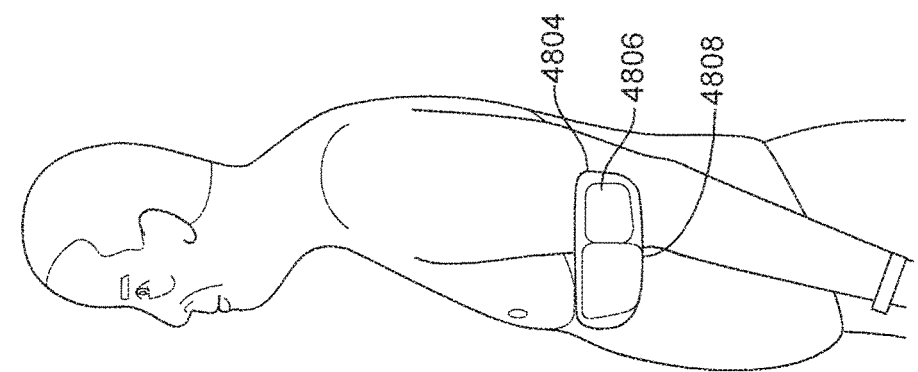
Figure 48B:
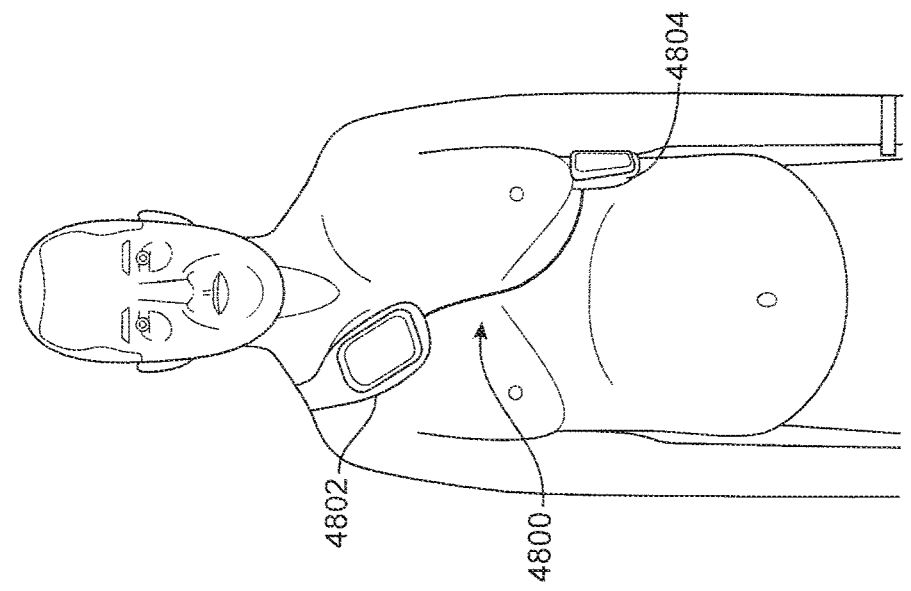
Figure 48A:
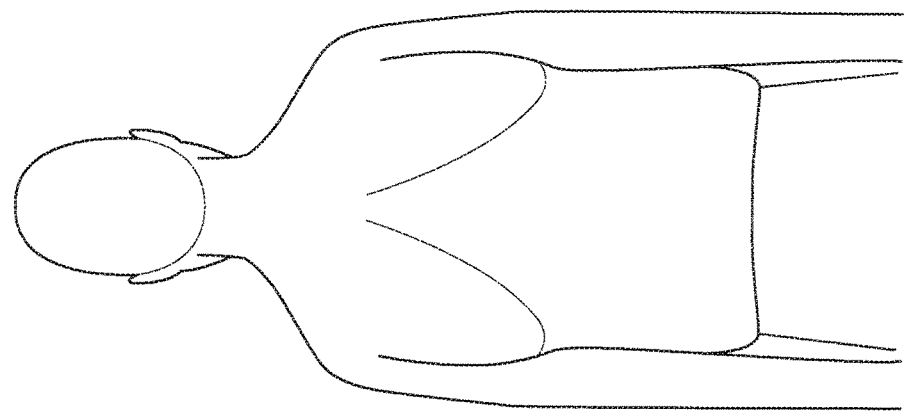

FIGS. 45A-48C illustrate various profiles and configurations of wearable defibrillators with an electrode on the upper chest of the patient and the electronics/battery and capacitor in separate pockets attached to the patient on the side of the patient under the arm. FIGS. 45A-45C illustrate a wearable defibrillator 4500 with an upper patch 4502 including a patient engagement substrate having a defibrillator pad electrode and ECG sensors and a lower patch 4504 including a patient engagement substrate having a defibrillator electrode and ECG sensors. The lower patch 4504 is supporting a first electronics module 4506 and a second electronics module 4508. FIGS. 46A-46C illustrate a wearable defibrillator 4600 with an upper patch 4602 including a patient engagement substrate having a defibrillator pad electrode and ECG sensors and a lower patch 4604 including a patient engagement substrate having a defibrillator electrode and ECG sensors. The lower patch 4604 is supporting a first electronics module 4606 and a second electronics module 4608. FIGS. 47A-47C illustrate a wearable defibrillator 4700 with an upper patch 4702 including a patient engagement substrate having a defibrillator pad electrode and ECG sensors and a lower patch 4704 including a patient engagement substrate having a defibrillator electrode and ECG sensors. The lower patch 4704 is supporting a first electronics module 4706 and a second electronics module 4708. The wearable defibrillator 4700 has an over the shoulder configuration. FIGS. 48A-48C illustrate a wearable defibrillator 4800 with an upper patch 4802 including a patient engagement substrate having a defibrillator pad electrode and ECG sensors and a lower patch 4804 including a patient engagement substrate having a defibrillator electrode and ECG sensors. The lower patch 4804 is supporting a first electronics module 4806 and a second electronics module 4808. The wearable defibrillator 4800 has an over the shoulder configuration.

FIGS. 49A-49D are pictures of a weighted model of a wearable defibrillator attached to a mannequin. FIGS. 49A-49D illustrate a wearable defibrillator 4900 with an upper patch 4902 including a patient engagement substrate having a defibrillator pad electrode and ECG sensors and a lower patch 4904 including a patient engagement substrate having a defibrillator electrode and ECG sensors. The lower patch 4904 is supporting a first electronics module 4906 and a second electronics module 4908. The first electronics module 4906 includes the battery 4910 and the second electronics module 4908 includes the capacitors 4912. One defibrillator electrode is attached to the upper chest of the mannequin and the capacitors, batteries, and second defibrillator electrode are adhered to the side of the mannequin's chest. The capacitors were modeled with 160 grams of weight and the battery section was modeled with 100 grams of weight. The adhesive supported the 260 gram weight on the mannequin's side.

FIGS. 50A-50D are pictures of a weighted model of a wearable defibrillator attached to a mannequin similar to FIGS. 49A-49D but with a different profile for the modules supporting the capacitors and battery sections of the device. FIGS. 50A-50D illustrate a wearable defibrillator 5000 with an upper patch 5002 including a patient engagement substrate having a defibrillator pad electrode and ECG sensors and a lower patch 5004 including a patient engagement substrate having a defibrillator electrode and ECG sensors. The lower patch 5004 is supporting a first electronics module 5006 and a second electronics module 5008. The first electronics module 5006 includes the battery 5010 and the second electronics module 5008 includes the capacitors 5012.

FIGS. 51A-51D are pictures of a weighted model of a wearable defibrillator 5100 attached to a mannequin. FIGS. 51A-51D illustrate a wearable defibrillator 5100 with an upper patch 5102 including a patient engagement substrate having a defibrillator pad electrode and ECG sensors, a lower patch 5104 including a patient engagement substrate having a defibrillator electrode and ECG sensors, and a second upper patch 5105. The second upper patch 5105 supports a first electronics module 5106. The lower patch 5104 is supporting a second electronics module 5108. The first electronics module 5106 includes the battery 5110 and the second electronics module 5108 includes the capacitors 5112. One defibrillator electrode is attached to the upper chest of the mannequin and a second defibrillator electrode is attached to the side of the mannequin. The battery and low voltage component model is also attached to the chest of the mannequin with a weight of 50 grams. The capacitor model is adhered to the side of the mannequin's chest with a weight of 160 grams.

FIGS. 52A-52D are pictures of a weighted model of a wearable defibrillator 5200 attached to a mannequin. FIGS. 52A-52D illustrate a wearable defibrillator 5200 with an upper patch 5202 including a patient engagement substrate having a defibrillator pad electrode and ECG sensors and a lower patch 5204 including a patient engagement substrate having a defibrillator electrode and ECG sensors. The lower patch 5204 is supporting a first electronics module 5206 and a second electronics module 5208. The first electronics module 5206 includes the battery 5210 and the second electronics module 5208 includes the capacitors 5212. One defibrillator electrode is attached to the upper chest of the mannequin and the capacitors, batteries, and second defibrillator electrode are adhered to the side of the mannequin's chest. The capacitors were modeled with 160 grams of weight and the battery section was modeled with 50 grams of weight.

Figures 53A, 53B, 53C, 53D:
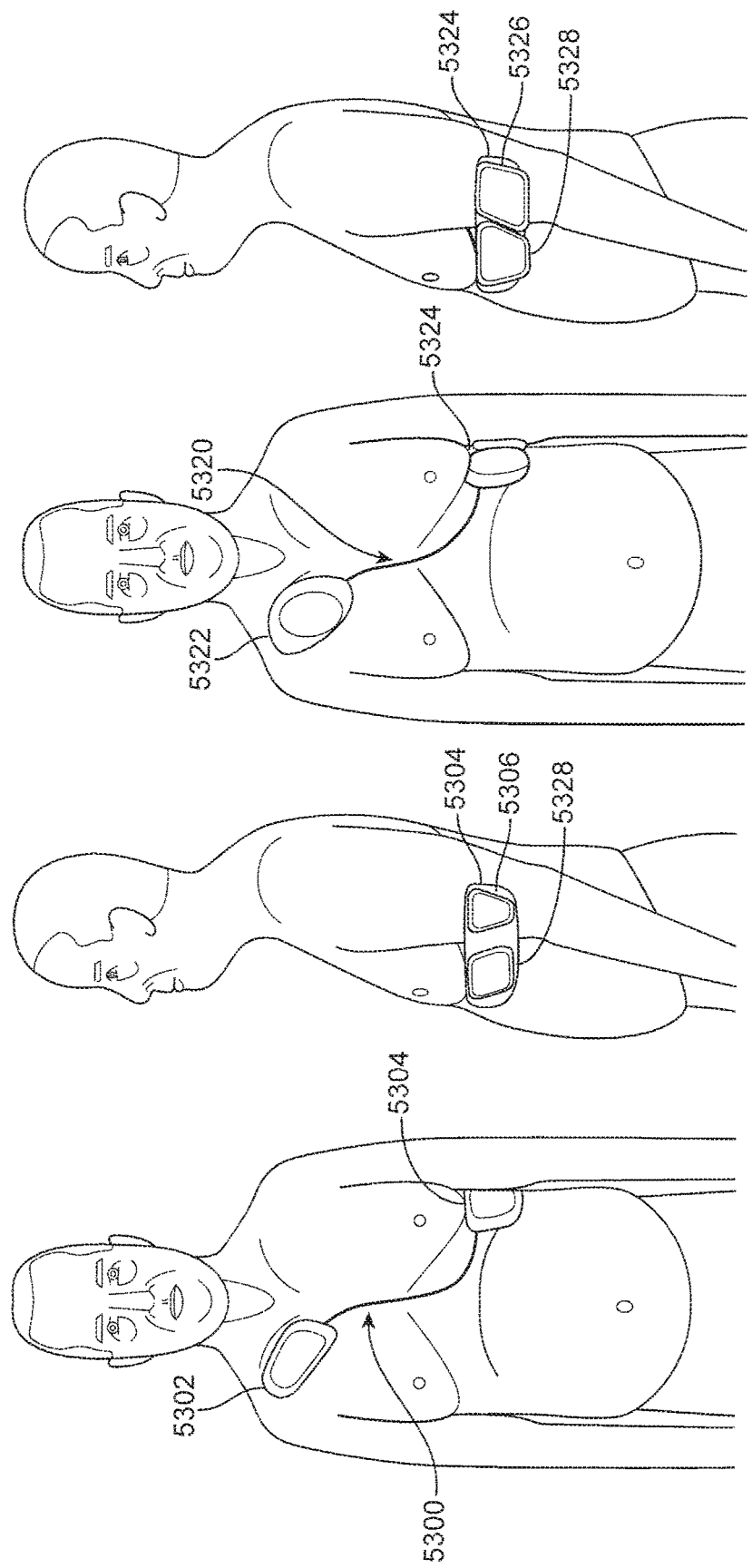

FIGS. 53A-53D illustrate two wearable defibrillators 5300 and 5320 with a patch attached to the chest with an electrode, capacitors, and battery supported on the patient's side under the arm. FIGS. 53A-53B illustrate a wearable defibrillator 5300 with an upper patch 5302 including a patient engagement substrate having a defibrillator pad electrode and ECG sensors and a lower patch 5304 including a patient engagement substrate having a defibrillator electrode and ECG sensors. The lower patch 5304 is supporting a first electronics module 5306 and a second electronics module 5308. FIGS. 53C-53D illustrate a wearable defibrillator 5320 with an upper patch 5322 including a defibrillator pad electrode and ECG sensors and a lower patch 5324 including a defibrillator electrode and ECG sensors. The lower patch 5324 is supporting a first electronics module 5326 and a second electronics module 5328.

FIGS. 54A-54D illustrate two configurations for a wearable defibrillator 5400, 5420. FIGS. 54A-54B illustrate a wearable defibrillator 5400 with an upper patch 5402 including a patient engagement substrate having a defibrillator pad electrode and ECG sensors and a lower patch 5404 including a patient engagement substrate having a defibrillator electrode and ECG sensors. The lower patch 5404 is supporting a first electronics module 5406 and a second electronics module 5408. FIGS. 53C-53D illustrate a wearable defibrillator 5420 with an upper patch 5422 including a patient engagement substrate having a defibrillator pad electrode and ECG sensors and a lower patch 5424 including a patient engagement substrate having a defibrillator electrode and ECG sensors. The lower patch 5424 is supporting a first electronics module 5426 and a second electronics module 5428. Each of the configurations supports the capacitors and the battery on the patient's side under the arm. The electrode is shown contacting either side of the chest and is in electrical communication with the capacitors. The wearable defibrillator can include a shoulder support strap that contacts the shoulder or that goes over the shoulder and down the patient's back to connect with the upper patch with the capacitor and battery sections.

Figure 55D:
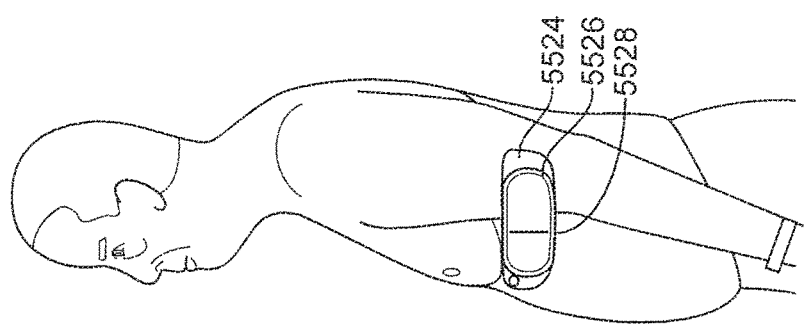
FIGS. 55A-55D show embodiments of wearable defibrillators with an upper patch and a lower patch.
Figure 55C:
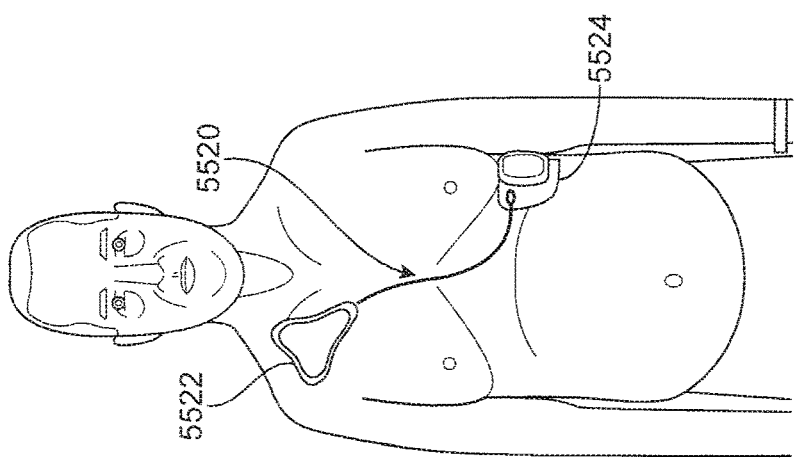
Figure 55B:
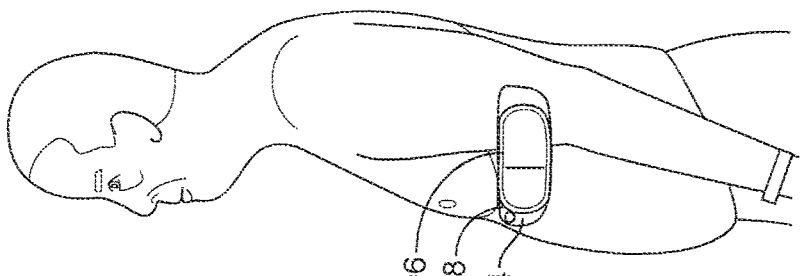
Figure 55A:
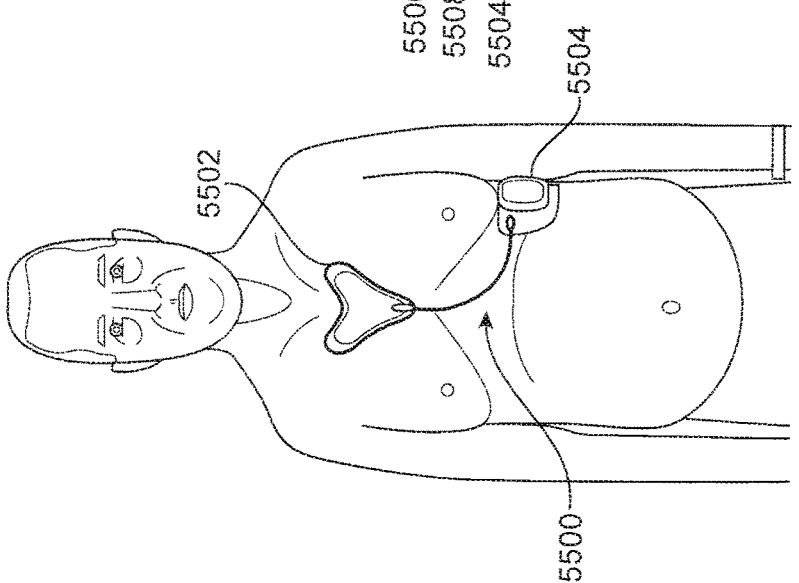

FIGS. 55A-55D illustrate two configurations for a wearable defibrillator 5500, 5520. FIGS. 55A-55B illustrate a wearable defibrillator 5500 with an upper patch 5502 including a patient engagement substrate having a defibrillator pad electrode and ECG sensors and a lower patch 5504 including a patient engagement substrate having a defibrillator electrode and ECG sensors. The lower patch 5504 is supporting a first electronics module 5506 and a second electronics module 5508. FIGS. 53C-53D illustrate a wearable defibrillator 5520 with an upper patch 5522 including a patient engagement substrate having a defibrillator pad electrode and ECG sensors and a lower patch 5524 including a patient engagement substrate having a defibrillator electrode and ECG sensors. The lower patch 5524 is supporting a first electronics module 5526 and a second electronics module 5528. Each of the configurations supports the capacitors, the battery, and an electrode on the patient's side under the arm. The upper patch has a triangular configuration and can be attached to the patient's sternum or upper chest as illustrated.

FIGS. 56A-56H3 illustrate additional embodiments of wearable defibrillators. FIG. 56A illustrates a wearable defibrillator 5600 with an upper patch 5602 having a chest electrode and with higher profile components (e.g., capacitors and batteries) located on a lower patch 5604 on the patient's side under the arm.

FIGS. 56B1-56B3 illustrate a wearable defibrillator 5610 with an over the shoulder support. The over the shoulder support allows the shoulder to support additional device weight. Defibrillator electrodes can be on the upper patch 5612 and lower patch 5614. The battery and electronics can be on a front pocket of the upper patch 5612 and the capacitors and electrode are illustrated on the back pocket 5616 of the device. Any remaining high profile components could be supported on the side of the user.

FIG. 56C illustrates a wearable defibrillator 5620 with an upper patch 5622 having a chest electrode and with higher profile components (e.g., capacitors and batteries) located on a lower patch 5624 on the patient's side under the arm. FIGS. 56D1-56D3 illustrate a wearable defibrillator 5630 with a support 5632 around the neck of the patient. The around the neck support 5632 could be used to support the weight of the electronics components on the back of the patient 5634 and the electrode components on the front of the patient 5636. Additional components can be supported on the patient's side 56388.

FIGS. 56E1-56E3 illustrate a wearable defibrillator 5640 that can be worn around the neck to support an electrode 5642 on the back and support an electrode and capacitor and batteries in front chest pockets 5644, 5646. FIGS. 56F1-56F3 illustrate a wearable defibrillator 5650 with a front chest pocket 5652 supporting an electrode and one of the capacitor/battery and a second pocket 5654 on the back supporting an electrode and the other of the capacitor/battery. FIGS. 56G1-56G3 illustrate a wearable defibrillator 5660 with two chest pockets 5662, 5664, one for the electrode and the other for the capacitor/battery along with a side pocket 5666 for supporting the other of the capacitor/battery. The defibrillator in FIGS. 56G1-56G3 also has an optional chest strap 5668 to provide additional device support. FIGS. 56H1-56H3 illustrate a setup similar to FIGS. 56G1-56G3 but without the chest strap. FIGS. 56H1-56H3 illustrate a wearable defibrillator 5670 with two chest pockets 5672, 5674, one for the electrode and the other for the capacitor/battery along with a side pocket 5676 for supporting the other of the capacitor/battery.

FIGS. 57A-57E illustrate a wearable defibrillator system including a wearable defibrillator 5700 and a bracelet 5702. The wearable defibrillator includes a connected capacitor bank 5704 and electronics/battery compartment 5706 that is supported on the patient's side by an adhesive pocket 5708. A second electrode 5710 is supported by the side adhesive pocket 5708. A chest pocket 5712 supports the first electrode 5714. The adhesive pockets are replaceable. The bracelet communicates 5702 wirelessly with the wearable defibrillator 5700.

FIGS. 58A-58C illustrate a wearable defibrillator 5800 including replaceable adhesive electrode assemblies 5802. The electrode assembly 5802 includes a pocket 5804 for supporting the capacitor 5806, electronics, and battery 5808. The electrode assembly includes a plug 5810 to connect the capacitors 5806 to the electrodes. After a set period of time, e.g., 10-14 days the adhesive electrode assembly 5802 is replaced with the capacitor, electronics, and battery unit installed in the new adhesive electrode assembly.

FIGS. 59A-59E illustrate a wearable defibrillator system 5900 including connected defibrillator pads 5902, 5904, capacitors 5906, and battery/electronics components 5908. The system also includes adhesive patches and pockets 5910, 5912, 5914 configured to support the defibrillator pads, capacitors, and battery/electronics components. The adhesive patches and pockets can be replaced.

FIGS. 60A-60D illustrate a wearable defibrillator 6000 with a flexible hinge 6002 between the capacitors 6006 and the electronics/battery components 6004. The flexible hinge 6002 can make the device more comfortable and less restrictive to wear. The capacitors 6006 and electronics/battery 6004 components can be received within an adhesive pocket 6008 including the electrodes 6010.

FIGS. 61A-61B illustrate a wearable defibrillator 6100 with the electronics and battery component 6102 connected to the capacitors 6104 by a bridge 6106. The defibrillator pad electrodes 6108, 6110 are receivable within adhesive pouches 6112, 6114, respectively. The electronics component 6102 and capacitors 6104 are also received by a pouch 6116.

FIGS. 62A-62E illustrate a wearable defibrillator 6200 with a lower patch 6202 supporting a capacitor module 6204 and a battery module 6206. The capacitor module 6204 includes capacitors 6208 and the battery module 6206 includes a battery 6210. The capacitor module 6204 and battery/electronics module 6206 are contained within waterproof enclosures 6212, 6214 on a lower patch 6202. The electronics/battery and capacitor components have trapezoidal foot prints. The lower patch 6202 includes a conductive material 6216 molded into the flexible pad of the lower patch 6202. The lower patch 6220 has a conductive material 6222 connected to the housing 6224 that is separate from the flexible adhesive portion of the lower patch 6220.

FIGS. 63A-63E are similar to FIGS. 62A-62E but with different foot prints for the electronics/battery and capacitor components. FIGS. 63A-63E illustrate a wearable defibrillator 6300 with a lower patch 6302 supporting a capacitor module 6304 and a battery module 6306. The capacitor module 6304 includes capacitors 6308 and the battery module 6306 includes a battery 6310. The capacitor module 6304 and battery/electronics module 6306 are contained within enclosures 6312, 6314 on a lower patch 6302. The lower patch 6302 has a conductive material 6316 connected to the housing 6318 that is separate from the flexible adhesive portion of the lower patch 6302. The lower patch 6322 includes a conductive material 6324 molded into the flexible pad of the lower patch 6322. The lower patch 6322 includes a flex point 6326 between the enclosures 6312, 6314.

FIGS. 64A-64F illustrate a wearable defibrillator similar to the devices depicted in FIGS. 62A-62E and 63A-63E but with a slit or cutout 6450 between the electronics/battery and capacitor components. FIGS. 64A-64F illustrate a wearable defibrillator 6400 with a lower patch 6402 supporting a capacitor module 6404 and a battery module 6406. The capacitor module 6404 includes capacitors 6408 and the battery module 6406 includes a battery 6410. The capacitor module 6404 and battery/electronics module 6406 are contained within enclosures 6412, 6414 on a lower patch 6402. The lower patch 6402 includes a conductive material 6416 molded into the flexible pad of the lower patch 6402 that is connected to the defibrillator pad electrode 6418 of the upper pad 6419. The lower patch 6422 has a conductive material 6424 connected to the housing 6426 that is separate from the flexible adhesive portion of the lower patch 6422. The lower patches 6402, 6422 each include a slit 6450 between the enclosures 6412, 6414 to improve the flexibility of the device.

Figure 65:
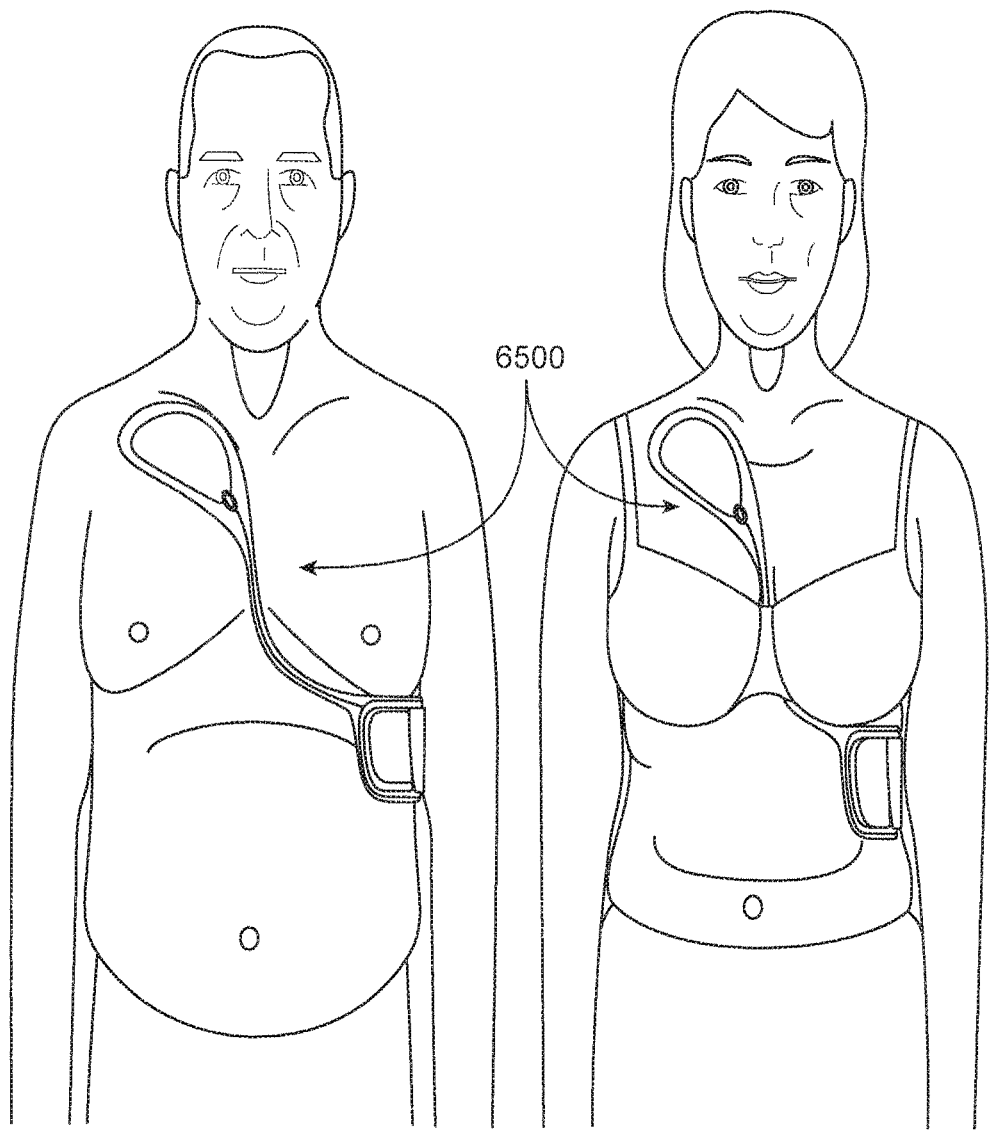
Figure 66:
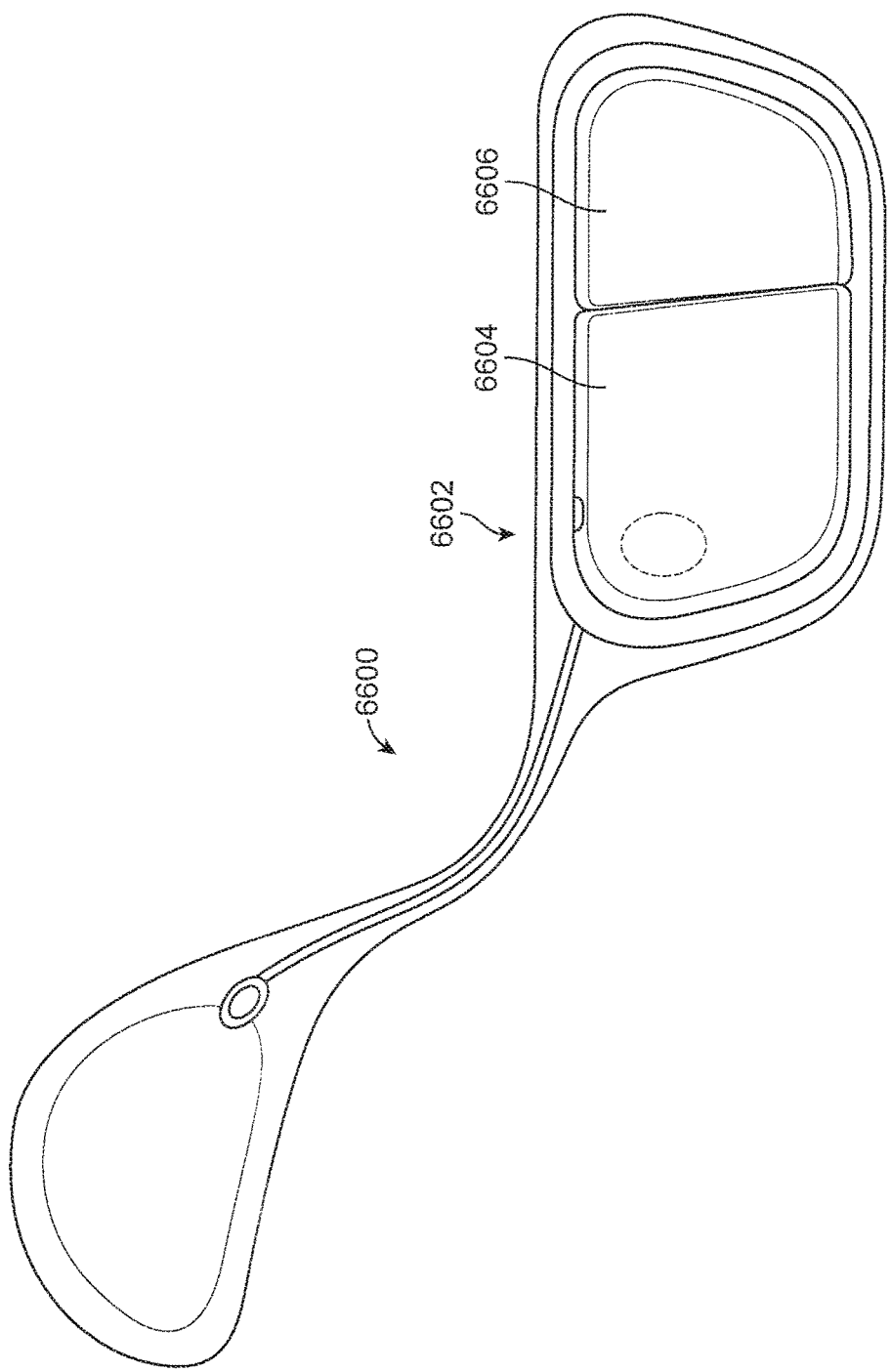

FIGS. 65-70H illustrate wearable defibrillators with various support designs and configurations. FIG. 65 illustrates a gender neutral wearable defibrillator 6500 on a male and female patient. FIG. 66 illustrates a wearable defibrillator 6600 with a side support/patch 6602 for second electrode, the capacitors 6604, and the battery/electronics 6606. FIGS. 67A-67H illustrate additional designs for the foot print of the upper patch (6702, 6706, 6710, and 6714) and lower patch/side support (6704, 6708, 6712, 6716) to support the capacitors and battery/electronics components.

Figures 68A, 68B:
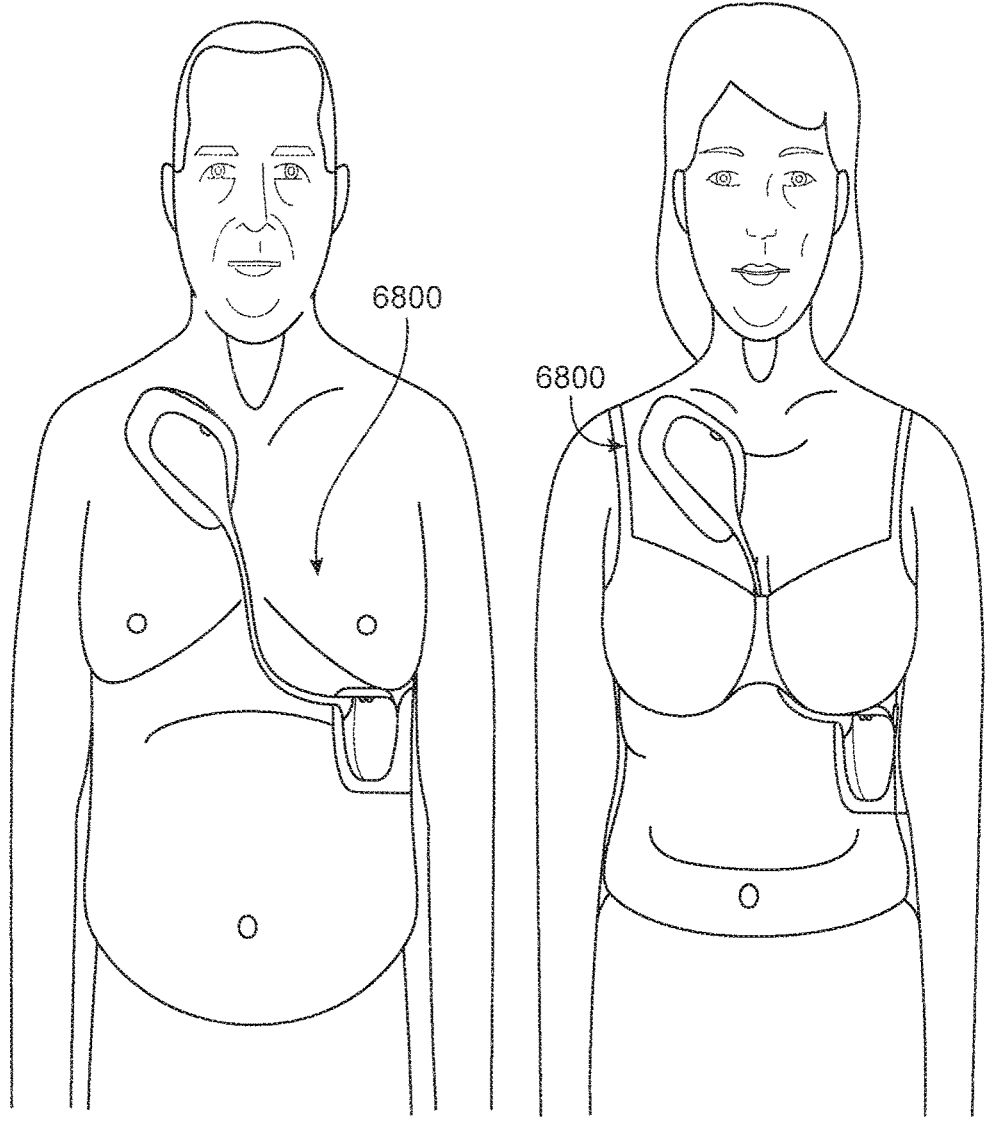
FIGS. 68A-68B illustrate an embodiment of a wearable defibrillator on a male and a female patient.
Figure 69:
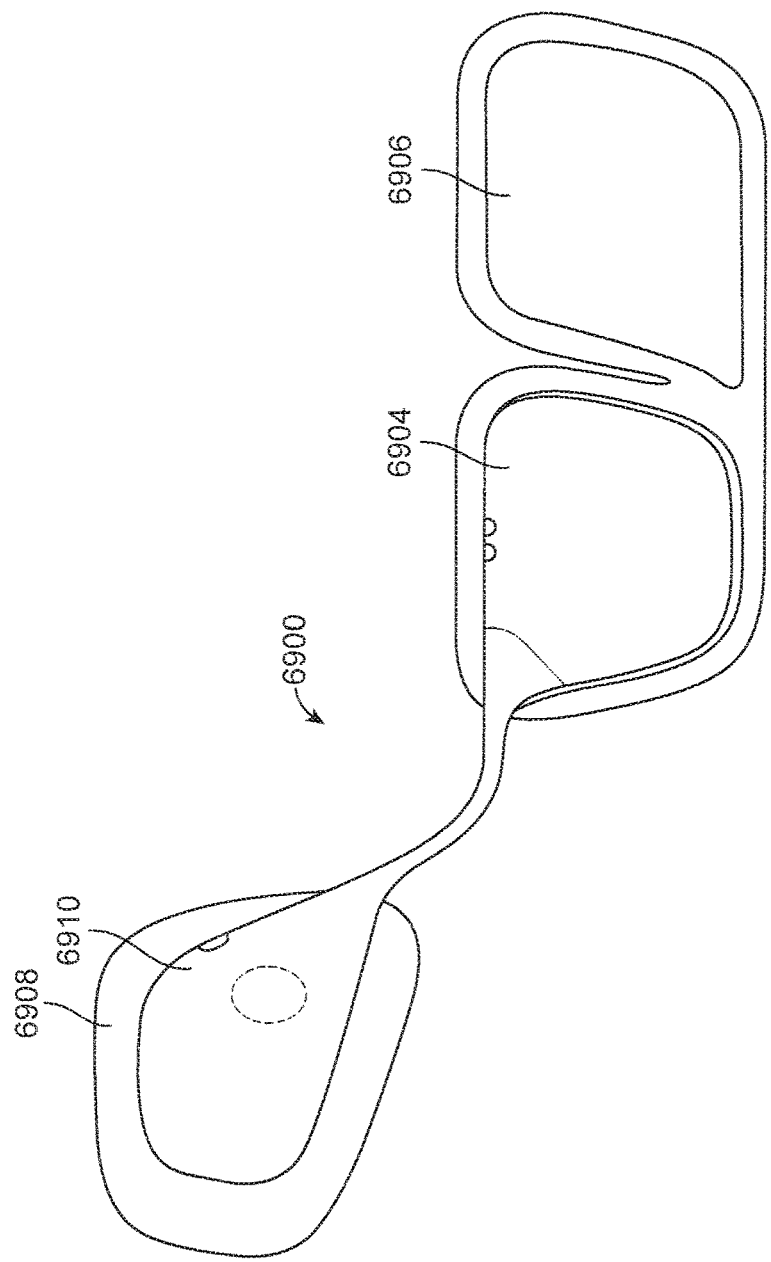

FIGS. 68A-69 illustrate another embodiment of a wearable defibrillator with the battery/electronics component supported on the upper chest of the patient. FIGS. 68A-68B illustrate the wearable defibrillator 6800 on a male and a female patient. The wearable defibrillator 6800 includes replaceable adhesive patches. The side support is configured to support the capacitor components. FIG. 69 illustrates a wearable defibrillator 6900 with a lower patch 6902 supporting a capacitor module 6904 and defibrillator pad electrode 6906. The upper patch 6908 supports the low voltage module 6910 and a second defibrillator pad electrode.

FIGS. 70A-70H illustrate additional foot prints for the upper patch (7002, 7006, 7010, 7014) and lower patch (7004, 7008, 7012, 7016).

Figures 71A, 71B:
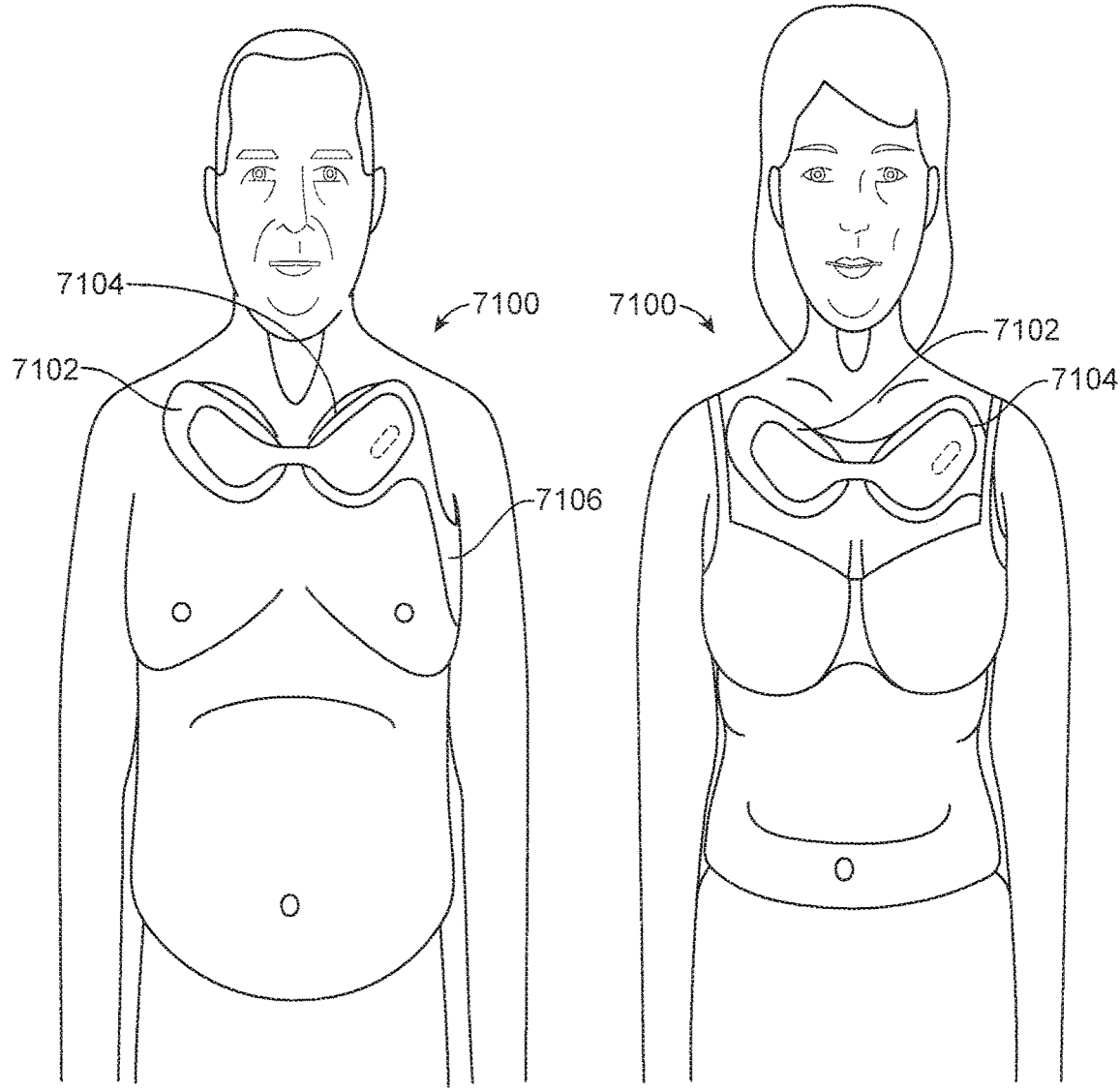
FIGS. 71A-71B illustrate a wearable defibrillator with two chest pockets and a side pocket on a male and a female patient.
Figure 72:
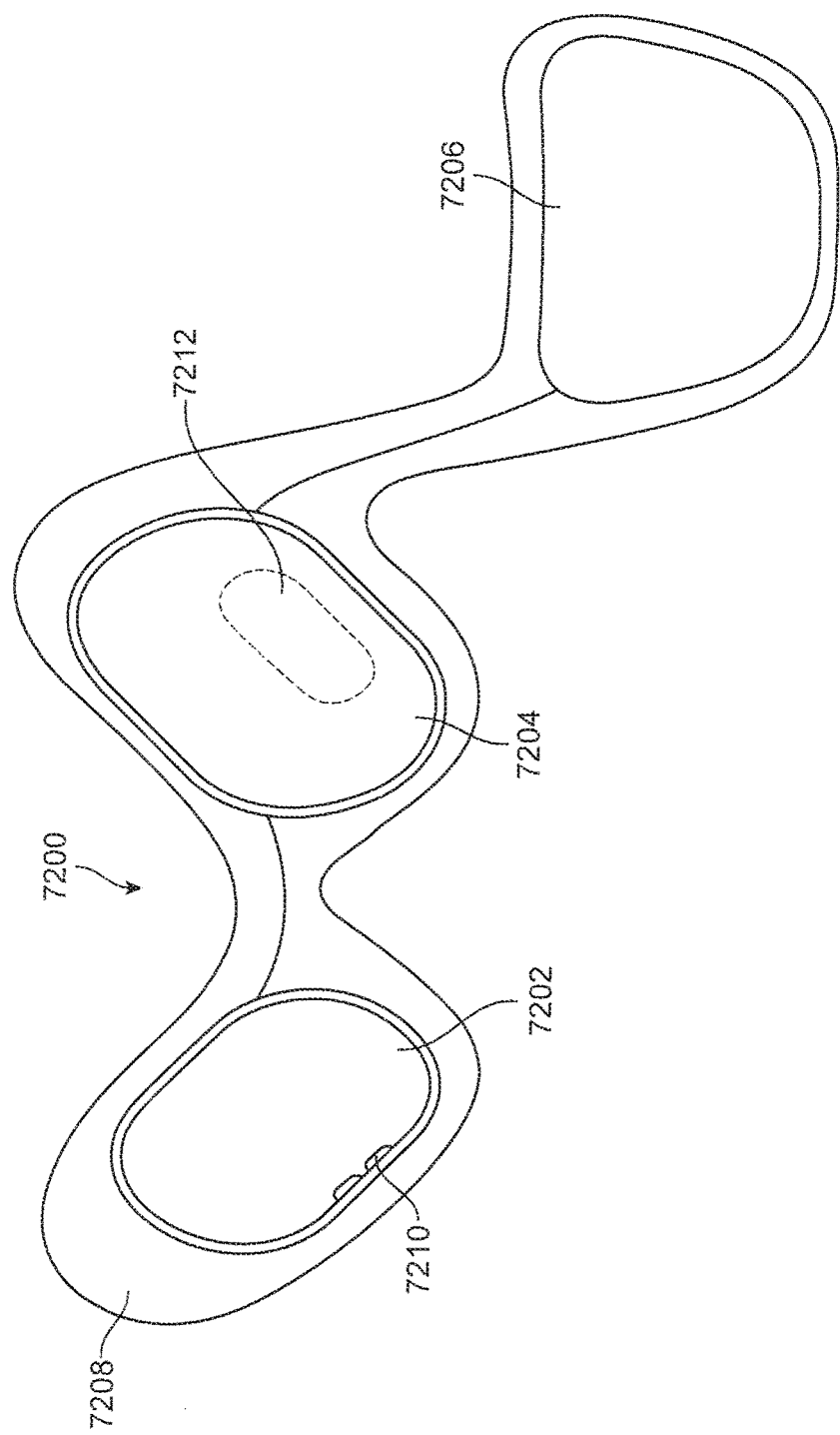
Figure 73B:
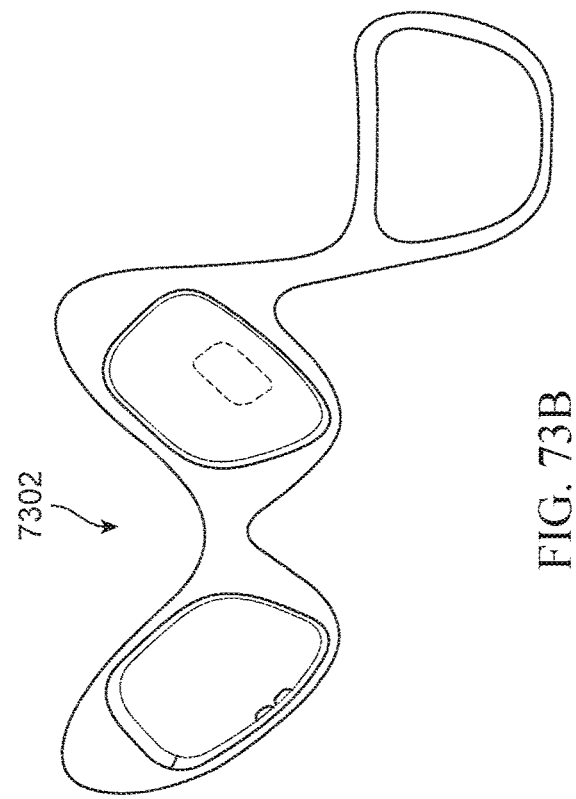
Figure 73A:
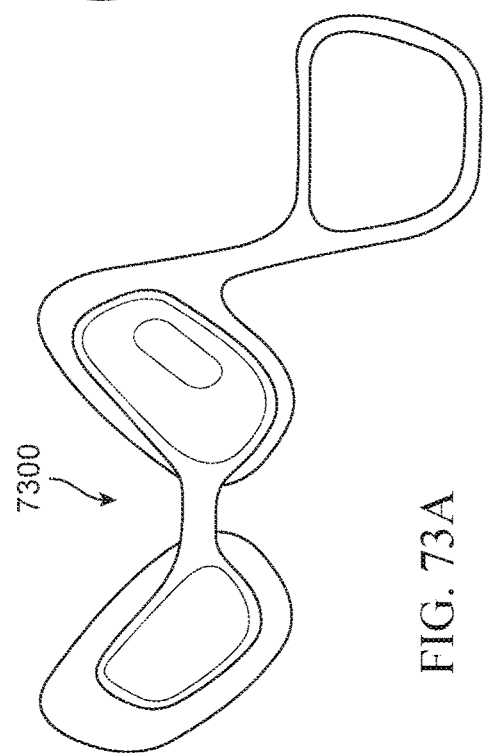
Figure 74:
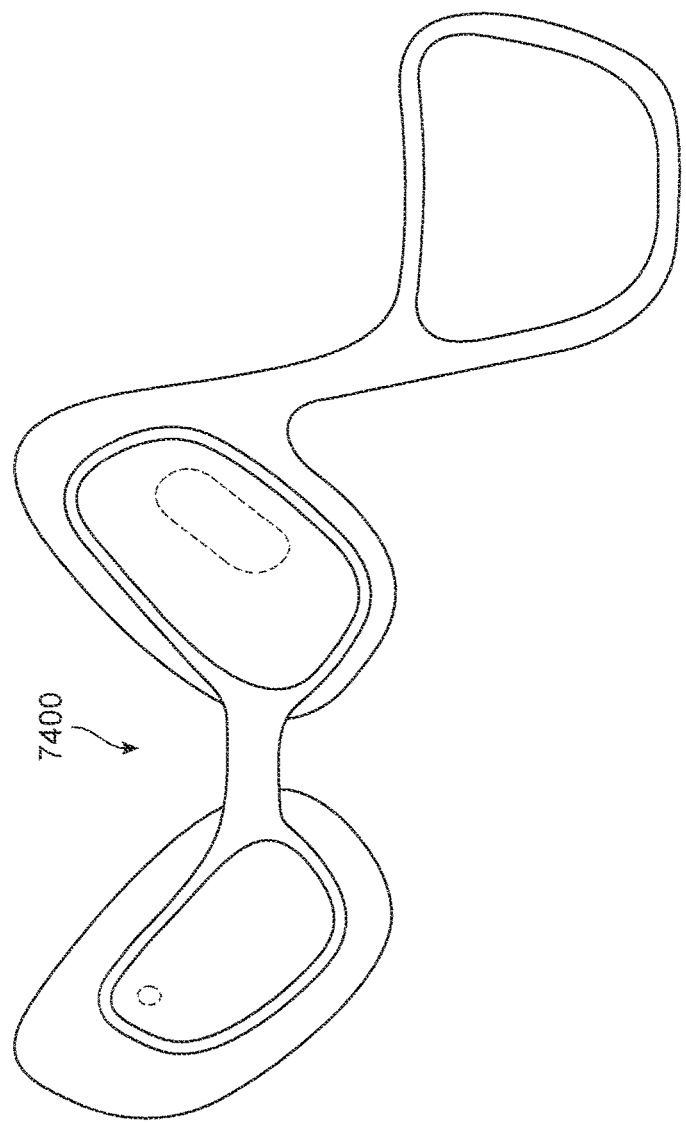

FIGS. 71A-74 illustrate wearable defibrillators with two chest pockets and a side pocket. FIGS. 71A-71B illustrate a wearable defibrillator 7100 with a first chest pocket 7102 and a second chest pocket 7104 and a side electrode 7106. A first chest pocket is configured to support the defibrillator electrode and electronics/battery. The second chest pocket is configured to support the capacitor components. The second defibrillator electrode can be located on the side of the patient. FIG. 72 illustrates an embodiment of a wearable defibrillator 7200 with a low voltage module 7202, high voltage module 7204, first defibrillator electrode 7206, second defibrillator electrode 7208, status indicator 7210, and capacitive switch 7212. FIGS. 73A-74 illustrate embodiments of wearable defibrillators 7300, 7302, and 7400 that are similar to 7200 but with different profiles to conform to the body.

Figure 75:
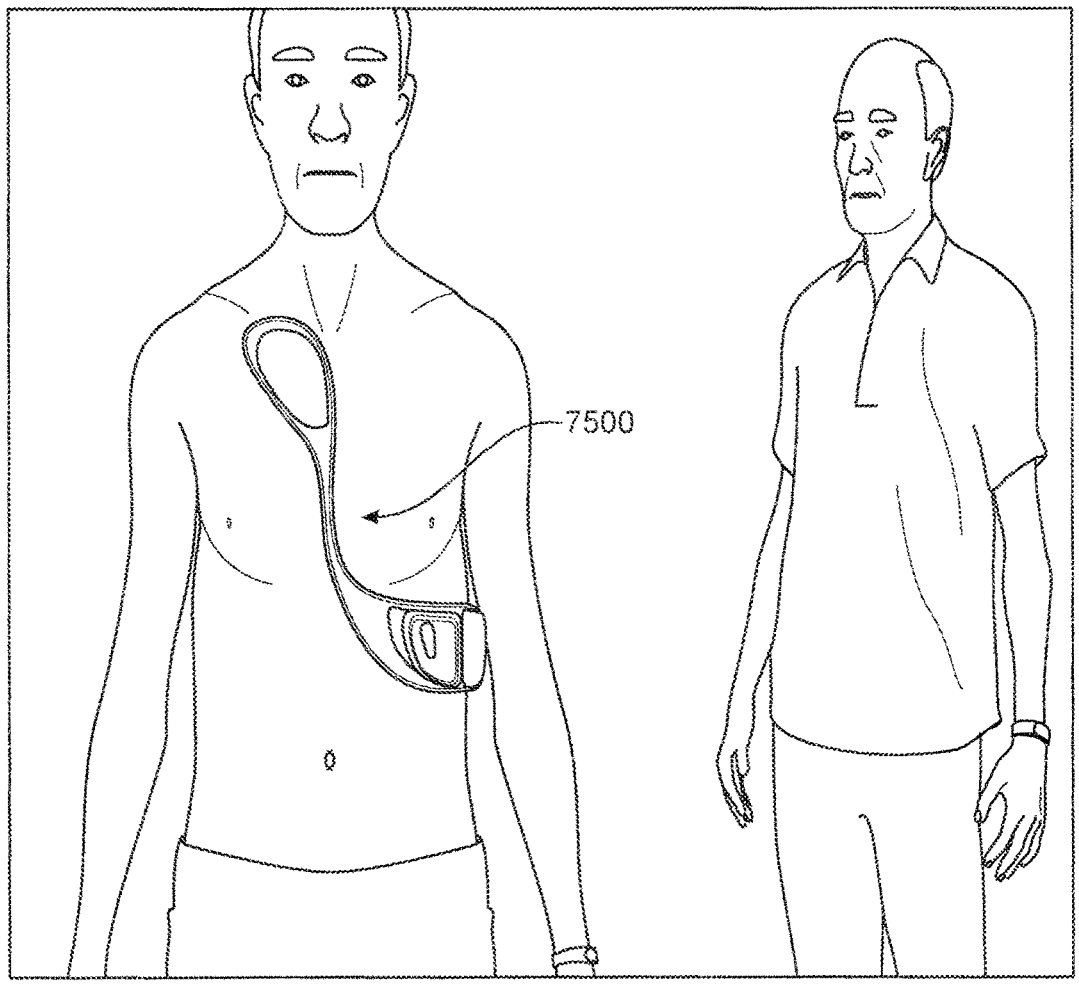
FIGS. 75-76 illustrate various embodiments of wearable defibrillators.
Figure 76:
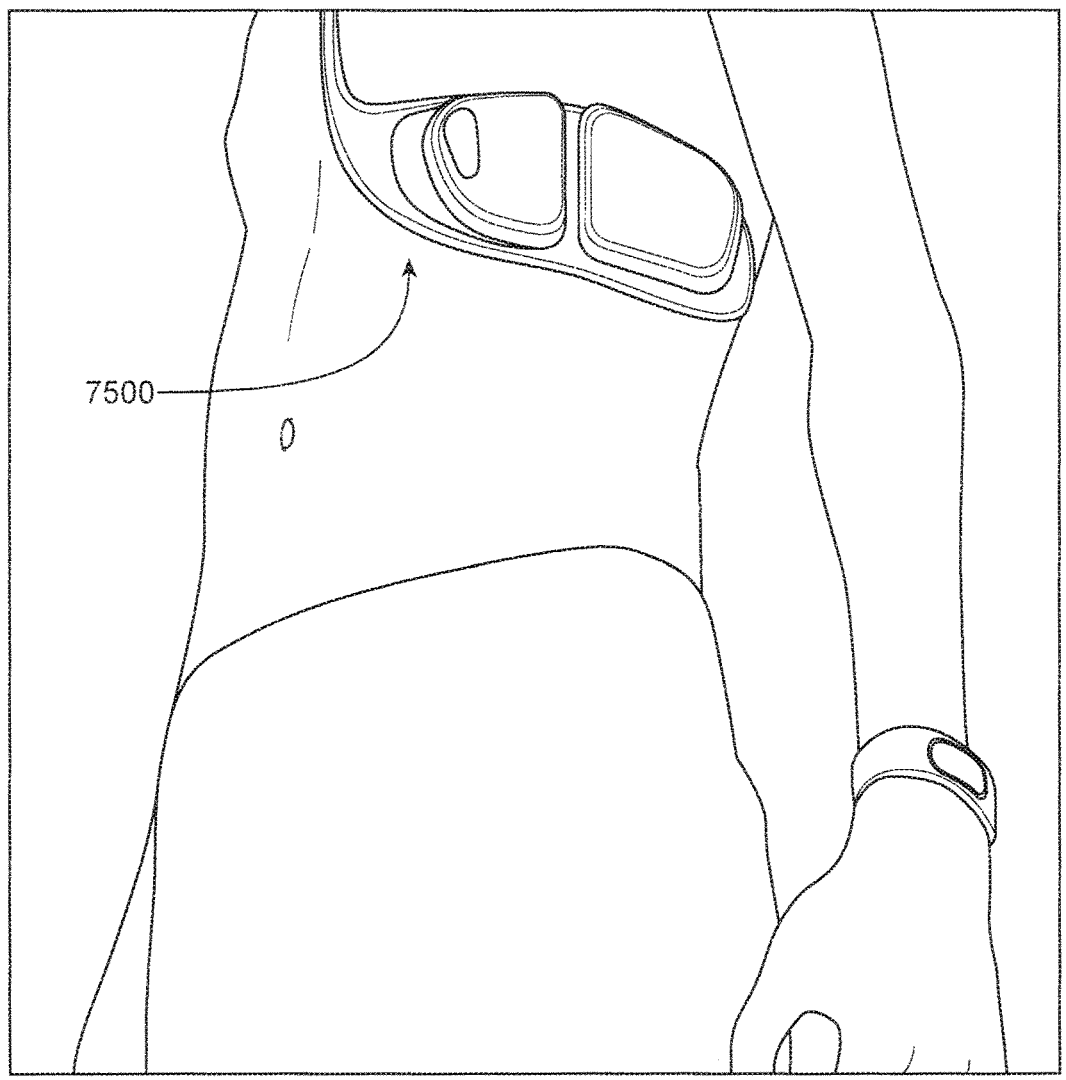

FIGS. 75-76 illustrate various views of a patient wearing an embodiment of wearable defibrillator 7500.

Figure 77:
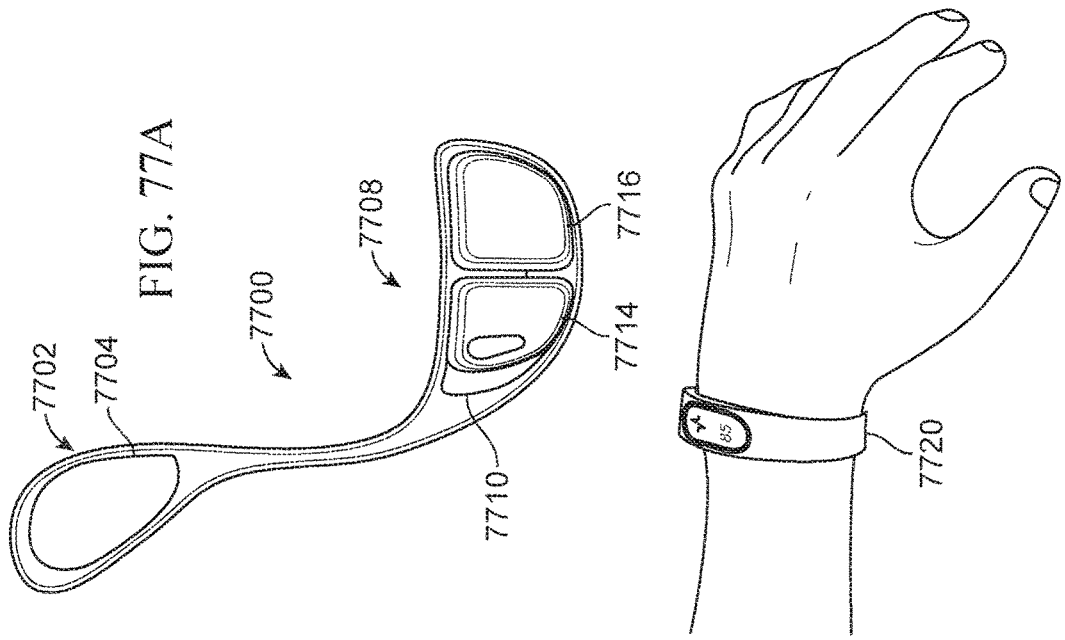
Figure 78:
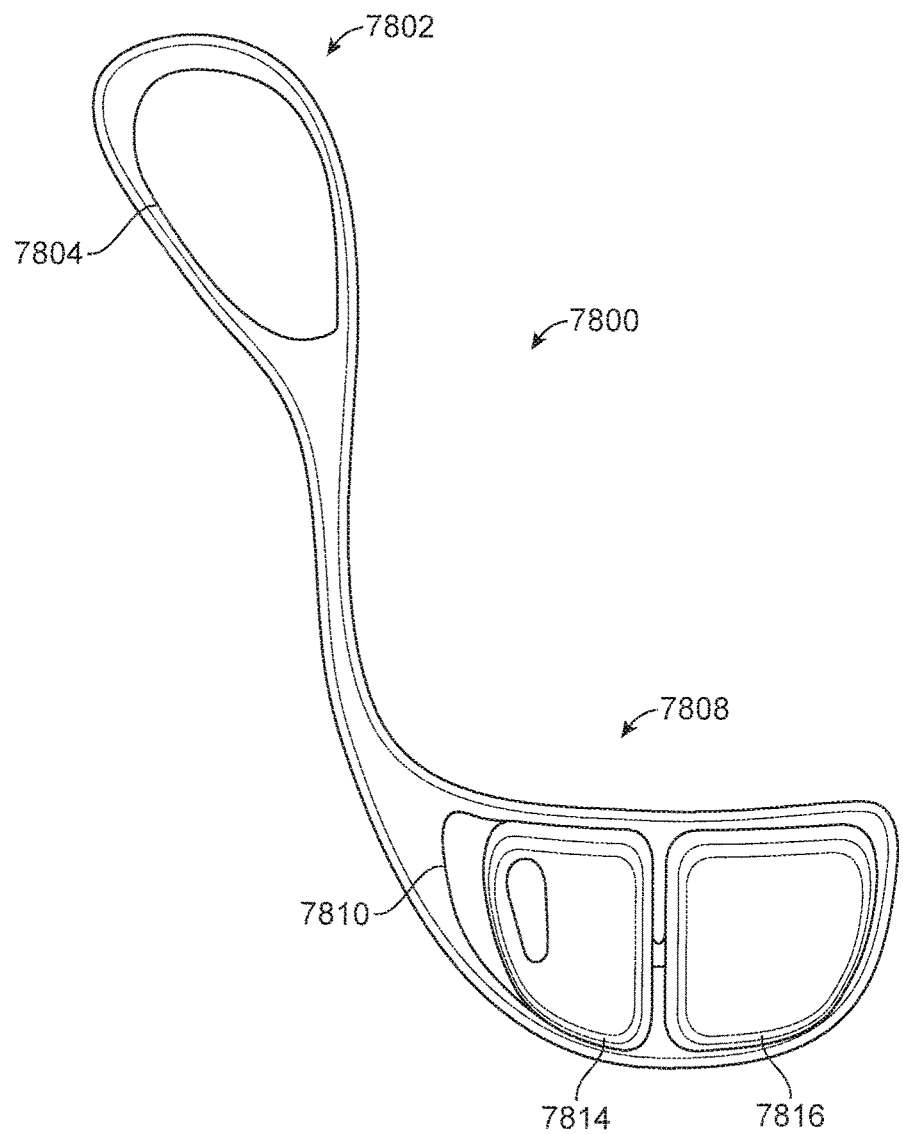

FIGS. 77A-78 illustrate various features of an embodiment of a wearable defibrillator. FIGS. 77A-77C illustrate a wearable defibrillator 7700 with an upper patch 7702 including a defibrillator pad electrode 7704 and ECG sensors 7706 and a lower patch 7708 including a defibrillator electrode 7710 and ECG sensors 7712. The lower patch 7708 is supporting a first electronics module 7714 and a second electronics module 7716. A bracelet 7720 can transmit data to the wearable defibrillator 7700. FIG. 78 illustrates a wearable defibrillator 7800 with an upper patch 7802 including a defibrillator pad electrode 7804 and ECG sensors and a lower patch 7808 including a defibrillator electrode 7810 and ECG sensors. The lower patch 7808 is supporting a first electronics module 7814 and a second electronics module 7816.

FIGS. 79A-80 illustrate embodiments of a wearable bracelet that can be used with the wearable defibrillators disclosed herein. FIGS. 79A-79D show a bracelet 7900 that can be used with any of the wearable defibrillators disclosed herein. The bracelet 7900 can communicate with the wearable defibrillator. The bracelet 7900 can generate an alert on the display 7902 prior to a shock. The display 7904 can be deactivated by touching the capacitive display. Display 7906 illustrates vital signs for the patient wearing a wearable defibrillator. FIG. 80 illustrates a bracelet 8000 with a touch display 8002 sized for a male wearer. FIG. 80 illustrates a bracelet 8005 with a touch display 8007 sized for a female wearer.

Figure 81A:
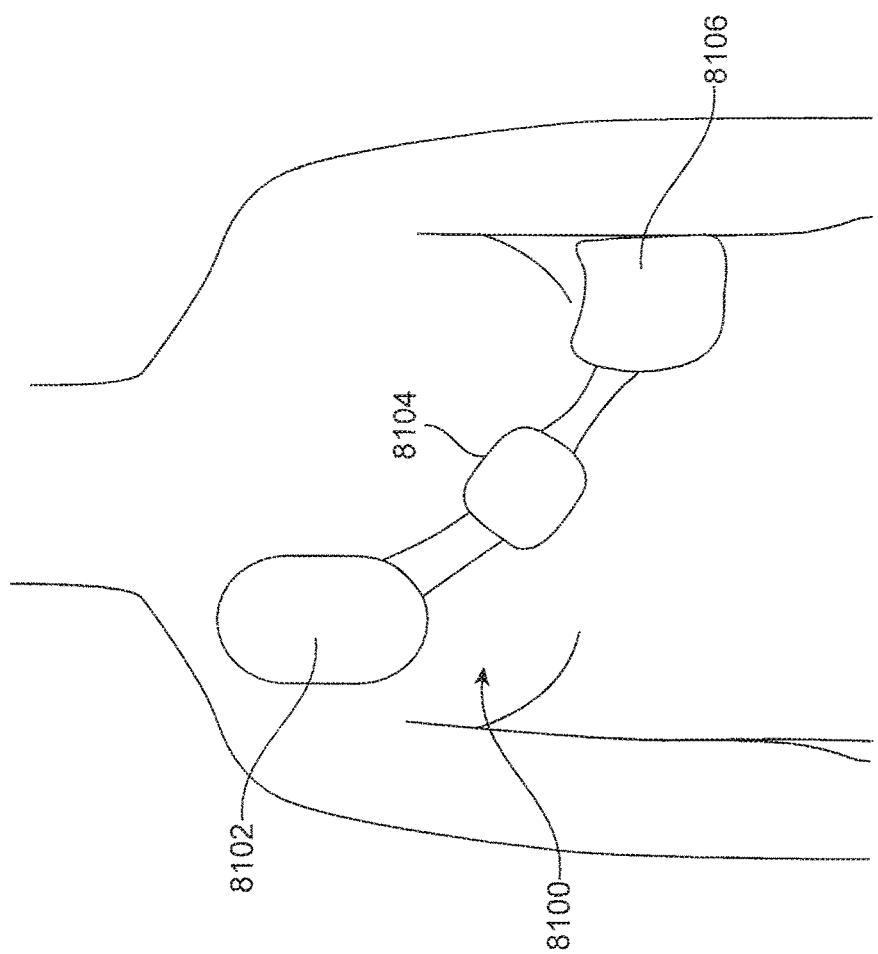
FIG. 81A illustrates a schematic sketch of a wearable defibrillator in accordance with some embodiments.
Figure 83A:
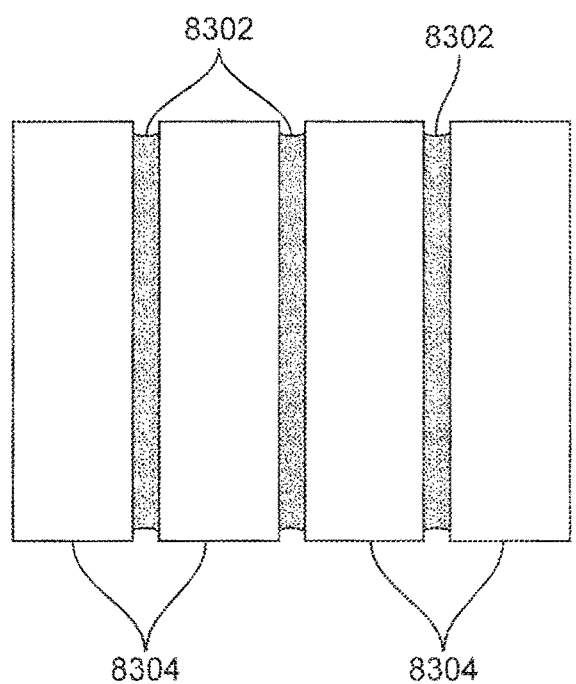
FIGS. 83A-83D illustrate cross-sectional and top views of a wearable defibrillator with various configurations of interconnect structures in accordance with some embodiments.
Figure 83B:
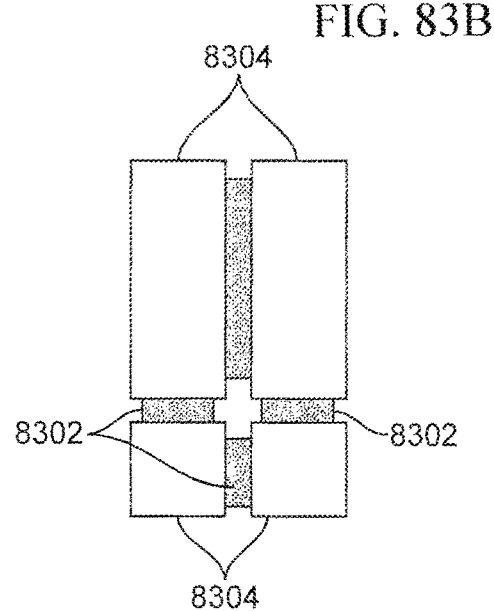
Figure 83C:
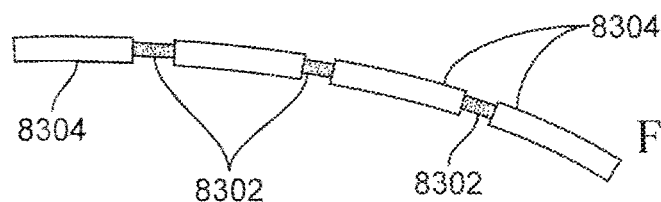
Figure 83D:
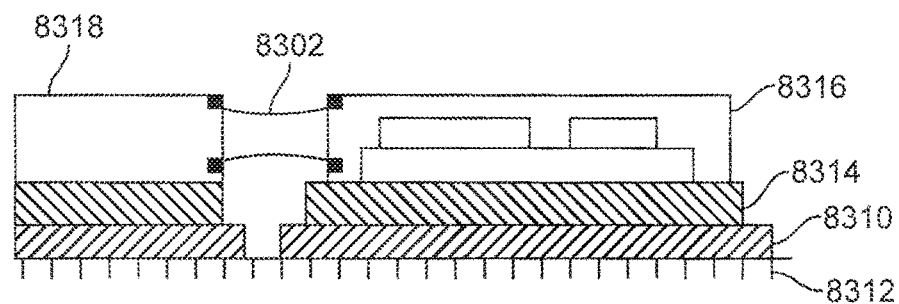

FIG. 81A is a drawing of a wearable defibrillator 8100 with a chest 8102, sternum 8104, and side pockets 8106 to support the components of the device.

FIG. 81B illustrates a cross-section 8110 of a wearable defibrillator having a layered design. The hydrocolloid adhesive 8112 is designed to contact the skin. A flexible substrate 8114 acts as a bridge between the adhesive and the heavier components 8116 (e.g., capacitors, battery, electronic, etc.). The flexible substrate can improve the comfort of the device and improve the ability of the device to support the heavier and rigid components.

FIGS. 82A-82C illustrate drawings of wearable defibrillators with supports over the shoulder and around the neck. The over the shoulder support can also attach to common points of anatomy on the patient's skeleton or body. The wearable defibrillator 8200 has a front chest pocket 8202 and a back pocket 8204. The wearable defibrillator 8201 includes a neck support and front pocket 8212 and back pocket similar to 8204. The pockets can support a defibrillator electrode and the electronic components.

FIGS. 83A-83D illustrate various configurations of interconnect structures to improve the ability of the device to conform to curves on the body. The wearable defibrillators can include rigid portions 8304 and flexible interconnect structures 8302. The adhesive layer 8310 can contact the skin 8312 and a compliant layer 8314. The compliant layer 8314 can engage with the electronics components 8316, 8318. The electronics components 8316, 8318 can be connected together by a flexible interconnect 8302.

FIGS. 84A1-84A2 illustrate cross-sectional and top views of portions of a wearable defibrillator device. In one drawing the electrode 8400 includes channels 8402 between spacers 8404 for deploying an electrode gel or liquid to contact the skin 8406 from a gel source 8408. The gel or liquid can improve the electrical contact between the electrodes and the skin.

FIG. 84B illustrates a device 8420 can include an adhesive 8422, a bonding layer 8424 and a stretchable anchor 8426 to support the defibrillator components 8428 off of the body. The stretchable anchors can be used with the bonding layer to improve attachment of the device to the body.

Figure 85A:
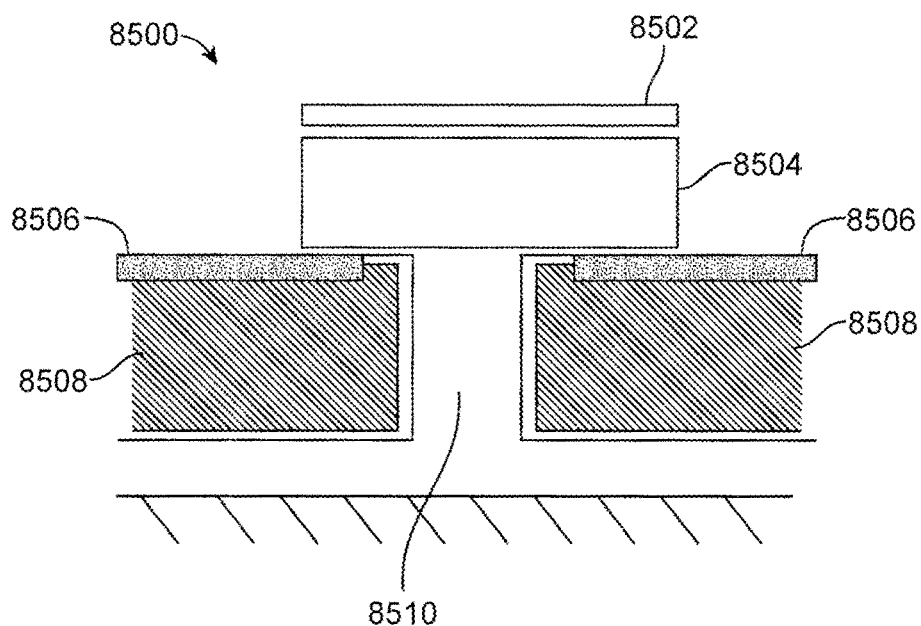
FIGS. 85A-85B illustrate cross-sectional and top views of wearable electrodes in accordance with some embodiments.
Figure 85B:
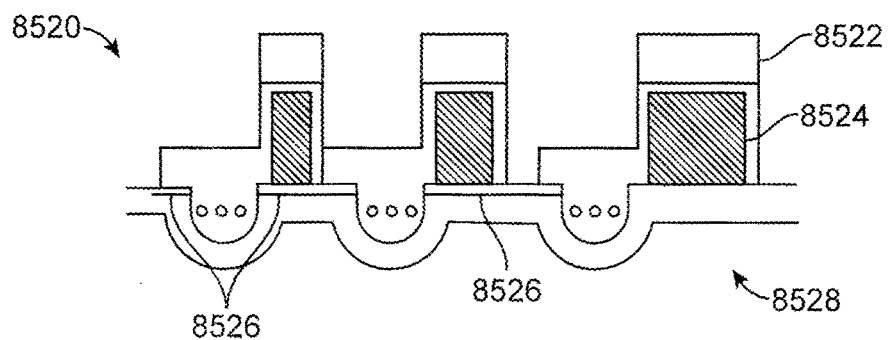

FIGS. 85A-85B illustrate cross-sectional and top views of wearable electrodes including thermal activated 8500 and pressure activated 8520 conductive gel deployment structures. The thermal activated 8500 structure includes a heating element 8502, thermos-activated hydrogel 8504, electrode 8506, gel 8508, and fluid via 8510. The thermos-activated hydrogel 8504 can be deployed through the via 8510 to contact the skin 8512. The pressure activated deployment structure 8520 includes a pressure source 8522, gel 8524, and electrodes 8526, for deploying the gel 8524 against the skin 8528.

Figure 86A:
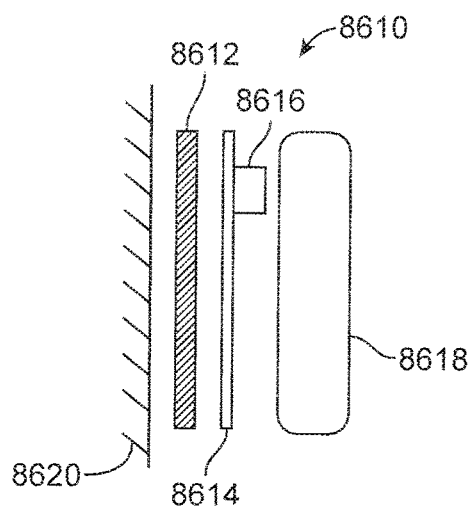
FIGS. 86A-86C illustrate cross-sectional views of portions of wearable defibrillators in accordance with some embodiments.
Figure 86B:
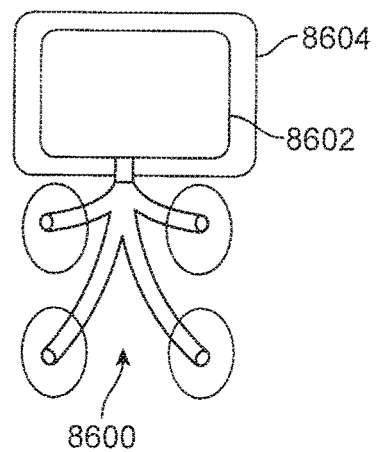
Figure 86C:
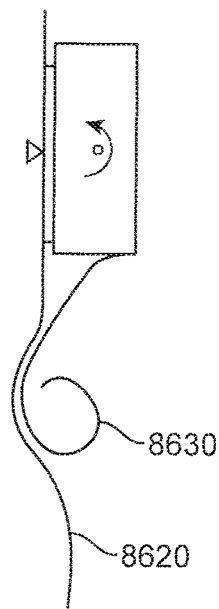

FIGS. 86A-86C illustrates various views of support structures to improve the ability to attach the rigid and heavy defibrillator components to the patient's body. FIG. 86B illustrates a buttressing structure 8600 is used to further support the heavy and rigid defibrillator components 8602 along with an adhesive border 8604. FIG. 86A illustrates a structure 8610 with a hydrocolloid adhesive 8612 that is coupled to a PET film 8614 with a bracket 8616 attached to an end of the rigid and heavy defibrillator components 8618. The anchor allows additional movement of the heavy components while providing a strong attachment structure to the skin 8620. FIG. 86C illustrates a device with a tail 8630 or similar structure can be used to contact the skin 8620 to provide a force on the device to improve engagement between the skin and adhesive 8632 and electronics components 8634 and to provide additional weight support for the device.

FIGS. 87A-87B illustrate a portion of a wearable defibrillator 8700 with an electrode 8702 that can be rotated to improve the skin comfort of the wearer. FIG. 87B also illustrates a portion of a wearable defibrillator 8710 with an electrode 8714 and adhesive wings 8712. The device can be rotated such that wings 8712 contact new portions of the skin. Alternating the sections of the skin contacted by the adhesive can minimize the skin irritation for the wearer.

The wearable defibrillators disclosed herein can meet various design criteria in accordance with some embodiments. In conventional biphasic waveforms about 150 joules to 360 joules can be delivered to the patient. A therapeutic energy of 200 joules or less can be used in some embodiments. A voltage of 3.7 can be used to supply the electronics and thus the milliamp-hours used per shock will be in the range of 11.2-27 mA-hours. The charging circuit can be capable of charging the 100 μF capacitor to 1800 volts in under 20 seconds. A fly-back transformer configuration can be used as the demands on the battery will be in the form of 6 μs pulses of 1.3-1.5 at a frequency of up to 10 KHz sustained for 30 seconds. During charging, the analysis circuit may need additional current in order to drive the DSP supply with a core clocked at 100 MHz or so. This could draw an additional 1 Amp load for approximately 30 seconds. The shelf life can be 3 months or greater. The device can retain enough energy and be ready to wear for the desired duration at the end of the shelf life. The device can be capable of delivering 10 shocks from a single charge of the batteries. The average load will likely remain in the range of 5-10 milliamps throughout most of the wear period with rare bursts of 2.5 Amp average sustained current for approximately 30 seconds. The device can be IEC60601 certified.

Figure 33:
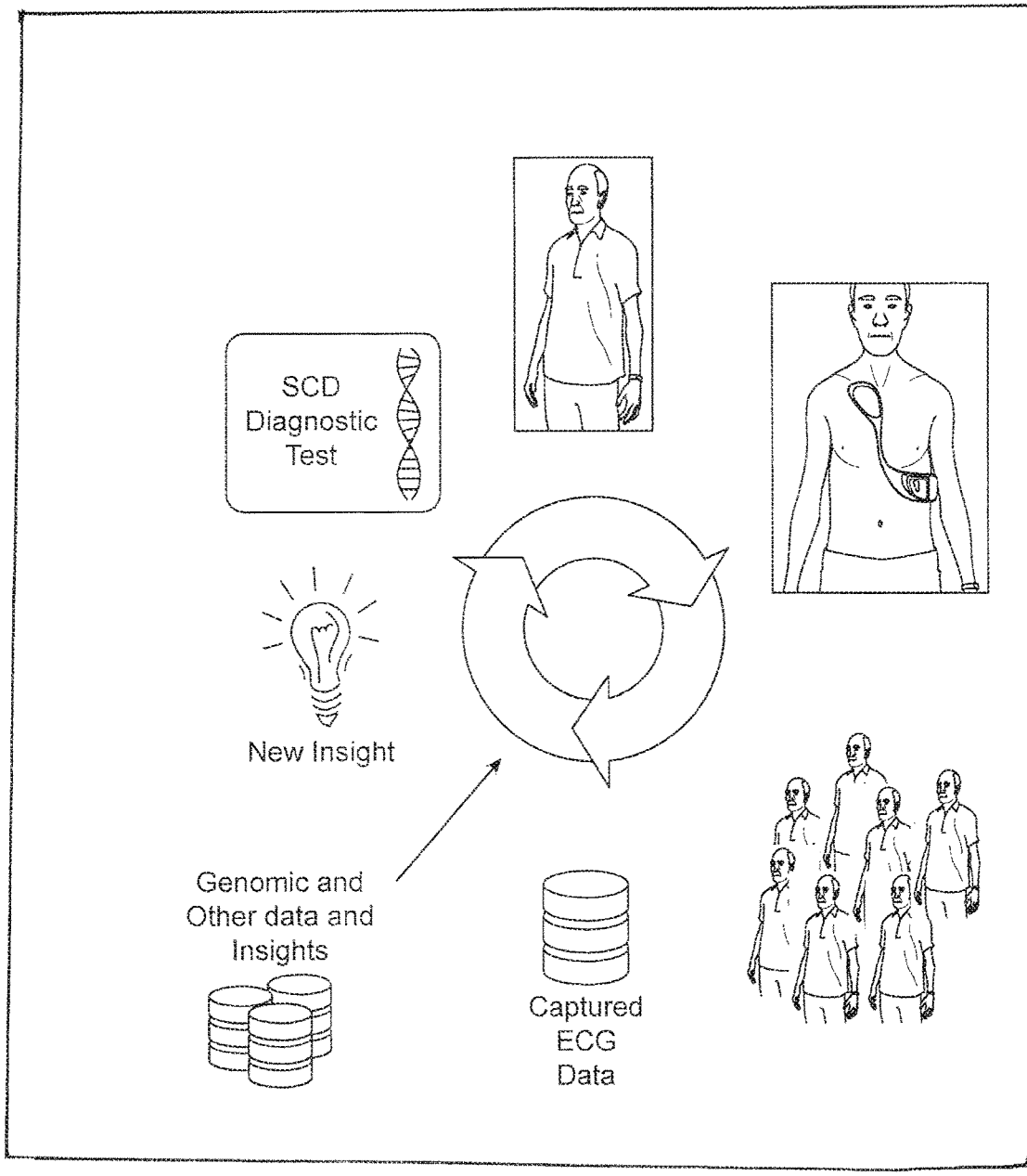
FIG. 33 is a schematic depicting a SCD diagnostic test in accordance with some embodiments.

FIG. 33 is a schematic depiction of a SCD diagnostic test developed in accordance with some embodiments. The wearable defibrillators disclosed herein can collect ECG and other patient data that can be analyzed and aggregated to learn more about SCD patterns and causes. The ECG data can be combined with genomic data and other patient data. The ECG, genomic, and other data can be combined and analyzed to develop an SCD diagnostic test that can be used to predict SCD and SCD risk factors based on health information for a single patient. The patient can then receive personalized treatment, including a wearable defibrillator, based on the SCD diagnostic test results.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable defibrillator comprising:
   a battery;
   one or more capacitors;
   first and second defibrillator electrode pads configured to engage with a patient's skin;
   a controller configured to charge the one or more capacitors with the battery and to discharge the one or more capacitors through the defibrillator electrode pads to the patient;
   a plurality of electrically connected housings enclosing the battery, the one or more capacitors, and the controller;
   a plurality of sensing electrodes configured to engage with the patient's skin and to provide a cardiac signal to the controller;
   a first patient engagement substrate comprising an adhesive and a fluid transport element, the first patient engagement substrate supporting the first defibrillator electrode pad and the housings, the first patient engagement substrate being adapted and configured to be adhesively attached to the patient's skin at a first location on the patient's torso;
   a second patient engagement substrate which is separate from the first patient engagement substrate, the second patient engagement substrate comprising an adhesive and a fluid transport element, the second patient engagement substrate supporting the second defibrillator electrode pad, the second patient engagement substrate being adapted and configured to be adhesively attached to the patient's skin at a second location on the patient's torso; and
   a cable extending between the first patient engagement substrate and the second patient engagement substrate,
   wherein at least one of the sensing electrodes is located on the first patient engagement substrate or the second patient engagement substrate,
   wherein the first patient engagement substrate and the second patient engagement substrate are electrically interconnected by the cable but are not mechanically interconnected.

2. The wearable defibrillator of claim 1, wherein the battery is disposed in one of the housings and the one or more capacitors are disposed in another of the housings.

3. The wearable defibrillator of claim 1, further comprising a flexible connection between two of the housings.

4. The wearable defibrillator of claim 1, wherein the housings are waterproof.

5. The wearable defibrillator of claim 1, wherein the housings are adapted and configured to conform to the patient's torso.

6. The wearable defibrillator of claim 1, wherein the first patient engagement substrate is adapted and configured to follow a lower rib line of the patient when adhesively attached to the first location.

7. The wearable defibrillator of claim 1, wherein the first location is on a side of the patient under an arm of the patient.

8. The wearable defibrillator of claim 1, wherein at least one of the first patient engagement substrate and the second patient engagement substrate has an average elasticity of about 0.40 MPa to about 0.90 MPa.

9. The wearable defibrillator of claim 1, wherein at least one of the first patient engagement substrate and the second patient engagement substrate comprises an elastic element having an elasticity similar to the elasticity of the patient's skin.

10. The wearable defibrillator of claim 1, further comprising user interface controls disposed on the housing.

11. A method of applying a wearable defibrillator to a patient's torso, the method comprising:
    adhering a first patient engagement substrate to a first skin location on the patient's torso, the first patient engagement substrate supporting a first defibrillator electrode pad and a plurality of housings, the housings enclosing a battery, one or more capacitors, and a controller;
    conforming the housings to the patient's torso; and
    adhering a second patient engagement substrate which is separate from the first patient engagement substrate to a second skin location on the patient's torso, the second patient engagement substrate supporting a second defibrillator electrode pad, a plurality of sensing electrodes being supported by the first patient engagement substrate and or the second patient engagement substrate engaging with the patient's skin and providing a cardiac signal to the controller, a cable extending from the second engagement substrate to the first engagement substrate such that the first patient engagement substrate and the second patient engagement substrate are electrically interconnected but are not mechanically interconnected.

12. The method of claim 11, wherein adhering the first patient engagement substrate comprises adhering the first patient engagement substrate to follow a lower rib line of the patient.

13. The method of claim 11, wherein the first skin location is under an arm of the patient.

14. The method of claim 13, wherein the second skin location is on an upper chest of the patient.

15. The method of claim 11, further comprising flexing the electrically connected housings about a flexible connection.

\* \* \* \* \*